(12) United States Patent
Iino et al.

(10) Patent No.: US 8,138,197 B2
(45) Date of Patent: Mar. 20, 2012

(54) SPIROCHROMANON DERIVATIVES

(75) Inventors: Tomoharu Iino, Tsukuba (JP); Hideki Jona, Moriya (JP); Hideki Kurihara, Tsukuba (JP); Masayuki Nakamura, Tsukuba (JP); Kenji Niiyama, Tsuchiura (JP); Jun Shibata, Tsukuba (JP); Tadashi Shimamura, Tsukuba (JP); Hitomi Watanabe, Tsukuba (JP); Takeru Yamakawa, Tsukuba (JP); Lihu Yang, Edison, NJ (US)

(73) Assignees: MSD K.K., Tokyo (JP); Merck Sharp & Dohme Corp., Rahway, NJ (US)

( * ) Notice: Subject to any disclaimer, the term of this patent is extended or adjusted under 35 U.S.C. 154(b) by 402 days.

(21) Appl. No.: 12/518,466

(22) PCT Filed: Jan. 8, 2008

(86) PCT No.: PCT/US2008/000247
§ 371 (c)(1),
(2), (4) Date: Jun. 10, 2009

(87) PCT Pub. No.: WO2008/088692
PCT Pub. Date: Jul. 24, 2008

(65) Prior Publication Data
US 2009/0270436 A1      Oct. 29, 2009

Related U.S. Application Data

(60) Provisional application No. 60/880,303, filed on Jan. 12, 2007.

(51) Int. Cl.
*A61K 31/438* (2006.01)
*C07D 221/20* (2006.01)
(52) U.S. Cl. .......................... 514/270; 546/16
(58) Field of Classification Search .............. 546/16; 514/270
See application file for complete search history.

(56) References Cited

U.S. PATENT DOCUMENTS

| 4,261,988 | A | 4/1981 | Widdig et al. |
| 5,206,240 | A | 4/1993 | Baldwin et al. |
| 5,633,247 | A | 5/1997 | Baldwin et al. |
| 5,688,997 | A | 11/1997 | Baldwin et al. |
| 5,885,999 | A | 3/1999 | Elliott et al. |
| 7,410,976 | B2 | 8/2008 | Yamakawa et al. |
| 2001/0039286 | A1 | 11/2001 | Dinnell et al. |
| 2002/0082264 | A1 | 6/2002 | Nikolic et al. |
| 2007/0021453 | A1 | 1/2007 | Yamakawa et al. |
| 2008/0171761 | A1 | 7/2008 | Iino et al. |

FOREIGN PATENT DOCUMENTS

| EP | 0 518 805 A1 | 12/1992 |
| EP | 0 431 943 B1 | 7/1998 |
| JP | 2005119987 A | 5/2005 |
| WO | WO94/17045 A1 | 8/1994 |
| WO | WO95/30642 A1 | 11/1995 |
| WO | WO96/39140 A1 | 12/1996 |
| WO | WO97/16569 A1 | 5/1997 |
| WO | WO97/16729 A1 | 7/2004 |
| WO | WO2004/058727 A1 | 7/2004 |
| WO | WO2004/092179 A1 | 10/2004 |
| WO | WO2006/040329 A1 | 4/2006 |
| WO | WO2006/055752 A2 | 5/2006 |
| WO | WO2006/055752 A3 | 5/2006 |
| WO | WO2006/117669 A1 | 11/2006 |
| WO | WO2007/011809 A1 | 1/2007 |
| WO | WO2007/011811 A1 | 1/2007 |
| WO | WO2008/065508 A1 | 6/2008 |

OTHER PUBLICATIONS

Abu-Elheiga, et al., "Continuous Fatty Acid Oxidation and Reduced Fat Storage in Mice Lacking Acetyl-CoA Carboxylase 2", Science, 2001, pp. 2613-2616, vol. 291.

(Continued)

*Primary Examiner* — Rita Desai
(74) *Attorney, Agent, or Firm* — Janet E. Fair; John C. Todaro

(57) ABSTRACT

The invention relates to a compound of a general formula (I): wherein Ar1 represents a group formed from an aromatic ring selected from a group consisting of benzene, pyrazole, isoxazole, pyridine, indole, 1H-indazole, 1H-furo[2,3-c]pyrazole, 1H-thieno[2,3-c]pyrazole, benzimidazole, 1,2-benzisoxazole, imidazo[1,2-a]pyridine, imidazo[1,5-a]pyridine and 1H-pyrazolo[3,4-a]pyridine, having Ar2, and optionally having one or two or more substituents selected from R3; R1 and R2 each independently represent a hydrogen atom, a halogen atom, a cyano group, a C2-C6 alkenyl group, a C1-C6 alkoxy group, a C2-C7 alkanoyl group, a C2-C7 alkoxycarbonyl group, an aralkyloxycarbonyl group, a carbamoyl-C1-C6 alkoxy group, a carboxy-C2-C6 alkenyl group, or a group of -Q1-N(Ra)-Q2-Rb; or a C1-C6 alkyl group optionally having a substituent; or an aryl or heterocyclic group optionally having a substituent; or a C1-C6 alkyl group or a C2-C6 alkenyl group having the aryl or heterocyclic group; T and U each independently represent a nitrogen atom or a methine group; and V represents an oxygen atom or a sulfur atom. The compound of the invention is useful as therapeutical agents for various ACC-related diseases.

(I)

3 Claims, No Drawings

OTHER PUBLICATIONS

Abu-Elheiga, et al., "Human acetyl-CoA carboxylase: Characterization, molecular cloning, and evidence for two isoforms", Proc. Natl. Acad. Sci., 1995, pp. 4011-4015, vol. 92.

Beckers, et al., "Chemical Inhibition of Acetyl-CoA Carboxylase Induces Growth Arrest and Cytotoxicity Selectively in Cancer Cells", Cancer Res., 2007, pp. 8180-8187, vol. 67, Issue 17.

Elliott, et al., "4-0xospiro[benzopyran-2,4'-piperidines] as Class III Antiarrhythmic Agents. Pharmacological Studies on 3,4-Dihydro-1'[2-(benzofurazan-5-yl)-ethyl]-6-methanesulfonamidospiro[(2H)-1-benzopyran-2,4'-piperidin]-4-one (L-691,121)", J. Med. Chem., 1992, pp. 3973-3976, vol. 35.

Freiberg, et al., "Identification and Characterization of the First Class of Potent Bacterial Acetyl-CoA Carboxylase Inhibitors with Antibacterial Activity", The Journal of Biological Chemistry, 2004, pp. 26066-26073, vol. 279, No. 25.

Harwood, et al., "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals", The Journal of Biological Chemistry, 2003, pp. 37099-37111, vol. 278, No. 39.

Nakamuta, et al., "Evaluation of fatty acid metabolism-related gene expression in nonalcoholic fatty liver disease", International Journal of Molecular Medicine, 2005, pp. 631-635, vol. 16.

Quaglia, et al., "1'-Benzyl-3,4-dihydrospirol[2H-1-benzothiopyran-2,4'-piperidine] (Spipethiane), a Potent and Highly Selective Ligand", American Chemical Society, 1998, pp. 1557-1560, vol. 41, No. 10.

Savage, et al., "Reversal of diet-induced hepatic steatosis and hepatic insulin resistance by antisense oligonucleotid inhibitors of acetyl-CoA carboxylases 1 and 2", The Journal of Clinical Investigaton, 2006, pp. 1-8.

Wilson, et al., "Synthesis and derivatisation of a novel spirol[1-benzofuran-2,4'-piperidin]-3-one scaffold", Org. Biomol. Chem., 2005, pp. 3228-3235, vol. 3.

Xu, et al., "The fat-derived hormone adiponectin alleviates alcoholic and nonalcoholic fatty liver diseases in mice", The Journal of Clinical Investigation, 2003, pp. 91-100, vol. 112, Nol. 1.

Database Chemcats Abstract, Cas-Registry Nos. 877811-12-6, 2006, 877811-11-5, 2008.

Database Chemcats Abstract, XP-002477903, Cas-Registry No. 887467-90-5, 2007.

SPIROCHROMANON DERIVATIVES

CROSS-REFERENCE TO RELATED APPLICATIONS

This application is a U.S. National Phase application under 35 U.S.C. §371 of PCT Application No. PCT/US2008/000247, filed Jan. 8, 2008, which claims priority from and the benefit of U.S. Provisional Application No. 60/880,303, filed Jan. 12, 2007.

BACKGROUND OF THE INVENTION

Acetyl CoA carboxylase (hereinafter this may be abbreviated to ACC) is an enzyme that carboxylates acetyl CoA to produce malonyl CoA, and mammals have two isozymes of ACC1 and ACC2 in their own bodies. Malonyl CoA produced by ACC may be a starting material for long-chain fatty acids or neutral fats, and in addition, it may negatively control carnitine palmitoyl transferase-1 (CPT-1) that participates in oxidative decomposition of fatty acids. Of the above isozymes, ACC1 exists in cytoplasm and is considered as a rate-limiting enzyme in biosynthesis of long-chain fatty acids, while, ACC2 exists predominantly on mitochondria and is said to participate principally in oxidation of fatty acids. Accordingly, compounds capable of inhibiting ACC1 and/or ACC2 are expected not only to inhibit synthesis of fatty acids but also to reduce accumulated fats. In fact, it is shown that, as compared with normal mice, ACC2-knocked out mice hardly get fat (see *Proceedings of the National Academy of Sciences of the United States of America*, 100 (18), pp. 10207-10212, 2003).

An excess of accumulated fats may cause, for example, insulin resistance, diabetes, hypertension, hyperlipemia and obesity, and it is known that a plurality of those factors, as combined, lead to an extremely higher risk of arteriosclerosis, and the symptom is referred to as a metabolic syndrome. Further, it is known that hypertriglyceridemia or obesity leads to a higher risk of, for example, pancreatitis, liver dysfunction, cancers such as breast cancer, uterine cancer, ovarian cancer, colon cancer and prostate cancer, emmeniopathy, arthritis, gout, cholecystitis, gastroesophageal reflux, pickwickian syndrome, sleep apnea syndrome. It is well known that diabetes often causes, for example, cardiac angina, heart failure, stroke, claudication, retinopathy, eyesight failure, renal failure, neuropathy, skin ulcer, infectious diseases (see *The Merck Manual of Medical Information*, second home edition, Merck & Co., 2003). Accordingly, ACC inhibitors are useful for the treatment and/or prevention of such disorders.

ACC exists also in plants, parasites, bacteria and fungi, and it is known that it participates in the growth of cells. For example, aryloxyphenoxypropionic acid-type herbicides represented by diclofop, and cyclohexanedione-type herbicides represented by setoxydim excert their activity by inhibiting ACC in plants (see *Biochemical Society of Transaction*, 22(3), p. 616 (1994)), and the aryloxyphenoxypropionic acids also exhibit a growth-inhibiting effect on parasites (see *Journal of Biological Chemistry*, 277 (26), pp. 23208-23215 (2002)). In addition, sorafen and moiramide B known as ACC inhibitors exhibit an antibacterial effect and an antifungal effect (see *Current Genetics*, 25 (2), pp. 95-100 (1994); *Journal of Biological Chemistry*, 279 (25), pp. 26066-26073 (2004)).

Tumor cells generally show an increased synthesis of fatty acids, and it is reported that some fatty acid synthesis inhibitors exhibit a cell growth-inhibiting effect.

Based on the above-mentioned information, ACC inhibitors are expected to be useful for the treatment and/or prevention of disorders such as hyperlipemia, fatty liver, dyslipidemia, hepatic dysfunction, obesity, diabetes, insulin resistance, metabolic syndrome, arteriosclerosis, hypertension, cardiac angina, heart failure, cardiac infarction, stroke, claudication, retinopathy, eyesight failure, renal failure, electrolyte metabolism disorder, neuropathy, skin ulcer, bulimia, pancreatitis, emmeniopathy, arthritis, gout, cholecystitis, gastroesophageal reflux, pickwickian syndrome, sleep apnea syndrome, neoplasm, infectious diseases, such as parasite infection, bacterial infection, viral infection, and fungal infection, and also as herbicides.

Up to the present, for example, those described in a pamphlet of WO 2003/094912, a pamphlet of WO 2003/072197, a pamphlet of WO 2003/059886, a pamphlet of WO 2003/059871 are known as compounds capable of inhibiting ACC, but the compounds described in these references are totally different from the compounds of the present invention in point of their structures.

On the other hand, various compounds having the same spirochromanone skeleton as that of the compounds of the present invention are disclosed in a pamphlet of WO 95/30642, EP 431973A or a pamphlet of WO 2004/092179. However, these references do neither disclose nor suggest the ACC-inhibiting effect of those compounds or the compounds of the present invention.

SUMMARY OF THE INVENTION

The present invention is useful in the field of medicines. More precisely, novel spirochromanone derivatives of the invention are acetyl CoA carboxylase inhibitors useful as therapeutical agents for various vascular diseases, nervous system diseases, metabolic diseases, genital diseases, digestive system diseases, respiratory diseases, neoplasm and infectious diseases. In addition, they are also useful as herbicides.

DETAILED DESCRIPTION OF THE INVENTION

The present invention provides compounds of the following general formula (I), and salts and esters thereof, which have a strong ACC-inhibiting effect:

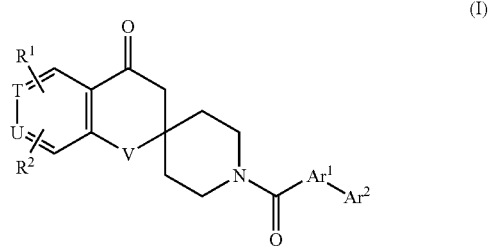

(I)

wherein $Ar^1$ represents a group formed from an aromatic ring selected from a group consisting of benzene, pyrazole, isoxazole, pyridine, indole, 1H-indazole, 1H-furo[2,3-c]pyrazole, 1H-thieno[2,3-c]pyrazole, benzimidazole, 1,2-benzisoxazole, imidazo[1,2-a]pyridine, imidazo[1,5-a]pyridine and 1H-pyrazolo[3,4-b]pyridine, having $Ar^2$, and optionally having one or two or more substituents selected from $R^3$;

$Ar^2$ represents an aromatic group selected from a group consisting of a phenyl group, a furyl group, a thienyl group, a pyrazolyl group, a thiazolyl group, an oxazolyl group, an isoxazolyl group, a 1,2,4-triazolyl group, a 1,2,4-oxadiazolyl group, a 1,3,4-oxadiazolyl group, a tetrazolyl group, a pyridyl group, a pyrazinyl group, a pyrimidinyl group, an indolyl group and a benzo[b]thienyl group, optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group;

$R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of -$Q^1$-N($R^a$)-$Q^2$-$R^b$;

a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group;

$R^3$ represents a halogen atom, a nitro group, a cyano group, a hydroxyl group, a carboxyl group, a C2-C6 alkenyl group, a cyclo-C3-C6 alkyl group, or a group of —N($R^e$)$R^f$, a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group may be interrupted by an oxygen atom, a sulfur atom or an imino group;

a C1-C6 alkyl group optionally having a substituent selected from a group consisting of a halogen atom, a hydroxyl group, a cyclo-C3-C6 alkyl group and a C1-C6 alkoxy group; or a phenyl group, a 1,2,4-triazolyl group or a tetrazolyl group optionally having a substituent selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group;

$Q^1$ and $Q^2$ each independently represent a single bond, or a group of —CO—, —SO$_2$— or —C($R^g$)($R^h$)—;

$R^a$ and $R^b$ each independently represent a hydrogen atom, a C2-C6 alkenyl group, a C——C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of —N($R^i$)$R^j$;

a C1-C6 alkyl group optionally having a substituent selected from a group consisting of a halogen atom, a C1-C6 alkoxy group, a carbamoyl group and a C2-C7 alkoxycarbonyl group; or a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group;

$R^c$, $R^d$, $R^g$, $R^h$, $R^i$ and $R^j$ each independently represent a hydrogen atom, a C1-C6 alkyl group, or a halo-C1-C6 alkyl group;

$R^e$ and $R^f$ each independently represent a hydrogen atom, a C1-C6 alkyl group, or a halo-C1-C6 alkyl group, or taken together, they may form a C2-C5 alkylene group optionally interrupted by an oxygen atom, a sulfur atom or an imino group;

T and U each independently represent a nitrogen atom or a methine group; and

V represents an oxygen atom or a sulfur atom.

The compounds (I) of the invention have an ACC-inhibiting effect and are useful as therapeutical agents for various ACC-related disorders, for example, vascular diseases such as hypertension, cardiac angina, heart failure, cardiac infarction, stroke, claudication, diabetic nephropathy, diabetic retinopathy, eyesight failure, electrolyte metabolism disorder, arteriosclerosis; nervous system diseases such as bulimia, diabetic neuropathy; metabolic diseases such as metabolic syndrome, obesity, diabetes, insulin resistance, hyperlipemia, hypercholesterolemia, hypertriglyceridemia, dyslipidemia, nonalcoholic fatty liver, hormone secretion failure, gout, and hepatic steatosis; genital diseases such as emmeniopathy, sexual dysfunction; digestive system diseases such as liver dysfunction, pancreatitis, cholecystitis, gastroesophageal reflux; respiratory diseases such as obesity-hypoventilation syndrome (pickwickian syndrome), sleep apnea syndrome; infectious diseases caused by bacteria, fungi or parasites; malignant neoplasm; and inflammatory diseases such as arthritis and skin ulcer. The compounds are also useful as herbicides.

In particular, the compounds (I) of the invention are useful as therapeutical agents, for example, for metabolic syndrome, fatty liver, hyperlipemia, obesity, diabetes, bulimia, malignant neoplasm and infectious diseases.

The invention relates to the compounds of formula (I), and their salts and esters, and to their production and use.

The meanings of the terms used herein are mentioned below, and the invention is described in more detail hereinunder.

"Halogen atom" includes a fluorine atom, a chlorine atom, a bromine atom, and an iodine atom.

"C1-C6 alkyl group" means a linear or branched alkyl group having from 1 to 6 carbon atoms, and it includes, for example, a methyl group, an ethyl group, a propyl group, an isopropyl group, a butyl group, an isobutyl group, a sec-butyl group, a tert-butyl group, a pentyl group, an isopentyl group, a hexyl group, and an isohexyl group.

"Halo-C1-C6 alkyl group" means the above-mentioned C1-C6 alkyl group which is substituted with the above-mentioned halogen atom(s) of the same type or different types and which has one or two or more, but preferably from 1 to 3 unlimited substitutable positions, and it includes, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group.

"Hydroxy-C1-C6 alkyl group" means the above-mentioned C1-C6 alkyl group which is substituted with hydroxyl group(s) and which has one or two or more, but preferably one or two unlimited substitutable positions, and it includes, for example, a hydroxymethyl group, a 2-hydroxyethyl group, a 1-hydroxy-1-methylethyl group, a 1,2-dihydroxyethyl group, and a 3-hydroxypropyl group.

"Cyclo-C3-C6 alkyl group" means a cycloalkyl group having from 3 to 6 carbon atoms, and it includes a cyclopropyl group, a cyclobutyl group, a cyclopentyl group, and a cyclohexyl group.

"C2-C6 alkenyl group" means a linear or branched alkenyl group having from 2 to 6 carbon atoms, and it includes, for example, a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group.

"C1-C6 alkoxy group" means a linear or branched alkoxy group having from 1 to 6 carbon atoms, and it includes, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, and an isohexyloxy group.

"Halo-C1-C6 alkoxy group" means the above-mentioned C1-C6 alkoxy group which is substituted with the above-mentioned halogen atom(s) of the same type or different types and which has one or two or more, but preferably from 1 to 3 unlimited substitutable positions, and it includes, for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group.

"C1-C6 alkylthio group" means a linear or branched alkylthio group having from 1 to 6 carbon atoms, and it includes, for example, a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, and an isohexylthio group.

"C2-C7 alkanoyl group" means an alkanoyl group having the above-mentioned C1-C6 alkyl group, or that is, an alkanoyl group having from 2 to 7 carbon atoms, and it includes, for example, an acetyl group, a propionyl group, a butyryl group, an isobutyryl group, a valeryl group, an isovaleryl group, and a pivaloyl group.

"Halo-C2-C7 alkanoyl group" means the above-mentioned C2-C7 alkanoyl group which is substituted with the above-mentioned halogen atom(s) of the same type or different types and which has one or two or more, but preferably from 1 to 3 unlimited substitutable positions, and it includes, for example, a chloroacetyl group, a dichloroacetyl group, a fluoroacetyl group, a difluoroacetyl group, a 3-chloropropionyl group, and a 3-fluoropropionyl group.

"C2-C7 alkanoylamino group" means an amino group that is mono-substituted or di-substituted, preferably mono-substituted with the above-mentioned C2-C7 alkanoyl group, and it includes, for example, an acetylamino group, a propionylamino group, a butyrylamino group, an isobutyrylamino group, a valerylamino group, an isovalerylamino group, a pivaloylamino group.

"C1-C6 alkylcarbamoyl group" means a carbamoyl group that is mono-substituted or di-substituted with the above-mentioned C1-C6 alkyl group, and it includes, for example, a methylcarbamoyl group, a dimethylcarbamoyl group, an ethylcarbamoyl group, a diethylcarbamoyl group, an ethyl(methyl)carbamoyl group, a propylcarbamoyl group, an isopropylcarbamoyl group.

"Cyclo-C3-C6 alkylcarbamoyl group" means a carbamoyl group that is mono-substituted or di-substituted, preferably mono-substituted with the above-mentioned cyclo-C3-C6 alkyl group, and it includes, for example, a cyclopropylcarbamoyl group, a cyclobutylcarbamoyl group, a cyclopentylcarbamoyl group, a cyclohexylcarbamoyl group.

"C1-C6 alkoxy-C1-C6 alkyl group" means the above-mentioned C1-C6 alkyl group which is substituted with the above-mentioned C1-C6 alkoxy group(s) of the same type or different types and which has one or two or more, but preferably from 1 or 2 unlimited substitutable positions, and it includes, for example, a methoxymethyl group, an ethoxymethyl group, a 2-methoxyethyl group, a 2-ethoxyethyl group, a 1-methoxy-1-methylethyl group, a 1,2-dimethoxyethyl group, a 3-methoxypropyl group.

"(C1-C6 alkoxy-C1-C6 alkyl)carbamoyl group" means a carbamoyl group that is mono-substituted or di-substituted, preferably mono-substituted with the above-mentioned C1-C6 alkoxy-C1-C6 alkyl group, and it includes, for example, a (methoxymethyl)carbamoyl group, an (ethoxymethyl)carbamoyl group, a (2-methoxyethyl)carbamoyl group, a (2-ethoxyethyl)carbamoyl group, a (1-methoxy-1-methylethyl)carbamoyl group, a (1,2-dimethoxyethyl)carbamoyl group, a (3-methoxypropyl)carbamoyl group.

"C2-C7 alkoxycarbonyl group" means an alkoxycarbonyl group having the above-mentioned C1-C6 alkoxy group, or that is, an alkoxycarbonyl group having from 2 to 7 carbon atoms, and it includes, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, and a pentyloxycarbonyl group.

"Halo-C2-C7 alkoxycarbonyl group" means a haloalkoxycarbonyl group having the above-mentioned halo-C1-C6 alkoxy group, and it includes, for example, a 2,2-difluoroethoxycarbonyl group.

"Carbamoyl-C1-C6 alkoxy group" means the above-mentioned C1-C6 alkoxy group substituted with one or two or more, preferably one carbamoyl group at the substitutable position thereof, and it includes, for example, a carbamoylmethoxy group, a 1-carbamoylethoxy group, a 2-carbamoylethoxy group, a 2-carbamoylpropoxy group, and a 3-carbamoylpropoxy group.

"Carboxy-C2-C6 alkenyl group" means the above-mentioned C2-C6 alkenyl group substituted with one or two or more, preferably one carboxyl group at the substitutable position thereof, and it includes, for example, a 1-carboxyvinyl group, a 2-carboxyvinyl group, a 2-carboxy-1-propenyl group, a 3-carboxy-1-propenyl group, a 3-carboxy-2-propenyl group, a 4-carboxy-3-butenyl group, and a 4-carboxy-2-butenyl group.

"C2-C7 alkanoyloxy group" means an alkanoyloxy group having the above-mentioned C2-C7 alkanoyl group, and it includes, for example, an acetyloxy group, a propionyloxy group, a butyryloxy group, an isobutyryloxy group, a valeryloxy group, an isovaleryloxy group, and a pivaloyloxy group.

"C1-C6 alkylsulfonyl group" means a linear or branched alkylsulfonyl group having from 1 to 6 carbon atoms, and it includes, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

"C1-C6 alkylsulfonylamino group" means an amino group that is mono-substituted or di-substituted, preferably mono-substituted with the above-mentioned C1-C6 alkylsulfonyl group, and it includes, for example, a methylsulfonylamino group, an ethylsulfonylamino group, a propylsulfonylamino group, an isopropylsulfonylamino group, a butylsulfonylamino group, a sec-butylsulfonylamino group, an isobutylsulfonylamino group, a tert-butylsulfonylamino group, a pentylsulfonylamino group, an isopentylsulfonylamino group, a hexylsulfonylamino group, an isohexylsulfonylamino group.

"C2-C7 alkanoyloxy-C1-C6 alkyl group" means the above-mentioned C1-C6 alkyl group substituted with one or two or more, preferably one C2-C7 alkanoyloxy group at any substitutable position thereof, and it includes, for example, an acetyloxymethyl group, a propionyloxymethyl group, a butyryloxymethyl group, an isobutyryloxymethyl group, a valeryloxymethyl group, an isovaleryloxymethyl group, and a pivaloyloxymethyl group.

"Aryl group" includes, for example, a phenyl group, a naphthyl group.

"Aralkyl group" means the above-mentioned C1-C6 alkyl group which is substituted one or two or more, preferably one aryl group at any substitutable position thereof, and it includes, for example, a benzyl group, a 1-phenylethyl group, a phenethyl group, a 1-naphthylmethyl group, and a 2-naphthylmethyl group.

"Aralkyloxy group" means an aralkyloxy group having the above-mentioned aralkyl group, and it includes, for example, a benzyloxy group, a 1-phenylethyloxy group, a phenethyloxy group, a 1-naphthylmethyloxy group, and a 2-naphthylmethyloxy group.

"Aralkyloxycarbonyl group" means an aralkyloxycarbonyl group having the above-mentioned aralkyloxy group, and it includes, for example, a benzyloxycarbonyl group, a 1-phenylethyloxycarbonyl group, a phenethyloxycarbonyl group, a 1-naphthylmethyloxycarbonyl group, and a 2-naphthylmethyloxycarbonyl group.

"Heteroaromatic group" means a 5-membered or 6-membered monocyclic aromatic heterocyclic group which has one or two or more, but preferably from 1 to 3 and the same or different hetero atoms selected from a group consisting of oxygen, nitrogen and sulfur atoms, or means a condensed-cyclic aromatic heterocyclic group which is constructed through condensation of the monocyclic aromatic heterocyclic group and the above-mentioned aryl group or through condensation of those, same or different monocyclic aromatic heterocyclic groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a, 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, and a pyrido[3,2-b]pyridyl group.

"Heterocyclic group" means a 3- to 7-membered monocyclic heterocyclic group which has one or two or more, but preferably from 1 to 3 and the same or different hetero atoms selected from a group consisting of oxygen, nitrogen and sulfur atoms, or means a condensed-cyclic heterocyclic group which is constructed through condensation of the monocyclic heterocyclic group and a 3- to 7-membered carbocyclic group or through condensation of those, same or different monocyclic heterocyclic groups; and it includes the above-mentioned heterocyclic aromatic groups. Its examples are, in addition to those listed hereinabove for the above-mentioned heterocyclic aromatic group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group, and a thiomorpholinyl group.

"Cyclo-C3-C6 alkyloxy group" means a cycloalkyloxy group having the above-mentioned cyclo-C3-C6 alkyl group, and it includes a cyclopropyloxy group, a cyclobutyloxy group, a cyclopentyloxy group, and a cyclohexyloxy group.

"Cyclo-C3-C6 alkyloxycarbonyl group" means a cycloalkyloxycarbonyl group having the above-mentioned cyclo-C3-C6 alkyloxy group, and it includes, for example, a cyclopropyloxycarbonyl group, a cyclobutyloxycarbonyl group.

"Cyclo-C3-C6 alkyl-C1-C6 alkoxy group" means the above-mentioned C1-C6 alkoxy group which is substituted with one or two or more, preferably one cyclo-C3-C6 alkyl group at any substitutable position thereof, and it includes, for example, a cyclopropylmethoxy group, a cyclobutylmethoxy group, a cyclopentylmethoxy group, a cyclopropylethoxy group, a cyclobutylethoxy group, and a cyclopropylpropoxy group.

"Cyclo-C3-C6 alkylthio group" means a cycloalkylthio group having the above-mentioned cyclo-C3-C6 alkyl group, and it includes a cyclopropylthio group, a cyclobutylthio group, a cyclopentylthio group, and a cyclohexylthio group.

"Cyclo-C3-C6 alkyl-C1-C6 alkylthio group" means the above-mentioned C1-C6 alkylthio group substituted with one or two or more, preferably one cyclo-C3-C6 alkyl group at any substitutable position thereof, and it includes, for example, a cyclopropylmethylthio group, a cyclobutylmethylthio group, a cyclopentylmethylthio group, a cyclopropylethylthio group, a cyclobutylethylthio group, and a cyclopropylpropylthio group.

"Cyclo-C3-C6 alkyl group optionally interrupted by an oxygen atom, a sulfur atom or an imino group" means that the cyclo-C3-C6 alkyl group is the above-mentioned cyclo-C3-C6 alkyl group, or means that the carbon atom(s) constituting the cyclo-C3-C6 alkyl group is/are replaced with one or two or more, preferably one oxygen atom, sulfur atom or imino group so that the cyclo-C3-C6 alkyl group is interrupted by it. The group includes, for example, those listed hereinabove as the above-mentioned cyclo-C3-C6 alkyl group, and in addition to these, an oxiranyl group, an oxetanyl group, a tetrahydrofuranyl group, a tetrahydro-2H-pyranyl group, a thiiranyl group, a thietanyl group, a tetrahydrothienyl group, a tetrahydro-2H-thiopyranyl group, an aziridinyl group, an azetidinyl group, a pyrrolidinyl group, and a piperidyl group.

"C1-C6 alkylene group" means a linear or branched alkylene group having from 1 to 6 carbon atoms, and it includes, for example, a methylene group, an ethylene group, a trimethylene group, a tetramethylene group, a pentamethylene group, and a hexamethylene group.

"C2-C5 alkylene group optionally interrupted by an oxygen atom, a sulfur atom or an imino group" means an alkylene group having from 2 to 5 carbon atoms, which is interrupted or not by one or two or more, but preferably one oxygen atom, sulfur atom or imino group at any position of the alkylene chain thereof capable of being interrupted by it, and this includes, for example, an ethylene group, a trimethylene group, a tetramethylene group, a pentamethylene group, a 2-oxatetramethylene group, a 2-oxapentamethylene group, 3-oxapentamethylene group, a 2-thiatetramethylene group, a 2-thiapentamethylene group, a 3-thiapentamethylene group, a 2-azatetramethylene group, 2-azapentamethylene group, and a 3-azapentamethylene group.

"Salts" of the compound of formula (I) means pharmaceutically acceptable common salts, including, for example, base addition salts of the compound having a carboxyl group, a hydroxyl group or an acidic heterocyclic group such as a tetrazolyl group, with a base added to the carboxyl group, the hydroxyl group or the acidic heterocyclic group of the compound; and acid addition salts of the compound having an amino group or a basic heterocyclic group, with an acid added to the amino group or the basic heterocyclic group of the compound.

The base addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"Esters" of the compound of formula (I) mean those of the compound having a carboxyl group, which are esterified at the carboxyl group of the compound and which are pharmaceutically acceptable common esters, including, for example, esters with a C1-C6 alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or cyclopentyl group; esters with an aralkyl group such as a benzyl group or a phenethyl group; esters with a C2-C6 alkenyl group such as an allyl group or a 2-butenyl group; esters with a C1-C6 alkoxy-C1-C6 alkyl group such as a methoxymethyl group, a 2-methoxyethyl group or a 2-ethoxyethyl group; esters with a C2-C7 alkanoyloxy-C1-C6 alkyl group such as an acetoxymethyl group, a pivaloyloxymethyl group or a 1-pivaloyloxyethyl group; esters with a C2-C7 alkoxycarbonyl-C1-C6 alkyl group such as a methoxycarbonylmethyl group or an isopropoxycarbonylmethyl group; esters with a carboxy-C1-C6 alkyl group such as a carboxymethyl group; esters with a C2-C7 alkoxycarbonyloxy-C1-C6 alkyl group such as a 1-(ethoxycarbonyloxy)ethyl group or a 1-(cyclohexyloxycarbonyloxy)ethyl group; esters with a carbamoyloxy-C1-C6 alkyl group such as a carbamoyloxymethyl group; esters with a phthalidyl group; and esters with a (5-substituted-2-oxo-1,3-dioxol-4-yl)methyl group such as a (5-methyl-2-oxo-1,3-dioxol-4-yl)methyl group.

"Therapeutical agent" means a medicine used for the treatment and/or prevention of various disorders.

For more concrete disclosure of the compounds of formula (I) of the invention, the symbols used in formula (I) are described in detail hereinunder with reference to their preferred examples.

$Ar^1$ is a group formed from an aromatic ring selected from a group consisting of benzene, pyrazole, isoxazole, pyridine, indole, 1H-indazole, 1H-furo[2,3-c]pyrazole, 1H-thieno[2,3-c]pyrazole, benzimidazole, 1,2-benzisoxazole, imidazo[1,2-a]pyridine, imidazo[1,5-a]pyridine and 1H-pyrazolo[3,4-b]pyridine, having $Ar^2$, and optionally having one or two or more substituents selected from $R^3$;

"Group formed from an aromatic ring selected from a group consisting of benzene, pyrazole, isoxazole, pyridine, indole, 1H-indazole, 1H-furo[2,3-c]pyrazole, 1H-thieno[2,3-c]pyrazole, benzimidazole, 1,2-benzisoxazole, imidazo[1,2-a]pyridine, imidazo[1,5-a]pyridine and 1H-pyrazolo[3,4-b]pyridine" means an atomic group formed by formally removing the hydrogen atom from the ring-constituting atoms of the aromatic ring. The group means at least 2-valent group necessarily bonding to the adjacent carbonyl group and $Ar^2$, and optionally it may have one or two or more substituents selected from $R^3$, and it may be 3- or 4-valent or more poly-valent group bonding to the substituent. One or two or more substituents selected from $Ar^2$ and $R^3$ may independently bond to any bondable position on $Ar^1$.

$Ar^1$ is, for example, preferably a group formed from an aromatic ring such as benzene, pyridine, indole, 1H-indazole, 1H-thieno[2,3-c]pyrazole and benzimidazole.

$Ar^2$ represents an aromatic group selected from a group consisting of a phenyl group, a furyl group, a thienyl group, a pyrazolyl group, a thiazolyl group, an oxazolyl group, an isoxazolyl group, a 1,2,4-triazolyl group, a 1,2,4-oxadiazolyl group, a 1,3,4-oxadiazolyl group, a tetrazolyl group, a pyridyl group, a pyrazinyl group, a pyrimidinyl group, an indolyl group and a benzo[b]thienyl group, optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonylamino group and a tetrazolyl group.

The aromatic group of $Ar^2$ may be unsubstituted or substituted with one or two or more, the same or different, preferably one substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, C1-C6 alkylsulfonyl group, a C1-C6 alkylsulfonylamino group and a tetrazolyl group.

The halogen atom for the substituent is, for example, preferably a fluorine atom, a chlorine atom.

The C1-C6 alkyl group for the substituent is, for example, preferably a methyl group, an ethyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The cyclo-C3-C6 alkyl group for the substituent is, for example, preferably a cyclopropyl group.

The C2-C6 alkenyl group for the substituent is, for example, preferably a 2-propenyl group, an isopropenyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The C2-C7 alkanoylamino group for the substituent is, for example, preferably an acetylamino group.

The C1-C6 alkylcarbamoyl group for the substituent is, for example, preferably a methylcarbamoyl group, a diethylcarbamoyl group.

The cyclo-C3-C6 alkylcarbamoyl group for the substituent is, for example, preferably a cyclopropylcarbamoyl group, a cyclopentylcarbamoyl group.

The (C1-C6 alkoxy-C1-C6 alkyl)carbamoyl group for the substituent is, for example, preferably a (methoxymethyl)carbamoyl group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group, an ethylsulfonyl group.

The C1-C6 alkylsulfonylamino group for the substituent is, for example, preferably a methylsulfonylamino group, an ethylsulfonylamino group.

The substituent is, for example, preferably a halogen atom, a cyano group, a C1-C6 alkyl group, a C1-C6 alkoxy group, a C2-C7 alkanoylamino group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group, a tetrazolyl group.

"Aromatic group" itself for $Ar^2$ is, for example, preferably a phenyl group, a furyl group, a thienyl group, a pyrazolyl group, a thiazolyl group, an oxazolyl group, an isoxazolyl group, a 1,2,4-triazolyl group, a tetrazolyl group, a pyridyl group, an indolyl group.

Examples of $Ar^2$ are, for example, a phenyl group, a 2-fluorophenyl group, a 3-fluorophenyl group, a 4-fluorophenyl group, a 3-chlorophenyl group, a 4-chlorophenyl group, a 4-bromophenyl group, a 3-nitrophenyl group, a 3-cyanophenyl group, a 3-hydroxyphenyl group, a 4-hydroxyphenyl group, a 3-methylphenyl group, a 4-methylphenyl group, a 3-difluoromethylphenyl group, a 4-difluoromethylphenyl group, a 3-hydroxymethylphenyl group, a 4-hydroxymethylphenyl group, a 3-cyclopropylphenyl group, a 4-cyclopropylphenyl group, a 3-(2-propenyl)phenyl group, a 2-methoxyphenyl group, a 3-methoxyphenyl group, a 4-methoxyphenyl group, a 3-difluoromethoxyphenyl group, a 4-difluoromethoxyphenyl group, a 4-trifluoromethoxyphenyl group, a 3-methylthiophenyl group, a 4-methylthiophenyl group, a 3-acetylaminophenyl group, a 4-acetylaminophenyl group, a 4-cyclopentylcarbamoylphenyl group, a 4-(methoxymethyl)carbamoylphenyl group, a 3-methoxycarbonylphenyl group, a 4-methoxycarbonylphenyl group, a 3-methylsulfonylphenyl group, a 4-methylsulfonylaminophenyl group, a 4-(5-tetrazolyl)phenyl group, a 2-furyl group, a 3-furyl group, a 2-thienyl group, a 3-thienyl group, a 3-pyrazolyl group, a 4-pyrazolyl group, a 1-methyl-4-pyrazolyl group, a 1-cyclopropyl-4-pyrazolyl group, a 1-difluoromethyl-4-pyrazolyl group, a 1-ethyl-4-pyrazolyl group, a 2-thiazolyl group, a 5-thiazolyl group, a 2-methyl-5-oxazolyl group, a 4-isoxazolyl group, a 1,2,4-triazol-3-yl group, a 3-ethyl-1,2,4-oxadiazol-5-yl group, a 5-tetrazolyl group, a 2-pyridyl group, a 3-pyridyl group, a 2-fluoro-4-pyridyl group, a 6-fluoro-3-pyridyl group, a 6-methoxy-3-pyridyl group, a 2-pyrazinyl group, a 5-pyrimidinyl group, a 2-indolyl group, a 3-indolyl group, a 4-indolyl group, a 5-indolyl group, a 2-benzo[b]thienyl group. Of those, preferred are a phenyl group, a 4-fluorophenyl group, a 4-(5-tetrazolyl)phenyl group, a 2-furyl group, a 3-furyl group, a 2-thienyl group, a 4-pyrazolyl group, a 1-methyl-4-pyrazolyl group, a 1-ethyl-4-pyrazolyl group, a 5-thiazolyl group, a 2-methyl-5-oxazolyl group, a 4-isoxazolyl group, a 1,2,4-triazol-3-yl group, a 5-tetrazolyl group, a 2-pyridyl group, a 5-indolyl group.

$R^3$ represents a halogen atom, a nitro group, a cyano group, a hydroxyl group, a carboxyl group, a C2-C6 alkenyl group, a cyclo-C3-C6 alkyl group, or a group of $-N(R^e)R^f$; a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group may be interrupted by an oxygen atom, a sulfur atom or an imino group;

a C1-C6 alkyl group optionally having a substituent selected from a group consisting of a halogen atom, a hydroxyl group, a cyclo-C3-C6 alkyl group and a C1-C6 alkoxy group; or a phenyl group, a 1,2,4-triazolyl group or a tetrazolyl group optionally having a substituent selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group. For $Ar^1$, if desired, one or two or more, the same or different substituents are selected from these groups.

The halogen atom for $R^3$ is, for example, preferably a fluorine atom, a chlorine atom.

The C2-C6 alkenyl group for $R^3$ is, for example, preferably a vinyl group, a 2-propenyl group.

The cyclo-C3-C6 alkyl group for $R^3$ is, for example, preferably a cyclopropyl group.

In the group of $-N(R^e)R^f$ for $R^3$, $R^e$ and $R^f$ each independently represent a hydrogen atom, a C1-C6 alkyl group or a halo-C1-C6 alkyl group, or taken together, they may form a C2-C5 alkylene group optionally interrupted by an oxygen atom, a sulfur atom or an imino group.

The C1-C6 alkyl group for $R^e$ and $R^f$ is, for example, preferably a methyl group, an ethyl group.

The halo-C1-C6 alkyl group for $R^e$ and $R^f$ is, for example, preferably a fluoromethyl group, a difluoromethyl group.

The C2-C5 alkylene group optionally interrupted by an oxygen atom, a sulfur atom or an imino group, which is formed by $R^e$ and $R^f$ taken together, is for example, preferably a tetramethylene group, a pentamethylene group, a 3-oxapentamethylene group. The group forms, along with the adjacent nitrogen atom, a 1-pyrrolidinyl group, a piperidino group, a morpholino group.

Preferably, for example, $R^e$ and $R^f$ each are a C1-C6 alkyl group, or taken together, form the above-mentioned C2-C5 alkylene group.

Accordingly, the group of —N($R^e$)$R^f$ is, for example, more concretely a dimethylamino group, a 1-pyrrolidinyl group, or a morpholino group.

In "a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, a cyclo-C3-C6 alkylthio group or the cyclo-C3-C6 alkyl-C1-C6 alkylthio group may be interrupted by an oxygen atom, a sulfur atom or an imino group" for $R^3$, the halogen atom for the substituent is, for example, preferably a fluorine atom, a chlorine atom.

The C1-C6 alkoxy group optionally substituted with a halogen atom or a hydroxyl group for $R^3$ is, for example, preferably a methoxy group, an ethoxy group, a propoxy group, an isopropoxy group, a difluoromethoxy group, a 2,2-difluoroethoxy group, a 2-hydroxyethoxy group, more preferably a methoxy group, an ethoxy group.

The C2-C7 alkoxycarbonyl group optionally substituted with a halogen atom or a hydroxyl group for $R^3$ is, for example, preferably a methoxycarbonyl group, an ethoxycarbonyl group, a propoxycarbonyl group, an isopropoxycarbonyl group, a difluoromethoxycarbonyl group, a 2,2-difluoroethoxycarbonyl group, a 2-hydroxyethoxycarbonyl group, more preferably a methoxycarbonyl group, an ethoxycarbonyl group.

The C1-C6 alkylthio group optionally substituted with a halogen atom or a hydroxyl group for $R^3$ is, for example, preferably a methylthio group, an ethylthio group, a difluoromethylthio group, a 2-hydroxyethylthio group.

The cyclo-C3-C6 alkyloxy group optionally substituted with a halogen atom or a hydroxyl group for $R^3$ is, for example, preferably a cyclopropyloxy group, a cyclobutyloxy group, a 3-tetrahydrofuranyloxy group.

The cyclo-C3-C6 alkyloxycarbonyl group optionally substituted with a halogen atom or a hydroxyl group for $R^3$ is, for example, preferably a cyclopropyloxycarbonyl group, a cyclobutyloxycarbonyl group, a 3-tetrahydrofuranyloxycarbonyl group.

The cyclo-C3-C6 alkyl-C1-C6 alkoxy group optionally substituted with a halogen atom or a hydroxyl group for $R^3$ is, for example, preferably a cyclopropylmethoxy group, a 3-tetrahydrofuranylmethoxy group.

The cyclo-C3-C6 alkylthio group optionally substituted with a halogen atom or a hydroxyl group for $R^3$ is, for example, preferably a cyclopropylthio group, a 3-tetrahydrothienylthio group.

The cyclo-C3-C6 alkyl-C1-C6 alkylthio group optionally substituted with a halogen atom or a hydroxyl group for $R^3$ is, for example, preferably a cyclopropylmethylthio group, a 3-tetrahydrothienylmethylthio group.

Of the phenoxy group, the C1-C6 alkoxy group, the C2-C7 alkoxycarbonyl group, the C1-C6 alkylthio group, the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group, optionally substituted with a halogen atom or a hydroxyl group, for $R^3$, for example, preferred is the C1-C6 alkoxy group or the cyclo-C3-C6 alkyloxy group optionally substituted with a halogen atom or a hydroxyl group.

"C1-C6 alkyl group optionally having a substituent selected from a group consisting of a halogen atom, a hydroxyl group, a cyclo-C3-C6 alkyl group and a C1-C6 alkoxy" for $R^3$ means the above-mentioned, unsubstituted C1-C6 alkyl group, or the above-mentioned C1-C6 alkyl group having the substituent at any substitutable position thereof, in which the substituent is one or two or more, preferably one or two, the same or different groups selected from a halogen atom, a hydroxyl group, a cyclo-C3-C6 alkyl group and a C1-C6 alkoxy group.

The halogen atom for the substituent is, for example, preferably a fluorine atom, a chlorine atom.

The cyclo-C3-C6 alkyl group for the substituent is, for example, preferably a cyclopropyl group.

The C1-C6 alkoxy group for the substituent is, for example, preferably a methoxy group, an ethoxy group.

The C1-C6 alkyl group optionally having the substituent for $R^3$ is, for example, preferably a methyl group, an ethyl group, an isopropyl group, a fluoromethyl group, a difluoromethyl group, a trifluoromethyl group, a 2-fluoroethyl group, a 2,2-difluoroethyl group, a hydroxymethyl group, a 2-hydroxyethyl group, a cyclopropylmethyl group, a methoxymethyl group.

"A phenyl group, a 1,2,4-triazolyl group, or a tetrazolyl group optionally having a substituent selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group" for $R^3$ means an unsubstituted phenyl, 1,2,4-triazolyl or tetrazolyl group, or a phenyl, 1,2,4-triazolyl or tetrazolyl group having the substituent at the substitutable position thereof, in which the substituent is one or two or more, preferably one or two, the same or different groups selected from a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group.

The halogen atom for the substituent is, for example, preferably a fluorine atom, a chlorine atom.

The C1-C6 alkyl group for the substituent is, for example, preferably a methyl group, an ethyl group.

The halo-C1-C6 alkyl group for the substituent is, for example, preferably a fluoromethyl group, a difluoromethyl group, a 2,2-difluoroethyl group.

The hydroxy-C1-C6 alkyl group for the substituent is, for example, preferably a hydroxymethyl group, a 2-hydroxyethyl group.

The cyclo-C3-C6 alkyl group for the substituent is, for example, preferably a cyclopropyl group.

The C2-C6 alkenyl group for the substituent is, for example, preferably a vinyl group, a 2-propenyl group, an isopropenyl group.

The C1-C6 alkoxy group for the substituent is, for example, preferably a methoxy group, an ethoxy group, an isopropoxy group.

The halo-C1-C6 alkoxy group for the substituent is, for example, preferably a fluoromethoxy group, a difluoromethoxy group, a 2,2-difluoroethyl group.

The C1-C6 alkylthio group for the substituent is, for example, preferably a methylthio group, an ethylthio group, an isopropylthio group.

The substituent is, for example, preferably a halogen atom, a C1-C6 alkyl group, a C1-C6 alkoxy group.

The optionally-substituted phenyl group includes, for example, a phenyl group, a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 4-methylphenyl group, a 4-methoxyphenyl group, a 4-ethoxyphenyl group. Of those, preferred are a phenyl group, a 2-fluorophenyl group, a 3-fluorophenyl group, a 4-fluorophenyl group, a 4-chlorophenyl group, a 4-methoxyphenyl group.

The optionally-substituted 1,2,4-triazolyl group is, for example, preferably a 1,2,4-triazol-3-yl group.

The optionally-substituted tetrazolyl group is, for example, preferably a 5-tetrazolyl group.

$R^3$ is, for example, preferably a halogen atom, a cyclo-C3-C6 alkyl group or a group of —N($R^e$)$R^f$; or a C1-C6 alkoxy group or a cyclo-C3-C6 alkyl group optionally substituted with a halogen atom or a hydroxyl group; or the above-mentioned, optionally-substituted C1-C6 alkyl group; or a phenyl group, a 1,2,4-triazolyl group or a tetrazolyl group optionally substituted with a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group.

Accordingly, in the compounds of the invention, the group of the following formula:

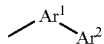

is preferably formed through combination of the above-mentioned preferred groups; for example, it is preferably a 5-methoxy-3-biphenylyl group, a 5-ethoxy-3-biphenylyl group, a 5-isopropyloxy-3-biphenylyl group, a 5-(1-pyrrolidinyl)-3-biphenylyl group, a 3'-cyano-5-methoxycarbonyl-3-biphenylyl group, a 5-methoxy-3'-methoxycarbonyl-3-biphenylyl group, a 3'-acetylamino-3-biphenylyl group, a 3'-acetylamino-5-methoxy-3-biphenylyl group, an m-terphenyl-5'-yl group, a 5-(5-tetrazolyl)-3-biphenylyl group, a 6-methyl-5-(5-tetrazolyl)-3-biphenylyl group, a 2-cyano-4-biphenylyl group, a 2-methoxy-4-biphenylyl group, a 2'-fluoro-2-methoxy-4-biphenylyl group, a 2,6-diethoxy-4-biphenylyl group, a 2-ethoxy-6-methoxy-4-biphenylyl group, a 2-(2,2-difluoroethoxy)-6-methoxy-4-biphenylyl group, a 2,3'-dimethoxy-4-biphenylyl group, a 2,6-dimethoxy-4-biphenylyl group, a 2'-fluoro-2,6-dimethoxy-4-biphenylyl group, a 3'-fluoro-2,6-dimethoxy-4-biphenylyl group, a 4'-difluoro-2,6-dimethoxy-4-biphenylyl group, a 3'-chloro-2,6-dimethoxy-4-biphenylyl group, a 4'-chloro-2,6-dimethoxy-4-biphenylyl group, a 3'-methyl-2,6-dimethoxy-4-biphenylyl group, a 4'-methyl-2,6-dimethoxy-4-biphenylyl group, a 2,3',6-trimethoxy-4-biphenylyl group, a 2,4',6-trimethoxy-4-biphenylyl group, a 2-ethoxy-3'-methoxy-4-biphenylyl group, a 2-ethoxy-4'-methoxy-4-biphenylyl group, a 2-(2-hydroxyethoxy)-4'-methoxy-4-biphenylyl group, a 2-(2-hydroxyethoxy)-6-methoxy-4-biphenylyl group, a 3-(5-indolyl)phenyl group, a 3-(5-indolyl)-5-methoxyphenyl group, a 4-(5-indolyl)-3,5-dimethoxyphenyl group, a 4-(2-furyl)-3,5-dimethoxyphenyl group, a 4-(3-furyl)-3,5-dimethoxyphenyl group, a 3,5-dimethoxy-4-(2-thienyl)phenyl group, a 3-ethoxy-4-(3-pyrazolyl)phenyl group, a 3,5-dimethoxy-4-(4-pyrazolyl)phenyl group, a 3-methoxy-4-(1-methyl-4-pyrazolyl)phenyl group, a 3,5-dimethoxy-4-(1-methyl-4-pyrazolyl)phenyl group, a 3-ethoxy-4-(4-pyrazolyl)phenyl group, a 3,5-diethoxy-4-(4-pyrazolyl)phenyl group, a 3-ethoxy-4-(1-methyl-4-pyrazolyl)phenyl group, a 3,5-diethoxy-4-(1-methylpyrazolyl)phenyl group, a 3,5-diethoxy-4-(1-ethyl-4-pyrazolyl)phenyl group, a 3-(2-hydroxyethoxy)-5-methoxy-4-(1-methyl-4-pyrazolyl)phenyl group, a 3-ethoxy-5-methoxy-4-(1-methyl-4-pyrazolyl)phenyl group, a 4-(1-cyclopropyl-4-pyrazolyl)-3,5-diethoxyphenyl group, a 4-(1-difluoromethyl-4-pyrazolyl)-3,5-diethoxyphenyl group, a 3,5-dimethoxy-4-(2-thiazolyl)phenyl group, a 3,5-dimethoxy-4-(5-thiazolyl)phenyl group, a 3,5-dimethoxy-4-(2-methyl-5-oxazolyl)phenyl group, a 3,5-diethoxy-4-(4-isoxazolyl)phenyl group, a 3-methoxy-5-(1,2,4-triazol-3-yl)phenyl group, a 3-ethoxy-5-(1,2,4-triazol-3-yl)phenyl group, a 3-morpholino-5-(1,2,4-triazol-3-yl)phenyl group, a 3,5-di-1,2,4-triazol-3-yl)phenyl group, a 3-methoxy-5-(5-tetrazolyl)phenyl group, a 3-ethoxy-5-(5-tetrazolyl)phenyl group, a 3-ethoxy-4-methyl-5-(5-tetrazolyl)phenyl group, a 3-cyclopropyl-5-(5-tetrazolyl)phenyl group, a 3-cyclopropyloxy-5-(5-tetrazolyl)phenyl group, a 3-cyclobutyloxy-5-(5-tetrazolyl)phenyl group, a 3-morpholino-5-(5-tetrazolyl)phenyl group, a 3-methoxy-5-(3-pyridyl)phenyl group, a 3-ethoxy-4-(6-fluoro-3-pyridyl)phenyl group, a 3-ethoxy-4-(6-methoxy-3-pyridyl)phenyl group, a 3,5-diethoxy-4-(5-pyrimidinyl)phenyl group, a 4-(5-indolyl)phenyl group, a 3-(1-pyrrolidinyl)-3-(2-benzo[b]thienyl)phenyl group, a 5-(2-benzo[b]thienyl)phenyl group, a 4,6-diphenyl-2-pyridyl group, a 6-(3-ethyl-1,2,4-oxadiazol-5-yl)-4-phenyl-2-pyridyl group, a 2-chloro-6-phenyl-4-pyridyl group, a 2-methoxy-6-phenyl-4-pyridyl group, a 2-ethoxy-6-phenyl-4-pyridyl group, a 2-difluoromethoxy-6-phenyl-4-pyridyl group, a 2-methoxy-6-(2-methoxyphenyl)-4-pyridyl group, a 2-methoxy-6-(3-methoxyphenyl)-4-pyridyl group, a 2-methoxy-6-(4-methoxyphenyl)-4-pyridyl group, a 2-cyclopropyloxy-6-phenyl-4-pyridyl group, a 2-phenoxy-6-phenyl-4-pyridyl group, a 2-phenyl-6-(3-tetrahydrofuranyloxy)-4-pyridyl group, a 2-dimethylamino-6-phenyl-4-pyridyl group, a 2,6-diphenyl-4-pyridyl group, a 2,6-bis(4-fluorophenyl)-4-pyridyl group, a 2-(4-bromophenyl)-6-(4-chlorophenyl)-4-pyridyl group, a 2-methoxy-6-(4-pyrazolyl)-4-pyridyl group, a 2-phenyl-6-(5-tetrazolyl)-4-pyridyl group, a 2-(2-fluorophenyl)-6-(5-tetrazolyl)-4-pyridyl group, a 2-(3-fluorophenyl)-6-(5-tetrazolyl)-4-pyridyl group, a 2-(4-fluorophenyl)-6-(5-tetrazolyl)-4-pyridyl group, a 2-(3-methoxyphenyl)-6-(5-tetrazolyl)-4-pyridyl group, a 2-(4-methoxyphenyl)-6-(5-tetrazolyl)-4-pyridyl group, a 2-(4-difluoromethoxyphenyl)-6-(5-tetrazolyl)-4-pyridyl group, a 2-(5-tetrazolyl)-6-(4-trifluoromethoxyphenyl)-4-pyridyl group, a 2-(3-methylsulfonylphenyl)-6-(5-tetrazolyl)-4-pyridyl group, a 2-(4-cyclopentylcarbamoylphenyl)-6-(5-tetrazolyl-4-pyridyl group, a 2-[4-(methoxymethyl)carbamoylphenyl]-6-(5-tetrazolyl)-4-pyridyl group, a 2-(3-acetylaminophenyl)-6-(5-tetrazolyl)-4-pyridyl group, a 2-(4-methylsulfonylaminophenyl)-6-(5-tetrazolyl)-4-pyridyl group, a 2-methoxy-6-[4-(5-tetrazolyl)phenyl]-4-pyridyl group, a 2-(5-indolyl)-6-methoxy-4-pyridyl group, a 1-phenyl-5-indolyl group, a 3-chloro-1-phenyl-5-indolyl group, a 3-methyl-1-phenyl-5-indolyl group, a 1-(2-pyridyl)-5-indolyl group, a 1-(2-pyrazinyl)-5-indolyl group, a 1-cyclopropyl-3-(5-tetrazolyl)-5-indolyl group, a 3-cyclopropyl-1-(5-tetrazolyl)-5-indolyl group, a 1-cyclopropyl-7-ethoxy-3-(5-tetrazolyl)-5-indolyl group, a 1,3-diphenyl-5-indolyl group, a 1-phenyl-6-indolyl group, a 3-bromo-1-phenyl-6-indolyl group, a 1-methyl-3-phenyl-6-indolyl group, a 4-methoxy-1-phenyl-6-indolyl group, a 1,3-diphenyl-6-indolyl group, a 1-cyclopropyl-3-(5-tetrazolyl)-6-indolyl group, a 1-cyclopropyl-4-ethoxy-3-(5-tetrazolyl)-6-indolyl group, a 1-cyclopropyl-4-(5-tetrazolyl)-6-indolyl group, a 4-methoxy-1-(5-tetrazolyl)-6-indolyl group, a 3-methyl-1-phenyl-5-indazolyl group, a 1-methyl-3-phenyl-6-indazolyl group, a 1-phenyl-1H-benzimidazol-5-yl group, a 1-methyl-2-phenyl-1H-benzimidazol-5-yl group, a 2-methyl-1-phenyl-1H-benzimidazol-5-yl group, a 1-cyclopropyl-2-phenyl-1H-benzimidazol-5-yl group, a 2-cyclopropyl-1-phenyl-1H-benzimidazol-5-yl group, a 1,2-diphenyl-1H-benzimidazol-5-yl group, a 1-phenyl-1H-benzopyrazol-5-yl group, a 1,3-diphenyl-1H-benzopyrazol-5-yl group, a 1,3-diphenyl-1H-benzopyrazol-6-yl group, a 3-phenyl-1,2-benzisoxazol-5-yl group, a 3-phenyl-1,2-benzisoxazol-6-yl group, a 3-methyl-1-phenyl-1H-furo[2,3-c]pyrazol-5-yl group, a 1-phenyl-1H-thieno[2,3-c]pyrazol-5-yl group, a 1-methyl-3-phenyl-1H-thieno[2,3-c]pyrazol-5-yl group, a 3-methyl-1-(4-fluorophenyl)-1H-thieno[2,3-c]pyrazol-5-yl group, a 3-cyclopropyl-1-(4-fluorophenyl)-1H-thieno[2,3-c]pyrazol-5-yl group, a 3-cyclopropyl-1-phenyl-1H-thieno[2,3-c]pyrazol-5-yl group, a 3-methyl-1-(2-pyridyl)-1H-thieno[2,3-c]pyrazol-5-yl group, a 3-ethyl-1-(2-pyridyl)-1H-thieno[2,3-c]pyrazol-5-yl group, a 3-cyclopropyl-1-(2-pyridyl)-1H-thieno[2,3-c]pyrazol-5-yl group, a 1,3-diphenyl-1H-thieno[2,3-c]pyrazol-5-yl group, a 3-methoxymethyl-1-(2-pyridyl)-1H-thieno[2,3-c]pyrazol-5-yl group, a 1-phenyl-3-(2-pyridyl)-1H-thieno[2,3-c]pyrazol-5-yl group, a 3-phenyl-1-(2-pyridyl)-1H-thieno[2,3-c]pyrazol-5-yl group, a 8-methoxy-3-phenylimidazo[1,2-a]pyridin-6-yl group, a 3-phenylimidazo[1,5-a]pyridin-7-yl group, a 1-isopropyl-6-phenyl-1H-pyrazolo[3,4-b]pyridin-4-yl group. Of those, for example, more preferred are a 5-(5-tetrazolyl)-3-biphenylyl group, a 2,6-diethoxy-4-biphenylyl group, a 2,6-dimethoxy-4-biphenylyl group, a 3,5-diethoxy-4-(4-pyrazolyl)phenyl group, a 3,5-diethoxy-4-(1-methyl-4-pyrazolyl)phenyl group, a 3-ethoxy-5-methoxy-4-(1-methyl-4-pyrazolyl)phenyl group, a 3,5-dimethoxy-4-(2-methyl-5-oxazolyl)phenyl group, a 1-phenyl-5-indolyl group, a 1-methyl-3-phenyl-6-indolyl group, a 1-cyclopropyl-4-(5-tetrazolyl)-6-indolyl group, a 1-methyl-3-phenyl-6-indazolyl group, a 3-methyl-1-phenyl-1H-furo[2,3-c]pyrazol-5-yl group, a 3-methyl-1-(2-pyridyl)-1H-thieno[2,3-c]pyrazol-5-yl group, a 1,3-diphenyl-1H-thieno[2,3-c]pyrazol-5-yl group, a 3-phenyl-1-(2-pyridyl)-1H-thieno[2,3-c]pyrazol-5-yl group.

$R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of -$Q^1$-N($R^a$)-$Q^2$-$R^b$;

a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group.

The halogen atom for $R^1$ and $R^2$ is, for example, preferably a chlorine atom, a bromine atom.

The C2-C6 alkenyl group for $R^1$ and $R^2$ is, for example, preferably a 2-propenyl group, an isopropenyl group.

The C1-C6 alkoxy group for $R^1$ and $R^2$ is, for example, preferably a methoxy group, an ethoxy group, a propoxy group.

The halo-C1-C6 alkoxy group for $R^1$ and $R^2$ is, for example, preferably a fluoromethoxy group, a difluoromethoxy group.

The C2-C7 alkanoyl group for $R^1$ and $R^2$ is, for example, preferably an acetyl group, a propionyl group.

The halo-C2-C7 alkanoyl group for $R^1$ and $R^2$ is, for example, preferably a difluoroacetyl group, a 3-fluoropropionyl group.

The C2-C7 alkoxycarbonyl group for $R^1$ and $R^2$ is, for example, preferably a methoxycarbonyl group, an ethoxycarbonyl group.

The halo-C2-C7 alkoxycarbonyl group for $R^1$ and $R^2$ is, for example, preferably a fluoromethoxycarbonyl group, a difluoromethoxycarbonyl group.

The cyclo-C3-C6 alkyloxycarbonyl group for $R^1$ and $R^2$ is, for example, preferably a cyclopropyloxycarbonyl group.

The aralkyloxycarbonyl group for $R^1$ and $R^2$ is, for example, preferably a benzyloxycarbonyl group.

The carbamoyl-C1-C6 alkoxy group for $R^1$ and $R^2$ is, for example, preferably a carbamoylmethoxy group, a 2-carbamoylethoxy group.

The carboxy-C2-C6 alkenyl group for $R^1$ and $R^2$ is, for example, preferably a 2-carboxyvinyl group, a 3-carboxy-1-propenyl group, a 3-carboxy-2-propenyl group.

In the group of -$Q^1$-N($R^a$)-$Q^2$-$R^b$ for $R^1$ and $R^2$, $Q^1$ and $Q^2$ each independently represent a single bond, or a group of —CO—, —SO$_2$— or —C($R^g$)($R^h$)—; $R^a$ and $R^b$ each independently represent a hydrogen atom, a C2-C6 alkenyl group, a C1-C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of —N($R^i$)$R^j$;

a C1-C6 alkyl group optionally having a substituent selected from a group consisting of a halogen atom, a C1-C6 alkoxy group, a carbamoyl group and a C2-C7 alkoxycarbonyl group; or a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group.

In the group of —C($R^g$)($R^h$)— for $Q^1$ and $Q^2$, $R^g$ and $R^h$ each independently represent a hydrogen atom, a C1-C6 alkyl group, or a halo-C1-C6 alkyl group.

$R^g$ and $R^h$ are, for example, preferably a hydrogen atom, a methyl group, an ethyl group.

$Q^1$ is, for example, preferably a single bond, or a group of —CO— or —C($R^g$)($R^h$)—; and $Q^2$ is, for example, preferably a single bond, or a group of —CO— or —C($R^g$)($R^h$)—. The group of —C($R^g$)($R^h$)— for $Q^1$ is more preferably —C(CH$_3$)$_2$—; and the group of —C($R^g$)($R^h$)— for $Q^2$ is more preferably —CH$_2$—.

The C2-C6 alkenyl group for $R^a$ and $R^b$ is, for example, preferably a vinyl group, a 2-propenyl group.

The cyclo-C3-C6 alkyloxy group for $R^a$ and $R^b$ is, for example, preferably a cyclopropyloxy group.

The C1-C6 alkoxy group for $R^a$ and $R^b$ is, for example, preferably a methoxy group, an ethoxy group.

The halo-C1-C6 alkoxy group for $R^a$ and $R^b$ is, for example, preferably a fluoromethoxy group, a difluoromethoxy group, a trifluoromethoxy group, a chloromethoxy group, a dichloromethoxy group.

The cyclo-C3-C6 alkyl group for $R^a$ and $R^b$ is, for example, preferably a cyclopropyl group.

The aralkyloxy group for $R^a$ and $R^b$ is, for example, preferably a benzyloxy group.

The C2-C7 alkoxycarbonyl group for $R^a$ and $R^b$ is, for example, preferably a methoxycarbonyl group, an ethoxycarbonyl group, a tert-butoxycarbonyl group.

In the group of —N($R^i$)$R^j$ for $R^a$ and $R^b$, $R^i$ and $R^j$ each independently represent a hydrogen atom, a C1-C6 alkyl group or a halo-C1-C6 alkyl group.

$R^i$ and $R^j$ are, for example, preferably a hydrogen atom, a methyl group or a 2,2,2-trifluoroethyl group.

The group of —N($R^i$)$R^j$ for $R^a$ and $R^b$ is, for example, preferably an amino group, a dimethylamino group, or a 2,2,2-trifluoroethylamino group.

"C1-C6 alkyl group optionally having a substituent selected from a group consisting of a halogen atom, a C1-C6 alkoxy group, a carbamoyl group and a C2-C7 alkoxycarbonyl group" for $R^a$ and $R^b$ means the above-mentioned unsubstituted C1-C6 alkyl group, or the above-mentioned C1-C6 alkyl group having a substituent at any substitutable position thereof, in which the substituent may be the same or different, one or two or more, preferably from 1 to 3 substituents selected from a group consisting of a halogen atom, a C1-C6 alkoxy group, a carbamoyl group and a C2-C7 alkoxycarbonyl group.

The halogen atom for the substituent is, for example, preferably a fluorine atom, a chlorine atom.

The C1-C6 alkoxy group for the substituent is, for example, preferably a methoxy group, an ethoxy group.

The C2-C7 alkoxycarbonyl group for the substituent is, for example, preferably a methoxycarbonyl group, an ethoxycarbonyl group, a tert-butoxycarbonyl group.

The substituent is, for example, preferably a halogen atom, a carbamoyl group, a C2-C7 alkoxycarbonyl group.

"C1-C6 alkyl group" itself of the above-mentioned, optionally-substituted C1-C6 alkyl group for $R^a$ and $R^b$ is, for example, preferably a methyl group, an ethyl group, a propyl group, an isopropyl group.

The above-mentioned, optionally-substituted C1-C6 alkyl group for $R^a$ and $R^b$ is, for example, preferably a methyl group, a difluoromethyl group, a trifluoromethyl group, a methoxymethyl group, a carbamoylmethyl group, a tert-butoxycarbonylmethyl group, an ethyl group, a propyl group, an isopropyl group.

"Heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group" for $R^a$ and $R^b$ means the above-mentioned, unsubstituted heteroaromatic group, or the above-mentioned heteroaromatic group having "a C1-C6 alkyl group optionally having a substituent selected from a group consisting of a halogen atom, a C1-C6 alkoxy group, a carbamoyl group and a C2-C7 alkoxycarbonyl group" as a substituent at any substitutable position thereof, in which the substituent on the heteroaromatic group may be the same or different, one or two or more, preferably one or two selected from them.

Preferred examples of the substituent on the heteroaromatic group, "C1-C6 alkyl group optionally having a substituent selected from a group consisting of a halogen atom, a C1-C6 alkoxy group, a carbamoyl group and a C2-C7 alkoxycarbonyl group" may be the same as those mentioned hereinabove for the "optionally-substituted C1-C6 alkyl group" for $R^a$ and $R^b$.

"Heteroaromatic group" itself of the heteroaromatic group optionally substituted with the above-mentioned, optionally-substituted C1-C6 alkyl group for $R^a$ and $R^b$ is, for example, preferably a pyrrolyl group, a pyrazolyl group, an isoxazolyl group, a 1,2,4-triazolyl group, a pyrimidinyl group.

The heteroaromatic group optionally substituted with the above-mentioned, optionally-substituted C1-C6 alkyl group for $R^a$ and $R^b$ is, for example, preferably a 2-pyrrolyl group, a 1-methyl-2-pyrrolyl group, a 3-pyrazolyl group, a 1-methyl-3-pyrazolyl group, a 2-methyl-3-pyrazolyl group, a 2,5-dimethyl-3-pyrazolyl group, a 2-ethyl-3-pyrazolyl group, a 2-methoxymethyl-3-pyrazolyl group, a 5-methyl-3-isoxazolyl group, a 1,2,4-triazol-3-yl group, a 1-methyl-1,2,4-triazol-3-yl group, a 2-methyl-1,2,4-triazol-3-yl group, a 2-pyrimidinyl group, a 5-pyrimidinyl group.

$R^a$ and $R^b$ are, for example, preferably a hydrogen atom, a C1-C6 alkoxy group, an aralkyloxy group, a carbamoyl group, a C2-C7 alkoxycarbonyl group, a group of —N($R^i$)$R^j$, a C1-C6 alkyl group optionally having the above-mentioned substituent, or a heteroaromatic group optionally substituted with the above-mentioned, optionally-substituted C1-C6 alkyl group.

The group of -$Q^1$-N($R^a$)-$Q^2$-$R^b$ of $R^1$ and $R^2$ is, for example, preferably such that $Q^1$ and $Q^2$ are a single bond, $R^a$ is a hydrogen atom, and $R^b$ is a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group; more preferably, it is a 2-methyl-3-pyrazolylamino group; or such that $Q^1$ is a group of —CO—, $Q^2$ is a group of —C($R^g$)($R^h$)—, $R^a$ is a hydrogen atom, and $R^b$ is a carbamoyl group; or such that $Q^1$ is a group of —CO—, $Q^2$ is a group of —C($R^g$)($R^h$)—, $R^a$ is a hydrogen atom, and $R^b$ is a C1-C6 alkyl group optionally having a substituent selected from a group consisting of a halogen atom, a C1-C6 alkoxy group, a carbamoyl group and a C2-C7 alkoxycarbonyl group.

Examples of the group of -$Q^1$-N($R^a$)-$Q^2$-$R^b$ for $R^1$ and $R^2$ include, for example, an isopropylamino group, a formylamino group, an acetylamino group, a methoxycarbonylamino group, a benzyloxycarbonylamino group, a carbamoylamino group, a 2,2,2-trifluoroethylcarbamoylamino group, a 2-pyrrolylcarbonylamino group, a 1-methyl-2-pyrrolylcarbonylamino group, a 3-pyrazolylamino group, a 1-methyl-3-pyrazolylamino group, a 2-methyl-3-pyrazolylamino group, a 2,5-dimethyl-3-pyrazolylamino group, a 2-ethyl-3-pyrazolylamino group, a 2-methoxymethyl-3-pyrazolylamino group, an N-methyl-N-(2-methyl-3-pyrazolyl)amino group, a 5-methyl-3-isoxazolylamino group, a 1,2,4-triazol-3-ylamino group, a 1-methyl-1,2,4-triazol-3-ylamino group, a 2-methyl-1,2,4-triazol-3-ylamino group, a 2-pyridinylamino group, a 5-pyridinylamino group, a carbamoyl group, a methylcarbamoyl group, a 2,2-difluoroethylcarbamoyl group, a 2,2,2-trifluoroethylcarbamoyl group, a (carbamoylmethyl)carbamoyl group, a (2-carbamoylethyl)carbamoyl group, a (1-carbamoyl-1-methylethyl)carbamoyl group, a (1-tert-butoxycarbonyl-1-methylethyl)carbamoyl group, a (2-tert-butoxycarbonylethyl)carbamoyl group, an aminosulfonyl group, a methylaminosulfonyl group, a dimethylaminosulfonyl group, an ethylaminosulfonyl group, a propylaminosulfonyl group, a butylaminosulfonyl group, an N-acetyl-N-methylaminosulfonyl group, an N-acetyl-N-ethylaminosulfonyl group, an N-acetyl-N-propylaminosulfonyl group, a 1-amino-1-methylethyl group, a 1-acetylamino-1-methylethyl group, a 1-(benzyloxycarbonylamino-1-methylethyl group. Of those, for example, preferred are a 1-methyl-3-pyrazolylamino group, a 2-methyl-3-pyrazolylamino group, a 2,5-dimethyl-3-pyrazolylamino group, a 5-methyl-3-isoxazolylamino group, a carbamoyl group, a 2,2,2-trifluoroethylcarbamoyl group, a (carbamoylmethyl) carbamoyl group; more preferred is a 2-methyl-3-pyrazolylamino group.

"C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group" for $R^1$ and $R^2$ means the above-mentioned unsubstituted C1-C6 alkyl group, or the above-mentioned C1-C6 alkyl group having the substituent at the substitutable position thereof, in which the substituent may be the same or different, one or two or more, preferably from 1 to 3 groups selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group.

The halogen atom for the substituent is, for example, preferably a fluorine atom, a chlorine atom.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The C2-C7 alkanoyloxy group for the substituent is, for example, preferably an acetyloxy group, a propionyloxy group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group, an ethylsulfonyl group.

The substituent is, for example, preferably a halogen atom, a hydroxyl group, a carboxyl group, a carbamoyl group, a C2-C7 alkoxycarbonyl group.

"C1-C6 alkyl group" itself of the above-mentioned, optionally-substituted C1-C6 alkyl group for $R^1$ and $R^2$ is, for example, preferably a methyl group, an ethyl group, a propyl group, an isopropyl group, a tert-butyl group.

The above-mentioned, optionally-substituted C1-C6 alkyl group for $R^1$ and $R^2$ is, for example, preferably a methyl group, a fluoromethyl group, a hydroxymethyl group, an azidomethyl group, a methoxymethyl group, a methylthiomethyl group, an acetyloxymethyl group, a methoxycarbonylmethyl group, a methylsulfonylmethyl group, an ethyl group, a 1-hydroxyethyl group, a 1-carboxy-1-methylethyl group, a 1-carbamoyl-1-methylethyl group, a 1-methoxycarbonyl-1-methylethyl group, a propyl group, an isopropyl group, a tert-butyl group.

"Aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$" for $R^1$ and $R^2$ means the above-mentioned unsubstituted aryl or heterocyclic group, or the above-mentioned aryl or heterocyclic group having the substituent at the substitutable position thereof, in which the substituent may be the same or different, one or two or more, preferably one or two groups selected from a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$.

The halogen atom for the substituent is, for example, preferably a fluorine atom, a chlorine atom.

The C1-C6 alkyl for the substituent is, for example, preferably a methyl group, an ethyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The C2-C7 alkanoyloxy-C1-C6 alkyl group for the substituent is, for example, preferably an acetyloxymethyl group, a pivaloyloxymethyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C2-C7 alkanoyl group for the substituent is, for example, preferably an acetyl group, a propionyl group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group.

In the group of —CO—N($R^c$)$R^d$ for the substituent, $R^c$ and $R^d$ each independently represent a hydrogen atom, a C1-C6 alkyl group or a halo-C1-C6 alkyl group.

The C1-C6 alkyl group for $R^c$ and $R^d$ is, for example, preferably a methyl group, an ethyl group.

The group of —CO—N($R^c$)$R^d$ for the substituent is, for example, preferably a carbamoyl group, a dimethylcarbamoyl group.

The substituent is, for example, preferably an oxo group, a C1-C6 alkyl group, a formyl group, a carboxyl group, a C2-C7 alkoxycarbonyl group, a C1-C6 alkylsulfonyl group, a group of —CO—N($R^c$)$R^d$.

"Aryl group" itself of the above-mentioned optionally-substituted aryl or heterocyclic group for $R^1$ and $R^2$ is, for example, preferably a phenyl group; "heterocyclic group" itself thereof is, for example, preferably a pyrrolyl group, an imidazolyl group, a pyrazolyl group, a 1,2,4-triazolyl group, a tetrazolyl group, a pyridyl group, a pyrimidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a dihydropyridyl group, a piperidyl group, a piperazinyl group, a morpholinyl group, a thiomorpholinyl group. Of those, more preferred is a tetrazolyl group.

The above-mentioned, optionally-substituted aryl or heterocyclic group for $R^1$ and $R^2$ is, for example, preferably a phenyl group optionally substituted with a halogen atom, a carboxyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a C1-C6 alkyl group, a C1-C6 alkoxy group, a carboxyl group, a C2-C7 alkoxycarbonyl group or a group of —CO—N($R^c$)$R^d$; a pyrimidinyl group; a dihydro-1,2,4-triazolyl group optionally substituted with an oxo group; a dihydro-1,2,4-oxadiazolyl group optionally substituted with an oxo group; a dihydropyridyl group optionally substituted with an oxo group; a thiomorpholinyl group optionally substituted with an oxo group; or a piperazinyl group optionally substituted with a C2-C7 alkanoyl group. More preferred is a tetrazolyl group optionally substituted with a C2-C7 alkanoyloxy-C1-C6 alkyl group.

Examples of the aryl group or the heterocyclic group for $R^1$ and $R^2$ include, for example, a phenyl group, a 3-carboxyphenyl group, a 3-carboxy-4-fluorophenyl group, a 3-carbamoylphenyl group, a 4-carbamoylphenyl group, a 1-pyrrolyl group, a 1-imidazolyl group, a 3-pyrazolyl group, a 4-pyrazolyl group, a 1-methyl-4-pyrazolyl group, a 1,2,4-triazol-3-yl group, a 1,2,4-triazol-4-yl group, a 5-carbamoyl-1,2,4-triazol-3-yl group, a 1-tetrazolyl group, a 5-tetrazolyl group, a 1-methyl-5-tetrazolyl group, a 2-methyl-5-tetrazolyl group, a 2-pivaloyloxymethyl-5-tetrazolyl group, a 2-dimethylcarbamoyl-5-tetrazolyl group, a 3-pyridyl group, a 6-methoxy-3-pyridyl group, a 5-methoxycarbonyl-3-pyridyl group, a 5-carboxy-3-pyridyl group, a 5-carboxy-6-methyl-3-pyridyl group, a 2-carboxy-4-pyridyl group, a 5-carboxy-2-pyridyl group, a 5-carbamoyl-2-pyridyl group, a 5-carbamoyl-3-pyridyl group, a 2-pyrimidinyl group, a 5-pyrimidinyl group, a 2-oxo-1-pyrrolidinyl group, a 5-oxo-4,5-dihydro-1,2,4-triazol-3-yl group, a 3-oxo-2,3-dihydro-1,2,4-triazol-4-yl group, a 5-oxo-4,5-dihydro-1,2,4-oxadiazol-3-yl group, a 5-thioxo-4,5-dihydro-1,2,4-oxadiazol-3-yl group, a 5-oxo-4,5-dihydro-1,3,4-oxadiazol-2-yl group, a 5-oxo-4,5-dihydro-1,2,4-thiadiazol-3-yl group, a 2-oxo-2,3-dihydro-1,2,3,5-oxathiadiazol-4-yl group, a 6-oxo-1,6-dihydro-3-pyridyl group, a 1-piperidyl group, a 4-oxo-1-piperidyl group, a 1-piperazinyl group, a 3-oxo-1-piperazinyl group, a 4-methyl-1-piperazinyl group, a 4-formyl-1-piperazinyl group, a 4-acetyl-1-piperazinyl group, a 4-methoxycarbonyl-1-piperazinyl group, a 4-carbamoyl-1-piperazinyl group, a 4-methylsulfonyl-1-piperazinyl group, a 4-morpholinyl group, a 1,1-dioxo-4-thiomorpholinyl group. Of those, preferred are a 3-carbamoylphenyl group, a 4-carbamoylphenyl group, a 3-pyrazolyl group, a 4-pyrazolyl group, a 1-methyl-4-pyrazolyl group, a 1,2,4-triazol-3-yl group, a 5-tetrazolyl group, a 2-pivaloyloxymethyl-5-tetrazolyl group, a 6-methoxy-3-pyridyl group, a 5-carboxy-3-pyridyl group, a 5-carbamoyl-2-pyridyl group, a 5-carbamoyl-3-pyridyl group, a 2-pyrimidinyl group, a 5-pyrimidinyl group, a 5-oxo-4,5-dihydro-1,2,4-triazol-3-yl group, a 5-oxo-4,5-dihydro-1,2,4-oxadiazol-3-yl group, a 6-oxo-1,6-dihydro-3-pyridyl group; more preferred are a 5-carboxy-3-pyridyl group, a 2-carboxy-4-pyridyl group, a 5-carbamoyl-3-pyridyl group, a 5-tetrazolyl group, a 1-methyl-4-pyrazolyl group, a 5-oxo-4,5-dihydro-1,2,4-triazol-3-yl group, a 5-oxo-4,5-dihydro-1,2,4-oxadiazol-3-yl group.

"C1-C6 alkyl or C2-C6 alkenyl group having the aryl or heterocyclic group" for $R^1$ and $R^2$ means a C1-C6 alkyl or C2-C6 alkenyl group having the same or different, one or two or more, preferably one aryl or heterocyclic group selected from the above-mentioned "aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^{d}$", and is, for example, preferably a 5-tetrazolylmethyl group, a 2-(5-tetrazolyl)ethyl group, a 2-(5-tetrazolyl)vinyl group, a 3-(5-tetrazolyl)-1-propenyl group.

Preferred embodiments of $R^1$ and $R^2$ are, for example, such that $R^1$ is a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group or a group of -$Q^1$-N($R^a$)-$Q^2$-$R^b$;

a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group; and $R^2$ is a hydrogen atom, a halogen atom, a C1-C6 alkyl group or a C1-C6 alkoxy group.

$R^1$ is, for example, preferably a group of -$Q^1$-N($R^a$)-$Q^2$-$R^b$; or a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group; or an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$.

T and U each independently represent a nitrogen atom or a methine group. In case where T or U is a methine group, the methine group may be substituted with $R^1$ or $R^2$.

T and U are preferably a methine group.

V represents an oxygen atom or a sulfur atom, and is preferably an oxygen atom.

In the compounds of formula (I), $R^1$ and $R^2$ may be positioned at any substitutable position of the skeleton of the following formula:

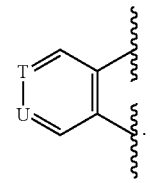

Preferred embodiments of the compounds of formula (I) are, for example, compounds of a general formula (I-1):

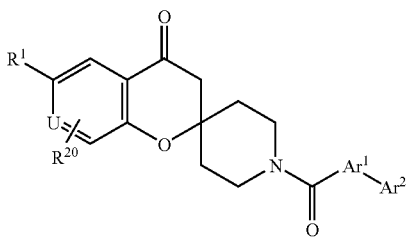

(I-1)

wherein R²⁰ represents a hydrogen atom, a halogen atom, a C1-C6 alkyl group or a C1-C6 alkoxy group; Ar¹, Ar², R¹ and U have the same meanings as above.

In formula (I-1), preferred embodiments of Ar¹, Ar², R¹ and U are the same as those of Ar¹, Ar², R¹ and U in formula (I). R²⁰ is preferably a hydrogen atom.

"A substitutable position" and "a bondable position" mean a position of a group at which the group has a chemically-substitutable hydrogen atom on the carbon atom, the nitrogen atom, the oxygen atom and/or the sulfur atom thereof, and the substitution gives a chemically-stable compound; or mean that a chemical bond gives a chemically-stable compound not resulting from the substitution of the type.

Depending on the type of the substituents therein and on the form of their salts, the compounds of the invention include stereoisomers and tautomers such as optical isomers, diastereoisomers and geometrical isomers, and the compounds of the invention encompass all these stereoisomers and tautomers and their mixtures.

The invention encompasses various crystals, amorphous phases, salts, hydrates and solvates of the compounds of the invention.

Further, prodrugs of the compounds of the invention are also within the scope of the invention. In general, such prodrugs are functional derivatives of the compounds of the invention, and they can be readily converted into the compounds that are needed in bodies. Accordingly, the term "administer" as referred to herein for the method of treating various disorders includes not only the administration of a specific compound but also the administration of a compound which, after administered to patients, may be converted into the specific compound in bodies. General methods for selection and production of suitable prodrug derivatives are described, for example, in *Design of Prodrugs*, ed. H. Bundgaard, Elsevier, 1985; and its entire description is referred to and incorporated herein as a part of the specification of the present application. Metabolites of these compounds include active compounds that are produced by leaving the compounds of the invention in a biological environment, and they are within a scope of the invention. Specific examples of the compounds of formula (I), and their salts and esters are, for example, as follows:

(1) 1'-{[4-(Benzo[b]thiophen-2-yl)phenyl]carbonyl}-6-(tetrazol-5-yl)-spiro[chroman-2,4'-piperidin]-4-one,
(2) 1'-{[2,6-Bis(4-fluorophenyl)pyridin-4-yl]carbonyl}-6-(tetrazol-5-yl)-spiro[chroman-2,4'-piperidin]-4-one,
(3) 1'-{[2-Methoxy-6-phenylpyridin-4-yl]carbonyl}-6-(tetrazol-5-yl)-spiro[chroman-2,4'-piperidin]-4-one,
(4) 1'-{[3-(1H-indol-5-yl)-5-methoxyphenyl]carbonyl}-6-(tetrazol-5-yl)-spiro[chroman-2,4'-piperidin]-4-one,
(5) 1'-{[2,6-Dimethoxybiphenyl-4-yl]carbonyl}-6-(tetrazol-5-yl)-spiro[chroman-2,4'-piperidin]-4-one,
(6) 1'-{[2,6-Dimethoxybiphenyl-4-yl]carbonyl}-6-(tetrazol-5-yl)-spiro[chroman-2,4'-piperidin]-4-one sodium salt,
(7) 1'-{[3-Pyrrolidin-1-yl-5-(1,2,4-triazol-3-yl)phenyl]carbonyl}-6-(tetrazol-5-yl)spiro[chroman-2,4'-piperidin]-4-one sodium salt,
(8) 6-[(1-Methyl-1H-pyrazol-5-yl)amino]-1'-{[2-phenyl-6-(tetrazol-5-yl)pyridin-4-yl]carbonyl}spiro[chroman-2,4'-piperidin]-4-one,
(9) [5-(4-Oxo-1'-{[3-(pyrrolidin-1-yl-5-(1,2,4-triazol-3-yl)phenyl]carbonyl}-spiro[chroman-2,4'-piperidin]-6-yl)-tetrazol-2-yl]methyl 2,2-dimethylpropanoate,
(10) [5-(1'-{[2,6-Dimethoxybiphenyl-4-yl]carbonyl}-4-oxospiro[chroman-2,4'-piperidin]-6-yl)-tetrazol-2-yl]methyl 2,2-dimethylpropanoate,
(11) 1'-{([3-Ethoxy-5-tetrazol-5-yl)phenyl]carbonyl}-6-[(1-methyl-1H-pyrazol-5-yl)amino]spiro[chroman-2,4'-piperidin]-4-one sodium salt,
(12) 1'-{[3,5-Diethoxy-4-(1-methyl-1H-pyrazol-4-yl)phenyl]carbonyl}-6-(tetrazol-5-yl)spiro[chroman-2,4'-piperidin]-4-one,
(13) 6-(1-Methylethyl)-1'-{[5-(tetrazol-5-yl)biphenyl-3-yl]carbonyl}spiro[7-azachroman-2,4'-piperidin]-4-one,
(14) 6-(1-Methyl-1H-pyrazol-4-yl)-1'-{[5-(tetrazol-5-yl)biphenyl-3-yl]carbonyl}spiro[chroman-2,4'-piperidin]-4-one,
(15) 1'-{[3-Ethoxy-4-(1-methyl-1H-pyrazol-4-yl)phenyl]carbonyl}-6-(tetrazol-5-yl)spiro[chroman-2,4'-piperidin]-4-one,
(16) 6-[(1-Methyl-1H-pyrazol-5-yl)amino]-1'-{[3-(pyrrolidin-1-yl)-5-(tetrazol-5-yl)phenyl]carbonyl}spiro[chroman-2,4'-piperidin]-4-one,
(17) 5-(4-Oxo-1'-{[5-(tetrazol-5-yl)biphenyl-3-yl]carbonyl}-spiro[chroman-2,4'-piperidin]-6-yl)pyridine-3-carboxamide sodium salt,
(18) 1'-{[3,5-Diethoxy-4-(1H-pyrazol-4-yl)phenyl]carbonyl}-6-(tetrazol-5-yl)spiro[chroman-2,4'-piperidin]-4-one,
(19) 1'-{[3,5-Diethoxy-4-(1H-pyrazol-4-yl)phenyl]carbonyl}-6-(5-oxo-4,5-dihydro-1,2,4-oxadiazol-3-yl)spiro[chroman-2,4'-piperidin]-4-one,
(20) 1'-{[3,5-Diethoxy-4-(1-methyl-1H-pyrazol-4-yl)phenyl]carbonyl}-6-(5-oxo-4,5-dihydro-1,2,4-oxadiazol-3-yl)spiro[chroman-2,4'-piperidin]-4-one,
(21) N-Carbamoylmethyl-1'-{[3,5-diethoxy-4-(1-methyl-1H-pyrazol-4-yl)phenyl]carbonyl}-4-oxospiro[chroman-2,4'-piperidine]-6-carboxamide,
(22) 1'-{[3,5-Diethoxy-4-(1-methyl-1H-pyrazol-4-yl)phenyl]carbonyl}-6-(5-oxo-4,5-dihydro-1H-1,2,4-triazol-3-yl)spiro[chroman-2,4'-piperidin]-4-one,
(23) 1'-{[3,5-Diethoxy-4-isoxazol-4-ylphenyl]carbonyl}-6-(tetrazol-5-yl)spiro[chroman-2,4'-piperidin]-4-one,
(24) 5-(1'-{[2,6-Dimethoxybiphenyl-4-yl]carbonyl}-4-oxospiro[chroman-2,4'-piperidin]-6-yl)pyridine-3-carboxylic acid,
(25) 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid,
(26) 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid sodium salt,
(27) [5-(1'-{[3,5-Diethoxy-4-(1-methyl-1H-pyrazol-4-yl)phenyl]carbonyl}-4-oxospiro[chroman-2,4'-piperidin]-6-yl)-2H-tetrazol-2-yl]methyl 2,2-dimethylpropanoate,
(28) Sodium 3-(1'-{[3,5-Diethoxy-4-(1-methyl-1H-pyrazol-4-yl)phenyl]carbonyl}-4-oxospiro[chroman-2,4'-piperidin]-6-yl)benzoate,
(29) 1'-{[3-Ethoxy-5-methoxy-4-(1-methyl-1H-pyrazol-4-yl)phenyl]carbonyl}-6-tetrazol-5-yl)spiro[chroman-2,4'-piperidin]-4-one,

(30) 1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one sodium salt,

(31) 1'-{[3,5-Diethoxy-4-(6-fluoropyridin-3-yl)phenyl]carbonyl}-6-(tetrazol-5-yl)spiro[chroman-2,4'-piperidin]-4-one,

(32) 1'-{[3,5-Diethoxy-4-(2-fluoropyridin-4-yl)phenyl]carbonyl}-6-(tetrazol-5-yl)spiro[chroman-2,4'-piperidin]-4-one,

(33) 1'-{[4-(2-Methyl-1,3-oxazol-5-yl)-3,5-dimethoxyphenyl]carbonyl}-6-(tetrazol-5-yl)spiro[chroman-2,4'-piperidin]-4-one,

(34) Sodium 5-(1'-{[3,5-diethoxy-4-(6-fluoropyridin-3-yl)phenyl]carbonyl}-4-oxo-spiro[chroman-2,4'-piperidin]-6-yl)pyridine-3-carboxylate,

(35) Sodium 5-(1'-{[3,5-Diethoxy-4-(1-methyl-1H-pyrazol-4-yl)phenyl]carbonyl}-4-oxospiro[chroman-2,4'-piperidin]-6-yl)pyridine-2-carboxylate,

(36) Sodium 2-(1'-{[3,5-Diethoxy-4-(1-methyl-1H-pyrazol-4-yl)phenyl]carbonyl}-4-oxospiro[chroman-2,4'-piperidin]-6-yl)pyridine-4-carboxylate,

(37) 4-(1'-{[3,5-Diethoxy-4-(1-methyl-1H-pyrazol-4-yl)phenyl]carbonyl}-4-oxospiro[chroman-2,4'-piperidin]-6-yl)pyridine-2-carboxylic acid,

(38) 1'-{[1-(1-Methylethyl)-6-phenyl-1H-pyrazolo[3,4-b]pyridin-4-yl]carbonyl}-6-(tetrazol-5-yl)spiro[chroman-2,4'-piperidin]-4-one,

(39) 1'-[(1,3-Diphenyl-1H-thieno[2,3-c]pyrazol-5-yl)carbonyl]-6-(tetrazol-5-yl)spiro[chroman-2,4'-piperidin]-4-one,

(40) 1'-{[1-Cyclopropyl-4-(tetrazol-5-yl)-1H-indol-6-yl]carbonyl}-6-[(1-methyl-1H-pyrazol-5-yl)amino]spiro[chroman-2,4'-piperidin]-4-one,

(41) 1'-{[1-Cyclopropyl-4-(tetrazol-5-yl)-1H-indol-6-yl]carbonyl}-6-(1-methylethyl)spiro[7-azachroman-2,4'-piperidin]-4-one,

(42) 1'-{[1-Cyclopropyl-4-(tetrazol-5-yl)-1H-indol-6-yl]carbonyl}-6-(1-methyl-1H-pyrazol-4-yl)spiro[chroman-2,4'-piperidin]-4-one,

(43) 1'-[(3-Cyclopropyl-1-pyridin-2-yl-1H-thieno[2,3-c]pyrazol-5-yl)carbonyl]-6-(tetrazol-5-yl)spiro[chroman-2,4'-piperidin]-4-one,

(44) 1'-{[1-Cyclopropyl-4-(tetrazol-5-yl)-1H-indol-6-yl]carbonyl}-6-[6-(methyloxy)pyridin-3-yl]spiro[chroman-2,4'-piperidin]-4-one,

(45) 1'-{[1-Cyclopropyl-4-(tetrazol-5-yl)-1H-indol-6-yl]carbonyl}-6-(6-oxo-1,6-dihydropyridin-3-yl)spiro[chroman-2,4'-piperidin]-4-one,

(46) 3-(1'-{[1-Cyclopropyl-4-(tetrazol-5-yl)-1H-indol-6-yl]carbonyl}-4-oxospiro[chroman-2,4'-piperidin]-6-yl)benzamide,

(47) 1'-[(1,3-Diphenyl-1H-indazol-6-yl)carbonyl]-6-(tetrazol-5-yl)spiro[chroman-2,4'-piperidin]-4-one,

(48) 1'-{[4-Methoxy-1-phenyl-1H-indol-6-yl]carbonyl}-6-(tetrazol-5-yl)spiro[chroman-2,4'-piperidin]-4-one,

(49) 1'-[(3-Phenyl-1-pyridin-2-yl-1H-thieno[2,3-c]pyrazol-5-yl)carbonyl]-6-(tetrazol-5-yl)spiro[chroman-2,4'-piperidin]-4-one,

(50) 1'-[(3-Chloro-1-phenyl-1H-indol-5-yl)carbonyl]-6-(tetrazol-5-yl)spiro[chroman-2,4'-piperidin]-4-one,

(51) 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one,

(52) 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one sodium salt,

(53) 1'-[(2-Cyclopropyl-1-phenyl-1H-benzimidazol-5-yl)carbonyl]-6-(tetrazol-5-yl)spiro[chroman-2,4'-piperidin]-4-one,

(54) 1'-[(1-Methyl-3-phenyl-1H-indol-6-yl)carbonyl]-6-(tetrazol-5-yl)spiro[chroman-2,4'-piperidin]-4-one,

(55) 1'-[(1-Ethyl-3-phenyl-1H-thieno[2,3-c]pyrazol-5-yl)carbonyl]-6-(tetrazol-5-yl)spiro[chroman-2,4'-piperidin]-4-one,

(56) 1'-[(1-Methyl-3-phenyl-1H-indazol-6-yl)carbonyl]-6-(tetrazol-5-yl)spiro[chroman-2,4'-piperidin]-4-one,

(57) 1'-[(3-Methyl-1-phenyl-1H-indazol-5-yl)carbonyl]-6-(tetrazol-5-yl)spiro[chroman-2,4'-piperidin]-4-one,

(58) Sodium 5-{1'-[(3-methyl-1-pyridin-2-yl-1H-thieno[2,3-c]pyrazol-5-yl)-carbonyl]-4-oxospiro[chroman-2,4'-piperidin]-6-yl}pyridine-3-carboxylate,

(59) Sodium 5-(1'-[(3-methyl-1-phenyl-1H-indazol-5-yl)carbonyl]-4-oxo-spiro[chroman-2,4'-piperidin]-6-yl)pyridine-3-carboxylate,

(60) Sodium 4-{1'-[(3-methyl-1-pyridin-2-yl-1H-thieno[2,3-c]pyrazol-5-yl)-carbonyl]-4-oxospiro[chroman-2,4'-piperidin]-6-yl}pyridine-2-carboxylate,

(61) 1'-{[3-(Difluoromethyl)-1-pyridin-2-yl-1H-thieno[2,3-c]pyrazol-5-yl]carbonyl}-6-(tetrazol-5-yl)spiro[chroman-2,4'-piperidin]-4-one,

(62) Methyl 5-{1'-[3-ethoxy-5-methoxy-4-(1-methyl-1H-pyrazol-4-yl)benzoyl]-4-oxospiro[chromman-2,4'-piperidin]-6-yl}nicotinate,

(63) (5-{1'-[3-ethoxy-5-methoxy-4-(1-methyl-1H-pyrazol-4-yl)benzoyl]-4-oxospiro[chromman-2,4'-piperidin]-6-yl}-2H-tetrazol-2-yl)methylpivalate,

(64) 4-{1'-[(3-methyl-1-phenyl-1H-indazol-5-yl)carbonyl]-4-oxospiro[chroman-2,4'-piperidin]-6-yl}-2-pyridinecarboxylic acid,

(65) 2-methyl-5-{1'-[(3-methyl-1-phenyl-1H-indazol-5-yl)carbonyl]-4-oxospiro[chroman-2,4'-piperidin]-6-yl}nicotinic acid,

(66) 3-carboxy-5-{1'-[4-(1-cyclopropyl-1H-pyrazol-4-yl)-3,5-diethoxybenzoyl]-4-oxospiro[chroman-2,4'-piperidin]-6-yl}pyridinium trifluoroacetate,

(67) 5-(1'-{4-[1-(difluoromethyl)-1H-pyrazol-4-yl]-3,5-diethoxybenzoyl}-4-oxospiro[chroman-2,4'-piperidin]-6-yl)nicotinic acid,

(68) 6-{1'-[3,5-dimethoxy-4-(1-methyl-1H-pyrazol-4-yl)benzoyl]-4-oxospiro[chroman-2,4'-piperidin]-6-yl}nicotinamide,

(69) Sodium 5-{1'-[3,5-diethoxy-4-(1-methyl-1H-pyrazol-4-yl)benzoyl]-4-oxospiro[chroman-2,4'-piperidin]-6-yl}-2-fluorobenzoate,

(70) Sodium 3-{1'-[3-ethoxy-5-methoxy-4-(1-methyl-1H-pyrazol-4-yl)benzoyl]-4-oxospiro[chroman-2,4'-piperidin]-6-yl}benzoate,

(71) Sodium 6-{1'-[3,5-diethoxy-4-(1-methyl-1H-pyrazol-4-yl)benzoyl]-4-oxospiro[chroman-2,4'-piperidin]-6-yl}nicotinate,

(72) 6-(1,1-dioxido-4-thiomorpholinyl)-1'-[3-ethoxy-5-methoxy-4-(1-methyl-1H-pyrazol-4-yl)benzoyl]spiro[chroman-2,4'-piperidin]-4-one,

(73) Methyl {1'-[3-ethoxy-5-methoxy-4-(1-methyl-1H-pyrazol-4-yl)benzoyl]-4-oxospiro[chroman-2,4'-piperidin]-6-yl}carbamate,

(74) 5-{1-[3-Ethoxy-5-methoxy-4-(1-methyl-1H-pyrazol-4-yl)benzoyl]-4-oxospiro[chroman-2,4'-piperidin]-6-yl}-2-fluorobenzoic acid,

(75) 5-{1'-[3-Ethoxy-5-methoxy-4-(1-methyl-1H-pyrazol-4-yl)benzoyl]-4-oxospiro[chroman-2,4'-piperidin]-6-yl}nicotinic acid,

(76) 6-(4-acetyl-1-piperazinyl)-1'-[3-ethoxy-5-methoxy-4-(1-methyl-1H-pyrazol-4-yl)benzoyl]spiro[chroman-2,4'-piperidin]-4-one,

(77) 6-{1'-[3-ethoxy-5-methoxy-4-(1-methyl-1H-pyrazol-4-yl)benzoyl]-4-oxospiro[chroman-2,4'-piperidin]-6-yl}nicotinamide,

(78) N-(2,2-difluoroethyl)-1'-[3-ethoxy-5-methoxy-4-(1-methyl-1H-pyrazol-4-yl)benzoyl]-4-oxospiro[chroman-2,4'-piperidine]-6-carboxamide,

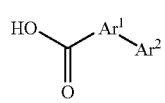

wherein $Ar^1$ and $Ar^2$ have the same meanings as above, according to a chemical process well known in the field of organic chemistry.

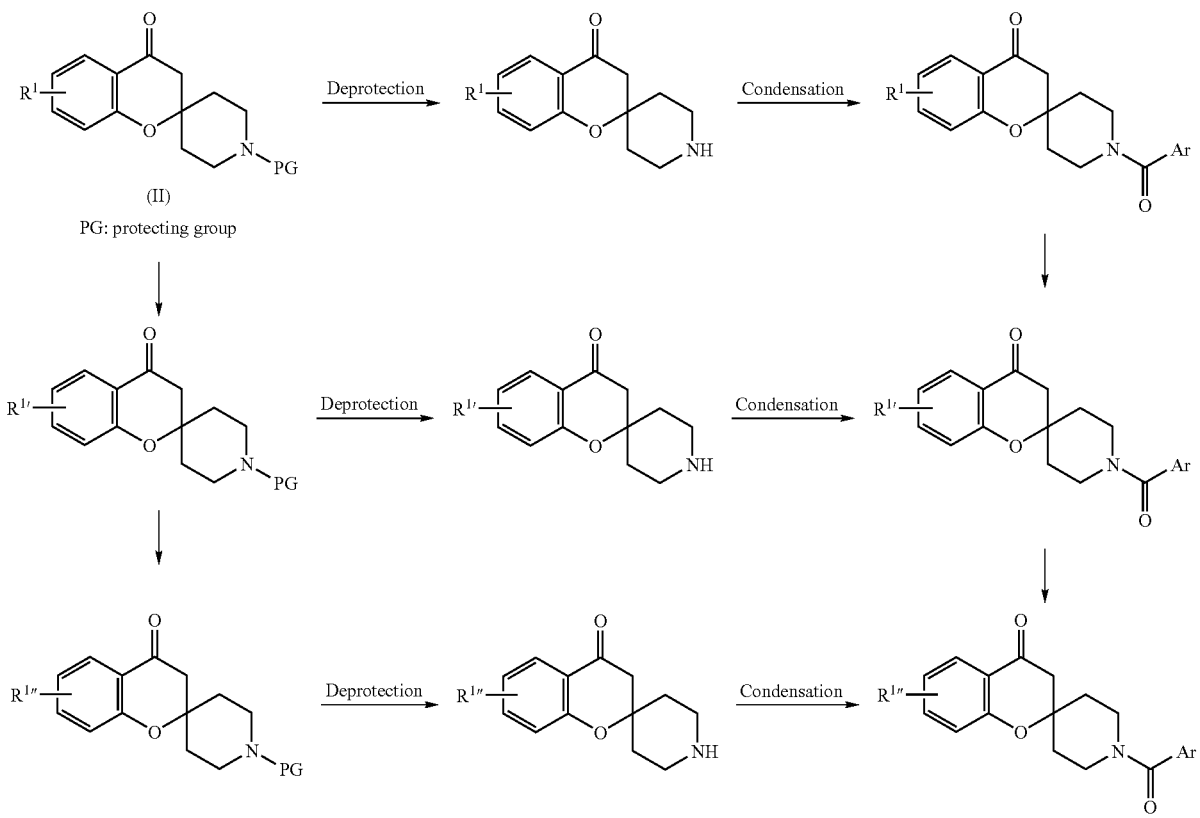

(79) 1'-[3-Ethoxy-5-methoxy-4-(1-methyl-1H-pyrazol-4-yl)benzoyl]-6-(1-methyl-1H-pyrazol-4-yl)spiro[chroman-2,4'-piperidin]-4-one,

(80) 1'-[(3-Methyl-1-phenyl-1H-furo[2,3-c]pyrazol-5-yl)carbonyl]-6-(tetrazol-5-yl)spiro[chroman-2,4'-piperidin]-4-one, or

(81) Sodium 5-[3-cyclopropyl-5-({6-[(1-methyl-1H-pyrazol-5-yl)amino]-4-oxospiro[chroman-2,4'-piperidin]-1'-yl}carbonyl)-1H-indol-1-yl]tetrazolide.

Methods for producing the compounds of the invention are described below.

The compounds (I) of the invention may be produced according to the production method mentioned below, or according to the methods shown in Examples and Reference Examples given hereinunder. However, the production of the compounds (I) of the invention should not be restricted by these reaction examples.

Production Method

A compound protected with a suitable group (II in the following drawing) is deprotected, and then condensed with an aromatic carboxylic acid or its reactive derivative of a formula (III):

wherein Ar represents a group of the following formula:

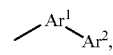

$Ar^1$ and $Ar^2$ have the same meanings as above.

The protective group (PG) may be, for example, a tert-butoxycarbonyl, benzyloxycarbonyl or benzoyl group, and may also be any other known protective group. For selecting suitable protective groups and their deprotection, for example, referred to is *Protective Groups in Organic Synthesis* (Theodora W. Greene & Peter G. M. Wuts, John Wiley & Sons, 1999).

In the above series of reaction, the functional groups such as hydroxyl group, amino group, imino group and carboxyl group not participating in the reaction may be suitably protected, if desired, and they may be deprotected after the reaction.

Not specifically defined, "protective group for hydroxyl group" may be any one having its function and includes, for example, a C1-C6 alkyl group such as a methyl group, an ethyl group, a propyl group, an isopropyl group, a tert-butyl group; a C1-C6 alkylsilyl group such as a trimethylsilyl group, a tert-butyldimethylsilyl group; a C1-C6 alkoxymethyl group such as a methoxymethyl group, a 2-methoxyethoxymethyl group; a tetrahydropyranyl group; a trimethylsilylethoxymethyl group, an aralkyl group such as a benzyl group, a p-methoxybenzyl group, a 2,3-dimethoxybenzyl group, an p-nitrobenzyl group, a p-nitrobenzyl group, a trityl group; an acyl group such as a formyl group, an acetyl group. Especially preferred are a methyl group, a methoxymethyl group, a tetrahydropyranyl group, a trityl group, a trimethylsilylethoxymethyl group, a tert-butyldimethylsilyl group, and an acetyl group.

Also not specifically defined, "protective group for amino group and imino group" may be any one having its function and includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a C2-C7 alkanoyl group such as a formyl group, an acetyl group, a propionyl group, a butyryl group, a pivaloyl group; a benzoyl group; an arylalkanoyl group such as a phenylacetyl group, a phenoxyacetyl group; a C2-C7 alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a C1-C6 alkylsilyl group such as a trimethylsilyl group, a tert-butyldimethylsilyl group; a tetrahydropyranyl group; a trimethylsilylethoxymethyl group; a C1-C6 alkylsulfonyl group such as a methylsulfonyl group, an ethylsulfonyl group; an arylsulfonyl group such as a benzenesulfonyl group, a toluenesulfonyl group. Especially preferred are an acetyl group, a benzoyl group, a tert-butoxycarbonyl group, a benzyloxycarbonyl group, a trimethylsilylethoxymethyl group, and a methylsulfonyl group.

Also not specifically defined, "protective group for carboxyl group" may be any one having its function and includes, for example, a C1-C6 alkyl group such as a methyl group, an ethyl group, a propyl group, an isopropyl group, a tert-butyl group; a halo-C1-C6 alkyl group such as a 2,2,2-trichloroethyl group; a C2-C6 alkenyl group such as a 2-propenyl group; an aralkyl group such as a benzyl group, a p-methoxybenzyl group, a p-nitrobenzyl group, a benzhydryl group, a trityl group. Especially preferred are a methyl group, an ethyl group, a tert-butyl group, a 2-propenyl group, a benzyl group, a p-methoxybenzyl group, and a benzhydryl group.

For the introduction and the removal of the protective groups, referred to is the above reference.

The substituent $R^1$ may be converted into a group of any other type ($R^{1'}$, $R^{1''}$) in any suitable stage according to a chemical process per-se well known in the field of organic chemistry.

For example, when $R^1$ is a bromide group, then it may be converted into a cyano group and may be further into a tetrazolyl group. The conversion reaction may be attained according to a chemical process well known in the field of organic chemistry.

In the above drawing, the condensation of the amino compound derived from the compound of formula (II), with an aromatic carboxylic acid may be attained in the same manner. In general, from 0.5 mol to an excessive molar amount, preferably from 1 mol to 1.5 mols of an aromatic carboxylic acid is used relative to one mol of the amino compound.

The reaction may be attained generally in an inert solvent. The insert solvent is preferably methylene chloride, chloroform, tetrahydrofuran, dimethylformamide, pyridine or their mixtures.

Preferably, the reaction is effected in the presence of a condensing agent. The condensing agent includes, for example, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris(dimethylamino) phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoryl azide, 1,1'-carbonyldiimidazole.

The condensing agent may be used in an amount of from 1 mol to an excessive molar amount, preferably from 1 mol to 1.5 mols relative to 1 mol of the aromatic carboxylic acid.

The reaction temperature may be generally from –50° C. to 120° C., preferably from –20° C. to 80° C.

The reaction time may be generally from 30 minutes to 7 days, preferably from 1 hour to 24 hours.

In place of the aromatic carboxylic acid, a reactive derivative of the carboxylic acid may be reacted with the amino compound to produce the intended product.

The reactive derivative of the aromatic carboxylic acid usable herein includes, for example, acid halides, mixed acid anhydrides, active esters, and active amides.

The acid halide may be prepared by reacting the aromatic carboxylic acid with a halogenating agent in an ordinary manner. The halogenating agent includes, for example, thionyl chloride, phosphorus trichloride, phosphorus pentachloride, phosphorus oxychloride, phosphorus tribromide, oxalyl chloride, and phosgene.

The mixed acid anhydride may be prepared by reacting the aromatic carboxylic acid with an alkyl chlorocarbonate such as ethyl chlorocarbonate or with an aliphatic carboxylic acid chloride such as pivaloyl chloride, in an ordinary manner.

The active ester may be prepared by reacting the aromatic carboxylic acid with an N-hydroxy compound such as N-hydroxysuccinimide, N-hydroxyphthalimide or 1-hydroxybenzotriazole, or with a phenol compound such as 4-nitrophenol, 2,4-dinitrophenol, 2,4,5-trichlorophenol or pentachlorophenol, in the presence of a condensing agent such as N,N'-dicyclohexylcarbodiimide or 1-(3-dimethylaminopropyl)-3-ethylcarbodiimide, in an ordinary manner.

The active amide may be prepared by reacting the aromatic carboxylic acid with, for example, 1,1'-carbonyldiimidazole or 1,1'-carbonylbis(2-methylimidazole) in an ordinary manner.

The reaction between the amino compound and the reactive derivative of the carboxylic acid may be attained, generally using from 0.5 mols to an excessive molar amount, preferably from 1 mol to 1.5 mols of the reactive derivative of the carboxylic acid, per 1 mol of the amino compound.

The reaction may be effected generally in an inert solvent. The inert solvent is, for example, preferably methylene chloride, chloroform, tetrahydrofuran, dimethylformamide, pyridine and their mixtures.

The reaction may go on in the absence of a base, but for more smoothly promoting it, the reaction is preferably effected in the presence of a base.

The base includes an organic base such as triethylamine, diisopropylethylamine, pyridine, 4-dimethylaminopyridine; and an inorganic base such as sodium hydroxide, potassium hydroxide, sodium carbonate, potassium carbonate, sodium hydrogencarbonate.

In general, the base is used preferably in an amount of from 1 mol to an excessive molar amount relative to 1 mol of the amino compound. When the base is liquid, then the base may serve also as a solvent.

The reaction temperature may be generally from −50° C. to 120° C., preferably from −20° C. to 80° C.

The reaction time may be generally from 5 minutes to 7 days, preferably from 30 minutes to 24 hours.

After the reaction, the system may be processed in an ordinary manner to give a crude product of the intended compound. The thus-obtained compound may be purified in an ordinary manner, or not purified, it may be subjected to the next reaction, if desired.

After the reaction, when the product has a protective group, then the protective group may be removed. When the product does not have a protective group, it may be processed in any ordinary manner, and the intended final product may be thus produced.

The compounds of formulae (II) and (III) may be commercial products, or may be prepared according to a known method or according to a method similar to a known method, or with reference to the methods described in Examples and Reference Examples, suitably as combined, if desired.

The compounds of formula (I) may be administered orally or parenterally, and after formulation into preparations suitable for the intended administration route, they can be used as therapeutic agents, for example, for vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy, sexual dysfunction; digestive system diseases such as liver dysfunction, pancreatitis, cholecystitis and gastroesophageal reflux; respiratory diseases such as Pickwickian syndrome and sleep apnea syndrome; infectious diseases caused by bacteria, fungi or parasites; malignant neoplasm; and inflammatory diseases such as arthritis and skin ulcer.

The following "diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, ACC 1/2 inhibitors may also be useful to treat hypertension associated with this condition.

One aspect of the present invention provides a method for the treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of disorders, diseases or conditions responsive to the modulation of ACC-1 or ACC-2 including, but not limited to, metabolic syndrome, fatty liver, hyperlipemia, dyslipidemia, non-alcoholic fatty liver disease, obesity, diabetes, bulimia, malignant neoplasm or an infectious disease in a subject in need thereof which comprises administering to said subject a therapeutically or prophylactically effective amount of a compound of formula (I), or a pharmaceutically acceptable salt or ester thereof.

Another aspect of the present invention provides a method for the treatment of metabolic syndrome, fatty liver, hyperlipemia, obesity, diabetes, bulimia, malignant neoplasm or infectious diseases, which comprises administering to a subject in need thereof a therapeutically effective amount of the compound or its salt or ester of claim 1.

Another aspect of the present invention provides a method for the treatment or prevention of diabetes in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of fatty liver in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of obesity in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoartritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of hyperlipemia or dyslipidemia in a subject in need thereof which comprises administering to the subject a therapeutically or prophylactically effective amount of a compound of formula (I), or a pharmaceutically acceptable salt or ester thereof.

Another aspect of the present invention provides a method for caloric intake in a subject in need thereof which comprises administering to the subject a therapeutically or prophylactically effective amount of a compound of formula (I), or a pharmaceutically acceptable salt or ester thereof. Another aspect of the present invention provides a method for reducing food intake in a subject in need thereof which comprises administering to the subject a therapeutically or prophylactically effective amount of a compound of formula (I), or a pharmaceutically acceptable salt or ester thereof. Another aspect of the present invention provides a method for increasing satiety in a subject in need thereof which comprises administering to the subject a therapeutically or prophylactically effective amount of a compound of formula (I), or a pharmaceutically acceptable salt or ester thereof. Another aspect of the present invention provides a method for reducing appetite in a subject in need thereof which comprises administering to the subject a therapeutically or prophylactically effective amount of a compound of formula (I), or a pharmaceutically acceptable salt or ester thereof.

The present invention also relates to methods for treating or preventing obesity by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing diabetes by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing hyperlipemia or dyslipidemia by administering a compound of formula (I), or a pharmaceutically acceptable salt or ester thereof, in combination with a therapeutically or prophylactically effective amount of another agent known to be useful to treat or prevent the condition.

Another aspect of the present invention provides a pharmaceutical composition comprising a compound of formula (I), or a pharmaceutically acceptable salt or ester thereof, and a pharmaceutically acceptable carrier.

Yet another aspect of the present invention relates to a compound of formula (I), or a pharmaceutically acceptable salt or ester thereof, for use in medicine.

Yet another aspect of the present invention relates to the use of a compound of formula (I), or a pharmaceutically acceptable salt or ester thereof, for the manufacture of a medicament useful for the treatment or prevention, or suppression of a disease mediated by ACC-1 or ACC-2 in a subject in need thereof.

Yet another aspect of the present invention relates to the use of a compound of formula (I), or a pharmaceutically acceptable salt or ester thereof, for the manufacture of a medicament useful for the treatment or prevention of metabolic syndrome, hyperlipemia, dyslipidemia, non-alcoholic fatty liver disease, obesity, diabetes, bulimia, malignant neoplasm or an infectious disease in a subject in need thereof.

Yet another aspect of the present invention relates to the use of a compound of formula (I), or a pharmaceutically acceptable salt or ester thereof, for the manufacture of a medicament useful for the treatment or prevention of obesity in a subject in need thereof.

Yet another aspect of the present invention relates to the use of a compound of formula (I), or a pharmaceutically acceptable salt or ester thereof, for the manufacture of a medicament useful for the treatment or prevention of diabetes in a subject in need thereof.

Yet another aspect of the present invention relates to the use of a compound of formula (I), or a pharmaceutically acceptable salt or ester thereof, for the manufacture of a medicament useful for the treatment or prevention of hyperlipemia or dyslipidemia in a subject in need thereof.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes, a diabetes related disorder, or an obesity-related disorder in a subject in need of such treatment.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes, a diabetes related disorder, or an obesity-related disorder which comprises an effective amount of a compound of formula (I), or a pharmaceutically acceptable salt or ester thereof, and an effective amount of the agent, together or separately.

Yet another aspect of the present invention relates to a product containing a therapeutically effective amount of a compound of formula (I), or a pharmaceutically acceptable salt or ester thereof; and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, a diabetes related disorder, or an obesity-related disorder.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, taranabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl) {3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Yet another aspect of the present invention relates to a method of treatment or prevention of disorders, diseases or conditions responsive to the modulation of ACC-1 or ACC-2 in a subject in need thereof comprising administration of a therapeutically or prophylactically effective amount of a compound of formula (I), or a pharmaceutically acceptable salt or ester thereof, and a therapeutically or prophylactically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeplide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes, a diabetes related disorder, or an obesity-related disorder in a subject in need of such treatment.

Yet another aspect of the present invention relates to a method of treatment or prevention of disorders, diseases or conditions responsive to the modulation of ACC-1 or ACC-2 in a subject in need thereof comprising administration of a therapeutically or prophylactically effective amount of a compound of formula (I), or a pharmaceutically acceptable salt or ester thereof, and a therapeutically or prophylactically effective amount of at least one agent selected from the group consisting of: simvastatin, mevastafin, ezetimibe, atorvastatin, sitagliptin, metformin, sibutramine, orlistat, Qnexa, topiramate, phentermine, losartan, losartan with hydrochlorothiazidc, or a CB1 antagonist/inverse agonist selected from: rimonabant, taranabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-4-chlorophenyl){3-[(1S)-1-(3,5-difluorophenyl)-2-hydroxy-2-methylpropyl]azetidin-1-yl}methyl)-benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl){3-[1-(3,5-difluorophenyl)-2,2-dimethylpropyl]azetidin-1-yl}methyl)benzonitrile, 3-(1S)-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[1-(3,5-difluorophenyl)-2-fluoro-2-methylpropyl]azetidin-1-yl}methyl)thiophene-3-Carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

In clinical use of the compounds of the invention, pharmaceutically-acceptable additives may be added thereto to formulate various preparations in accordance with the intended administration route thereof, and the preparations may be administered. Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals including humans and other mammals and plants that require the treatment with the compound. For the mammals, humans are preferred and they may be either men or women. The mammals except humans are, for example, companion animals such as dogs and cats. The compounds of the invention are effective also for obesity and obesity-related disorders of dogs and cats. Any ordinary physicians, veterinarians and clinicians may readily determine the necessity, if any, of the treatment with the compound of the invention.

When the compound of the invention is, for example, put into clinical use, then its dose and its administration frequency may vary depending on the sex, the age, the body weight and the condition of the patient and on the type and the range of the necessary treatment with the compound. In oral administration, in general, the dose of the compound may be from 0.01 to 100 mg/kg of adult/day, preferably from 0.03 to 1 mg/kg of adult/day, and the administration frequency is preferably from one to a few times; and in parenteral administration, the dose may be from 0.001 to 10 mg/kg of adult/day, preferably from 0.001 to 0.1 mg/kg of adult/day, more preferably from 0.01 to 0.1 mg/kg of adult/day, and the administration frequency is preferably from one to a few times. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing obesity and/or diabetes mellitus and/or hyperlipemia and/or dyslipidemia and/or non-alcoholic fatty liver disease, or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The preparation may contain the compound of the invention in an amount of from 1.0 to 100% by weight, preferably from 1.0 to 60% by weight of the preparation. The preparation may contain any other therapeutically-effective compound.

In their use, the compounds of the invention may be combined with any other therapeutic agents that are useful for the treatment of disorders, for example, vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, pre-diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy and sexual dysfunction; digestive tract diseases such as liver dysfunction, pancreatitis, cholecystitis and gastroesophageal reflux; respiratory system diseases such as Pickwickian syndrome and sleep apnea syndrome; infectious diseases caused by bacteria, fungi or parasites; malignant neoplasm; and inflammatory diseases such as arthritis and skin ulcer. The individual ingredients to be combined may be administered at the same time or at different times during the treatment period, either as one preparation or as different preparations. Accordingly, the invention should be so interpreted that it encompasses any and every administration mode at the same time or at different times, and the administration in the invention should be interpreted so. The range of the combination of the compound of the invention and the other therapeutic agent useful for the above-mentioned disorders encompasses, in principle, all combinations of the compound of the invention and any and every pharmaceutical agent useful for the above-mentioned disorders.

The combination includes not only the composition of compounds of the invention and one other active substance but also the composition of compounds of the invention and two or more other active substances. There are a lot of examples of the combinations of a compound of the invention and one, two or more active substances selected from the therapeutic agents for the above-mentioned disorders. For example, for the treatment, management and prevention of metabolic syndrome, a combination of a compound of the invention and one, two or more active substances selected from hypolipidemic agents, lipid lowering agents, and anti-diabetic agents is useful. In particular, a composition that also contains an anti-obesity agent and an anti-hypertension agent, in addition to an anti-diabetic agent and/or a hypolipidemic agent or lipid lowering agent, may exhibit a synergistic effect for treatment, management and prevention of metabolic syndrome.

The pharmaceutical agents that may be combined with the compound of the invention are, for example, ACAT inhibitor, $\alpha$-blocker, aldose reductase inhibitor, $\alpha$-amylase inhibitor, angiotensin-converting enzyme inhibitor, angiotensin receptor antagonist, anion exchange resin, anorectic, antioxidant, antiplatelet, $\beta$-blocker, biguanide agent, calcium antagonist, CB1 receptor inverse agonist/antagonist, CETP inhibitor, cholesterol absorption inhibitor, DGAT inhibitor, DP-IV inhibitor, diuretic, eicosapentaenoic acid, endothelin antagonist, FLAP inhibitor, FXR modulator, Ghrelin antagonist, GLP-1 agonist, GLP-1 secretagogue, glucagon antagonist, glucokinase activator, glucocorticoid receptor ligand, $\alpha$-glucosidase inhibitor, GPAT inhibitor, histamine-H3 receptor ligand, HMG-CoA reductase inhibitor, HSD inhibitor, 11 beta HSD-1 inhibitor, insulin and insulin mimetics, kinase inhibitors such as VEGF inhibitor and PDGF inhibitor, leptin, lipase inhibitor, 5-LO inhibitor, LXR ligand, melanocortin agonist, MCH antagonist, MTTP inhibitor, orexin antagonist, opioid antagonist, neuropeptide Y antagonist, nicotinic acid agonist, PPAR ligand, PTP-1B inhibitor, SCD-1 inhibitor, serotonin transporter inhibitor, SGLT inhibitor, SUR ligand, thyroid hormone agonist, UCP activator, VPAC receptor agonist.

More concretely, examples of the other active ingredients that can be combined with a compound of the invention as different or the same pharmaceutical compositions are shown below, which, however, do not restrict the invention.

(a) Anti-diabetic medicines or agents, for example, (1) glitazones (e.g., ciglitazone, darglitazone, englitazone, isaglitazone (MCC-555), pioglitazone, rosiglitazone, troglitazone, tularik, BRLA9653, CLX-0921, 5-BTZD), and PPAR-$\gamma$ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and A1-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-$NH_2$; (12) non-thiazolidinediones such as JT-501, farglitazar (GW-2570/GI-262579), and muraglitazar; PPAR α/δ agonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTCO179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, for example, (1) 5HT (serotonin) transporter inhibitors such as paroxetine, fluoxetine, fenfluramine, fluvoxamine, sertraline, and imipramine; (2) NE (norepinephrine) transporter inhibitors such as GW320659, despiramine, talsupram, nomifensine, and the like; (3) CB-1 (cannabinoid-1 receptor) antagonists/inverse agonists such as rimonabant (Sanofi Synthelabo), SR-147778 (Sanofi Synthelabo), BAY65-2520 (Bayer), SLV319 (Solvey); and the compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, WO04/048317, WO05/000809, and EPO NO. EP-658546, EP656354, EP576357; (4) ghrelin antagonists such as those disclosed in WO01/87335, WO02/08250; (5) H3 (histamine H3) antagoniststinverse agonists such as thioperamide, 3-(1H-imidazol-4-yl)propyl N-(4-pentenyl) carbamate, clobenpropit, iodophenpropit, imoproxifan, GT2394 (Gliatech), A331440, and those disclosed in WO02/15905, O-[3-(1H-imidazol-4-yl)propanol]carbamates (Kiec-Kononowicz, K. et al., *Pharmazie,* 55:349-355 (2000)), piperidine-containing histamine H3-receptor antagonists (Lazewska, D. et al., *Pharmazie,* 56:927-932 (2001)), benzophenone derivatives and related compounds (Sasse, A. et al., *Arch. Pharm.* (Weinheim) 334:45-52 (2001)), substituted N-phenylcarbamates (Reidemeister, S. et al., Pharmazie, 55:83-86 (2000)), and proxifan derivatives (Sasse, A. et al., *J. Med. Chem.,* 43:3335-3343 (2000)); (6) melanin-concentrating hormone-1 receptor (MCH1R) antagonists such as T-226296 (Takeda), SNP-7941 (Synaptic), and those disclosed in WO01/82925, WO01/87834, WO02/051809, WO02/06245, WO02/076929, WO02/076947, WO02/04433, WO02/51809, WO02/083134, WO02/094799, WO03/004027, and Japanese Patent Application No. JP13226269, JP2004-139909; (7) MCH2R (melanin-concentrating hormone 2R) agonists/antagonists; (8) NPY1 (neuropeptide Y Y1) antagonists such as BIBP3226, 2-[1-(5-chloro-3-isopropyloxycarbonylaminophenyl)ethyl-amino]-6-[2-(5-ethyl-4-methyl-1,3-thiazol-2-yl)ethyl]-4-morpholinopyridine, BIBO3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; (9) NPY5 (neuropeptide Y Y5) antagonists such as L-152,804, GW-569180A, GW-594884A, GW-587081X, GW-548118X, FR235,208, FR-226928, FR240662, FR252384,1229U91, GI-264879A, CGP71683A, LY-377897, LY366377, PD-160170, SR-120562A, SR-120819A, JCF-104, H409/22, and the compounds disclosed in U.S. Pat. Nos. 6,057,335, 6,043,246, 6,140,354, 6,166,038, 6,180,653, 6,191,160, 6,258,837, 6,313,298, 6,337,332, 6,329,395, 6,340,683, 6,326,375, 6,329,395, 6,337,332, 6,335,345, 6,388,077, 6,462,053, 6,649,624, 6,723,847, EPO EP-01010691, EP-01044970, PCT WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/094789, WO02/094825, WO03/014083, WO03/10191, WO03/092889, WO2004/002986, WO2004/031175, and Norman et al., *J. Med. Chem.*, 43:4288-4312 (2000); (10) leptins such as recombinant human leptin (PEG-OB, Hoffman La Roche), and recombinant methionyl human leptin (Amgen); (11) leptin derivatives such as those disclosed in U.S. Pat. Nos. 5,552,524, 5,552,523, 5,552,522, 5,521,283, PCT WO96/23513, WO96/23514, WO96/23515, WO96/23516, WO96/23517, WO96/23518, WO96/23519, and WO96/23520; (12) opioid antagonists such as nalmefene (Revex®), 3-methoxynaltrexone, naloxone, naltrexone, and the compounds disclosed in WO00/21509; (13) orexin antagonists such as SB-334867-A, and the compounds disclosed in WO01/96302, WO01/68609, WO02/51232, WO02/51838, and WO03/023561; (14) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (15) CCK-A (cholecystokinin-A) agonists such as AR-R15849, GI181771, JMV-180, A-71378, A-71623, SR146131, and the compounds disclosed in U.S. Pat. No. 5,739,106; (16) CNTF (ciliary neurotrophic factors) such as GI-181771 (Glaxo-SmithKline), SR146131 (Sanofi Synthelabo), butabindide, and PD170292 and PD149164 (Pfizer); (17) CNTF derivatives such as axokine (Regeneron), and the compounds disclosed in WO94/09134, WO98/22128, and WO99/43813; (18) GHS (growth hormone secretagogue receptor) agonists such as NN703, hexarelin, MK-0677, SM-130686, CP-424,391, L-692,429, L-163,255, and the compounds disclosed in U.S. Pat. Nos. 5,536,716, 6,358,951, USP Application Nos. 2002/049196, 2002/022637, WO01/56592, and WO02/32888; (19) 5HT2c (serotonin receptor 2c) agonists such as BVT933, DPCA37215, IK264, PNU22394, WAY161503, R-1065, YM348, and the compounds disclosed in U.S. Pat. No. 3,914,250, WO02/36596, WO02/48124, WO02/10169, WO01/66548, WO02/44152, WO02/51844, WO02/40456, and WO02/40457; (20) Mc3r (melanocortin-3 receptor) agonists; (21) Mc4r (melanocortin-4 receptor) agonists such as CHIR86036 (Chiron), ME-10142 and ME-10145 (Melacure), PT-141 and PT-14 (Palatin), and the compounds disclosed in U.S. Pat. Nos. 6,410,548, 6,294,534, 6,350,760, 6,458,790, 6,472,398, 6,376,509, and 6,818,658, USP Application No. US2002/0137664, US2003/0236262, US2004/009751, US2004/0092501, WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847, WO04/024720, WO04/078716, WO04/078717, WO04/087159, WO04/089307 and WO05/009950; (22) monoamine reuptake inhibitors such as sibutramine (Meridia®/Reductil®) and its salts, and the compounds disclosed in U.S. Pat. Nos. 4,746,680, 4,806,570, 5,436,272, USP Publication No. 2002/0006964, and WO01/27068, and WO0/62341; (23) serotonin reuptake inhibitors such as dexfenfluramine, fluoxetine, paroxetine, sertraline, and the compounds disclosed in U.S. Pat. No. 6,365,633, and WO01/27060, and WO01/162341; (24) GLP-1 (glucagon-like peptide-1) agonists; (25) topiramate (Topimax®); (26) Phytopharm compound 57 (CP644,673); (27) ACC2 (acetyl-CoA carboxylase-2) inhibitors; (28) β3 (β-adrenergic receptor-3) agonists such as AD9677/TAK677 (Dainippon/Takeda), CL-316,243, SB418790, BRL-37344, L-796568, BMS-196085, BRL-35135A, CGP12177A, BTA-243, GW427353, trecadrine, Zeneca D7114, SR59119A, and the compounds disclosed in USP Application No. 5,705,515, U.S. Pat. No. 5,451,677, and WO94/18161, WO95/29159, WO97/46556, WO98/04526, WO98/32753, WO01/74782 and WO02/32897; (29) DGAT1 (diacylglycerol acyltransferase-1) inhibitors; (30) DGAT2 (diacylglycerol acyltransferase-2) inhibitors; (31) FAS (fatty acid synthase) inhibitors such as cerulenin, C75; (32) PDE (phosphodiesterase) inhibitors such as theophylline, pentoxifylline, zaprinast, sildenafil, aminone, milrinone, cilostamide, rolipram, and cilomilast; (33) thyroid hormone-β agonists such as KB-2611 (KaroBioBMS), and the compounds disclosed in WO02/15845 and Japanese Patent Application No. JP2000256190; (34) UCP-1 (uncoupling protein-1), 2 and 3 activators such as phytanic acid, 4-[(E)-2-(5,6,7,8-tetrahydro-5,5,8,8-tetramethyl-2-naphthalenyl)-1-propenyl] benzoic acid (TTNPB), retinoic acid, and the compounds disclosed in WO99/00123; (35) acyl-estrogens such as oleoyl-estrones disclosed in del Mar-Grasa, M. et al., *Obesity Research*, 9:202-209 (2001); (36) glucocorticoid antagonists; (37) 11βHSD-1 (11-β-hydroxysteroid dehydrogenase type 1) inhibitors such as BVT3498, BVT2733, and the compounds disclosed in WO01/90091, WO01/90090, and WO01/90092, and U.S. Pat. No. 6,730,690 and USP Application No. 2004/0133011; (38) SCD-1 (stearoyl-CoA desaturase-1) inhibitors; (39) dipeptidyl peptidase IV (DP-IV) inhibitors such as isoleucine thiazolidide, valine pyrrolidide, NVP-DPP728, LAF237, P93/01, TSL225, TMC-2A/2B/2C, FE999011, P9310/K364, VIP0177, SDZ274-444, and the compounds disclosed in U.S. Pat. No. 6,699,871, WO03/004498, WO03/004496, EP 1258476, WO02/083128, WO02/062764, WO03/000250, WO03/002530, WO03/002531, WO03/002553, WO03/002593, WO03/000180, and WO03/000181; (40) lipase inhibitors such as tetrahydrolipstatin (orlistat/Xenical®), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and the compounds disclosed in WO01/77094, U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; (44) phosphate transporter inhibitors; (45) melanocortin agonists such as melanotan II and the compounds described in WO99/64002, and WO00/746799; (46) melanin condensating hormone antagonists such as the compounds disclosed in WO01/21577 and WO01/21169; (47) galanin antagonists; (48) CCK agonists; (49) corticotropin-releasing hormone agonists; and (50) phosphodiesterase-3B (PDE3B) inhibitors; (51) 5HT-2 agonists; (52) histamine receptor-3 (H3) modulators; (53) β-hydroxy steroid dehydrogenase-1 inhibitors (β-HSD-1); (54) anti-obesity serotonergic agents, such as fenfluramine, dexfenfluramine, phentermine, and sibutramine; (55) peptide YY, PYY 3-36, peptide YY analogs, derivatives, and fragments such as BIM-43073D, BIN-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936, 092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (56) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (57) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (58) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof, (59) aminorex; (60) amphechloral; (61) amphetamine; (62) benzphetamine; (63) chlorphentermine; (64) clobenzorex; (65) cloforex; (66) clominorex; (67) clortermine; (68) cyclexedrine; (69) dextroamphetamine; (70) diphemethoxidine, (71) N-ethylamphetamine; (72) fenbutrazate; (73) fenisorex; (74) fenproporex; (75) fludorex; (76) fluminorex; (77) furfurylmethylamphetamine; (78) levamfetamine; (79) levophacetoperane; (80) mefenorex; (81) metamfepramone; (82) methamphetamine; (83) norpseudoephedrine; (84) pentorex; (85) phendimetrazine; (86) phenmetrazine; (87) picilorex; (88) zonisamide, and (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; (90) Qnexa; and (91) bupropion; and (e) (1) Glucagon Receptor Agonists; (2) G Protein Receptor Agonist-40 (GPR-40) also called SNORF 55 such as BG 700, and those disclosed in WO 04/041266, 04/022551, 03/099793; (3) G Protein Receptor Agonist-119 (GPR119, also called RUP3; SNORF 25)—such as RUP3, HGPRBMY26, PFI 007, SNORF 25; (4) G Protein Receptor Agonist 131; (5) Selective Peroxisome Proliferator Activator Receptor Modulator (SPPARMS, also known as selective PPAR gamma modulators)—such as T131 (Amgen), FK614 (Fujisawa), netoglitazone, and metaglidasen; (6) oxyntomodulin; (7) SGLT inhibitors (sodium dependent glucose transporter inhibitors)—such as AVE 2268, KGT 1251, T1095/RWJ 394718.

The present agent may be combined with non-drug therapy such as kinesitherapy, dietetic treatment, and radiation therapy.

The compound and the combined compositions of the invention are effective for treating and preventing diabetes. The term "diabetes" as used herein includes both insulin-dependent diabetes (that is, also known as IDDM, type-1 diabetes), and insulin-independent diabetes (that is, also known as NIDDM, type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geqq$140 mg/dl and <200 mg/dl); or insulin resistance, resulting in an increased risk of developing diabetes.

The compounds and compositions of the invention are useful for treatment of both type-1 diabetes and type-2 diabetes. The compounds and compositions are especially useful for treatment of type-2 diabetes. The compounds and compositions of the invention are especially useful for treatment and/or prevention of pre-diabetes. Also, the compounds and compositions of the invention are especially useful for treatment and/or prevention of gestational diabetes mellitus.

Treatment of diabetes mellitus refers to the administration of a compound or combination of the present invention to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes. Yet another outcome of treatment is to increase hepatic insulin sensitivity.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The invention is described more concretely with reference to Examples and Reference Examples mentioned below, which, however, do not restrict the invention.

In thin-layer chromatography in Examples, Silica gel$_{60}$F$_{254}$ (Merck) was used as the plate; and a UV detector was used for detection. In column silica gel, used was Wakogel™ C-300 or C-200 (Wako Jun-yaku), FLASH+ cartridge (Biotage) or Chromatorex (FUJI SELYSIA CHEMICAL). In high-performance partitioning liquid chromatography, used was ODS (C18) filler. The MS spectrum was determined through electrospray ionization (ESI), using Micromass ZQ 2000 (Waters). In NMR spectrometry, used was dimethylsulfoxide as the internal standard in a heavy dimethylsulfoxide solution, or used was tetramethylsilane as the internal standard in a heavy chloroform solution. For it, used was a spectrophotometer of JNM-AL400 (JEOL), Mercury 400 (400 MHz; Varian) or Inova 400 (400 MHz; Varian), and the total δ value was shown as ppm.

Abbreviations in NMR have the following meanings: s: singlet; d: doublet; dd: double doublet; t: triplet; dt: double triplet; q: quartet; m: multiplet; br: broad; br m: broad multiplet; J: coupling constant; Hz: hertz; DMSO-d$_6$: heavy dimethylsulfoxide; CDCl$_3$: heavy chloroform.

Abbreviations in Examples and Reference Examples have the following meanings: HOBT: 1-hydroxybenzotriazole hydrate; NMP: N-methylpyrrolidone; WSC: 1-(3-dimethylaminopropyl)-3-ethylcarbodiimide; DMF: dimethylformamide; Et$_3$N: triethylamine; EDCI: 1-(3-dimethylaminopropyl)-3-ethylcarbodiimide hydrochloride; TEA: triethylamine; HCl: hydrochloric acid; Et2O: diethyl ether; MeOH: methanol; THF: tetrahydrofuran; TFA: trifluoroacetic acid; CHCl$_3$: chloroform; μL: microliter; ml or mL: milliliter; mol: mole; mmol: millimole; ca: circa; Et or et: ethyl; AcOEt: ethyl acetate; Me or me: methyl; N: normal; h: hour(s); min: minute(s); kg: kilogram; mg: milligram; g: gram; dil: dilute; sat: saturated; aq: aqueous; t-Bu or t-bu: tert-butyl; t-BuOH: tert-butanol; Boc: tert-butoxy; CDI: carbonyl diimidazole; ODS: octadecylsilica; and DBU: 1,8-diazabicyclo[5.4.0]undec-7-ene.

Example 1

Production of 1'-{[4-(Benzo[b]thiophen-2-yl)phenyl]carbonyl}-6-(tetrazol-5-yl)spiro[chroman-2,4'-piperidin]-4-one

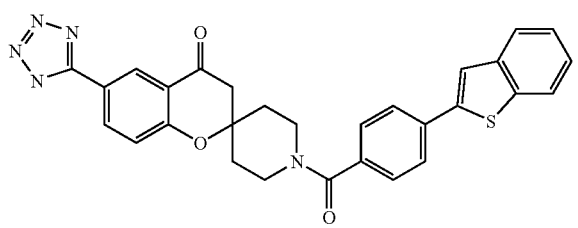

WSC hydrochloride (69.0 mg, 0.36 mmol) was added to a mixture of 4-(benzo[b]thiophen-2-yl)benzoic acid (76.3 mg, 0.300 mmol), 6-(tetrazol-5-yl)spiro[chroman-2,4'-piperidin]-4-one hydrochloride (96.5 mg, 0.300 mmol), HOBT (45.9 mg, 0.300 mmol), triethylamine (0.042 mL, 0.300 mmol) and NMP (1.5 mL), and stirred at room temperature for 20 hours. The reaction mixture was concentrated under reduced pressure, and the residue was purified through high-performance preparative liquid chromatography (0.1% TFA, water/acetonitrile) to obtain the title compound as a pale yellow solid. $^1$H-NMR (400 MHz, DMSO-d$_6$) δ: 8.44 (1H, d J=2.2 Hz), 8.25 (11, dd, J=8.5, 2.2 z), 8.00 (1H, d, J=8.3 Hz), 7.96 (1H, s), 7.89-7.83 (3H, m), 7.54 (2H, d, J=7.8 Hz), 7.44-7.33 (3H, m), 4.37-4.18 (1H, m), 3.65-3.18 (3H, m), 3.00 (2H, s), 2.13-1.75 (4H, m). MS [M–H]$^-$=520.

Example 2

Production of 1'-{[2,6-Bis(4-fluorophenyl)pyridin-4-yl]carbonyl}-6-(tetrazol-5-yl)spiro[chroman-2,4'-piperidin]-4-one

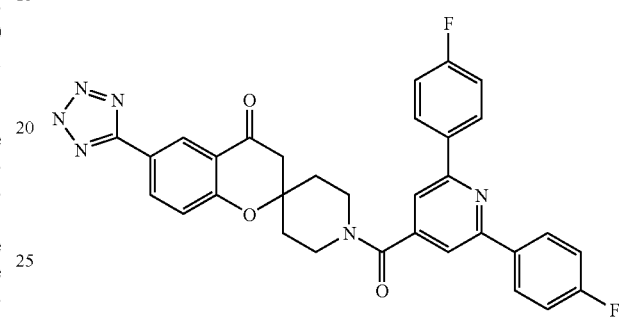

Triethylamine (71.0 μl, 0.51 mol), 1-hydroxybenzotriazole hydrate (35 mg, 0.26 mmol) and 1-(3-dimethylaminopropyl)-3-ethylcarbodiimide hydrochloride (49.0 mg, 0.26 mol) were added to an N,N-dimethylformamide solution (0.5 mL) of 2,6-bis(4-fluorophenyl)pyridine-4-carboxylic acid (53.0 mg, 0.17 mmol) and 6-(tetrazol-5-yl)spiro[chroman-2,4'-piperidin]-4-one hydrochloride (82.0 mg, 0.26 mol), and stirred at 60° C. for 3 hours. The reaction liquid was concentrated under reduced pressure, and the resulting residue was purified through high-performance preparative liquid chromatography (0.1% TFA, water/acetonitrile) to obtain the title compound as a white solid. $^1$H-NMR (400 MHz, DMSO-d$_6$) δ: 8.42 (1H, d, J=2.0 Hz), 8.31 (4H, dd, J=8.7, 5.7 Hz), 8.25 (1H, dd, J=8.7, 2.3 Hz), 7.94 (2H, s), 7.39-7.33 (5H, m), 4.35-4.32 (1H, m), 3.46-3.32 (3H, m), 2.99 (2H, s), 2.13-2.10 (1H, m), 1.91-1.87 (3H, m). MS [M+H]$^+$=579.

Example 3

Production of 1'-{[2-Methoxy-6-phenylpyridin-4-yl]carbonyl}-6-(tetrazol-5-yl)spiro[chroman-2,4'-piperidin]-4-one

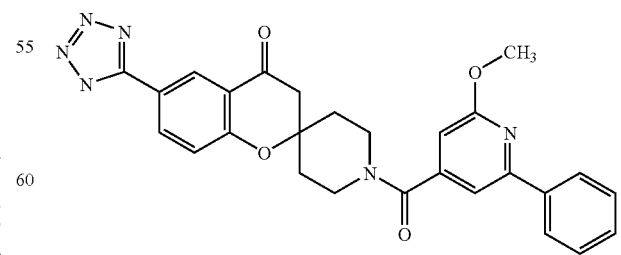

6-(Tetrazol-5-yl)spiro[chroman-2,4'-piperidin]-4-one hydrochloride (42 mg), 1-hydroxybenzotriazole monohydrate (20 mg), 1-(3-dimethylaminopropyl)-3-ethylcarbodiimide hydrochloride (25 mg), triethylamine (21 μL) and water (1 mL) were added in that order to a DMF (3 mL) solution of 2-methoxy-6-phenyl-isonicotinic acid (25 mg), and stirred at room temperature for 2 hours. Water was added to the reaction liquid, the formed precipitate was taken out through filtration, washed with water, and dried to obtain the title compound as a white solid. $^1$H-NMR (400 MHz, DMSO-d$_6$) δ: 8.41 (1.0H, d, J=2.0 Hz), 8.23 (1.0H, dd, J=8.6, 2.4 Hz), 8.13 (2.0H, d, J=6.8 Hz), 7.57 (1.0H, br s), 7.51-7.44 (3.0H, m), 7.32 (1.0H, d, J=8.6 Hz), 6.78 (1.0H, br s), 4.31-4.27 (1.0H, m), 3.97 (3.0H, s), 3.40-3.20 (3.0H, m), 2.97 (2.0H, s), 2.10-2.05 (1.0H, m), 1.90-1.83 (3.0H, m). MS [M−H]$^−$=495.

Example 4

Production of 1'-{[3-(1H-indol-5-yl)-5-methoxyphenyl]carbonyl}-6-(tetrazol-5-yl)spiro[chroman-2,4'-piperidin]-4-one

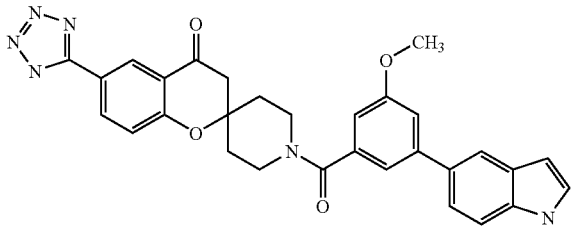

WSC hydrochloride (52.5 mg, 0.274 mmol) was added to a mixture of 3-(1H-indol-5-yl)-5-methoxybenzoic acid (61.0 mg, 0.228 mmol), 6-(tetrazol-5-yl)spiro[chroman-2,4'-piperidin]-4-one hydrochloride (73.4 mg, 0.228 mmol), HOBT (34.9 mg, 0.228 mmol), triethylamine (0.048 mL, 0.34 mmol), chloroform (0.4 mL) and NMP (0.8 mL), and stirred at room temperature for 20 hours. The reaction mixture was concentrated under reduced pressure, and the residue was purified through high-performance preparative liquid chromatography (0.1% TFA, water/acetonitrile) to obtain the title compound as a pale yellow solid. $^1$H-NMR (400 MHz, DMSO-d$_6$) δ: 11.18 (1H, s), 8.43 (1H, d J=2.3 Hz), 8.25 (1H, dd, J=8.8, 2.3 Hz), 7.87-7.86 (1H, m), 7.47 (1H, d, J=8.4 Hz), 7.41 (1H, dd, J=8.4, 1.7 Hz), 7.39 (1H, t, J=2.8 Hz), 7.35 (1H, d, J=8.8 Hz), 7.26 (1H, dd, J=2.4, 1.5 Hz), 7.24 (1H, t, J=1.5 Hz), 6.87 (1H, dd, J=2.4, 1.5 Hz), 6.49 (1H, ddd, J=2.8, 2.1, 0.7 Hz), 4.37-4.23 (1H, m), 3.86 (3H, s), 3.66-3.18 (3H, m), 2.99 (2.0H, s), 2.14-1.81 (4H, m). MS [M−H]$^−$=533.

Example 5

Production of 1'-{[2,6-dimethoxybiphenyl-4-yl]carbonyl}-6-tetrazol-5-yl)spiro[chroman-2,4'-piperidin]-4-one

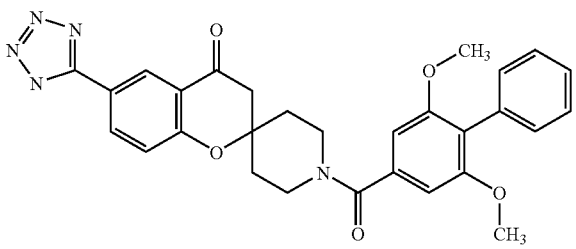

Triethylamine (10.4 mL) and water (100 mL) were added to a DMF (300 mL) solution of 2,6-dimethoxybiphenyl-4-carboxylic acid (12.0 g), 6-(tetrazol-5-yl)spiro[chroman-2, 4'-piperidin]-4-one hydrochloride (16.4 g), WSC (13.4 g) and HOBT (9.42 g), and stirred at 90° C. for 1 hour. Water was added to it at room temperature, and a white precipitate was thus obtained. This was dried under reduced pressure to obtain the title compound as a colorless solid. $^1$H-NMR (DMSO-d$_6$) δ: 8.43 (1H, d, J=2.2 Hz), 8.24 (1H, dd, J=8.8, 2.2 Hz), 7.37-7.31 (3H, m), 7.29-7.24 (1H, m), 7.22-7.18 (2H, m), 6.75 (2H, s), 4.34-4.21 (1H, m), 3.68 (6H, s), 3.67-3.15 (3H, m), 2.99 (2H, s), 2.14-1.92 (2H, m), 1.89-1.78 (2H, m). MS [M+H]$^+$=526.

Example 6

Production of 1'-{[2,6-Dimethoxybiphenyl-4-yl]carbonyl}-6-(tetrazol-5-yl)spiro[chroman-2,4'-piperidin]-4-one sodium salt

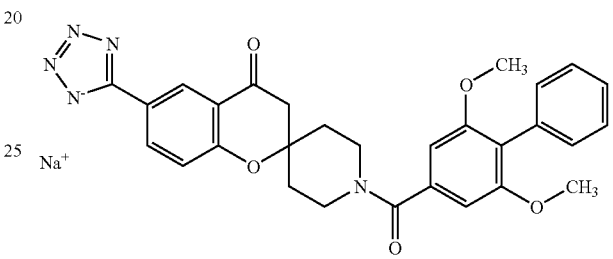

Aqueous 1 N sodium hydroxide solution (50 mL) was added to a suspension in water (50 mL) of 1'-{[2,6-dimethoxybiphenyl-4-yl]carbonyl}-6-(tetrazol-5-yl)spiro[chroman-2,4'-piperidin]-4-one (21.2 g), and stirred at room temperature for 30 minutes. Next, this was purified through ODS reversed-phase chromatography (water/methanol) to obtain the title compound as a colorless amorphous substance. $^1$H-NMR (400 MHz, DMSO-d$_6$) δ: 8.33 (1H, d, J=2.2 Hz), 8.17 (1H, dd, J=8.5, 2.2 Hz), 7.37-7.32 (2H, m), 7.29-7.19 (3H, m), 7.11 (1H, d, J=8.5 Hz), 6.76 (2H, s), 4.36-4.20 (1H, m), 3.72-3.64 (2H, m), 3.68 (6H, s), 3.35-3.17 (1H, m), 2.90 (2H, s), 2.14-1.89 (2H, m), 1.86-1.75 (2H, m). MS [M+H]$^+$=526.

Example 7

Production of 1'-{[3-Pyrrolidin-1-yl-5-(1,2,4-triazol-3-yl)phenyl]-carbonyl}-6-(tetrazol-5-yl)spiro[chroman-2,4'-piperidin]-4-one sodium salt

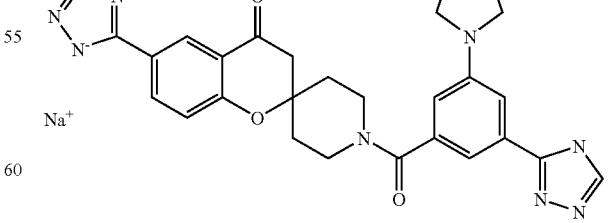

WSC hydrochloride (69.0 mg, 0.36 mmol) was added to a mixture of 3-(pyrrolidin-1-yl)-5-(1,2,4-triazol-3-yl)-benzoic acid (80.2 mg, 0.30 mmol), 6-(tetrazol-5-yl)spiro[chroman-2,4'-piperidin]-4-one hydrochloride (96.5 mg, 0.30 mmol), HOBT (45.9 mg, 0.30 mmol), triethylamine (0.063 ml, 0.45 mmol), chloroform (0.5 ml) and DMF (1.0 ml), and then stirred at room temperature for 16 hours. The reaction mixture was concentrated under reduced pressure, and the residue was purified through high-performance preparative liquid chromatography (0.1% TFA, water/acetonitrile). The obtained product was suspended in water, and aqueous 1 N sodium hydroxide solution was added to it until it became dissolved, and then purified through ODS reversed-phase chromatography (water/methanol) to obtain the intended compound as a yellow solid. $^1$H-NMR (400 MHz, DMSO-d$_6$) δ: 8.33-8.29 (1H, br. m), 8.31 (1H, d J=2.1 Hz), 8.15 (1H, dd, J=8.7, 2.1 Hz), 7.25-7.22 (2H, m), 7.11 (1H, d, J=8.7 Hz), 6.56-6.54 (1H, m), 4.33-4.18 (1H, m), 3.67-3.09 (7H, m), 2.91 (2H, s), 2.13-1.69 (8H, m).

MS [M−H]$^−$=524.

Example 8

Production of 6-[(1-methyl-1H-pyrazol-5-yl)amino]-1'-{[2-phenyl-6-(tetrazol-5-yl)pyridin-4-yl]carbonyl}spiro[chroman-2,4'-piperidin]-4-one

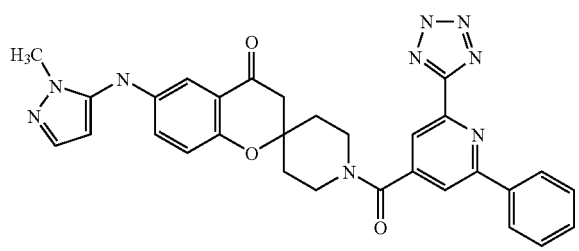

6-[(1-Methyl-1H-pyrazol-5-ylamino)]spiro[chroman-2,4'-piperidin]-4-one hydrochloride (117 mg), 1-hydroxybenzotriazole monohydrate (53 mg), 1-(3-dimethylaminopropyl)-3-ethylcarbodiimide hydrochloride (68 mg), triethylamine (94 μL) and water (1 mL) were added in that order to a DMF (3 mL) solution of 2-phenyl-6-(tetrazol-5-yl)-isonicotinic acid (75 mg), and stirred at 60° C. for 1 hour. Water was added to the reaction liquid, and the resulting precipitate was taken out through filtration, washed with hexane/ethyl acetate=2/1, and dried to obtain the title compound as a yellow solid. $^1$H-NMR (400 MHz, DMSO-d$_6$) δ: 8.37 (2.0H, d, J=6.8 Hz), 8.17 (1.0H, s), 8.08 (1.0H, br s), 7.93 (1.0H, s), 7.61-7.50 (3.0H, m), 7.32 (1.0H, d, J=2.0 Hz), 7.18-7.12 (2.0H, m), 6.99 (1.0H, d, J=8.4 Hz), 5.89 (1.0H, s), 4.31-4.27 (1.0H, m), 3.60 (3.0H, s), 3.50-3.20 (3.0H, m), 2.82 (2.0H, s), 2.12-2.05 (1.0H, m), 1.90-1.78 (3.0H, m). MS [M−H]$^+$=560.

Example 9

Production of [5-(4-Oxo-1'-{[3-(pyrrolidin-1-yl-5-(1,2,4-triazol-3-yl)phenyl]carbonyl}-spiro[chroman-2,4'-piperidin]-6-yl)-tetrazol-2-yl]methyl 2,2-dimethyl-proyanoate

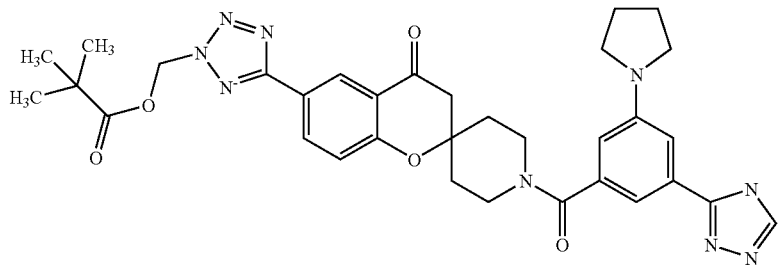

WSC hydrochloride (92.0 mg, 0.48 mmol) was added to a mixture of 3-(pyrrolidin-1-yl)-5-(1,2,4-triazol-3-yl)benzoic acid (103 mg, 0.40 mmol), [5-(4-oxospiro[chroman-2,4'-piperidin]-6-yl)-tetrazol-2-yl]methyl 2,2-dimethylpropanoate hydrochloride (174 mg, 0.40 mmol), HOBT (61.3 mg, 0.40 mmol), triethylamine (0.084 ml, 0.60 mmol) and DMF (2.0 ml), and stirred at room temperature for 12 hours. The reaction mixture was concentrated under reduced pressure, water was added to the residue, and extracted with ethyl acetate. The organic layer was washed with water and aqueous saturated sodium hydrogencarbonate solution, dried with sodium sulfate, and concentrated under reduced pressure. The residue was purified through silica gel column chromatography to obtain the title compound as a colorless solid. $^1$H-NMR (400 MHz, DMSO-d$_6$) δ: 8.48-8.19 (1H, br m), 8.39 (1H, d J=2.3 Hz), 8.25 (1H, dd, J=8.7, 2.3 Hz), 7.31 (1H, d, J=8.7 Hz), 7.22 (2H, s), 6.63 (2H, s), 6.55 (1H, s), 4.32-4.18 (1H, m), 3.64-3.16 (7H, m), 2.98 (2H, s), 2.12-1.71 (8H, m), 1.13 (9H, s). MS [M+H]$^+$=640.

Example 10

Production of [5-(1'-{[2,6-Dimethoxybiphenyl-4-yl]carbonyl}-4-oxospiro[chroman-2,4'-piperidin]-6-yl)-tetrazol-2-yl]methyl 2,2-dimethylpropanoate

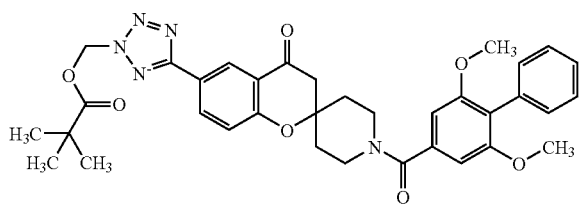

Triethylamine (0.23 mL) and water (2.0 mL) were added to a DMF (6.0 mL) solution of 2,6-dimethoxy-biphenyl-4-carboxylic acid (258 mg), [5-(4-oxospiro[chroman-2,4'-piperidin]-6-yl)-tetrazol-2-yl]methyl 2,2-dimethylpropanoate hydrochloride (500 mg), WSC (288 mg) and HOBT (202 mg), and stirred at 90° C. for 1 hour. Water was added to it at room temperature, and a white precipitate was thus obtained.

This was dried under reduced pressure to obtain the title compound as a colorless solid. ¹H-NMR (400 MHz, DMSO-$d_6$) δ: 8.40 (1H, d, J=2.2 Hz), 8.26 (1H, dd, J=8.8, 2.2 Hz), 7.38-7.18 (6H, m), 6.75 (2H, s), 6.64 (2H, s), 4.35-4.21 (1H, m), 3.68 (6H, s), 3.65-3.39 (2H, m), 3.29-3.25 (1H, m), 2.98 (2H, s), 2.14-1.92 (2H, m), 1.89-1.78 (2H, m), 1.14 (9H, s). MS [M+H]⁺=640.

Example 11

Production of 1'-{[3-Ethoxy-5-(tetrazol-5-yl)phenyl]carbonyl}-6-[(1-methyl-1H-pyrazol-5-yl)amino]spiro[chroman-2,4'-piperidin]-4-one sodium salt

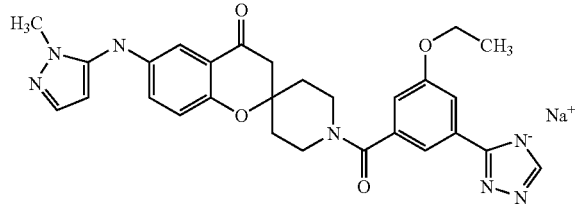

WSC hydrochloride (92.0 mg, 0.48 mmol) was added to a mixture of 3-ethoxy-5-(tetrazol-5-yl)benzoic acid (93.7 mg, 0.40 mmol), 6-[(1-methyl-1H-pyrazol-5-yl)amino]spiro[chroman-2,4'-piperidin]-4-one hydrochloride (140 mg, 0.40 mmol), HOBT (61.3 mg, 0.40 mmol), triethylamine (0.112 ml, 0.80 mmol) and DMF (2.0 ml), and stirred at room temperature for 15 hours. The reaction mixture was concentrated under reduced pressure, the residue was purified through high-performance preparative liquid chromatography (0.11% TFA, water/acetonitrile) to obtain the title compound as a yellow solid. ¹H-NMR (400 MHz, DMSO-$d_6$) δ: 7.93 (1H, s), 7.56-7.53 (2H, m), 7.33 (1H, d, J=1.9 Hz), 7.18-7.12 (2H, m), 7.01 (1H, d, J=8.2 Hz), 6.80-6.78 (1H, m), 5.91 (1H, d, J=1.9 Hz), 4.32-4.15 (1H, m), 4.09 (2H, q, J=6.9 Hz), 3.62 (3H, s), 3.58-3.11 (3H, m), 2.82 (2H, s), 2.07-1.66 (4H, m), 1.36 (3H, t, J=6.9 Hz). MS [M+H]⁺=529.

Example 12

Production of 1'-{[3,5-Diethoxy-4-(1-methyl-1H-pyrazol-4-yl)phenyl]carbonyl}-6-(tetrazol-5-yl)spiro[chroman-2,4'-piperidin]-4-one

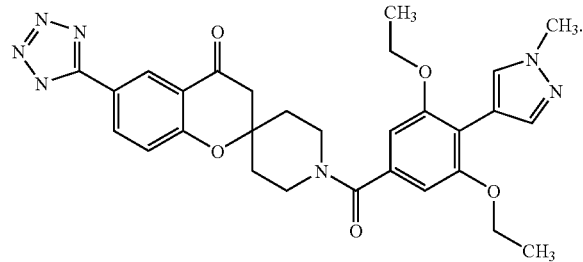

Et3N (38 μL), HOBT (41 mg) and WSC hydrochloride (52 mg) were added to a DMF (3 ml) solution of 3,5-diethoxy-4-(1-methyl-1H-pyrazol-4-yl)benzoic acid (65 mg), 6-(tetrazol-5-yl)spiro[chroman-2,4'-piperidin]-4-one hydrochloride (87 mg), and stirred overnight at room temperature. Water was added to the reaction liquid, the formed solid was taken out through filtration, then fully washed with water and ether. The solid was dried under reduced pressure to obtain the title compound. ¹H-NMR (400 MHz, DMSO-$d_6$) δ: 8.41 (1H, d, J=4.0 Hz), 8.23 (11, dd, J=8.0, 4.0 Hz), 8.04 (1H, s), 7.92 (1H, s), 7.32 (1H, d, J=8.0 Hz), 6.68 (2H, s), 4.32-4.18 (1H, m), 4.08 (4H, q, J=8.0 Hz), 3.86 (3H, s), 3.64-3.20 (3H, m), 2.97 (2H, s), 2.10-1.75 (4H, m), 1.37 (6H, t, J=8.0 Hz). MS [M+H]⁺=558.

Example 13

Production of 6-(1-Methylethyl)-1'-{[5-(tetrazol-5-yl)biphenyl-3-yl]carbonyl}spiro[7-azachroman-2,4'-piperidin]-4-one

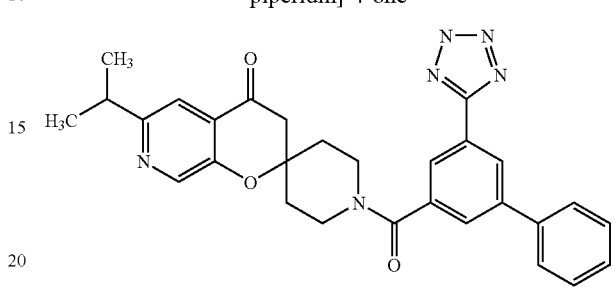

6-(1-Methylethyl)spiro[7-azachroman-2,4'-piperidin]-4-one hydrochloride (94 mg), 1-hydroxybenzotriazole monohydrate (36 mg), 1-(3-dimethylaminopropyl)-3-ethylcarbodiimide hydrochloride (57 mg), triethylamine (73 μL) and water (1 mL) were added in that order to a DMF (3 mL) solution of 5-(tetrazol-5-yl)biphenyl-3-carboxylic acid (50 mg), and stirred at 90° C. for 1 hour and 30 minutes. Water was added to the reaction liquid, the formed precipitate was taken out through filtration, washed with hexane/ethyl acetate=2/1, and dried to obtain the title compound as a white solid. ¹H-NMR (400 MHz, DMSO-$d_6$) δ: 8.50 (1.0H, s), 8.38 (1.0H, s), 8.04 (1.0H, s), 7.87 (1.0H, s), 7.79 (2.0H, d, J=7.6 Hz), 7.54 (2H, t, J=7.6 Hz), 7.45 (1.011, t, J=7.6 Hz), 7.40 (1.0H, s), 4.40-4.22 (1.0H, m), 3.65-3.20 (3.0H, m), 3.01 (1.0H, q, J=6.8 Hz), 2.97 (2.0H, s), 2.15-2.05 (1.0H, m), 1.95-1.78 (3.0H, m), 1.18 (6.0H, d, J=6.8 Hz). MS [M+H]⁺=509.

Example 14

Production of 6-(1-Methyl-1H-pyrazol-4-yl)-1'-{[5-(tetrazol-5-yl)biphenyl-3-yl]carbonyl}spiro[chroman-2,4'-piperidin]-4-one

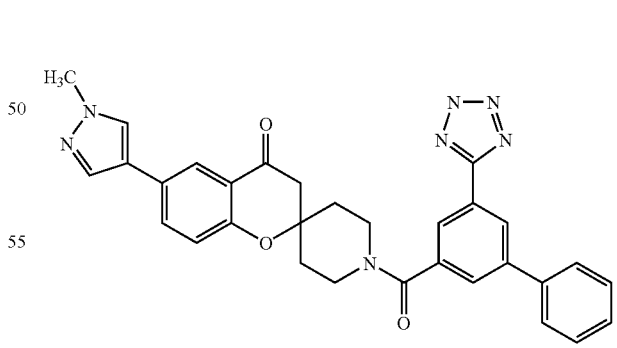

6-(1-Methyl-1H-pyrazol-4-yl)spiro[chroman-2,4'-piperidin]-4-one hydrochloride (93 mg), 1-hydroxybenzotriazole monohydrate (36 mg), 1-(3-dimethyl aminopropyl)-3-ethylcarbodiimide hydrochloride (57 mg), triethylamine (0.73 mL) and water (1 mL) were added in that order to a DMF (3 mL) solution of 5-(tetrazol-5-yl)biphenyl-3-carboxylic acid (50 mg), and stirred at 90° C. for 2 hours and 30 minutes.

Water was added to the reaction liquid, and the formed precipitate was taken out through filtration, washed with hexane/ethyl acetate=3/2, and dried to obtain the title compound as a white solid. $^1$H-NMR (400 MHz, DMSO-d$_6$) δ: 8.36 (1.0H, s), 8.13 (1.0H, s), 8.03 (1.0H, s), 7.85-7.77 (6.0H, m), 7.53 (2.0H, d, J=7.2 Hz), 7.44 (1.0H, t, J=7.2 Hz), 7.10 (1.0H, d, J=8.4 Hz), 4.40-4.22 (1.0H, m), 3.83 (3.0H, s), 3.65-3.20 (3.0H, m), 2.89 (2.0H, s), 2.15-2.05 (1.0H, m), 1.95-1.78 (3.0H, m). MS [M+H]$^+$=546.

Example 15

Production of 1'-{[3-Ethoxy-4-(1-methyl-1H-pyrazol-4-yl)phenyl]carbonyl}-6(tetrazol-5-yl)spiro[chroman-2,4'-piperidin]-4-one

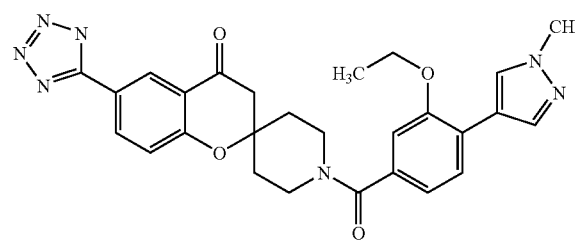

Triethylamine (136 μL, 0.97 mol), 1-hydroxybenzotriazole hydrate (99.0 mg, 0.73 mmol) and 1-(3-dimethylaminopropyl)-3-ethylcarbodiimide hydrochloride (140 mg, 0.73 mol) were added to an N,N-dimethylformamide solution (4.0 mL) of 3-ethoxy-4-(1-methyl-1H-pyrazol-4-yl)benzoic acid (120 mg, 0.49 mmol) and 6-(tetrazol-5-yl)spiro[chroman-2,4'-piperidin]-4-one hydrochloride (204 mg, 0.63 mol), and then stirred at 90° C. for 30 minutes. The reaction liquid was cooled to room temperature, and water was added thereto. The formed solid was taken out through filtration, and dried overnight at 75° C. under reduced pressure to obtain the title compound as a white solid. $^1$H-NMR (400 MHz, DMSO-d$_6$) δ: 8.41 (1H, d, J=2.2 Hz), 8.23 (1H, dd, J=8.5, 2.2 Hz), 8.12 (1H, s), 7.93 (1H, br s), 7.63 (1H, d, J=8.0 Hz), 7.32 (1H, d, J=8.8 Hz), 7.03 (1H, br s), 6.97 (1H, dd, J=7.9, 1.6 Hz), 4.14 (2H, q, J=6.9 Hz), 3.87 (3H, s), 3.31-3.28 (4H, m), 2.97 (2H, s), 1.92-1.79 (4H, m), 1.43 (3H, t, J=7.0 Hz). MS [M+H]$^+$= 514.

Example 16

Production of 6-[(1-Methyl-1H-pyrazol-5-yl)amino]-1'-{[3-(pyrrolidin-1-yl)-5-(tetrazol-5-yl)phenyl]carbonyl}spiro[chroman-2,4'-piperidin]-4-one

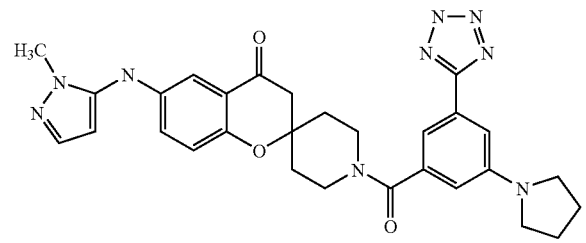

6-[(1-Methyl-1H-pyrazol-5-yl)amino]spiro[chroman-2,4'-piperidin]-4-one hydrochloride (46 mg), 1-hydroxybenzotriazole monohydrate (17 mg), 1-(3-dimethylaminopropyl)-3-ethylcarbodiimide hydrochloride (27 mg), triethylamine (34 μL) and water (660 μL) were added in that order to a DMF (2 mL) solution of 3-(pyrrolidin-1-yl)-5-(tetrazol-5-yl)benzoic acid (27 mg), and stirred at 90° C. for 2 hours and 30 minutes. Water was added to the reaction liquid, and the formed precipitate was taken out through filtration, once dried, then washed with hexane/ethyl acetate=3/2, and taken out through filtration. After dried, the title compound was obtained as a yellow solid. $^1$H-NMR (400 MHz, DMSO-d$_6$) δ: 7.92 (1.0H, s), 7.32 (1.0H, d, J=2.0 Hz), 7.21 (2.0H, s), 7.18-7.13 (2.0H, m), 6.99 (1.0H, d, J=9.2 Hz), 6.67 (1.0H, s), 5.89 (1.0H, s), 4.30-4.22 (1.0H, m), 3.61 (3.0H, s), 3.65-3.20 (3.0H, m), 2.81 (2.0H, s), 2.05-1.85 (9.0H, m), 1.85-1.70 (3.0H, m). MS [M+H]$^+$=554.

Example 17

Production of 5-(4-Oxo-1'-{[5-(tetrazol-5-yl)biphenyl-3-yl]carbonyl}-spiro[chroman-2,4'-piperidin]-6-yl)pyridine-3-carboxamide sodium salt

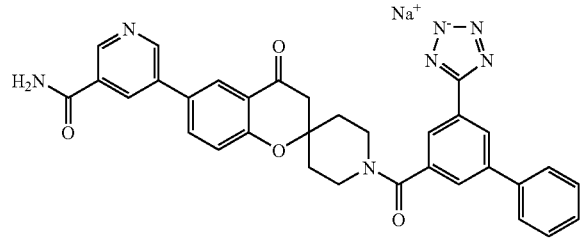

5-(4-Oxospiro[chroman-2,4'-piperidin]-6-yl)pyridine-3-carboxamide dihydrochloride (94 mg), 1-hydroxybenzotriazole monohydrate (36 mg), 1-(3-dimethylaminopropyl)-3-ethylcarbodiimide hydrochloride (57 mg), triethylamine (73 μL) and water (660 μL) were added in that order to a DMF (2 mL) of 5-(tetrazol-5-yl)biphenyl-3-carboxylic acid (50 mg), and stirred at 90° C. for 2 hours. 1-Hydroxybenzotriazole monohydrate (36 mg), 1-(3-dimethylaminopropyl)-3-ethylcarbodiimide hydrochloride (57 mg) and triethylamine (73 μL) were added thereto, and stirred at room temperature for 3 days. The reaction liquid was concentrated, and the residue was purified through high-performance preparative liquid chromatography (0.1% TFA, water/acetonitrile), then water and aqueous 1 N sodium hydroxide solution (380 μL) were added to it, and purified through ODS reversed-phase chromatography (water/methanol) to obtain the title compound as a yellow solid. $^1$H-NMR (400 MHz, DMSO-d$_6$) δ: 9.00 (1.0H, d, J=2.0 Hz), 8.97 (1.0H, d, J=2.0 Hz), 8.47 (1.0H, t, J=2.0 Hz), 8.29 (1.0H, t, J=1.6 Hz), 8.30-8.26 (1.0H, br s), 8.119 (1.0H, d, J=2.5 Hz), 8.05 (1.0H, dd, J=8.8, 2.5 Hz), 7.97 (1.0H, t, J=1.6 Hz), 7.72 (2.0H, d, J=7.2 Hz), 7.63-7.61 (1.0H, br s), 7.54 (1.0H, t, J=1.6 Hz), 7.51 (2.0H, t, J=7.2 Hz), 7.40 (1.0H, t, J=7.2 Hz), 7.29 (1.0H, d, J=8.8 Hz), 4.40-4.28 (1.0H, m), 3.40-3.20 (3.0H, m), 2.97 (2.0H, s), 2.11-1.90 (1.0H, m), 1.90-1.80 (3.0H, m). MS [M+H]$^+$=586.

Example 18

Production of 1'-{[3,5-Diethoxy-4-(1H-pyrazol-4-yl)phenyl]carbonyl}-6-(tetrazol-5-yl)spiro[chroman-2,4'-piperidin]-4-one

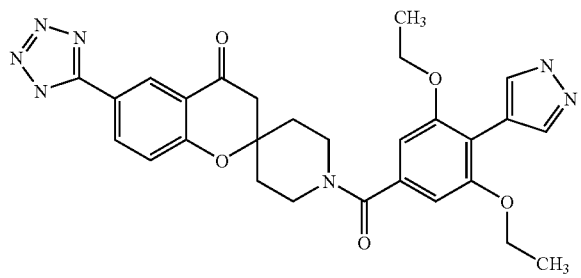

Et3N (83 μL), HOBT (46 mg) and WSC hydrochloride (58 mg) were added to a DMF (4 mL) solution of 3,5-diethoxy-4-(1H-pyrazol-4-yl)benzoic acid (97 mg) and 6-(tetrazol-5-yl)spiro [chroman-2,4'-piperidin]-4-one hydrochloride (70 mg), stirred overnight at room temperature. Water was added to the reaction liquid, the formed solid was taken out through filtration, and the solid was washed with water and ether. The solid was dried under reduced pressure to obtain the title compound. $^1$H-NMR (400 MHz, DMSO-$d_6$) δ: 8.41 (1H, d, J=4.0 Hz), 8.23 (1H, dd, J=8.0, 4.0 Hz), 8.04 (2H, s), 7.32 (1H, d, J=8.0 Hz), 6.68 (2H, s), 4.32-4.18 (1H, m), 4.08 (4H, q, J=8.0 Hz), 3.64-3.20 (3H, m), 2.97 (2H, s), 2.10-1.75 (4H, m), 1.37 (6H, t, J=8.0 Hz). MS [M+H]$^+$=544.

Example 19

Production of 1'-{[3,5-Diethoxy-4-(1H-pyrazol-4-yl)phenyl]carbonyl}-6-(5-oxo-4,5-dihydro-1,2,4-oxadiazol-3-yl)spiro[chroman-2,4'-piperidin]-4-one

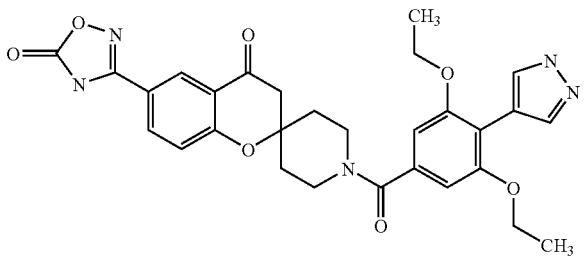

Et3N (83 μL), HOBT (46 mg) and WSC hydrochloride (58 mg) were added to a DMF (4 mL) solution of 3,5-diethoxy-4-(1H-pyrazol-4-yl)benzoic acid (101 mg) and 6-(5-oxo-4,5-dihydro-1,2,4-oxadiazol-3-yl)spiro[chroman-2,4'-piperidin]-4-one hydrochloride (70 mg), and stirred overnight at room temperature. Water was added to the reaction liquid, the formed solid was taken out through filtration, the solid was washed with water and ether. The solid was dried under reduced pressure to obtain the title compound. $^1$H-NMR (400 MHz, DMSO-$d_6$) δ: 12.96 (1H, s), 8.21 (1H, d, J=4.0 Hz), 8.06 (2H, s), 8.00 (11, dd, J=8.0, 4.0 Hz), 7.30 (1H, d, J=8.0 Hz), 6.68 (2H, s), 4.32-4.18 (1H, m), 4.08 (4H, q, J=8.0 Hz), 3.64-3.20 (3H, m), 2.97 (2H, s), 2.10-1.75 (4H, m), 1.37 (6H, t, J=8.0 Hz). MS [M+H]$^+$=560.

Example 20

Production of 1'-{[3,5-Diethoxy-4-(1-methyl-1H-pyrazol-4-yl)phenyl]carbonyl}-6-(5-oxo-4,5-dihydro-1,2,4-oxadiazol-3-yl)spiro[chroman-2,4'-piperidin]-4-one

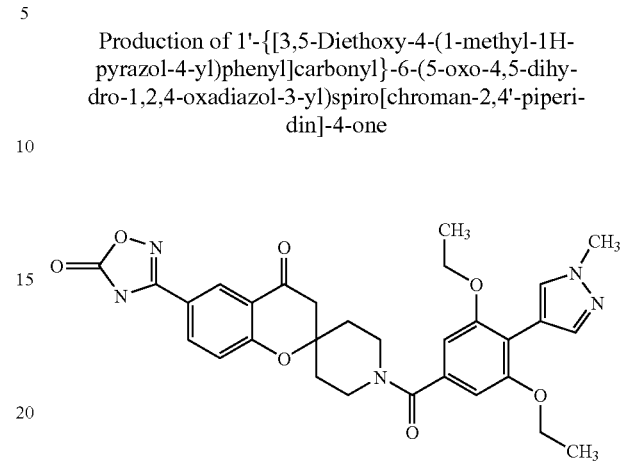

Et3N (58 μL), HOBT (32 mg) and WSC hydrochloride (40 mg) were added to a DMF (4 mL) solution of 3,5-diethoxy-4-(1-methyl-1H-pyrazol-4-yl)benzoic acid (50 mg) and 6-(5-oxo-4,5-dihydro-1,2,4-oxadiazol-3-yl)spiro[chroman-2,4'-piperidin]-4-one hydrochloride (70 mg), and stirred overnight at room temperature. Water was added to the reaction liquid, the formed solid was taken out through filtration, and the solid was fully washed with water and ether. The solid was dried under reduced pressure to obtain the title compound. $^1$H-NMR (400 MHz, DMSO-$d_6$) δ: 12.96 (1H, s), 8.21 (1H, d, J=4.0 Hz), 8.06 (1H, s), 8.00 (1H, dd, J=8.0, 4.0 Hz), 7.92 (1H, s), 7.30 (1H, d, J=8.0 Hz), 6.68 (2H, s), 4.32-4.18 (1H, m), 4.08 (4H, q, J=8.0 Hz), 3.86 (3H, s), 3.64-3.20 (3H, m), 2.97 (2H, s), 2.10-1.75 (4H, m), 1.37 (6H, t, J=8.0 Hz). MS [M+H]$^+$=574.

Example 21

Production of N-Carbamoylmethyl-1'-{[3,5-diethoxy-4-(1-methyl-1H-pyrazol-4-yl)phenyl]carbonyl}-4-oxospiro[chroman-2,4'-piperidine]-6-carboxamide

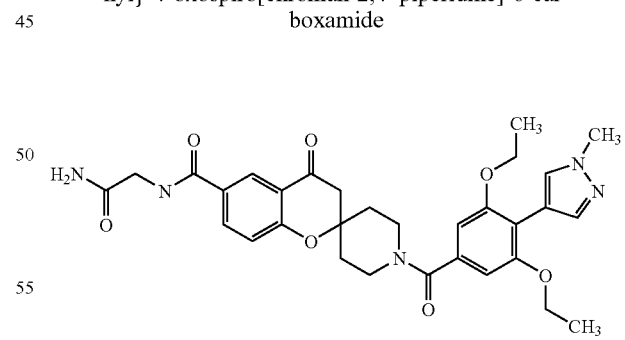

N-Carbamoylmethyl-4-oxospiro[chroman-2,4'-piperidine]-6-carboxamide hydrochloride (354 mg), 3,5-diethoxy-4-(1-methyl-1H-pyrazol-4-yl)benzoic acid (145 mg), WSC hydrochloride (115 mg), HOBT (91.2 mg) and triethylamine (0.209 mL) were suspended in DMF (3 mL), and stirred at 50° C. for 16 hours. Water was added to it, the formed solid was taken out through filtration, and the resulting solid was purified through silica gel column chromatography (chloroform/methanol), and crystallized from chloroform/diethyl ether to obtain the title compound. $^{1}$H-NMR (400 MHz, DMSO-$d_6$) δ: 8.75 (1.0H, t, J=5.6 Hz), 8.35-8.28 (1.0H, m), 8.09 (1.0H, dd, J=8.8, 2.2 Hz), 8.04 (1.0H, s), 7.92 (1.0H, s), 7.35 (1.0H, s), 7.17 (1.0H, d, J=8.8 Hz), 7.00 (1.0H, s), 6.68 (2.0H, s), 4.31-4.02 (1.0H, m), 4.08 (4.0H, q, J=7.0 Hz), 3.86 (3.0H, s), 3.77 (2.0H, d, J=5.9 Hz), 3.64-3.02 (3.0H, m), 2.93 (2.0H, s), 2.10-1.72 (4.0H, m), 1.37 (6.0H, t, J=7.0 Hz). MS [M+H]$^+$=590.

Example 22

Production of 1'-{[3,5-Diethoxy-4-(1-methyl-1H-pyrazol-4-yl)phenyl]carbonyl}-6-(5-oxo-4,5-dihydro-1H-1,2,4-triazol-3-yl)spiro[chroman-2,4'-piperidin]-4-one

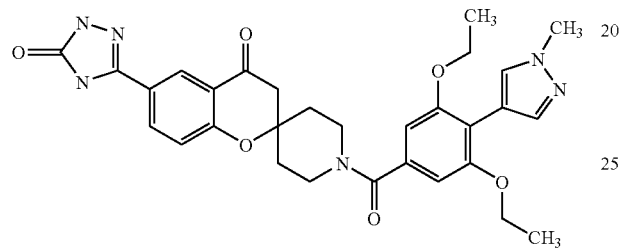

6-(5-Oxo-4,5-dihydro-1H-1,2,4-triazol-3-yl)spiro[chroman-2,4'-piperidin]-4-one hydrochloride (202 mg), 3,5-diethoxy-4-(1-methyl-1H-pyrazol-4-yl)benzoic acid (145 mg), EDCI (115 mg), HOBT (91.2 mg) and triethylamine (0.209 mL) were suspended in DMF (3 mL), and stirred at 50° C. for 16 hours. Water was added to it, the formed solid was taken out through filtration, and the resulting solid was recrystallized from methanol to obtain the title compound. $^{1}$H-NMR (400 MHz, DMSO-$d_6$) δ: 8.08-8.04 (2.0H, m), 8.00 (1.0H, dd, J=8.8, 2.2 Hz), 7.93-7.91 (1.0H, m), 7.25 (1.0H, d, J=8.5 Hz), 7.22 (2.0H, br s), 6.68 (2.0H, s), 4.37-4.13 (1.0H, m), 4.08 (4.0H, q, J=6.8 Hz), 3.86 (3.0H, s), 3.66-3.13 (3.0H, m), 2.95 (2.0H, s), 2.14-1.69 (4.0H, m), 1.37 (6.0H, t, J=7.0 Hz). MS [M+H]$^+$=573.

Example 23

Production of 1'-{[3,5-Diethoxy-4-isoxazol-4-ylphenyl]carbonyl}-6-(tetrazol-5-yl)spiro[chroman-2,4'-piperidin]-4-one

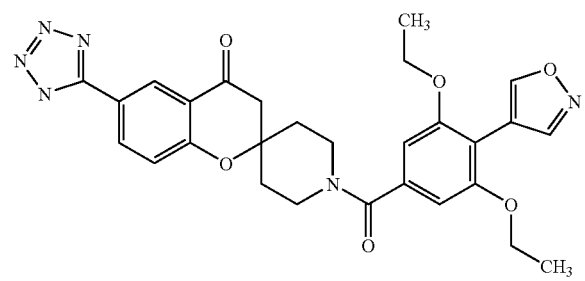

Et3N (104 μL), HOBT (57 mg) and WSC hydrochloride (71 mg) were added to a DMF (4 mL) solution of 3,5-diethoxy-4-isoxazol-4-yl-benzoic acid (86 mg) and 6-(tetrazol-5-yl)spiro[chroman-2,4'-piperidin]-4-one hydrochloride (119 mg), and stirred overnight at room temperature. Water was added to the reaction liquid, the formed solid was taken out through filtration, and washed with water and ether. The resulting solid was purified through high-performance preparative liquid chromatography (0.1% TFA, water/acetonitrile) to obtain the title compound. $^{1}$H-NMR (400 MHz, DMSO-$d_6$) δ: 9.18 (1H, s), 8.96 (1H, s), 8.42 (1H, d, J=4.0 Hz), 8.21 (1H, dd, J=8.0, 4.0 Hz), 7.33 (1H, d, J=8.0 Hz), 6.74 (2H, s), 4.32-4.18 (1H, m), 4.08 (4H, q, J=8.0 Hz), 3.64-3.20 (3H, m), 2.97 (2H, s), 2.10-1.75 (4H, m), 1.37 (6H, t, J=8.0 Hz). MS [M+H]$^+$=545.

Example 24

Production of 5-(1'-{[2,6-Dimethoxybiphenyl-4-yl]carbonyl}-4-oxospiro[chroman-2,4'-piperidin]-6-yl)pyridine-3-carboxylic acid

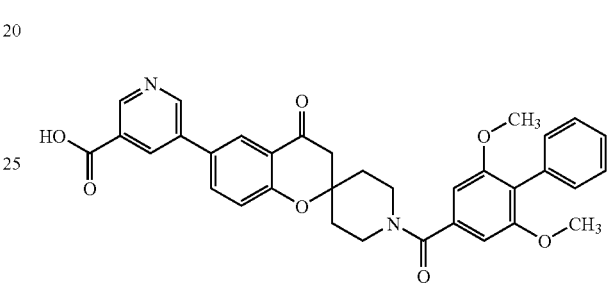

Carbonyldiimidazole (81 mg) was added to a DMF solution (2 mL) of 2,6-dimethoxybiphenyl-4-carboxylic acid (129 mg), and stirred at 60° C. for 2.5 hours. To the reaction liquid, added were 5-(4-oxospiro[chroman-2,4'-piperidin]-6-yl)pyridine-3-carboxylic acid dihydrochloride (246 mg) and triethylamine (209 ml), and stirred at that temperature for 17 hours. 1 N hydrochloric acid and water were added to the reaction liquid, and the resulting solid was purified through high-performance preparative liquid chromatography (0.1% TFA, water/acetonitrile). Then, this was further purified through silica gel thin-layer chromatography (chloroform/methanol) to obtain the title compound. $^{1}$H-NMR (400 MHz, DMSO-$d_6$) δ: 9.06 (1.0H, d, J=2.4 Hz), 9.02 (1.0H, d, J=2.0 Hz), 8.41 (1.0H, dd, J=2.4, 2.0 Hz), 8.12-8.01 (2.0H, m), 7.38-7.32 (2.0H, m), 7.29-7.24 (2.0H, m), 7.23-7.19 (2.0H, m), 6.75 (2.0H, s), 4.36-4.22 (1.0H, br m), 3.69-3.12 (3.0H, m), 3.68 (6.0H, s), 2.95 (2.0H, s), 2.15-1.93 (2.0H, m), 1.91-1.75 (2.0H, m). MS [M+H]$^+$=579.

Example 25

Production of 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid

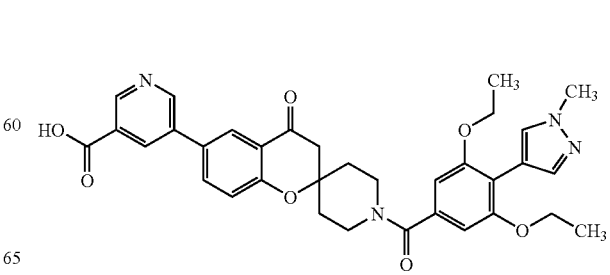

Carbonyldiimidazole (130 mg) and triethylamine (0.446 mL) were added to a DMF solution (4 mL) of 3,5-diethoxy-4-(1-methyl-1H-pyrazol-4-yl)benzoic acid (232 mg), and stirred at 70° C. for 2 hours. To the reaction liquid, added was a DMF suspension (2 ml) of 5-(4-oxospiro[chroman-2,4'-piperidin]-6-yl)pyridine-3-carboxylic acid dihydrochloride (370 mg) and triethylamine (0.335 ml) that had been prepared separately, and further stirred at that temperature for 1 hour. 1 N hydrochloric acid and water were added to the reaction liquid, the resulting solid was taken out through filtration, and recrystallized from methanol to obtain the title compound.

$^1$H-NMR (400 MHz, DMSO-d$_6$) δ: 9.02 (1.0H, d, J=2.2 Hz), 9.00 (1.0H, d, J=1.7 Hz), 8.40-8.38 (1.0H, m), 8.29 (1.0H, s), 8.06-8.01 (2.0H, m), 7.93-7.91 (1.0H, m), 7.25 (1.0H, dd, J=6.6, 2.7 Hz), 6.68 (2.0H, s), 4.31-4.18 (1.0H, br m), 4.08 (4.0H, q, J=7.0 Hz), 3.86 (3.0H, s), 3.79-3.08 (3.0H, m), 2.94 (2.0H, s), 2.11-1.88 (2.0H, m), 1.85-1.74 (2.0H, m), 1.37 (6.0H, t, J=7.0 Hz). MS [M+H]$^+$=611.

Example 26

Production of 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid sodium salt

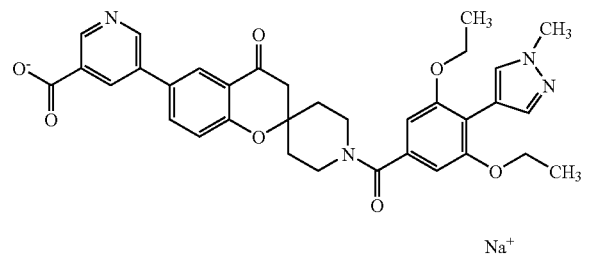

5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid (285 mg) was suspended in water (6 mL), and aqueous 1 N sodium hydroxide solution (0.624 mL) was added to it at room temperature, and stirred for 1 hour. The reaction liquid was purified through ODS reversed-phase chromatography (water/methanol) to obtain the title compound. $^1$H-NMR (400 MHz, DMSO-d$_6$) δ: 8.90-8.87 (1.0H, m), 8.74-8.72 (1.0H, m), 8.28-8.26 (1.0H, m), 8.05 (1.0H, s), 7.99-7.95 (2.0H, m), 7.93-7.92 (1.0H, m), 7.22 (1.0H, d, J=9.3 Hz), 6.69 (2.0H, s), 4.35-4.18 (1.0H, br m), 4.08 (4.0H, q, J=6.8 Hz), 3.86 (3.0H, s), 3.69-3.17 (3.0H, m), 2.93 (2.0H, s), 2.15-1.86 (2.0H, m), 1.85-1.74 (2.0H, m), 1.38 (6.0H, t, J=7.0 Hz). MS [M+Na]$^+$=633.

Example 27

Production of [5-(1'-{[3,5-Diethoxy-4-(1-methyl-1H-pyrazol-4-yl)phenyl]carbonyl}-4-oxospiro[chroman-2,4'-piperidin]-6-yl)-2H-tetrazol-2-yl]methyl 2,2-dimethylpropanoate

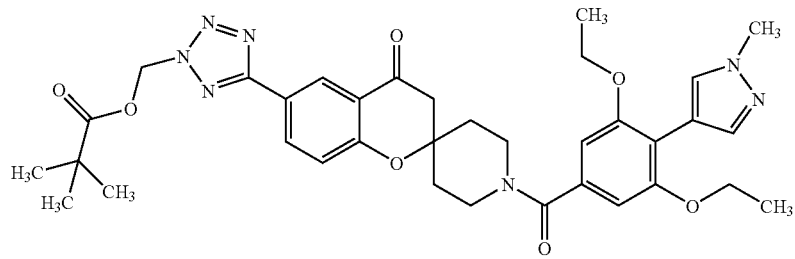

Et3N (223 μL), HOBT (123 mg) and WSC hydrochloride (154 mg) were added to a DMF (8 mL) solution of 3,5-diethoxy-4-(1-methyl-1H-pyrazol-4-yl)benzoic acid (194 mg) and [5-(4-oxospiro[chroman-2,4'-piperidin]-6-yl)-2H-tetrazol-2-yl]methyl 2,2-dimethylpropanoate hydrochloride (349 mg), and stirred overnight at room temperature. The reaction liquid was poured into saturated saline water, extracted with ethyl acetate, and the organic layer was washed with water and saturated saline water. The organic layer was dried with sodium sulfate, filtered, concentrated, and purified through silica gel column chromatography (hexane/EtOAc) to obtain the title compound. $^1$H-NMR (400 MHz, CDCl3) δ: 8.69 (1H, d, J=4.0 Hz), 8.32 (1H, dd, J=8.0, 4.0 Hz), 8.14 (1H, s), 7.97 (1H, s), 7.17 (1H, d, J=8.0 Hz), 6.64 (2H, s), 6.50 (2H, s), 4.32-4.18 (1H, m), 4.08 (4H, q, J=8.0 Hz), 3.94 (3H, s), 3.64-3.20 (3H, m), 2.97 (2H, s), 2.10-1.75 (4H, m), 1.37 (6H, t, J=8.0 Hz), 1.22 (9H, s). MS [M+H]$^+$=672.

Example 28

Production of Sodium 3-(1'-{[3,5-Diethoxy-4-(1-methyl-1H-pyrazol-4-yl)phenyl]carbonyl}-4-oxospiro[chroman-2,4'-piperidin]-6-yl)benzoate

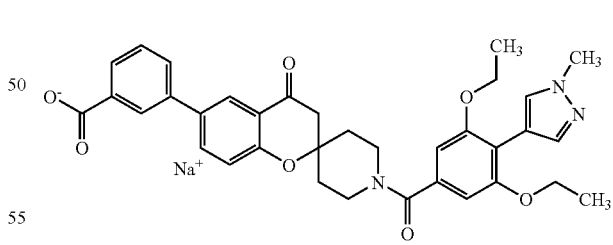

N,N'-carbonyldiimidazole (130 mg) and triethylamine (0.446 mL) were added to a DMF solution (4 mL) of 3,5-diethoxy-4-(1-methyl-1H-pyrazol-4-yl)benzoic acid (232 mg), and stirred at 70° C. for 20 hours. 3-(4-Oxo-spiro[chroman-2,4'-piperidin]-6-yl)benzoic acid hydrochloride (374 mg) was added to the reaction liquid, and further stirred at that temperature for 6 hours. 1 N hydrochloric acid and water were added to the reaction liquid, the formed solid was taken out through filtration, and the resulting solid was purified through silica gel column chromatography (chloroform/methanol) to obtain a carboxylic acid (240 mg). The obtained carboxylic acid was suspended in water (5 mL), and aqueous 1 N sodium hydroxide solution (0.393 mL) was added thereto and stirred at room temperature for 30 minutes. The resulting solution was purified through ODS reversed-phase chromatography (water/methanol) to obtain the title compound. $^1$H-NMR (400 MHz, DMSO-$d_6$) δ: 8.10 (1.0H, s), 8.05 (1.0H, s), 7.96-7.91 (2.0H, m), 7.90 (1.0H, dd, J=8.7, 2.3 Hz), 7.80 (1.0H, t, J=4.3 Hz), 7.55-7.50 (1.0H, m), 7.32 (1.0H, dd, J=7.8, 7.8 Hz), 7.18 (1.0H, d, J=8.5 Hz), 6.69 (2.0H, s), 4.38-4.16 (1.0H, m), 4.09 (4.0H, q, J=6.9 Hz), 3.86 (3.0H, s), 3.68-3.13 (3.0H, m), 2.92 (2.0H, s), 2.13-1.89 (2.0H, br m), 1.85-1.72 (2.0H, m), 1.38 (6.0H, t, J=6.9 Hz). MS [M+H]$^+$=632.

Example 29

Production of 1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one

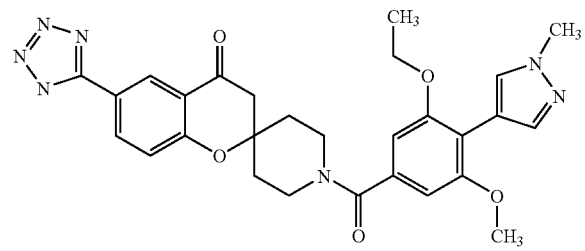

Et3N (170 μL), HOBT (94 mg) and WSC hydrochloride (118 mg) were added to a DMF (4 mL) solution of [3-ethoxy-5-methoxy-4-(1-methyl-1H-pyrazol-4-yl)]benzoic acid (141 mg) and 6-(tetrazol-5-yl)spiro[chroman-2,4'-piperidin]-4-one hydrochloride (196 mg), and stirred overnight at room temperature. Water was added to the reaction liquid, the formed solid was taken out through filtration, and the solid was washed with water and ether. The solid was dried under reduced pressure to obtain the title compound. $^1$H-NMR (400 MHz, DMSO-$d_6$) δ: 8.41 (1H, d, J=4.0 Hz), 8.23 (1H, dd, J=8.0, 4.0 Hz), 8.04 (1H, s), 7.88 (1H, s), 7.30 (1H, d, J=12.0 Hz), 6.70 (2H, s), 4.32-4.18 (1H, m), 4.08 (2H, q, J=8.0 Hz), 3.85 (3H, s), 3.83 (3H, s), 3.64-3.20 (3H, m), 2.97 (2H, s), 2.10-1.75 (4H, m), 1.37 (3H, t, J=8.0 Hz). MS [M+H]$^+$=544.

Example 30

Production of 1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one sodium salt

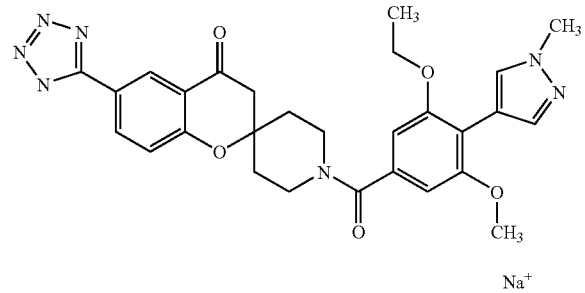

1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one (257 mg) was suspended in water, then 1 N sodium hydroxide (473 μL) was added thereto to dissolve it, and this was purified through ODS reversed-phase chromatography (water/methanol) to obtain the title compound. $^1$H-NMR (400 MHz, DMSO-$d_6$) δ: 8.30 (1H, d, J=4.0 Hz), 8.16 (1H, dd, J=8.0, 4.0 Hz), 8.04 (1H, s), 7.88 (1H, s), 7.10 (1H, d, J=12.0 Hz), 6.71 (2H, s), 4.32-4.18 (1H, m), 4.08 (2H, q, J=8.0 Hz), 3.85 (3H, s), 3.83 (3H, s), 3.64-3.20 (3H, m), 2.89 (2H, s), 2.10-1.75 (4H, m), 1.37 (3H, t, J=8.0 Hz). MS [M+H]$^+$=544.

Example 31

Production of 1'-{[3,5-Diethoxy-4-(6-fluoropyridin-3-yl)phenyl]carbonyl}-6-(tetrazol-5-yl)spiro[chroman-2,4'-piperidin]-4-one

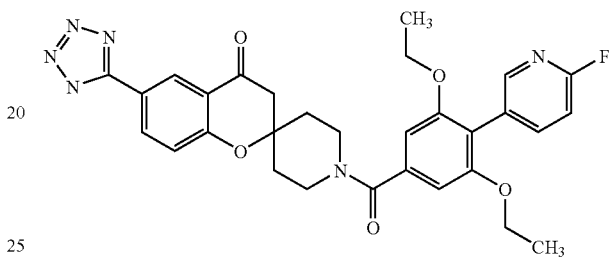

Et3N (200 μL), HOBT (110 mg) and WSC hydrochloride (138 mg) were added to a DMF (4 mL) solution of 3,5-diethoxy-4-(6-fluoropyridin-3-yl)benzoic acid (186 mg) and 6-(tetrazol-5-yl)spiro[chroman-2,4'-piperidin]-4-one hydrochloride (231 mg), and stirred overnight at room temperature. Water was added to the reaction liquid, the formed solid was taken out through filtration, and the solid was washed with water and ether. The solid was dried under reduced pressure to obtain the title compound. $^1$H-NMR (400 MHz, DMSO-$d_6$) δ: 8.42 (1H, d, J=4.0 Hz), 8.24 (1H, dd, J=8.0, 4.0 Hz), 8.13 (1H, s), 7.89 (1H, dt, J=8.0, 4.0 Hz), 7.32 (1H, d, J=8.0 Hz), 7.18 (1H, dd, J=8.0, 4.0 Hz), 6.75 (2H, s), 4.32-4.18 (1H, m), 4.08 (4H, q, J=8.0 Hz), 3.64-3.20 (3H, m), 2.98 (2H, s), 2.10-1.75 (4H, m), 1.17 (6H, t, J=8.0 Hz). MS [M+H]$^+$=573.

Example 32

Production of 1'-{[3,5-Diethoxy-4-(2-fluoropyridin-4-yl)phenyl]carbonyl}-6-(tetrazol-5-yl)spiro[chroman-2,4'-piperidin]-4-one

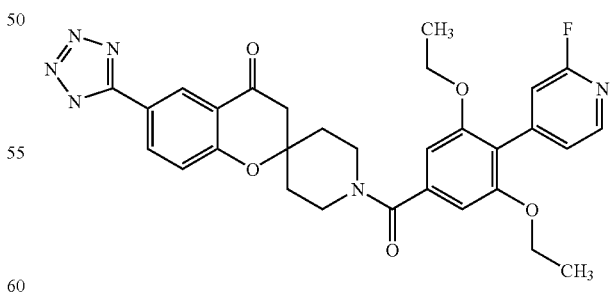

Et3N (290 μL), HOBT (160 mg) and WSC hydrochloride (200 mg) were added to a DMF (8 mL) solution of 3,5-diethoxy-4-(2-fluoropyridin-4-yl)benzoic acid (266 mg) and 6-(tetrazol-5-yl)spiro[chroman-2,4'-piperidin]-4-one hydrochloride (325 mg), and stirred overnight at room temperature. Water was added to the reaction liquid, the formed solid was taken out through filtration, and the solid was washed with water and ether. The solid was dried under reduced pressure to obtain the title compound. $^1$H-NMR (400 MHz, DMSO-$d_6$) δ: 8.42 (1H, d, J=4.0 Hz), 8.25-8.20 (2H, m), 7.32 (1H, d, J=8.0 Hz), 7.29-7.26 (1H, m), 7.10 (1H, s), 6.76 (2H, s), 4.32-4.18 (1H, m), 4.08 (4H, q, J=8.0 Hz), 3.64-3.20 (3H, m), 2.98 (2H, s), 2.10-1.75 (4H, m), 1.17 (6H, t, J=8.0 Hz). MS [M+H]$^+$=573.

Example 33

Production of 1'-{[4-(2-Methyl-1,3-oxazol-5-yl)-3,5-dimethoxyphenyl]carbonyl}-6-(tetrazol-5-yl)spiro[chroman-2,4'-piperidin]-4-one

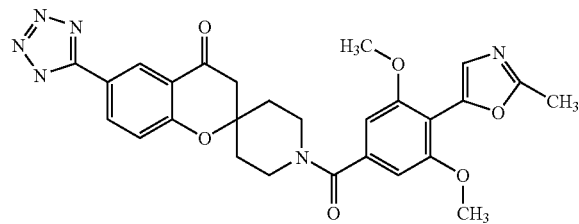

Et3N (28 μL), HOBT (15 mg) and WSC hydrochloride (19 mg) were added to a DMF (3 mL) solution of 4-(2-methyl-1,3-oxazol-5-yl)-3,5-dimethoxybenzoic acid (22 mg) and 6-(tetrazol-5-yl)spiro[chroman-2,4'-piperidin]-4-one hydrochloride (32 mg), and stirred overnight at room temperature. Water was added to the reaction liquid, the formed solid was taken out through filtration, and the solid was washed with water and ether. The solid was dried under reduced pressure to obtain the title compound. $^1$H-NMR (400 MHz, DMSO-$d_6$) δ: 8.42 (1H, d, J=4.0 Hz), 8.23 (1H, dd, J=8.0, 4.0 Hz), 7.32 (1H, d, J=8.0 Hz), 7.08 (1H, s), 6.75 (2H, s), 4.32-4.18 (1H, m), 3.79 (6H, s), 3.64-3.20 (3H, m), 2.97 (2H, s), 2.41 (3H, s), 2.10-1.75 (4H, m). MS [M+H]$^+$=531.

Example 34

Production of Sodium 5-(1'-{[3,5-diethoxy-4-(6-fluoropyridin-3-yl)phenyl]carbonyl}-4-oxo-spiro[chroman-2,4'-piperidin]-6-yl)pyridine-3-carboxylate

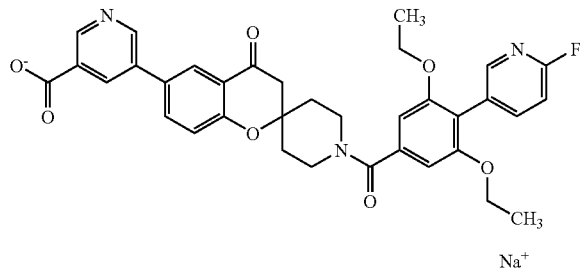

Et3N (1.42 mL), HOBT (551 mg) and WSC hydrochloride (691 mg) were added to a DMF (15 mL) solution of 3,5-diethoxy-4-(6-fluoropyridin-3-yl)benzoic acid (930 mg) and methyl 5-(4-oxospiro[chroman-2,4'-piperidin]-6-yl)pyridine-3-carboxylate dihydrochloride (1520 mg), and stirred overnight at room temperature. The reaction liquid was added to saturated saline water, extracted with ethyl acetate, and the extract was washed with water and saturated saline water. The organic layer was dried with sodium sulfate, filtered, concentrated, and the residue was purified through silica gel column chromatography (chloroform/methanol). The resulting amide was dissolved in a mixed solvent of methanol and THF, and aqueous 1 M NaOH solution (3 mL) was added to it, and stirred overnight at room temperature. The reaction liquid was concentrated under reduced pressure, and the residue was purified through ODS reversed-phase chromatography (water/methanol) to obtain the title compound. $^1$H-NMR (400 MHz, DMSO-$d_6$) δ: 8.90 (1H, s), 8.74 (1H, s), 8.29 (1H, s), 8.14 (1H, s), 8.00-7.95 (2H, m), 7.94-7.87 (1H, m), 7.23 (1H, d, J=8.0 Hz), 7.18 (1H, d, J=8.0 Hz), 6.75 (2H, s), 4.32-4.18 (1H, m), 4.08 (4H, q, J=8.0 Hz), 3.64-3.20 (3H, m), 2.94 (2H, s), 2.10-1.75 (4H, m), 1.17 (6H, t, J=8.0 Hz). MS [M+H]$^+$=626.

Example 35

Production of Sodium 5-(1'-{[3,5-Diethoxy-4-(1-methyl-1H-pyrazol-4-yl)phenyl]carbonyl}-4-oxospiro[chroman-2,4'-piperidin]-6-yl)pyridine-2-carboxylate

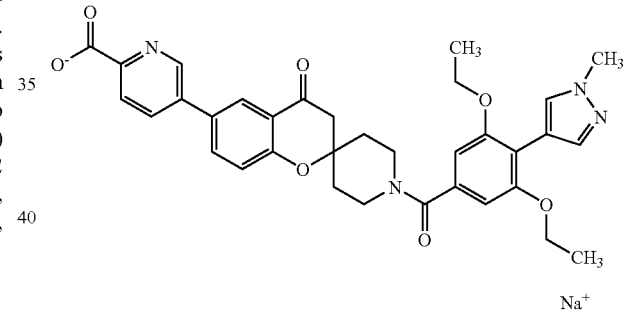

Et3N (108 μL), HOBT (74 mg) and WSC hydrochloride (93 mg) were added to a DMF (3 mL) solution of 3,5-diethoxy-4-(1-methyl-1H-pyrazol-4-yl)benzoic acid (94 mg) and methyl 5-(4-oxospiro[chroman-2,4'-piperidin]-6-yl)pyridine-2-carboxylate dihydrochloride (150 mg), and stirred overnight at room temperature. Water was added to the reaction liquid, the formed solid was taken out through filtration, and dried under reduced pressure. The resulting solid was purified through silica gel column chromatography (chloroform/methanol). The resulting amide was dissolved in a mixed solvent of methanol and THF, and aqueous 1 M NaOH solution (570 μL) was added to it, and stirred overnight at 50° C. The reaction liquid was concentrated under reduced pressure, and the residue was purified through ODS reversed-phase chromatography (water/methanol) to obtain the title compound. $^1$H-NMR (400 MHz, DMSO-$d_6$) δ: 8.69 (1H, d, J=4.0 Hz), 8.05 (1H, s), 8.00-7.90 (5H, m), 7.23 (1H, d, J=8.0 Hz), 6.69 (2H, s), 4.32-4.18 (1H, m), 4.08 (4H, q, J=8.0 Hz), 3.86 (3H, s), 3.64-3.20 (3H, m), 2.94 (2H, s), 2.10-1.75 (4H, m), 1.37 (6H, t, J=8.0 Hz). MS [M+H]$^+$=611.

Example 36

Production of Sodium 2-(1'-{[3,5-diethoxy-4-(1-methyl-1H-pyrazol-4-yl)phenyl]carbonyl}-4-oxospiro[chroman-2,4'-piperidin]-6-yl)pyridine-4-carboxylate

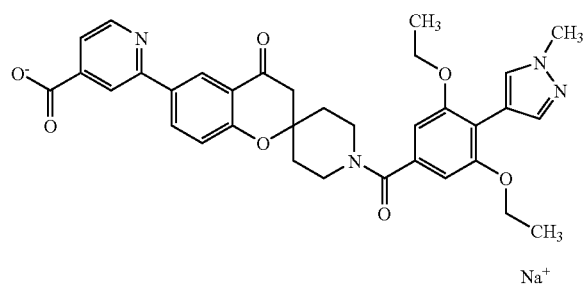

Et₃N (142 µL), HOBT (98 mg) and WSC hydrochloride (122 mg) were added to a DMF (3 mL) solution of 3,5-diethoxy-4-(1-methyl-1H-pyrazol-4-yl)benzoic acid (124 mg), methyl 2-(4-oxospiro[chroman-2,4'-piperidin]-6-yl)pyridine-4-carboxylate dihydrochloride (200 mg), and stirred overnight at room temperature. Water was added to the reaction liquid, the formed solid was taken out through filtration, and dried under reduced pressure. The resulting solid was purified through silica gel column chromatography (chloroform/methanol). The resulting amide was dissolved in a mixed solvent of methanol and THF, and aqueous 1 M NaOH solution (540 µL) was added to it, and stirred overnight at 50° C. The reaction liquid was concentrated under reduced pressure, and the residue was purified through ODS reversed-phase chromatography (water/methanol) to obtain the title compound. ¹H-NMR (400 MHz, DMSO-d₆) δ: 8.53 (1H, d, J=8.0 Hz), 8.40 (1H, d, J=4.0 Hz), 8.30 (1H, dd, J=8.0, 4.0 Hz), 8.14 (1H, s), 8.05 (1H, s), 7.92 (1H, s), 7.59 (1H, dd, J=8.0, 4.0 Hz), 7.20 (1H, d, J=8.0 Hz), 6.69 (2H, s), 4.32-4.18 (1H, m), 4.08 (4H, q, J=8.0 Hz), 3.86 (3H, s), 3.64-3.20 (3H, m), 2.94 (2H, s), 2.10-1.75 (4H, m), 1.37 (6H, t, J=8.0 Hz). MS [M+H]⁺=611.

Example 37

Production of 4-(1'-{[3,5-Diethoxy-4-(1-methyl-1H-pyrazol-4-yl)phenyl]carbonyl}-4-oxospiro[chroman-2,4'-piperidin]-6-yl)pyridine-2-carboxylic acid

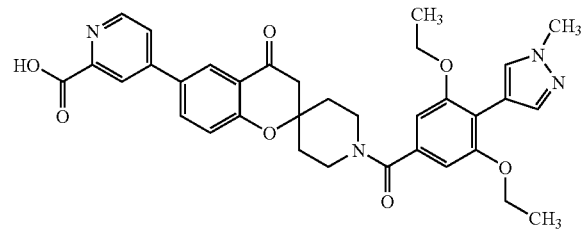

Et3N (142 µL), HOBT (98 mg) and WSC hydrochloride (122 mg) were added to a DMF (3 mL) solution of 3,5-diethoxy-4-(1-methyl-1H-pyrazol-4-yl)benzoic acid (124 mg) and methyl 4-(4-oxospiro[chroman-2,4'-piperidin]-6-yl)pyridine-2-carboxylate dihydrochloride (200 mg), and stirred overnight at room temperature. Water was added to the reaction liquid, the formed solid was taken out through filtration, and dried under reduced pressure. The resulting solid was purified through silica gel column chromatography (chloroform/methanol) to obtain an amide (237 mg). The amide was dissolved in a mixed solvent of methanol and THF, and aqueous 1 M NaOH solution (570 µL) was added to it, and stirred overnight at 50° C. The reaction liquid was concentrated under reduced pressure, and the residue was purified through ODS reversed-phase chromatography (water/methanol) to obtain the title compound. ¹H-NMR (400 MHz, DMSO-d₆) δ: 8.71 (1H, d, J=4.0 Hz), 8.24 (1H, s), 8.14-8.11 (2H, m), 8.05 (1H, s), 7.94 (1H, dd, J=8.0, 4.0 Hz), 7.92 (1H, s), 7.27 (1H, d, J=8.0 Hz), 6.68 (2H, s), 4.32-4.18 (1H, m), 4.08 (4H, q, J=8.0 Hz), 3.86 (3H, s), 3.64-3.20 (3H, m), 2.94 (2H, s), 2.10-1.75 (4H, m), 1.17 (6H, t, J=8.0 Hz). MS [M+H]⁺=611.

Example 38

Production of 1'-{[1-(1-Methylethyl)-6-phenyl-1H-pyrazolo[3,4-b]pyridin-4-yl]carbonyl}-6-(tetrazol-5-yl)spiro[chroman-2,4'-piperidin]-4-one

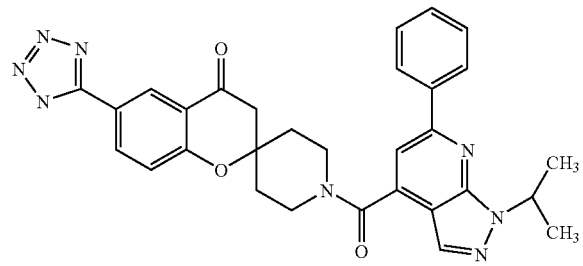

TEA (0.2 mL) was added to a DMF suspension (2 mL) of 1-(1-methylethyl)-6-phenyl-1H-pyrazolo[3,4-b]pyridine-4-carboxylic acid, 6-(tetrazol-5-yl)spiro[chroman-2,4'-piperidin]-4-one hydrochloride, EDCI and HOBT.H₂O, heated at 80° C. and stirred for 2 hours. This was cooled to room temperature, iced water was added thereto, and its pH was adjusted to 2.5 with 1 N HCl solution added thereto. The resulting crystal was taken out through filtration, washed with water, washed with Et2O, and dried in vacuum at 70° C. to obtain the title compound as a pale brown powder. ¹H-NMR (400 MHz, DMSO-d₆) δ: 8.34 (1H, d, J=2.2 Hz), 8.26-8.21 (2H, m), 8.19 (1H, s), 8.19 (1H, dd, J=8.4, 2.6 Hz), 7.82 (1H, s), 7.58-7.47 (3H, m), 7.20 (1H, d, J=8.4 Hz), 5.33 (1H, sept, J=6.8 Hz), 4.45-4.30 (1H, m), 3.70-3.00 (3H, m), 2.95 (2H, s), 2.20-1.70 (4H, m), 1.55 (6H, d, J=6.8 Hz). MS [M+H]⁺=549.

Example 39

Production of 1'-[(1,3-Diphenyl-1H-thieno[2,3-c]pyrazol-5-yl)carbonyl]-6-(tetrazol-5-yl)spiro[chroman-2,4'-piperidin]-4-one

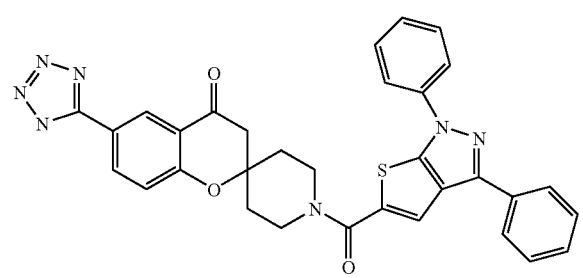

In the same manner as in Example 38, the title compound was obtained as a pale yellow powder from 6-(tetrazol-5-yl)

spiro[chroman-2,4'-piperidin]-4-one hydrochloride and 1,3-diphenyl-1H-thieno[2,3-c]pyrazole-5-carboxylic acid. ¹H-NMR (400 MHz, DMSO-d₆) δ: 8.33 (1H, d, J=2.2 Hz), 8.18 (1H, dd, J=8.2, 2.2 Hz), 8.13-8.09 (2H, m), 7.97 (1H, s), 7.89-7.85 (2H, m), 7.67-7.61 (2H, m), 7.53 (2H, t, J=7.8 Hz), 7.48-7.36 (2H, m), 7.14 (1H, d, J=8.5 Hz), 4.30-4.21 (2H, br m), 3.46 (2H, br s), 2.92 (2H, s), 2.12-2.04 (2H, br m), 1.91-1.80 (2H, m).
MS [M+H]⁺=588.

Example 40

Production of 1'-{[1-Cyclopropyl-4-(tetrazol-5-yl)-1H-indol-6-yl]carbonyl}-6-[(1-methyl-1H-pyrazol-5-yl)amino]spiro[chroman-2,4'-piperidin]-4-one

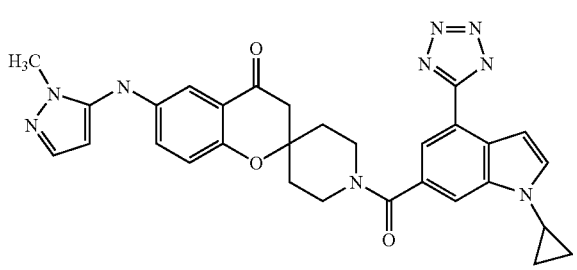

Triethylamine and water (1.5 mL) were added to a DMF (6 mL) solution of 1-cyclopropyl-4-(tetrazol-5-yl)-1H-indole-6-carboxylic acid (348 mg), 6-[(1-methyl-1H-pyrazol-5-yl)amino]spiro[chroman-2,4'-piperidin)]one hydrochloride, WSC hydrochloride and HOBT, and stirred at 90° C. for 30 minutes. Water was added to it at room temperature to obtain a white precipitate. This was dried under reduced pressure, washed with a mixed solvent of methanol and diethyl ether, and again dried under reduced pressure to obtain the title compound as a colorless solid. ¹H-NMR (400 MHz, DMSO-d₆) δ: 7.92 (1H, s), 7.83 (2H, d, J=3.2 Hz), 7.64 (1H, d, J=3.2 Hz), 7.32 (1H, d, J=1.7 Hz), 7.17-7.12 (3H, m), 7.00 (1H, d, J=9.0 Hz), 5.90 (1H, d, J=1.7 Hz), 4.45-4.05 (1H, br m), 3.60 (3H, s), 3.60-3.53 (1H, m), 3.47-3.21 (3H, br m), 2.83 (2H, s), 2.14-1.70 (4H, br m), 1.14-0.98 (4H, m). MS [M+H]⁺=564.

Example 41

Production of 1'-{[1-Cyclopropyl-4-(tetrazol-5-yl)-1H-indol-6-yl]carbonyl}-6-(1-methylethyl)spiro[7-azachroman-2,4'-piperidin]-4-one

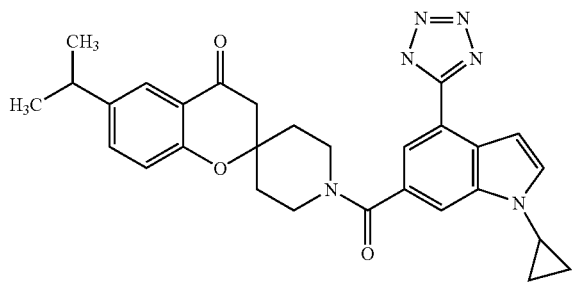

In the same manner as in Example 40, the title compound was obtained as a colorless solid from 6-(1-methylethyl)spiro [7-azachroman-2,4'-piperidin]-4-one dihydrochloride (166 mg) and 1-cyclopropyl-4-(tetrazol-5-yl)-1H-indole-6-carboxylic acid corresponding thereto. ¹H-NMR (400 MHz, DMSO-d₆) δ: 8.51 (1H, s), 7.83 (2H, s), 7.64 (1H, d, J=3.2 Hz), 7.41 (1H, s), 7.13 (1H, d, J=3.2 Hz), 4.41-4.13 (1H, br m), 3.82-3.19 (4H, br m), 3.07-3.00 (1H, m), 2.99 (2H, s), 2.10-1.71 (4H, br m), 1.20 (6H, d, J=7.1 Hz), 1.14-0.98 (4H, m). MS [M+H]⁺=512.

Example 42

Production of 1'-{[1-Cyclopropyl-4-(tetrazol-5-yl)-1H-indol-6-yl]carbonyl}-6-(1-methyl-1H-pyrazol-4-yl)spiro[chroman-2,4'-piperidin]-4-one

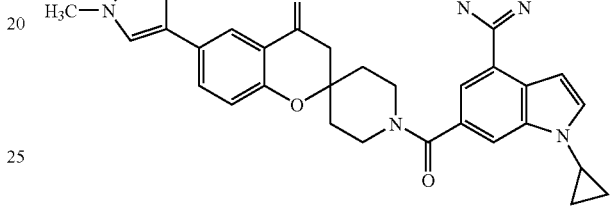

In the same manner as in Example 40, the title compound was obtained as a colorless solid from 6-(1-methyl-1H-pyrazol-4-yl)spiro[chroman-2,4'-piperidin]-4-one hydrochloride (166 mg) and 1-cyclopropyl-4-(tetrazol-5-yl)-1H-indole-6-carboxylic acid corresponding thereto. ¹H-NMR (400 MHz, DMSO-d₆) δ: 8.12 (1H, s), 7.85-7.76 (5H, m), 7.60 (1H, d, J=3.2 Hz), 7.16 (1H, d, J=3.2 Hz), 7.12 (1H, d, J=8.5 Hz), 4.34-4.17 (1H, br m), 3.83 (3H, s), 3.58-3.52 (1H, m), 3.58-3.18 (3H, br m), 2.91 (2H, s), 2.11-1.73 (4H, br m), 1.14-0.97 (4H, m). MS [M+H]⁺=549.

Example 43

Production of 1'-[(3-Cyclopropyl-1-pyridin-2-yl-1H-thieno[2,3-c]pyrazol-5-yl)carbonyl]-6-(tetrazol-5-yl) spiro[chroman-2,4'-piperidin]-4-one

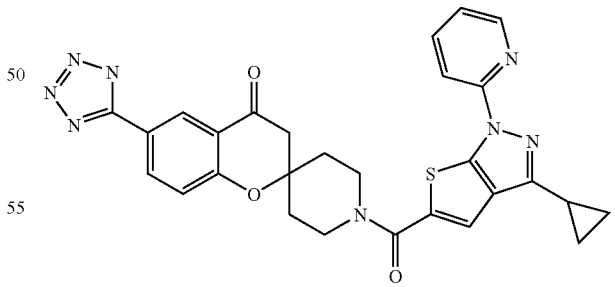

DMF (5 mL) and TEA (0.2 mL) were added to 3-cyclopropyl-1-pyridin-2-yl-1H-thieno[2,3-c]pyrazole-5-carboxylic acid (143 mg), 6-(tetrazol-5-yl)spiro[chroman-2,4'-piperidin]-4-one hydrochloride (177 mg), EDCI (119 mg) and HOBT (90 mg), heated at 80° C. and stirred for 2 hours. This was cooled to room temperature, iced water was added to it, and its pH was adjusted at 2.5 with 1 N HCl added thereto. The formed crystal was taken out through filtration, washed with water, washed with Et2O and dried in vacuum at 70° C. to obtain the title compound as a pale brown powder. ¹H-NMR (400 MHz, DMSO-d₆) δ: 8.54-8.51 (1H, br m), 8.43 (1H, d, J=2.2 Hz), 8.25 (1H, dd, J=8.3, 2.2 Hz), 8.03-7.97 (1H, m), 7.88 (1H, d, J=8.3 Hz), 7.51 (1H, s), 7.36-7.27 (2H, m), 4.24-4.14 (2H, br m), 3.4-3.6 (2H, br m), 3.00 (2H, s), 2.31-2.22 (1H, m), 2.10-2.02 (2H, br m), 1.93-1.81 (2H, br m), 1.11-1.04 (4H, m). MS [M+H]⁺=553.

Example 44

Production of 1'-{[1-Cyclopropyl-4-(tetrazol-5-yl)-1H-indol-6-yl]carbonyl}-6-[6-(methyloxy)pyridin-3-yl]spiro[chroman-2,4'-piperidin]-4-one

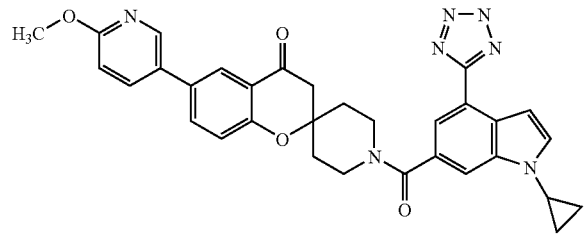

6-[6-(Methyloxy)pyridin-3-yl]spiro[chroman-2,4'-piperidin]-4-one dihydrochloride (238 mg), 1-cyclopropyl-4-(tetrazol-5-yl)-1H-indole-6-carboxylic acid (135 mg), EDCI (115 mg), HOBT (91.2 mg) and triethylamine (0.209 ml) were suspended in DMF (3 ml), and stirred at 50° C. for 16 hours. 1N hydrochloric acid and water were added to the reaction liquid, the formed solid was taken out through filtration, and the resulting solid was recrystallized from methanol to obtain the title compound. ¹H-NMR (400 MHz, DMSO-d₆) δ: 8.43 (1.0H, d, J=2.7 Hz), 7.98 (1.0H, dd, J=8.7, 2.7 Hz), 7.93-7.88 (2.0H, m), 7.87-7.83 (2.0H, m), 7.65 (1.0H, d, J=3.2 Hz), 7.21 (1.0H, d, J=8.3 Hz), 7.12 (1.0H, d, J=3.2 Hz), 6.88 (1.0H, d, J=8.3 Hz), 4.50-3.97 (1.0H, m), 3.88 (3.0H, s), 3.80-3.17 (4.0H, m), 2.94 (2.0H, s), 2.17-1.91 (2.0H, br m), 1.89-1.77 (2.0H, m), 1.16-1.09 (2.0H, m), 1.04-0.99 (2.0H, m). MS [M+H]⁺=576.

Example 45

Production of 1'-{[1-Cyclopropyl-4-(tetrazol-5-yl)-1H-indol-6-yl]carbonyl}-6-(6-oxo-1,6-dihydropyridin-3-yl)spiro[chroman-2,4'-piperidin]-4-one

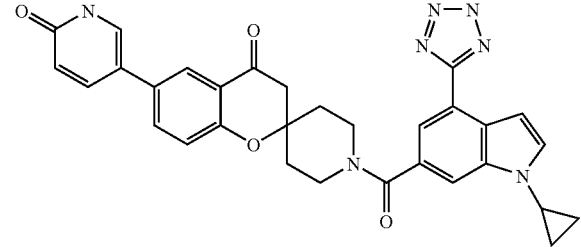

6-(6-Oxo-1,6-dihydropyridin-3-yl)spiro[chroman-2,4'-piperidin]-4-one hydrochloride (208 mg), 1-cyclopropyl-4-(tetrazol-5-yl)-1H-indole-6-carboxylic acid (135 mg), EDCI (115 mg), HOBT (91.2 mg) and triethylamine (0.209 ml) were suspended in DMF (3 ml), and stirred at 50° C. for 16 hours. 1N hydrochloric acid and water were added to the reaction liquid, the formed solid was taken out through filtration, and the resulting solid was recrystallized from methanol to obtain the title compound. ¹H-NMR (400 MHz, DMSO-d₆) δ: 11.78 (1.0H, s), 7.85-7.82 (2.0H, m), 7.81-7.75 (3.0H, m), 7.67 (1.0H, d, J=2.4 Hz), 7.64 (1.0H, d, J=3.2 Hz), 7.17-7.11 (2.0H, m), 6.40 (1.0H, d, J=9.5 Hz), 4.46-4.12 (1.0H, m), 3.93-3.13 (4.0H, m), 2.92 (2.0H, s), 2.15-1.90 (2.0H, m), 1.88-1.75 (2.0H, m), 1.16-1.08 (2.0H, m), 1.04-0.98 (2.0H, m). MS [M+H]⁺=562.

Example 46

Production of 3-(1'-{[1-Cyclopropyl-4-(tetrazol-5-yl)-1H-indol-6-yl]carbonyl}-4-oxospiro[chroman-2,4'-piperidin]-6-yl)benzamide

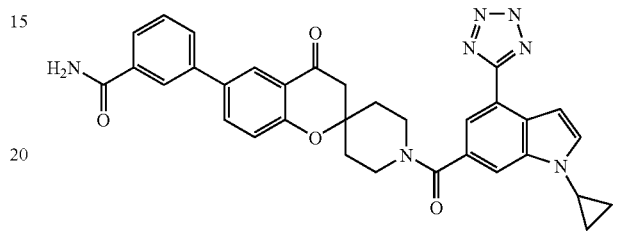

3-(4-Oxospiro[chroman-2,4'-piperidin]-6-yl)benzamide hydrochloride (224 mg), 1-cyclopropyl-4-(tetrazol-5-yl)-1H-indole-6-carboxylic acid (135 mg), EDCI (115 mg), HOBT (91.2 mg) and triethylamine (0.209 ml) were dissolved in DMF (3 mL), and stirred at 50° C. for 23 hours. 1N hydrochloric acid and water were added to the reaction liquid, the formed solid was taken out through filtration, and the resulting solid was purified through silica gel thin-layer column chromatography (chloroform/methanol) to obtain the title compound. ¹H-NMR (400 MHz, DMSO-d₆) δ: 8.17-8.10 (2.0H, br m), 8.05 (1.0H, d, J=2.2 Hz), 7.99 (1.0H, dd, J=8.5, 2.2 Hz), 7.86-7.78 (4.0H, m), 7.63 (1.0H, d, J=2.9 Hz), 7.52 (1.0H, dd, J=7.7, 7.7 Hz), 7.40 (1.0H, s), 7.25 (1.0H, d, J=8.5 Hz), 7.15-7.13 (1.0H, m), 4.50-4.08 (1.0H, br m), 3.88-3.08 (4.0H, m), 2.96 (2.0H, s), 2.23-1.68 (4.0H, m), 1.15-1.08 (2.0H, m), 1.06-0.96 (2.0H, m). MS [M+H]⁺=588.

Example 47

Production of 1'-[(1,3-Diphenyl-1H-indazol-6-yl)carbonyl]-6-(tetrazol-5-yl)spiro[chroman-2,4'-piperidin]-4-one

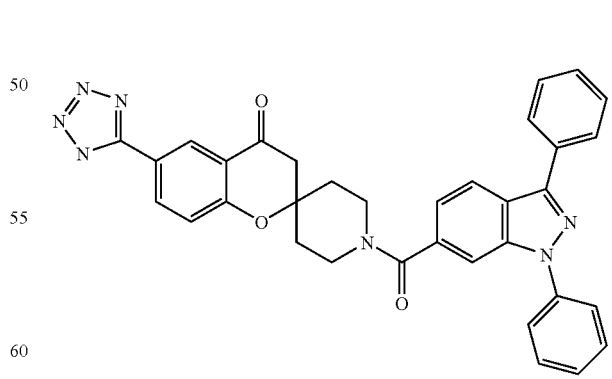

In the same manner as in Example 40, the title compound was obtained as a colorless solid from 1,3-diphenyl-1H-indazole-6-carboxylic acid (131 mg) and 6-(tetrazol-5-yl)spiro[chroman-2,4'-piperidin]-4-one hydrochloride. ¹H-NMR (400 MHz, DMSO-d₆) δ: 8.41 (1H, d, J=2.2 Hz), 8.23 (2H, dd, J=8.5, 2.2 Hz), 8.05 (2H, d, J=8.5 Hz), 7.87-7.83 (3H, m), 7.64 (2H, dd, J=8.5, 8.5 Hz), 7.58 (2H, dd, J=8.5, 8.5 Hz), 7.51-7.45 (2H, m), 7.38 (1H, dd, J=8.5, 1.2 Hz), 7.32 (1H, d, J=8.5 Hz), 4.36-4.22 (1H, br m), 3.60-3.19 (3H, br m), 2.97 (2H, s), 2.12-1.71 (4H, br m). MS [M+H]$^+$=582.

Example 48

Production of 1'-{[4-Methoxy-1-phenyl-1H-indol-6-yl]carbonyl}-6-(tetrazol-5-yl)spiro[chroman-2,4'-piperidin]-4-one

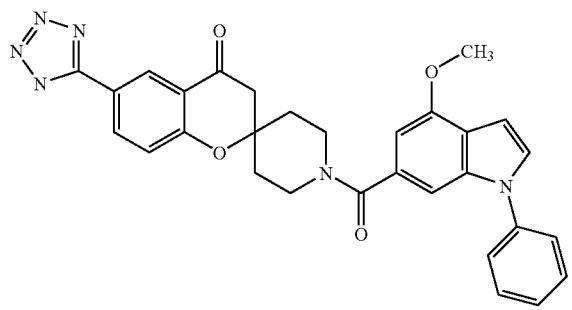

In the same manner as in Example 40, the title compound was obtained as a colorless solid from 6-(tetrazol-5-yl)spiro[chroman-2,4'-piperidin]-4-one hydrochloride and 4-methoxy-1-phenyl-1H-indole-6-carboxylic acid (253 mg). $^1$H-NMR (400 MHz, DMSO-d$_6$) δ: 8.40 (1H, d, J=2.2 Hz), 8.22 (1H, dd, J=8.7, 2.2 Hz), 7.63 (1H, d, J=3.2 Hz), 7.61-7.56 (4H, m), 7.45-7.40 (1H, m), 7.31 (1H, d, J=8.7 Hz), 7.16 (1H, s), 6.71 (1H, dd, J=3.2, 0.7 Hz), 6.67 (1H, s), 4.30-4.09 (1H, br m), 3.93 (3H, s), 3.80-3.17 (3H, br m), 2.95 (2H, s), 2.05-1.71 (4H, br m). MS [M+H]$^+$=535.

Example 49

Production of 1'-[(3-Phenyl-1-pyridin-2-yl-1H-thieno[2,3-c]pyrazol-5-yl)carbonyl]-6-(tetrazol-5-yl)spiro[chroman-2,4'-piperidin]-4-one

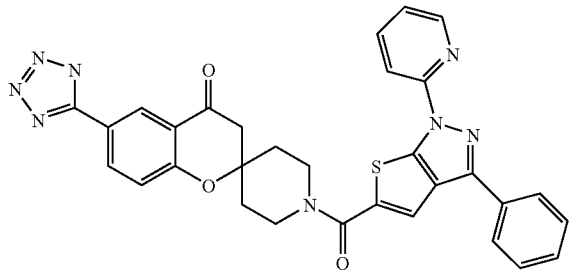

DMF (10 mL) and Et3N (1 mL) were added to 3-phenyl-1-pyridin-2-yl-1H-thieno[2,3-c]pyrazole-5-carboxylic acid (160 mg), 6-tetrazol-5-yl)spiro[chroman-2,4'-piperidin]-4-one hydrochloride (190 mg), EDCI (120 mg) and HOBT (90 mg), heated at 50° C. and stirred overnight. This was further stirred at 110° C. for 1 hour, then restored to room temperature, diluted with water, and its pH was adjusted at 1.5 with 1 N HCl added thereto. The formed crystal was taken out through filtration, washed with water, n-hexane and water, and dried in vacuum at 60° C. to obtain the title compound as a pale brown power. $^1$H-NMR (400 MHz, DMSO-d$_6$) δ: 8.62-8.57 (1H, m), 8.44 (1H, d, J=2.2 Hz), 8.26 (1H, dd, J=8.0, 2.2 Hz), 8.16-8.06 (4H, m), 7.92 (1H, s), 7.55 (2H, t, J=8.0 Hz), 7.50-7.45 (1H, m), 7.41-7.34 (2H, m), 4.30-4.20 (2H, br m), 3.53 (2H, s), 3.01 (2H, s), 2.12-2.04 (2H, br m), 1.95-1.84 (2H, br m). MS [M+H]$^+$=589.

Example 50

Production of 1'-[(3-Chloro-1-phenyl-1H-indol-5-yl)carbonyl]-6-(tetrazol-5-yl)spiro[chroman-2,4'-Piperidin]-4-one

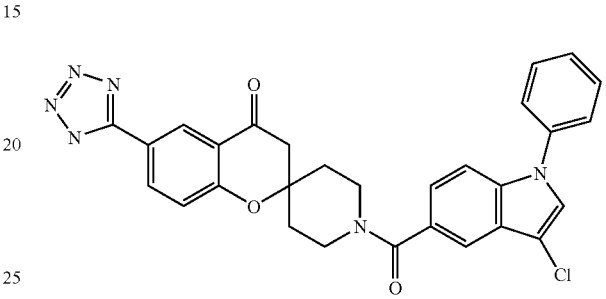

In the same manner as in Example 40, the title compound was obtained as a colorless solid from 3-chloro-1-phenyl-1H-indole-5-carboxylic acid (136 mg) and 6-(tetrazol-5-yl)spiro[chroman-2,4'-piperidin]-4-one hydrochloride. $^1$H-NMR (400 MHz, DMSO-d$_6$) δ: 8.41 (1H, d, J=2.2 Hz), 8.23 (1H, dd, J=8.5, 2.2 Hz), 8.02 (1H, s), 7.66 (1H, s), 7.63-7.58 (5H, m), 7.48-7.42 (1H, m), 7.37-7.31 (2H, m), 4.43-4.05 (1H, br m), 3.72-3.18 (3H, br m), 2.98 (2H, s), 2.10-1.77 (4H, br m). MS [M+H]$^+$=539.

Example 51

Production of 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one

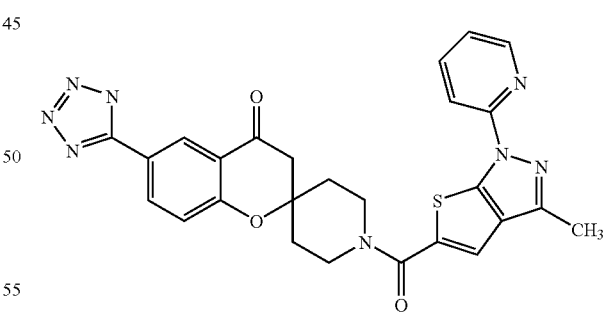

6-(Tetrazol-5-yl)spiro[chroman-2,4'-piperidin]-4-one hydrochloride (232 mg), 3-methyl-1-pyridin-2-yl-1H-thieno[2,3-c]pyrazole-5-carboxylic acid (155 mg), EDCI (153 mg) and HOBT (122 mg) were suspended in Et3N (1 mL) and DMF (8 mL). The suspension was stirred at 80° C. for 1.5 hours under heat, then cooled to room temperature, and chloroform (1.8 mL) was added thereto. Its pH was adjusted at 2.5 with 1 N HCl added thereto, and this was diluted with water, and Et2O was added thereto. The formed crystal was taken out through filtration, washed with water and Et$_2$O—CHCl$_3$, and dried in vacuum to obtain the title compound as a pale yellow powder. ¹H-NMR (400 MHz, DMSO-d₆): δ 8.53 (1H, d, J=4.4 Hz), 8.44 (1H, s), 8.25 (1H, d, J=8.5 Hz), 8.01 (1H, t, J=7.8 Hz), 7.90 (1H, d, J=8.5 Hz), 7.61 (1H, s), 7.37 (1H, d, J=8.8 Hz), 7.31 (1H, t, J=5.9 Hz), 6.44 (2H, s), 4.20 (2H, d, J=12.9 Hz), 3.48 (2H, br s), 2.52 (3H, s), 2.06 (2H, d, J=13.7 Hz), 1.94-1.81 (2H, m). MS [M+H]⁺=527.

Example 52

Production of 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one sodium salt

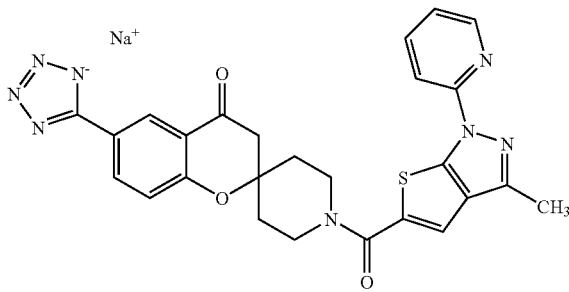

1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one (328 mg) was suspended in MeOH (10 mL), and 1 N NaOH (0.68 mL) was added thereto to dissolve it. The solution was purified through ODS reversed-phase column chromatography (water/methanol) to obtain the title compound as a pale brown powder. ¹H-NMR (400 MHz, DMSO-d₆) δ: 8.56-8.52 (1H, m), 8.33-8.30 (1H, m), 8.17 (1H, dd, J=8.5, 2.2 Hz), 8.04-7.98 (1H, m), 7.92-7.88 (1H, m), 7.61 (1H, s), 7.32-7.28 (1H, m), 7.13 (1H, d, J=8.5 Hz), 4.19 (2H, d, J=13.4 Hz), 3.48 (2H, br s), 2.92 (2H, s), 2.51 (3H, s), 2.05 (2H, d, J=13.4 Hz), 1.89-1.77 (2H, m). MS [M+Na]⁺=549.

Example 53

Production of 1'-[(2-Cyclopropyl-1-phenyl-1H-benzimidazol-5-yl)carbonyl]-6-(tetrazol-5-yl)spiro[chroman-2,4'-piperidin]-4-one

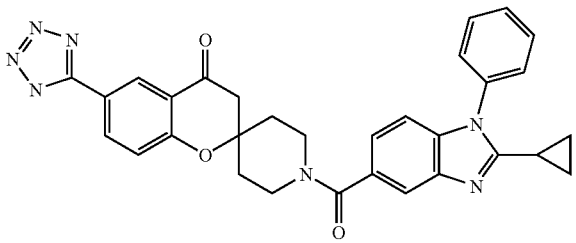

Methyl 2-cyclopropyl-1-phenyl-1H-benzimidazole-5-carboxylate (194 mg, 0.664 mmol) was dissolved in THF (6 mL) and MeOH (6 mL), and aqueous 5 N sodium hydroxide solution (0.66 mL, 3.30 mmol) was added to it and stirred at 60° C. for 2 hours. This was restored to room temperature, 5 N hydrochloric acid (0.66 mL, 3.30 mmol) was added thereto, the solvent was evaporated away under reduced pressure, and the residue was azeotroped with toluene. DMF (4 mL) and water (1 mL) were added to it, and 6-(tetrazol-5-yl)spiro[chroman-2,4'-piperidin]-4-one hydrochloride (256 mg, 0.797 mmol), triethylamine (0.14 mL, 0.996 mmol), HOBT (135 mg, 0.996 mmol) and WSC hydrochloride (191 mg, 0.996 mmol) were added thereto. The reaction liquid was stirred at 90° C. for 2 hours, restored to room temperature, and water was added thereto. The precipitated solid was taken out through filtration, and dried under reduced pressure to obtain the title compound as a white solid. ¹H-NMR (400 MHz, DMSO-d₆) δ: 8.42 (1H, d, J=2.2 Hz), 8.23 (1H, dd, J=8.8, 2.2 Hz), 7.69-7.59 (6H, m), 7.34 (1H, d, J=8.8 Hz), 7.23 (1H, dd, J=8.4, 1.6 Hz), 7.14 (1H, d, J=8.4 Hz), 4.50-3.29 (5H, m), 2.98 (2H, s), 2.06-1.77 (4H, m), 1.15-1.11 (2H, m), 1.04-1.00 (2H, m). MS [M+H]⁺=546.

Example 54

Production of 1'-[(1-Methyl-3-phenyl-1H-indol-6-yl)carbonyl]-6-(tetrazol-5-yl)spiro[chroman-2,4'-piperidin]-4-one

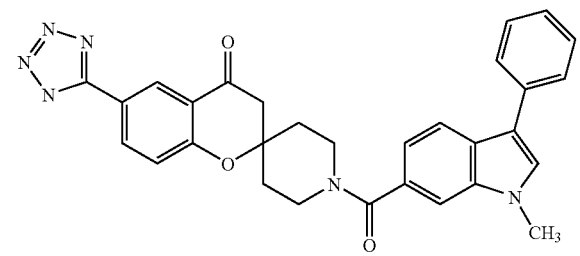

In the same manner as in Example 40, the title compound was obtained as a colorless solid from 6-(tetrazol-5-yl)spiro[chroman-2,4'-piperidin]-4-one hydrochloride and 1-methyl-3-phenyl-1H-indole-6-carboxylic acid (85 mg). ¹H-NMR (400 MHz, DMSO-d₆) δ: 8.42 (1H, d, J=2.2 Hz), 8.24 (1H, dd, J=8.5, 2.2 Hz), 7.89 (1H, d, J=8.5 Hz), 7.79 (1H, s), 7.65 (2H, dd, J=8.5, 1.2 Hz), 7.60 (1H, s), 7.43 (2H, dd, J=8.5, 8.5 Hz), 7.34 (1H, d, J=8.5 Hz), 7.24 (1H, dd, J=8.5, 8.5 Hz), 7.19 (1H, dd, J=8.5, 1.2 Hz), 4.39-4.14 (1H, br m), 3.87 (3H, s), 3.79-3.19 (3H, br m), 2.99 (2H, s), 2.10-1.77 (4H, br m). MS [M+H]⁺=519.

Example 55

Production of 1'-[(1-Ethyl-3-phenyl-1H-thieno[2,3-c]pyrazol-5-yl)carbonyl]-6-(tetrazol-5-yl)spiro[chroman-2,4'-piperidin]-4-one

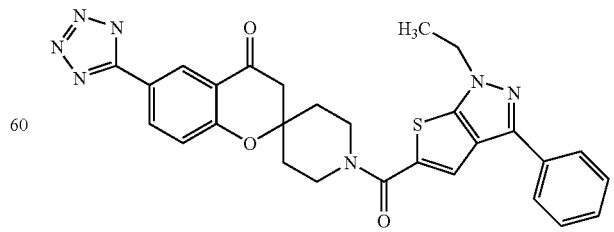

In the same manner as in Example 43, the title compound was obtained from 6-(tetrazol-5-yl)spiro[chroman-2,4'-piperidin]-4-one hydrochloride and 1-ethyl-3-phenyl-1H-thieno[2,3-c]pyrazole-5-carboxylic acid. $^1$H-NMR (400 MHz, DMSO-d$_6$) δ: 8.44 (1H, d, J=2.2 Hz), 8.31-8.23 (1H, m), 7.94 (2H, d, J=7.3 Hz), 7.79 (1H, s), 7.46 (2H, t, J=7.6 Hz), 7.39-7.32 (2H, m), 4.33 (2H, q, J=7.2 Hz), 4.27-4.15 (2H, m), 3.66-3.43 (2H, br m), 3.00 (2H, s), 2.11-2.00 (2H, br m), 1.93-1.80 (2H, m), 1.47 (3H, t, J=7.6 Hz). MS [M+H]$^+$=540.

Example 56

Production of 1'-[(1-Methyl-3-phenyl-1H-indazol-6-yl)carbonyl]-6-(tetrazol-5-yl)spiro[chroman-2,4'-piperidin]-4-one

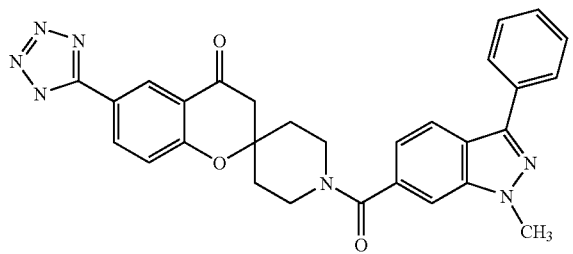

In the same manner as in Example 40, the title compound was obtained as a colorless solid from 1-methyl-3-phenyl-1H-indazole-6-carboxylic acid (549 mg) and 6-(tetrazol-5-yl)spiro[chroman-2,4'-piperidin]-4-one hydrochloride. $^1$H-NMR (400 MHz, DMSO-d$_6$) δ: 8.42 (1H, d, J=2.2 Hz), 8.24 (1H, dd, J=8.8, 2.2 Hz), 8.12 (1H, d, J=8.8 Hz), 7.96 (2H, d, J=7.8 Hz), 7.78 (1H, s), 7.52 (2H, dd, J=7.8, 7.8 Hz), 7.41 (1H, t, J=7.8 Hz), 7.34 (1H, d, J=8.5 Hz), 7.25 (1H, d, J=8.5 Hz), 4.41-4.24 (1H, br m), 4.13 (3H, s), 3.58-3.20 (3H, br m), 2.99 (2H, s), 2.15-1.79 (4H, br m). MS [M+H]$^+$=520.

Example 57

Production of 1'-[(3-Methyl-1-phenyl-1H-indazol-5-yl)carbonyl]-6-(tetrazol-5-yl)spiro[chroman-2,4'-piperidin]-4-one

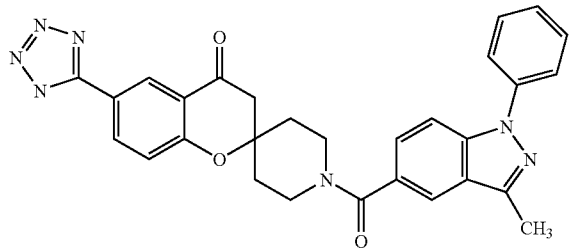

In the same manner as in Example 40, the title compound was obtained as a colorless solid from 3-methyl-1-phenyl-1H-indazole-5-carboxylic acid (561 mg) and 6-(tetrazol-5-yl)spiro[chroman-2,4'-piperidin]-4-one hydrochloride. $^1$H-NMR (400 MHz, DMSO-d$_6$) δ: 8.42 (1H, d, J=2.2 Hz), 8.24 (1H, dd, J=8.7, 2.2 Hz), 7.94 (1H, s), 7.83 (1H, d, J=8.7 Hz), 7.74 (2H, d, J=8.7 Hz), 7.59-7.52 (3H, m), 7.38 (1H, dd, J=8.7, 8.7 Hz), 7.33 (1H, d, J=8.7 Hz), 4.43-4.16 (1H, br m), 3.67-3.15 (3H, br m), 2.99 (2H, s), 2.60 (3H, s), 2.09-1.79 (4H, br m). MS [M+H]$^+$=520.

Example 58

Production of Sodium 5-{1'-[(3-methyl-1-pyridin-2-yl-1H-thieno[2,3-c]pyrazol-5-yl)carbonyl]-4-oxospiro[chroman-2,4'-piperidin]-6-yl}pyridine-3-carboxylate

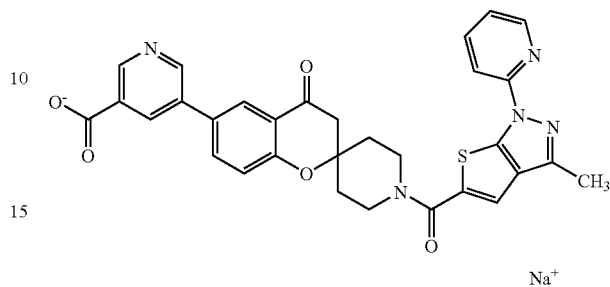

Triethylamine (2.78 mL) was added to a DMF (30 mL) solution of 3-methyl-1-pyridin-2-yl-1H-thieno[2,3-c]pyrazole-5-carboxylic acid (1.03 g), methyl 5-(4-oxospiro[chroman-2,4'-piperidin]-6-yl)pyridine-3-carboxylate dihydrochloride (1.70 g), WSC hydrochloride (843 mg) and HOBT (674 mg), and stirred at 60° C. for 1 hour. At room temperature, this was diluted with ethyl acetate, then washed with water, aqueous saturated sodium bicarbonate and saturated saline water in that order, and dried with sodium sulfate. This was filtered, concentrated, and purified through silica gel column chromatography (chloroform/methanol) to obtain the intended ester compound. Aqueous 5 N sodium hydroxide solution (1.2 mL) was added to a methanol (25 mL)/THF (25 mL) solution of the ester compound (2.81 g), and stirred at 60° C. for 4 hours. The organic solvent was evaporated away, the residue was diluted with water and then purified through ODS reversed-phase column chromatography (water/methanol) to obtain the title compound as a colorless amorphous substance. $^1$H-NMR (400 MHz, DMSO-d$_6$) δ: 8.92 (1H, s), 8.76 (1H, s), 8.53 (1H, s), 8.31 (1H, s), 8.04-7.97 (3H, m), 7.91 (1H, d, J=8.3 Hz), 7.62 (1H, s), 7.33-7.24 (2H, br m), 4.25-4.16 (2H, br m), 3.56-3.41 (2H, br m), 2.97 (2H, s), 2.52 (3H, s), 2.12-2.02 (2H, br m), 1.91-1.81 (2H, br m). MS [M+H]$^+$=580.

Example 59

Production of Sodium 5-{1'-[(3-methyl-1-phenyl-1H-indazol-5-yl)carbonyl]-4-oxo-spiro[chroman-2,4'-piperidin]-6-yl}pyridine-3-carboxylate

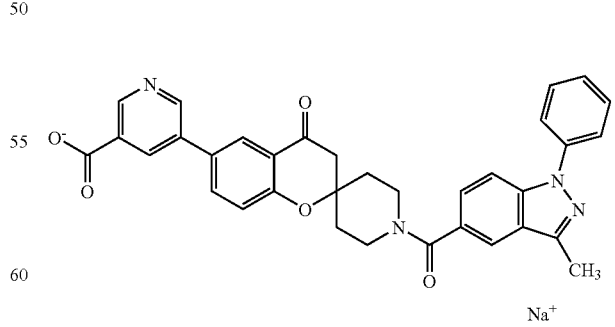

In the same manner as in Example 58, the title sodium salt compound was obtained as a colorless amorphous substance from 3-methyl-1-phenyl-1H-indazole-5-carboxylic acid (1.01 g) and methyl 5-(4-oxo-spiro[chroman-2,4'-piperidin]-

6-yl)pyridine-3-carboxylate dihydrochloride corresponding thereto. ¹H-NMR (400 MHz, DMSO-d₆) δ: 8.90 (1H, d, J=1.7 Hz), 8.74 (1H, d, J=2.4 Hz), 8.29 (1H, dd, J=2.4, 1.7 Hz), 7.99-7.95 (3H, m), 7.84 (1H, d, J=8.8 Hz), 7.75 (2H, d, J=8.8 Hz), 7.57 (2H, dd, J=8.8, 8.8 Hz), 7.55-7.52 (1H, m), 7.38 (1H, t, J=8.8 Hz), 7.24 (1H, d, J=8.8 Hz), 4.41-4.24 (1H, br m), 3.48-3.25 (3H, br m), 2.95 (2H, s), 2.61 (3H, s), 2.13-1.75 (4H, br m). MS [M+H]⁺=573.

Example 60

Production of Sodium 4-{1'-[(3-methyl-1-pyridin-2-yl-1H-thieno[2,3-c]pyrazol-5-yl)carbonyl]-4-oxospiro[chroman-2,4'-piperidin]-6-yl}pyridine-2-carboxylate

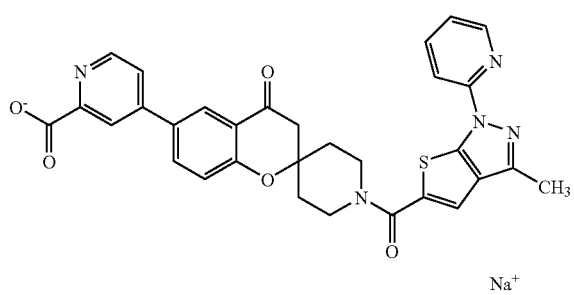

In the same manner as in Example 58, the title compound was obtained as a colorless amorphous substance from 3-methyl-1-pyridin-2-yl-1H-thieno[2,3-c]pyrazole-5-carboxylic acid (259 mg) and methyl 4-(4-oxospiro[chroman-2,4'-piperidin]-6-yl)pyridine-2-carboxylate dihydrochloride corresponding thereto. ¹H-NMR (400 MHz, DMSO-d₆) δ: 8.55-8.53 (1H, m), 8.48 (1H, d, J=5.4 Hz), 8.16 (1H, d, J=1.5 Hz), 8.11-7.99 (3H, m), 7.91 (1H, d, J=8.3 Hz), 7.62-7.60 (2H, m), 7.33-7.26 (2H, m), 4.24-4.17 (2H, br m), 3.63-3.36 (2H, br m), 2.98 (2H, s), 2.52 (3H, s), 2.11-2.04 (2H, br m), 1.92-1.82 (2H, br m). MS [M+S]⁺=580.

Example 61

Production of 1'-{[3-(Difluoromethyl)-1-pyridin-2-yl-1H-thieno[2,3-c]pyrazol-5-yl]carbonyl}-6-(tetrazol-5-yl)spiro[chroman-2,4'-piperidin]-4-one

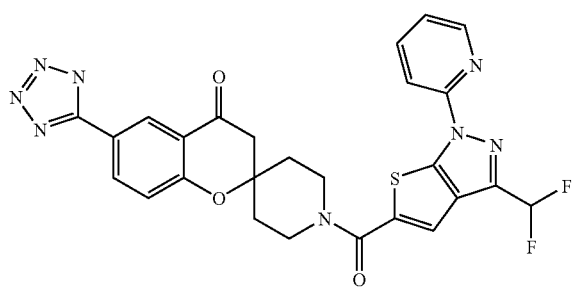

In the same manner as in Example 38, the title compound was obtained as a pale yellow powder from 6-(tetrazol-5-yl)spiro[chroman-2,4'-piperidin]-4-one hydrochloride and 3-(difluoromethyl)-1-pyridin-2-yl-1H-thieno[2,3-c]pyrazole-5-carboxylic acid. ¹H-NMR (400 MHz, DMSO-d₆) δ: 8.62 (1H, ddd, J=4.9, 2.2, 1.1 Hz), 8.44 (1H, d, J=2.2 Hz), 8.25 (1H, dd, J=8.3, 2.2 Hz), 8.11 (1H, td, J=8.3, 1.5 Hz), 8.01 (1H, d, J=8.3 Hz), 7.59 (1H, s), 7.47-7.42 (1H, m), 7.39 (1.0H, t, J=53.7 Hz), 7.36 (1H, d, J=8.3 Hz), 4.23-4.13 (2H, br m), 3.64-3.40 (2H, br m), 3.00 (2H, s), 2.11-2.02 (2H, br m), 1.95-1.82 (2H, br m). MS [M+H]⁺=563.

Example 62

Methyl 5-{1'-[3-ethoxy-5-methoxy-4-(1-methyl-1H-pyrazol-4-yl)benzoyl]-4-oxospiro[chromman-2,4'-piperidin]-6-yl}nicotinate

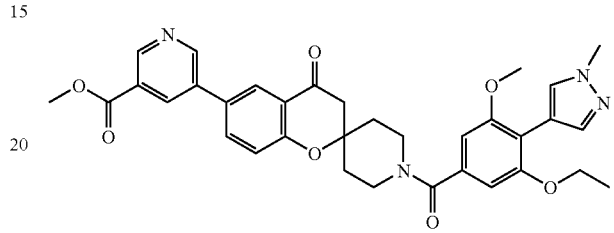

TEA (0.209 ml, 1.500 mmol) was added to a suspension of HOBT (92 mg, 0.600 mmol), EDCI (115 mg, 0.600 mmol), Methyl 5-(4-oxospiro[chroman-2,4'-piperidin]-6-yl)nicotinate dihydrochloride (233 mg, 0.600 mmol) and 3-Ethoxy-5-methoxy-4-(1-methyl-1H-pyrazol-4-yl)benzoic acid (138 mg, 0.5 mmol) in DMF (2 ml) and the mixture was stirred at room temperature for over night. Water (ca. 50 ml) was added to the mixture and stirred for 1 h. Resulted solid was collected by filtration. The solid was purified by silicagel column chromatography (CHCl₃/MeOH) and then precipitated by EtOAc/hexane to obtain the intended compound as a pale yellow solid. ¹H-NMR (DMSO-D₆) δ: 9.08 (1.0H, d, J=2.3 Hz), 9.00 (1.0H, d, J=2.0 Hz), 8.39 (1.0H, dd, J=2.3, 2.0 Hz), 8.04-7.99 (3.0H, m), 7.84 (1.0H, s), 7.22 (1.0H, dd, J=7.4, 1.6 Hz), 6.68-6.65 (2.0H, m), 4.31-4.12 (1.0H, m), 4.04 (2.0H, q, J=7.0 Hz), 3.87 (3.0H, s), 3.81 (3.0H, s), 3.79 (3.0H, s), 3.61-3.12 (3.0H, br m), 2.90 (2.0H, s), 2.08-1.85 (2.0H, br m), 1.81-1.71 (2.0H, m), 1.33 (3.0H, t, J=7.0 Hz). MS [M+H]+= 611.

Example 63

(5-{1'-[3-ethoxy-5-methoxy-4-(1-methyl-1H-pyrazol-4-yl)benzoyl]-4-oxospiro[chroman-2,4'-piperidin]-6-yl}-2H-tetrazol-2-yl)methylpivalate

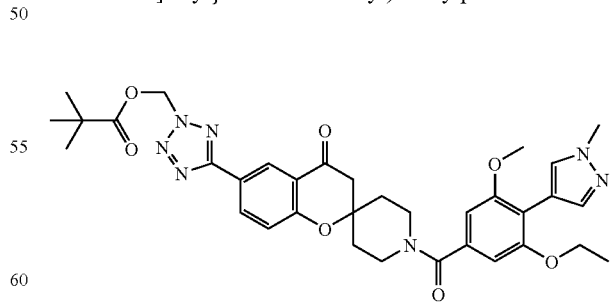

In the same manner as in Example 62, the title compound was obtained as a pale yellow solid from 3-ethoxy-5-methoxy-4-(1-methyl-1H-pyrazol-4-yl)benzoic acid and [5-(4-oxospiro-[chroman-2,4'-piperidin]-6-yl)-2H-tetrazol-2-yl] methyl 2,2-dimethylpropanoate hydrochloride. ¹H-NMR (CDCl₃) δ: 8.65 (1.0H, d, J=2.3 Hz), 8.30 (1.0H, dd, J=8.6, 2.3 Hz), 8.04 (1.0H, s), 7.89 (1.0H, s), 7.13 (1.0H, d, J=8.6 Hz), 6.62 (2.0H, d, J=7.0 Hz), 6.48 (2.0H, s), 4.59-4.37 (1.0H, br m), 4.06 (2.0H, q, J=6.9 Hz), 3.91 (3.0H, s), 3.85 (3.0H, s), 3.82-3.63 (1.0H, br m), 3.59-3.23 (2.0H, br m), 2.79 (2.0H, s), 2.29-1.93 (2.0H, br m), 1.84-1.54 (2.0H, br m), 1.44 (3.0H, t, J=7.0 Hz), 1.19 (9.0H, s). MS [M+H]+=658.

Example 64

4-{1'-[(3-methyl-1-phenyl-1H-indazol-5-yl)carbonyl]-4-oxospiro[chroman-2,4'-piperidin]-6-yl}-2-pyridinecarboxylic acid

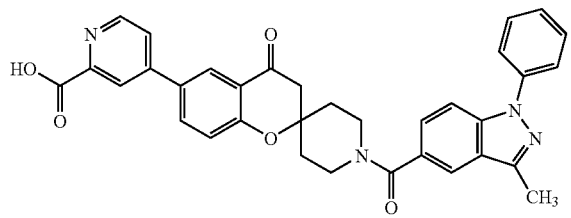

TEA (0.28 mL) was added to a DMF (3 mL) suspension of EDCI (137 mg), HOBT (92 mg), 3-methyl-1-phenyl-1H-indazole-5-carboxylic acid (126 mg), and methyl 4-(4-oxospiro[chroman-2,4'-piperidin]-6-yl)pyridine-2-carboxylate dihydrochloride (213 mg), and stirred at room temperature for over night. The organic solvent was evaporated away and the residue was purified by silica gel column chromatography to obtain the ester of intended compound as a colorless amorphous substance. Aqueous 1 N sodium hydroxide solution (1 mL) was added to a solution of the ester in methanol (5 ml) and THF (5 ml) and stirred at room temperature for over night. The organic solvent was evaporated away and diluted with water. Aqueous 1N hydrochloric acid solution (1 ml) was added thereto at room temperature, extracted with a mixed solvent of chloroform and methanol, and dried over sodium sulfate. After filtered, concentrated, and crystallized from hexane and EtOAc to afford the title compound was obtained as a colorless solid. 1H-NMR (DMSO-d₆) δ: 8.74 (1H, d, J=4.4 Hz), 8.25 (1H, d, J=1.5 Hz), 8.18-8.12 (2H, m), 7.96-7.93 (2H, m), 7.84 (1H, d, J=9.3 Hz), 7.79-7.73 (2H, m), 7.61-7.51 (3H, m), 7.41-7.35 (1H, m), 7.29 (1H, dd, J=6.8, 2.9 Hz), 4.40-4.15 (1H, m), 3.73-3.70 (3H, br m), 2.97 (2H, s), 2.60 (3H, s), 1.65-1.65 (4H, m). MS[M+H]+=573.

Example 65

2-methyl-5-{1'-[(3-methyl-1-phenyl-1H-indazol-5-yl)carbonyl]-4-oxospiro[chroman-2,4'-piperidin]-6-yl}nicotinic acid

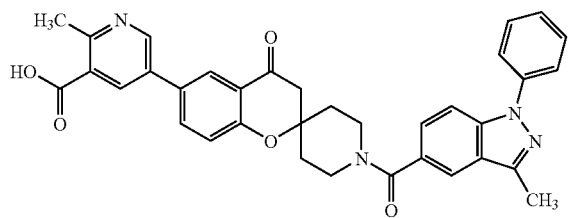

Triethylamine (0.28 mL) was added to a DMF (3 mL) suspension of EDCI (137 mg), HOBT (92 mg), 3-methyl-1-phenyl-1H-indazole-5-carboxylic acid (126 mg), and methyl 2-methyl-5-(4-oxospiro[chroman-2,4'-piperidin]-6-yl)nicotinate dihydrochloride (220 mg), and stirred at room temperature for over night. The organic solvent was evaporated away, and the residue was purified by silica gel column chromatography to obtain the ester of intended compound as colorless foam. Aqueous 1 N sodium hydroxide solution (1 mL) was added to a solution of the ester in methanol (5 ml) and THF (5 ml), stirred at room temperature for over night and then at 50° C. for over night. The organic solvent was evaporated away, diluted with water. Aqueous 1 N hydrochloric acid solution (1 ml) was added thereto at room temperature, extracted with a mixed solvent of chloroform and methanol, and dried over sodium sulfate. After filtered, concentrated and crystallized from hexane and EtOAc to afford the title compound as a colorless solid. ¹H-NMR (DMSO-d₆) δ: 13.34 (1H, s), 8.89 (1H, d, J=2.4 Hz), 8.33 (1H, d, J=2.4 Hz), 8.02-7.99 (2H, m), 7.94 (1H, s), 7.84 (1H, d, J=8.8 Hz), 7.74 (2H, dd, J=8.8, 1.2 Hz), 7.60-7.51 (3H, m), 7.40-7.35 (1H, m), 7.24 (1H, dd, J=6.3, 3.4 Hz), 4.42-4.14 (1H, br m), 3.67-3.19 (3H, br m), 2.95 (2H, s), 2.73 (3H, s), 2.60 (3H, s), 2.14-1.77 (4H, br m). MS[M+H]+=587

Example 66

3-carboxy-5-{1'-[4-(1-cyclopropyl-1H-pyrazol-4-yl)-3,5-diethoxybenzoyl]-4-oxospiro[chroman-2,4'-piperidin]-6-yl}pyridinium trifluoroacetate

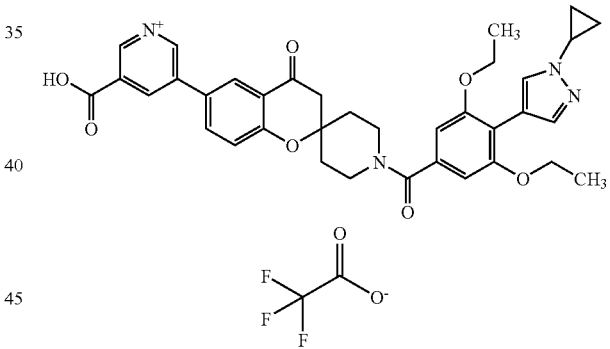

To a mixture of 4-(1-cyclopropyl-1H-pyrazolyl)-3,5-diethoxybenzoic acid (19.3 mg) and Methyl 5-(4-oxospiro[chroman-2,4'-piperidin]-6-yl)nicotinate dihydrochloride (31.1 mg) in DMF were added TEA (20 uL), HOBT (14 mg) and EDCI (17.5 mg) at room temperature, and the reaction mixture was stirred at room temperature, and the reaction mixture was stirred at room temperature for over night. The reaction mixture was poured into H2O, extracted with EtOAc. The combined organic layer was washed with H2O, brine, and dried over sodium sulfate. After concentrating the solvent, the residue was purified by preparative TLC eluting (CHCl3/MeOH) to give the title compound as a colorless solid. To a solution of the ester in MeOH was added aqueous 1N NaOH (65 ul) at room temperature, and the reaction mixture was stirred at room temperature for over night. The reaction mixture was concentrated under reduced pressure, and the residue was purified by p-HPLC (ODS, H2O/MeCN/0.1% TFA) to give the title compound as a white solid. ¹H-NMR (400 MHz, DMSO-d₆) δ: 8.91 (1H, d, J=2.0 Hz), 8.75 (1H, d, J=2.0 Hz), 8.39 (1H, t, J=2.0 Hz), 8.11 (1H, s), 7.99-7.97 (2H, m), 7.92 (1H, s), 7.21 (1H, d, J=8.0 Hz), 6.68 (2H, s), 4.30-4.18 (1H, m), 4.09 (4H, q, J=8.0 Hz), 3.78-3.73 (1H, m), 3.60-3.15 (3H, m), 2.93 (2H, s), 2.19-1.74 (4H, m), 1.37 (6H, t, J=8.0 Hz), 1.05-0.95 (4H, m). MS [M+H]+=637.

Example 67

5-(1'-{4-[1-(difluoromethyl)-1H-pyrazol-4-yl]-3,5-diethoxybenzoyl}-4-oxospiro[chroman-2,4'-piperidin]-6-yl)nicotinic acid

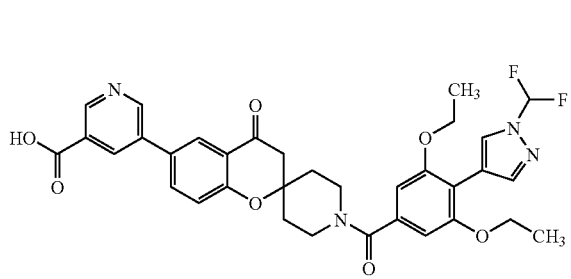

In the same manner as in Example 64, the title compound was obtained as a colorless foam from 4-[1-(difluoromethyl)-1H-pyrazol-4-yl]-3,5-diethoxybenzoic acid and Methyl 5-(4-oxospiro[chroman-2,4'-piperidin]-6-yl)nicotinate dihydrochloride. $^1$H-NMR (400 MHz, DMSO-d$_6$) δ: 9.07 (1H, d, J=2.0 Hz), 9.01 (1H, d, J=2.0 Hz), 8.44 (1H, s), 8.39 (1H, t, J=2.0 Hz), 8.20 (1H, s), 8.04-8.02 (2H, m), 7.85 (1H, t, J=60.0 Hz), 7.23 (1H, d, J=8.0 Hz), 6.70 (2H, s), 4.30-4.18 (1H, m), 4.09 (4H, q, J=8.0 Hz), 3.60-3.15 (3H, m), 2.92 (2H, s), 2.08-1.74 (4H, m), 1.35 (6H, t, J=8.0 Hz). MS[M+H]+=647.

Example 68

6-{1'-[3,5-dimethoxy-4-(1-methyl-1H-pyrazol-4-yl)benzoyl]-4-oxospiro[chroman-2,4'-piperidin]-6-yl}nicotinamide

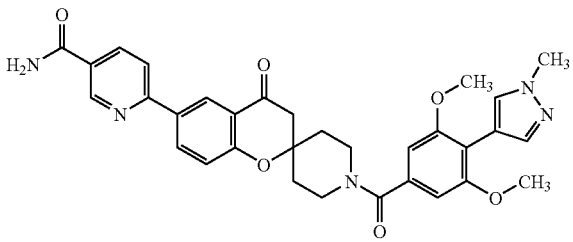

In the same manner as in Example 62, the title compound was obtained as a colorless foam from 3,5-dimethoxy-4-(1-methyl-1H-pyrazol-4-yl)benzoic acid and 6-(4-oxospiro[chroman-2,4'-piperidin]-6-yl)nicotinamide dihydrochloride. $^1$H-NMR (DMSO-D6) δ: 9.08 (1.0H, dd, J=2.2, 0.7 Hz), 8.52 (1.0H, d, J=2.2 Hz), 8.39 (1.0H, dd, J=8.8, 2.4 Hz), 8.27 (1.0H, dd, J=8.5, 2.4 Hz), 8.18 (1.0H, s), 8.07 (1.0H, d, J=8.5 Hz), 8.03 (1.0H, s), 7.83 (1.0H, d, J=0.7 Hz), 7.59 (1.0H, s), 7.24 (1.0H, d, J=8.7 Hz), 6.73 (2.0H, s), 4.34-4.20 (1.0H, br m), 3.85 (3.0H, s), 3.83 (6.0H, s), 3.66-3.18 (3.0H, br m), 2.95 (2.0H, s), 2.13-1.89 (2.0H, br m), 1.88-1.72 (2.0H, m). MS [M+H]+=582.

Example 69

Sodium 5-{1'-[3,5-diethoxy-4-(1-methyl-1H-pyrazol-4-yl)benzoyl]-4-oxospiro[chroman-2,4'-piperidin]-6-yl}-2-fluorobenzoate

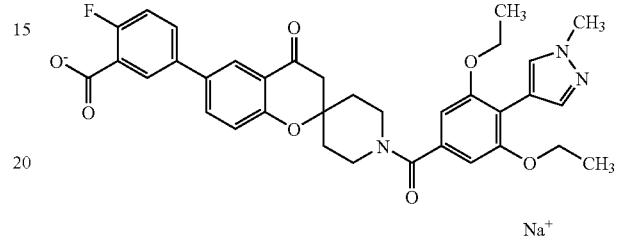

In the same manner as in Example 36, the title compound was obtained as a colorless foam from 3,5-diethoxy-4-(1-methyl-1H-pyrazol-4-yl)benzoic acid and Methyl 2-fluoro-5-(4-oxoospiro[chroman-2,4'-piperidin]-6-yl)benzoate hydrochloride. $^1$H-NMR (DMSO-D6) δ: 8.05 (1.0H, s), 7.92 (1.0H, d, J=0.5 Hz), 7.88 (1.0H, d, J=2.4 Hz), 7.85 (1.0H, dd, J=8.5, 2.4 Hz), 7.72 (1.0H, dd, J=6.8, 2.7 Hz), 7.45 (1.0H, ddd, J=8.5, 4.5, 2.7 Hz), 7.17 (1.0H, d, J=8.5 Hz), 7.05 (1.0H, dd, J=9.8, 8.5 Hz), 6.68 (2.0H, s), 4.30-4.18 (1.0H, br m), 4.08 (4.0H, q, J=7.0 Hz), 3.86 (3.0H, s), 3.66-3.15 (3.0H, br m), 2.89 (2.0H, s), 2.11-1.88 (2.0H, br m), 1.83-1.73 (2.0H, m), 1.37 (6.0H, t, J=7.0 Hz). MS [M+H]+=628.

Example 70

Sodium 3-{1'-[3-ethoxy-5-methoxy-4-(1-methyl-1H-pyrazol-4-yl)benzoyl]-4-oxospiro[chroman-2,4'-piperidin]-6-yl}benzoate

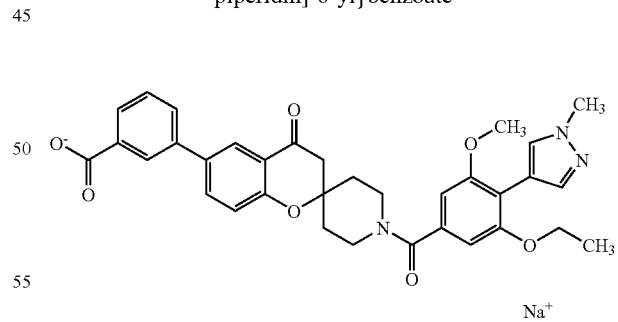

In the same manner as in Example 36, the title compound was obtained as a colorless foam from 3-ethoxy-5-methoxy-4-(1-methyl-1H-pyrazol-4-yl)benzoic acid and methyl 3-(4-oxospiro[chroman-2,4'-piperidin]-6-yl)benzoate hydrochloride. $^1$H-NMR (CD$_3$OD) δ: 8.20 (1.0H, s), 8.10 (1.0H, d, J=2.7 Hz), 8.06 (1.0H, s), 8.01 (1.0H, s), 7.93-7.88 (2.0H, m), 7.66-7.62 (1.0H, m), 7.42 (1.0H, dd, J=7.4, 7.4 Hz), 7.18 (1.0H, d, J=8.6 Hz), 6.77-6.74 (2.0H, m), 4.55-4.41 (1.0H, br m), 4.13 (2.0H, q, J=7.0 Hz), 3.91 (3.0H, s), 3.89 (3.0H, s), 3.78-3.26 (3.0H, br m), 2.95-2.80 (2.0H, m), 2.28-1.99 (2.0H, br m), 1.95-1.72 (2.0H, br m), 1.45 (3.0H, t, J=7.0 Hz). MS [M+H]⁺=596.

Example 71

Sodium 6-{1'-[3,5-diethoxy-4-(1-methyl-1H-pyrazol-4-yl)benzoyl]-4-oxospiro[chroman-2,4'-piperidin]-6-yl}nicotinate

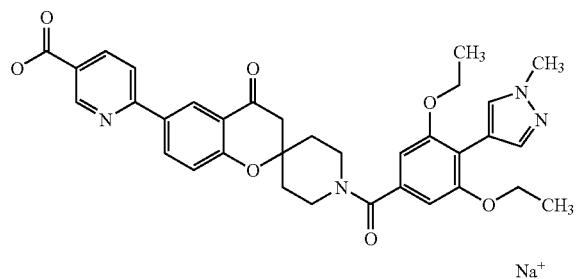

In the same manner as in Example 36, the title compound was obtained as a pale yellow foam from 3,5-diethoxy-4-(1-methyl-1H-pyrazol-4-yl)benzoic acid and Methyl 6-(4-oxospiro-[chroman-2,4'-piperidin]-6-yl)nicotinate dihydrochloride. ¹H-NMR (DMSO-D6) δ: 8.98-8.97 (1.0H, m), 8.44 (1.0H, d, J=2.2 Hz), 8.32 (1.0H, dd, J=8.7, 2.2 Hz), 8.13 (1.0H, dd, J=8.2, 2.2 Hz), 8.05 (1.0H, s), 7.92 (1.0H, d, J=0.5 Hz), 7.82 (1.0H, d, J=8.2 Hz), 7.19 (1.0H, d, J=8.8 Hz), 6.68 (2.0H, s), 4.31-4.19 (1.0H, br m), 4.08 (4.0H, q, J=6.9 Hz), 3.86 (3.0H, s), 3.63-3.15 (3.0H, br m), 2.93 (2.0H, s), 2.13-1.88 (2.0H, br m), 1.85-1.74 (2.0H, m), 1.37 (6.0H, t, J=6.9 Hz). MS [M+H]+=611.

Example 72

6-(1,1-dioxido-4-thiomorpholinyl)-1'-[3-ethoxy-5-methoxy-4-(1-methyl-1H-pyrazol-4-yl)benzoyl]spiro[chroman-2,4'-piperidin]-4-one

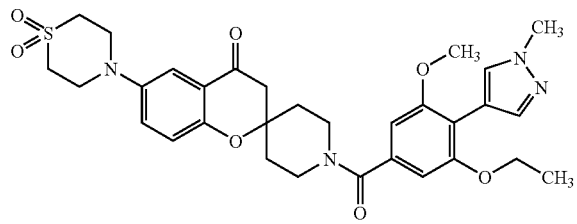

In the same manner as in Example 62, the title compound was obtained as a pale yellow foam from 3-ethoxy-5-methoxy-4-(1-methyl-1H-pyrazol-4-yl)benzoic acid and 6-(1,1-dioxido-4-thiomorpholinyl)spiro[chroman-2,4'-piperidin]-4-one hydrochloride. ¹H-NMR (DMSO-D6) δ: 8.04 (1.0H, s), 7.88 (1.0H, d, J=0.5 Hz), 7.39 (1.0H, dd, J=9.0, 3.2 Hz), 7.22 (1.0H, d, J=3.2 Hz), 7.02 (1.0H, d, J=9.0 Hz), 6.70-6.68 (2.0H, m), 4.30-4.16 (1.0H, hr m), 4.07 (2.0H, q, J=7.0 Hz), 3.85 (3.0H, s), 3.82 (3.0H, s), 3.67-3.61 (5.0H, m), 3.59-3.10 (6.0H, br m), 2.82 (2.0H, s), 2.05-1.82 (2.0H, br m), 1.80-1.68 (2.0H, m), 1.36 (3.0H, t, J=7.0 Hz). MS [M+H]⁺=609.

Example 73

Methyl {1'-[3-ethoxy-5-methoxy-4-(1-methyl-1H-pyrazol-4-yl)benzoyl]-4-oxospiro[chroman-2,4'-piperidin]-6-yl}carbamate

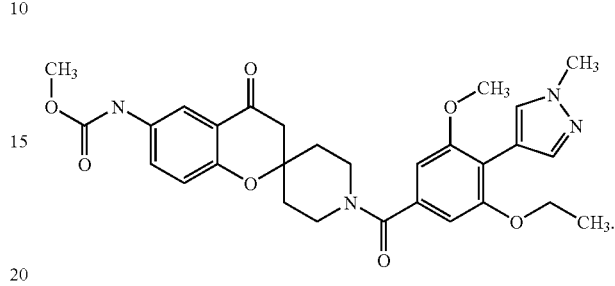

In the same manner as in Example 62, the title compound was obtained as a colorless foam from 3-ethoxy-5-methoxy-4-(1-methyl-1H-pyrazol-4-yl)benzoic acid and methyl (4 oxospiro[chroman-2,4'-piperidin]-6-yl)carbamate hydrochloride. ¹H-NMR (DMSO-D6) δ: 9.64 (1.0H, s), 8.04 (1.0H, s), 7.88 (1.0H, d, J=0.7 Hz), 7.84 (1.0H, s), 7.61 (1.0H, dd, J=9.0, 2.7 Hz), 7.03 (2.0H, d, J=9.0 Hz), 6.70-6.68 (2.0H, m), 4.32-4.15 (1.0H, br m), 4.07 (2.0H, q, J=7.0 Hz), 3.85 (3.0H, s), 3.82 (3.0H, s), 3.64 (3.0H, s), 3.61-3.08 (3.0H, br m), 2.83 (2.0H, s), 2.05-1.82 (2.0H, br m), 1.79-1.69 (2.0H, m), 1.36 (3.0H, t, J=7.0 Hz). MS [M+H]+=549.

Example 74

5-{1'-[3-Ethoxy-5-methoxy-4-(1-methyl-1H-pyrazol-4-yl)benzoyl]-4-oxospiro[chroman-2,4'-piperidin]-6-yl}-2-fluorobenzoic acid

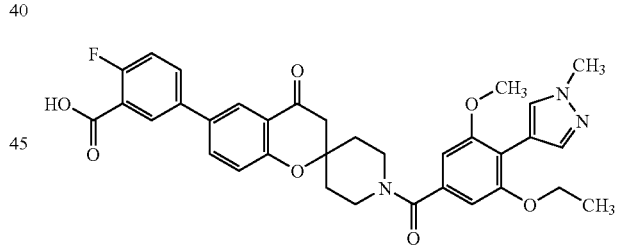

TEA (0.209 ml, 1.500 mmol) was added to a suspension of HOBT (92 mg, 0.600 mmol), EDCI (115 mg, 0.600 mmol), Methyl 2-fluoro-5-(4-oxospiro[chroman-2,4'-piperidin]-6-yl)benzoate hydrochloride (265 mg, 0.600 mmol) and 3-ethoxy-5-methoxy-4-(1-methyl-1H-pyrazol-4-yl)benzoic acid (138 mg, 0.5 mmol) in DME (2 ml) and the mixture was stirred at room temperature for over night. Water (ca 50 ml) was added to the mixture and stirred for 1 h. Resulted precipitate was collected by filtration. The solid was purified by silicagel column chromatography (CHCl3/MeOH) and then precipitated by EtOAc/hexane to obtain the ester of intended compound as pale yellow foam. Aqueous 1 N sodium hydroxide solution (0.75 mL) was added to a solution of the ester in methanol (2 ml) and THF (2 ml), stirred at room temperature for over night. The organic solvent was evaporated away and the residue was diluted with water. Aqueous 1N HCl aq. (1 ml) was added thereto at room temperature, and the resulted precipitate was collected, recrystallized from MeOH to afford the intended compound as a colorless solid. $^1$H-NMR (DMSO-d$_6$) δ: 8.04 (1.0H, s), 8.02 (1.0H, dd, J=7.0, 2.6 Hz), 7.95-7.91 (2.0H, m), 7.91-7.86 (2.0H, m), 7.37 (1.0H, dd, J=10.5, 8.8 Hz), 7.21 (1.0H, dd, J=6.0, 3.3 Hz), 6.72-6.70 (2.0H, m), 4.34-4.18 (1.0H, br m), 4.08 (2.0H, q, J=7.0 Hz), 3.85 (3.0H, s), 3.83 (3.0H, s), 3.64-3.10 (3.0H, m), 2.93 (2.0H, s), 2.12-1.88 (2.0H, m), 1.85-1.74 (2.0H, m), 1.37 (3.0H, t, J=7.0 Hz). MS [M+H]+=614.

Example 75

5-{1'-[3-Ethoxy-5-methoxy-4-(1-methyl-1H-pyrazol-4-yl)benzoyl]-4-oxospiro[chroman-2,4'-piperidin]-6-yl}nicotinic acid

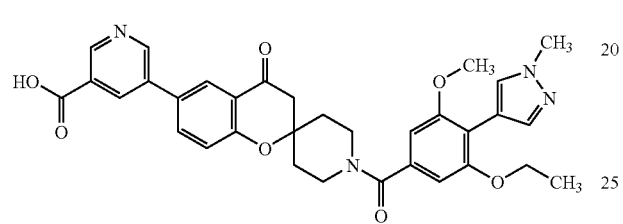

Aqueous 1 N sodium hydroxide solution (0.75 mL) was added to a solution of Methyl 5-{1'-[3-ethoxy-5-methoxy-4-(1-methyl-1H-pyrazol-4-yl)benzoyl]-4-oxospiro[chroman-2,4'-piperidin]-6-yl}nicotinate in MeOH (2 ml) and THF (2 ml) and stirred at room temperature for over night. The organic solvent was evaporated and diluted with water. Aqueous 1N HCl aq. (1 ml) was added thereto at room temperature, and the resulted solid was collected and recrystallized from MeOH to afford the intended compound as a colorless solid. $^1$H-NMR (DMSO-d$_6$) δ: 9.08 (1.0H, d, J=2.2 Hz), 9.02 (1.0H, d, J=1.7 Hz), 8.41 (1.0H, dd, J=2.2, 1.7 Hz), 8.07-8.03 (3.0H, m), 7.88 (1.0H, d, J=0.5 Hz), 7.27-7.24 (1.0H, m), 6.72-6.70 (2.0H, m), 4.33-4.19 (1.0H, br m), 4.09 (2.0H, q, J=7.0 Hz), 3.85 (3.0H, s), 3.83 (3.0H, s), 3.67-3.11 (3.0H, br m), 2.94 (2.0H, s), 2.12-1.89 (2.0H, br m), 1.84-1.77 (2.0H, m), 1.37 (3.0H, t, J=7.0 Hz). MS [M+H]+=597.

Example 76

6-(4-acetyl-piperazinyl)-1'-[3-ethoxy-5-methoxy-4-(1-methyl-1H-pyrazol-4-yl)benzoyl]spiro[chroman-2,4'-piperidin]-4-one

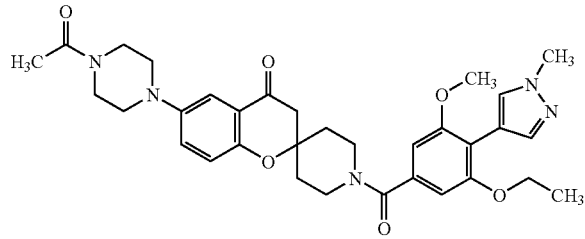

In the same manner as in Example 62, the title compound was obtained as a yellow foam from 3-ethoxy-5-methoxy-4-(1-methyl-1H-pyrazol-4-yl)benzoic acid and 6-(4-acetyl-1-piperazinyl)spiro[chroman-2,4'-piperidin]-4-one hydrochloride. $^1$H-NMR (DMSO-D6) δ: 8.04 (1.0H, s), 7.88 (1.0H, s), 7.35 (1.0H, dd, J=9.1, 3.0 Hz), 7.15 (1.0H, d, J=3.0 Hz), 7.00 (1.0H, d, J=9.1 Hz), 6.70-6.68 (2.0H, m), 4.28-4.16 (1.0H, br m), 4.08 (2.0H, q, J=7.0 Hz), 3.85 (3.0H, s), 3.82 (3.0H, s), 3.56-3.54 (4.0H, m), 3.38-3.18 (3.0H, m), 3.07-3.02 (2.0H, m), 3.01-2.96 (2.0H, m), 2.81 (2.0H, s), 2.06-1.83 (2.0H, br m), 2.02 (3.0H, s), 1.78-1.68 (2.0H, m), 1.36 (3.0H, t, J=7.0 Hz). MS [M+H]+=602.

Example 77

6-{1'-[3-ethoxy-5-methoxy-4-(1-methyl-1H-pyrazol-4-yl)benzoyl]-4-oxospiro[chroman-2,4'-piperidin]-6-yl}nicotinamide

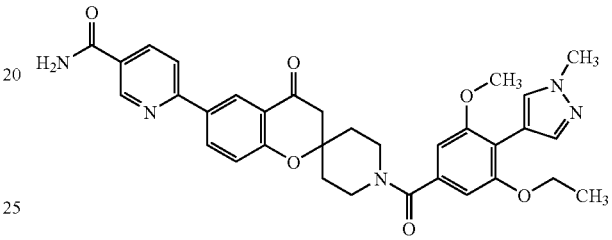

In the same manner as in Example 62, the title compound was obtained as a colorless solid from 3-ethoxy-5-methoxy-4-(1-methyl-1H-pyrazol-4-yl)benzoic acid and 6-(4-oxospiro[chroman-2,4'-piperidin]-6-yl)nicotinamide dihydrochloride. $^1$H-NMR (DMSO-D$_6$) δ: 9.08 (1.0H, dd, J=2.3, 0.6 Hz), 8.52 (1.0H, d, J=2.4 Hz), 8.39 (1.0H, dd, J=8.8, 2.4 Hz), 8.27 (1.0H, dd, J=8.5, 2.3 Hz), 8.18 (1.0H, s), 8.07 (1.0H, d, J=8.5 Hz), 8.04 (1.0H, s), 7.88 (1.0H, d, J=0.6 Hz), 7.59 (1.0H, s), 7.24 (1.0H, d, J=8.8 Hz), 6.72-6.70 (2.0H, m), 4.33-4.20 (1.0H, br m), 4.08 (2.0H, q, J=7.0 Hz), 3.85 (3.0H, s), 3.83 (3.0H, s), 3.65-3.19 (3.0H, br m), 2.95 (2.0H, s), 2.11-1.88 (2.01, br m), 1.86-1.76 (2.0H, m), 1.37 (3.0H, t, J=7.0 Hz). MS [M+H]+=596.

Example 78

N-(2,2-difluoroethyl)-1'-[3-ethoxy-5-methoxy-4-(1-methyl-1H-pyrazol-4-yl)benzoyl]-4-oxospiro[chroman-2,4'-piperidine]-6-carboxamide

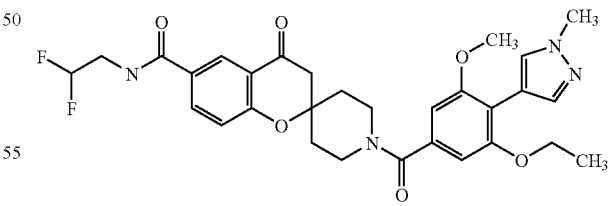

In the same manner as in Example 62, the title compound was obtained as a colorless solid from 3-ethoxy-5-methoxy-4-(1-methyl-1H-pyrazol-4-yl)benzoic acid and N-(2,2-difluoroethyl)-4-oxospiro[chroman-2,4'-piperidine]-6-carboxamide hydrochloride. $^1$H-NMR (DMSO-D$_6$) δ: 8.95 (1.0H, t, J=6.0 Hz), 8.32 (1.0H, d, J=2.4 Hz), 8.09 (1.0H, dd, J=8.8, 2.4 Hz), 8.04 (1.0H, s), 7.88 (1.0H, d, J=0.7 Hz), 7.19 (1.0H, d, J=8.8 Hz), 6.71-6.69 (2.0H, m), 6.09 (1.0H, U, J=56.0, 4.1 Hz), 4.33-4.16 (1.0H, br m), 4.08 (2.0H, q, J=7.0

Hz), 3.85 (3.0H, s), 3.81 (3.0H, d, J=13.7 Hz), 3.70-3.58 (2.0H, m), 3.60-3.13 (3.0H, br m), 2.91 (2.0H, s), 2.08-1.86 (2.0H, br m), 1.85-1.73 (2.0H, m), 1.37 (3.0H, t, J=7.0 Hz). MS [M+H]+=583.

Example 79

1'-[3-Ethoxy-5-methoxy-4-(1-methyl-1H-pyrazol-4-yl)benzoyl]-6-(1-methyl-1H-pyrazol-4-yl)spiro[chroman-2,4'-piperidin]4-one

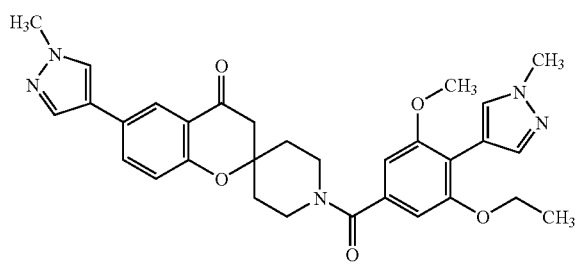

In the same manner as in Example 62, the title compound was obtained as a colorless solid from 3-ethoxy-5-methoxy-4-(1-methyl-1H-pyrazol-4-yl)benzoic acid and 6-(1-methyl-1H-pyrazol-4-yl)spiro[chroman-2,4'-piperidin]-4-one hydrochloride. $^1$H-NMR (DMSO-D$_6$) δ: 8.13 (1.0H, s), 8.04 (1.0H, s), 7.88 (1.0H, d, J=0.7 Hz), 7.83 (1.0H, d, J=2.2 Hz), 7.82 (1.0H, d, J=0.7 Hz), 7.78 (1.0H, dd, J=8.5, 2.2 Hz), 7.09 (1.0H, d, J=8.5 Hz), 6.71-6.69 (2.0H, m), 4.31-4.17 (10H, br m), 4.08 (2.0H, q, J=7.0 Hz), 3.85 (3.0H, s), 3.83 (3.0H, s), 3.83 (3.0H, s), 3.63-3.14 (3.0H, m), 2.88 (2.0H, s), 2.10-1.87 (2.0H, m), 1.81-1.72 (2.0H, m), 1.37 (3.0H, t, J=7.0 Hz). MS [M+H]+=556.

Example 80

1'-[(3-Methyl-1-phenyl-1H-furo[2,3-c]pyrazol-5-yl)carbonyl]-6-(tetrazol-5-yl)spiro[chroman-2,4'-piperidin]-4-one

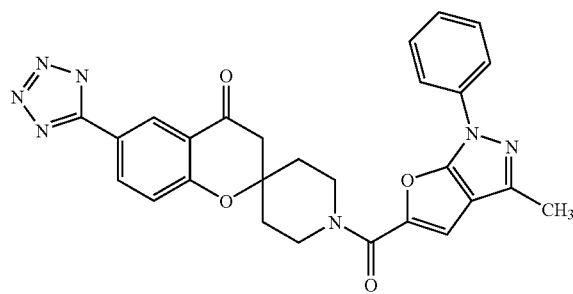

In the same manner as in Example 36, the title compound was obtained as a colorless solid from 3-methyl-1-phenyl-1H-furo[2,3-c]pyrazole-5-carboxylic acid and 6-(tetrazol-5-yl)spiro[chroman-2,4'-piperidin]-4-one hydrochloride. $^1$H-NMR (400 MHz, DMSO-D6) δ: 8.44 (1H, d, J=2.2 Hz), 8.25 (1H, dd, J=8.6, 2.2 Hz), 7.77 (2H, d, J=8.3 Hz), 7.54 (2H, s), 7.38-7.25 (3H, m), 4.25-4.16 (2H, br m), 3.60-3.33 (2H, br m), 3.00 (2H, s), 2.39 (3H, s), 2.11-1.80 (4H, m). MS [M+H]+=510.

Example 81

Sodium 5-[3-cyclopropyl-5-({6-[(1-methyl-1H-pyrazol-5-yl)amino]-4-oxospiro[chroman-2,4'-piperidin]-1'-yl}carbonyl)-1H-indol-1-yl]tetrazolide

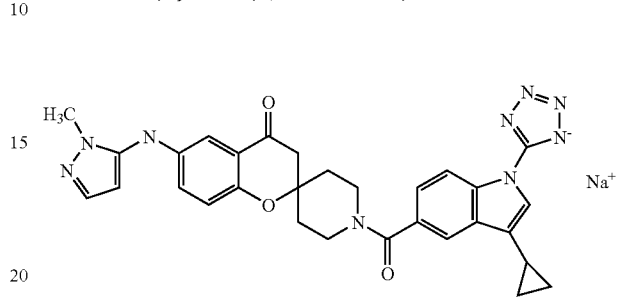

Aqueous 5N sodium hydroxide (0.5 mL) was added to a solution of Methyl 3-cyclopropyl-1-(tetrazol-5-yl)-1H-indole-5-carboxylate (200 mg) in MeOH and stirred at 60° C. for over night. Aqueous 5N hydrochloric acid (0.52 mL) was added to the reaction mixture and the solvent was removed under reduced pressure. The residue was dissolved in DMF (4 mL), and 6-[(1-methyl-1H-pyrazol-5-yl)amino]spiro[chroman-2,4'-piperidin]-4-one hydrochloride (244 mg), triethylamine (0.2 mL), HOBt (128 mg) and EDCI (160 mg) were added thereto. The reaction mixture was stirred at 90° C. for 1 hour. Water was added thereto at room temperature, and resulted precipitate was collected, dried under reduced pressure. The solid washed with a mixed solvent of MeOH and diethyl ether, and dried under reduced pressure to obtain the intended compound as a colorless solid. $^1$H-NMR (DMSO-D$_6$) δ: 8.27 (1H, d, J=8.5 Hz), 7.93 (1H, s), 7.82 (1H, d, J=1.0 Hz), 7.65 (1H, d, J=1.0 Hz), 7.44 (1H, dd, J=8.5, 1.7 Hz), 7.33 (1H, d, J=1.7 Hz), 7.17-7.13 (2H, m), 7.02-6.98 (1H, m), 5.90 (1H, d, J=1.7 Hz), 4.35-4.12 (1H, br m), 3.61 (3H, s), 3.47-3.30 (3H, br m), 2.82 (2H, s), 2.10-1.70 (5H, br m), 0.99-0.93 (2H, m), 0.75-0.70 (2H, m). MS[M+H]+=564

REFERENCE EXAMPLES

Abbreviations in Reference Examples and Examples have the following meanings. MeOH: methanol; MeO: methoxy; DMF: N,N-dimethylformamide; Zn(CN)2: zinc cyanide; Pd(PPh3)4: tetrakis(triphenylphosphine)palladium(0); EtOAc: ethyl acetate; HCl: hydrogen chloride or hydrochloric acid; CHCl3: chloroform; BuOH: butanol; WSC: 1-(3-dimethylaminopropyl)-3-ethylcarbodiimide; DMAP: 4-dimethylaminopyridine; NaOH: sodium hydroxide; MgSO4: magnesium sulfate; Pd(OAc)$_2$: palladium(II) acetate; DPPF: 1,1'-bis(diphenylphosphino)ferrocene; AcOK: potassium acetate; Na2CO3: sodium carbonate; AcOEt: ethyl acetate; Et$_2$O: diethyl ether; EtOH: ethanol; EtO: ethoxy; THF: tetrahydrofuran; NaBH4: sodium borohydride; NH4Cl: ammonium chloride; Na2SO4: sodium sulfate; TBSCl: tert-butyldimethylchlorosilane; Et3N: triethylamine; NaHCO3: sodium bicarbonate; CH3CN: acetonitrile; MS 4A: molecular sieves 4A; NMO: 4-methylmorpholine N-oxide; TPAP: tetrapropylammonium perruthenate; K3PO4: potassium phosphate, tribasic; DME: 1,2-dimethoxyethane; DIBOC: di-tert-butyl dicarbonate; EDCI: 1-(3-dimethylaminopropyl)-3-ethylcarbodiimide hydrochloride; HOBT: 1-hydroxybenzotriazole hydrate; TEA: triethylamine; tBu2-P-Ph-Ph: 2-(di-t-butylphosphino)biphenyl; PdCl2(PPh3)2: bis(triphenylphosphine)palladium(II) chloride; NaOMe: sodium methoxide; DMA: N,N-dimethylacetamide; Pd2(dba)3: tris(dibenzylideneacelone)dipalladium(0); POCl₃: phosphorus oxychloride; Bu4NBr: tetrabutylammonium bromide; PdCl2(dppf): 1,1'-bis(diphenyl-phosphino)ferrocenedichloro palladium(II); KHSO4: potassium hydrogen sulfate; TBAF: tetrabutylammonium fluoride; rt: room temperature; SEM: trimethylsilylethoxymethyl; Bn: benzyl.

Reference Example 1 tert-Butyl 6-bromo-4-oxospiro[chroman-2,4'-piperidine]-1'-carboxylate

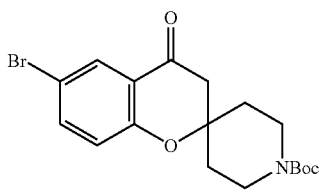

A mixture of 5-bromo-2-hydroxyacetophenone (104.35 g, 485.26 mmol), N-Boc-piperidin-4-one (98.62 g, 494.96 mmol), 20 mL of pyrrolidine (17.26 g, 242.63 mmol) and 261 mL of MeOH was heated under reflux until the reaction was complete. The mixture was cooled, then 87 mL of H₂O were added, and the mixture was filtered and dried to give tert-butyl 6-bromo-4-oxospiro-[chroman-2,4'-piperidine]-1'-carboxylate. Alternatively, 10 mL of pyrrolidine (121.31 mmol) may be used in this procedure.

Reference Example 2 tert-Butyl 6-cyano-4-oxospiro[chroman-2,4'-piperidine]-1'-carboxylate

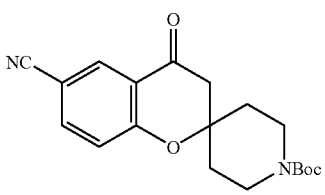

To a solution of tert-butyl 6-bromo-4-oxospiro[chroman-2,4'-piperidine]-1'-carboxylate (6593 g, 16.6 mol) and DMF (33 L) was added Zn(CN)₂ (1947 g, 16.6 mol) and Pd(PPh₃)₄ (192 g, 0.17 mol). The slurry was heated to 90° C. for 3 hours, then cooled to room temperature and filtered. Water (16 L) was added to the filtrate. The resulting slurry was cooled to 5° C., stirred for 1 hour and filtered. The solid was washed with DMF/water (2:1) and dried under vacuum to give tert-butyl 6-cyano-4-oxospiro[chroman-2,4'-piperidine]-1'-carboxylate.

Reference Example 3 tert-Butyl 4-oxo-6-(tetrazol-5-yl)spiro[chroman-2,4'-piperidine]-1'-carboxylate

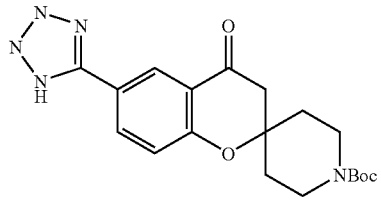

A solution of 23 g of tert-butyl 6-cyano-4-oxospiro[chroman-2,4'-piperidine]-1'-carboxylate (67.17 mmol), 13.10 g sodium azide (201.52 mmol), 27.74 g of triethylamine hydrochloride (201.52 mmol), and 460 mL of dry DMF was stirred under a nitrogen atmosphere at 100° C. for 12 hours. After cooling to room temperature, 506 mL of EtOAc were added, followed by 322 mL of 1M HCl (322 mmol). Alternatively, 0.5M HCl maybe added until pH=3. The resulting layers were separated, the organic layer was washed with water/methanol (115 mL/46 mL), and then concentrated to give tert-butyl 4-oxo-6-(tetrazol-5-yl)spiro[chroman-2,4'-piperidine]-1'-carboxylate.

Reference Example 4

6-(Tetrazol-5-yl)spiro[chroman-2,4'-piperidin]-4-one hydrochloride salt

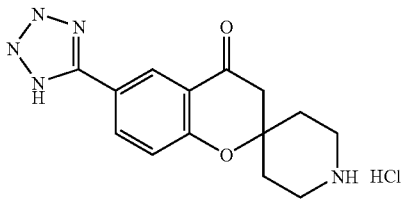

A solution of 5.08 g of tert-butyl 4-oxo-6-(tetrazol-5-yl)spiro[chroman-2,4'-piperidine]-1'-carboxylate (13.18 mmol), 8.8 mL of 12 M HCl (105.44 mmol) and 8 mL of methanol was heated to 50° C. until the reaction was complete. The resulting slurry was filtered, washed with 25 mL of methanol at room temperature, and dried to give 6-(tetrazol-5-yl)spiro[chroman-2,4'-piperidin]-4-one hydrochloride salt.

Reference Example 5

5-Bromonicotinic acid tert-butyl ester

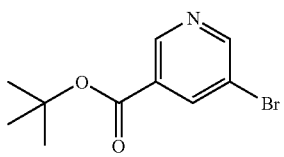

5-Bromo-nicotinic acid (20.2 g, 100 mmol) was dissolved in CHCl₃ (200 mL) and tert-BuOH (40 mL); and WSC-HCl (21.1 g, 110 mmol) and DMAP (21.1 g, 110 mmol) was added thereto in order, and stirred at room temperature over night. The reaction mixture was diluted with chloroform, washed with 0.5N HCl aq. (220 mL), 0.5N NaOH aq. (100 mL), brine Reference Example 6

5-{1'-tert-Butoxycarbonyl-4-oxospiro[chroman-2,4'-piperidin]-6-yl}nicotinic acid tert-butyl ester

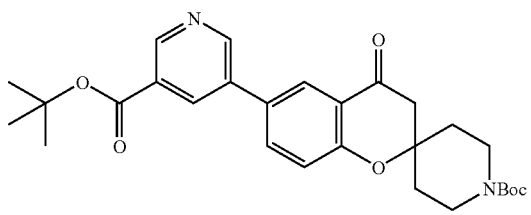

Tert-butyl 6-bromo-4-oxospiro[chroman-2,4'-piperidine]-1'-carboxylate (19.8 g, 50.0 mmol), bis(pinacolato)diboran (14.0 g, 55.0 mmol), Pd(OAc)$_2$ (560 mg, 2.50 mmol), DPPF (2.77 g, 5.00 mmol), and AcOK (5.82 g, 60.0 mmol) were suspended in dioxane (250 mL) and heated at 100° C. for 10 hours. After cooling down to room temperature, 5-bromo-nicotinicacid tert-butyl ester (14.2 g, 55.0 mmol), Pd(PPh$_3$)$_4$ (5.78 g, 5.00 mmol) and 2M Na$_2$CO$_3$ aq. (125 mL, 250 mmol) were added to the reaction mixture; and then heated at 100° C. for 15 hours. The reaction mixture was diluted with EtOAc and H$_2$O, organic layer was washed with brine and dried over MgSO$_4$. After filtration, the solvents were removed in vacuo and the residue was purified by silica gel column chromatography (hexane/EtOAc=10/0 to 6/4) and the obtained brown solid was crystallized from EtOAc/hexane (1/1) to afford 5-{1'-tert-butoxycarbonyl-4-oxospiro[chroman-2,4'-piperidin]-6-yl}nicotinic acid tert-butyl ester as a pale yellow solid.

Reference Example 7

5-{4-Oxospiro[chroman-2,4'-piperidin]-6-yl}nicotinic acid di-hydrochloride

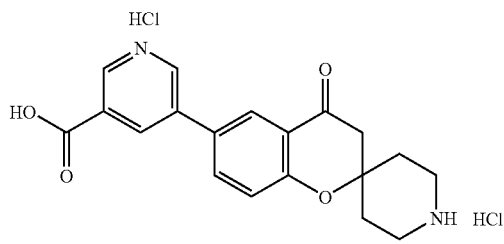

5-{1'-tert-butoxycarbonyl-4-oxospiro[chroman-2,4'-piperidin]-6-yl}nicotinic acid tert-butyl ester (14.0 g, 28.3 mmol) was dissolved in CHCl$_3$ (70 mL) and 4N HCl in dioxane (210 mL) was added thereto, and stirred at room temperature for 20 h. The resulted precipitate was filtered and washed with CHCl$_3$ and Et$_2$O to afford 5-{4-oxospiro[chroman-2,4'-piperidin]-6-yl}nicotinic acid di-hydrochloride as a colorless solid.

Reference Example 8 tert-Butyl 6-cyano-4-hydroxy-spiro[chroman-2,4'-piperidine]-1'-carboxylate

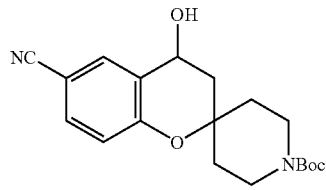

To a solution of 15 g of tert-butyl 6-cyano-4-oxospiro[chroman-2,4'-piperidine]-1'-carboxylate in 250 mL of EtOH-THF(1:4) at 0° C. was added NaBH$_4$ portionwise, and the reaction mixture was allowed to warm up to rt. After stirring for 1 h, NH$_4$Cl aqueous was added to the reaction mixture and the aqueous mixture was extracted with AcOEt twice. The combined organic layers were washed with brine, dried over Na$_2$SO$_4$, filtered, and concentrated in reduced pressure to give the intended compound as a pale yellow solid.

Reference Example 9 tert-Butyl 4-{[tert-butyl(dimethyl)silyl]oxy}-6-cyano-spiro[chroman-2,4'-piperidine]-1'-carboxylate

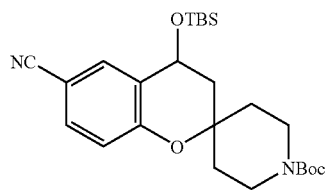

To a solution of 15.1 g of tert-butyl 6-cyano-4-hydroxy-spiro[chroman-2,4'-piperidine]-1'-carboxylate in DMF were added 3.6 g of imidazole and 7.95 g of TBSCl at rt, and the reaction mixture was stirred at rt for 1d. To this reaction mixture was added 598 mg of imidazole and 1.3 g of TBSCl at rt, and the reaction mixture was stirred at rt for 1d. The reaction mixture was poured into ice-cold brine, and the aqueous mixture was extracted with AcOEt twice. The combined organic layers were washed with H$_2$O and brine, dried over Na$_2$SO$_4$, filtered, and concentrated in reduced pressure. The residue was purified by column chromatography on silica gel using a mixture of hexane and AcOEt (100/0-80/20) as eluent to give the intended compound.

Reference Example 10 tert-Butyl 6-[amino(hydroxyimino)methyl]-4-{[tert-butyl(dimethyl)silyl]oxy}-spiro[chroman-2,4'-piperidine]-1'-carboxylate

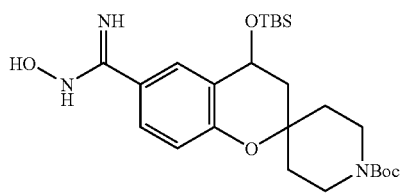

To a suspension of 18.2 g of tert-butyl 4-{[tert-butyl(dimethyl)silyl]oxy}-6-cyano-spiro[chroman-2,4'-piperidine]-1'-carboxylate in EtOH was added 16.3 mL of $Et_3N$ and 8.12 g of hydroxyamine hydrochloride at rt, and the reaction mixture was stirred at 85° C. for 1d. The resultant solution was cooled to rt, and concentrated in reduced pressure. To the residue was added $H_2O$, the resultant white solid was filtered, washed with $H_2O$, and dried in vacuo to give a crude product, which was used in the next step without further purification.

Reference Example 11 tert-Butyl 6-{amino[({[(2-ethylhexyl)oxy]carbonyl}oxy)-imino]methyl}-4-{[tert-butyl(dimethyl)silyl]oxy}spiro[chroman-2,4'-piperidine]-1'-carboxylate

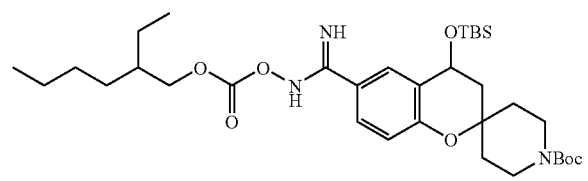

To a solution of tert-butyl 6-[amino(hydroxyimino)methyl]-4-{[tert-butyl(dimethyl)silyl]oxy}-spiro[chroman-2,4'-piperidine]-1'-carboxylate in 80 mL of DMF were added 3.78 mL of pyridine and 8.4 mL of 2-Ethylhexyl chloroformate at 0° C., and the reaction mixture was stirred at 0° C. for 1.5 h. The reaction mixture was poured into ice-cold brine, and extracted with AcOEt twice. The combined organic layers were washed with $H_2O$ and brine, dried over $Na_2SO_4$, filtered, and concentrated in reduced pressure to give a crude product, which was used in the next step without further purification.

Reference Example 12 tert-Butyl 4-{[tert-butyl(dimethyl)silyl]oxy}-6-(5-oxo-4,5-dihydro-1,2,4-oxadiazol-3-yl)-spiro[chroman-2,4'-piperidine]-1'-carboxylate

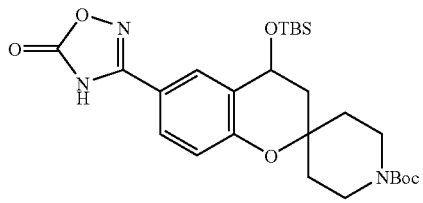

A solution of tert-butyl 6-{amino[({[(2-ethylhexyl)oxy]carbonyl}oxy)imino]methyl}-4-{[tert-butyl(dimethyl)silyl]oxy}-spiro[chroman-2,4'-piperidine]-1'-carboxylate in 100 mL of xylene was stirred at 145° C. for 14 h. The reaction mixture was cooled to rt, and concentrated in reduced pressure. The residue was purified by column chromatography on silica gel using a mixture of hexane-AcOEt (100/1-35/65) as an eluent to give the product as an off-white solid.

Reference Example 13 tert-Butyl 4-hydroxy-6-(5-oxo-4,5-dihydro-1,2,4-oxadiazol-3-yl)-spiro[chroman-2,4'-piperidine]-1'-carboxylate

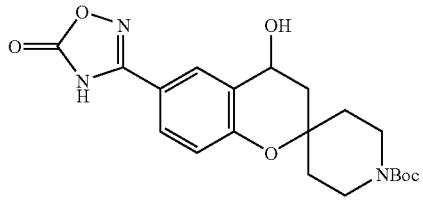

To a solution of 13.4 g of tert-butyl 4-([tert-butyl(dimethyl)silyl]oxy)-6-(5-oxo-4,5-dihydro-1,2,4-oxadiazol-3-yl)-spiro[chroman-2,4'-piperidine]-1'-carboxylate in 200 mL of EtOH-THF (5.5:1) at 0° C. was added 67 ml of 1M HClaq dropwise, and the reaction mixture was stirred at rt for 18 h. The reaction mixture was cooled to 0° C., and the mixture was basified with $NaHCO_3$. The mixture was concentrated in reduced pressure, and the residue was acidified with 1M HClaq. The aqueous mixture was extracted with a mixture of $CHCl_3$-MeOH (9:1) three times, and the combined organic layers was washed with brine, dried over $Na_2SO_4$, and concentrated in reduces pressure to give the product as a pale brown solid.

Reference Example 14 tert-Butyl 4-oxo-6-(5-oxo-4,5-dihydro-1,2,4-oxadiazol-3-yl)-spiro[chroman-2,4'-piperidine]-1'-carboxylate

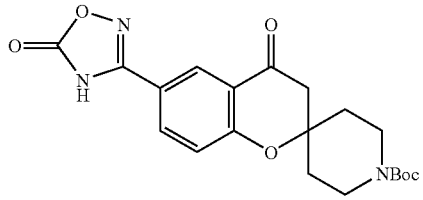

To a solution of 1.0 g of tert-butyl 4-hydroxy-6-(5-oxo-4,5-dihydro-1,2,4-oxadiazol-3-yl)-spiro[chroman-2,4'-piperidine]-1'-carboxylate in 40 ml of THF-CH₃CN (1:1) ar rt were added 2.0 g of MS 4A, 435 mg of NMO, and 88 mg of TPAP, and the reaction mixture was stirred at rt overnight. The mixture was filtered through a Celite pad, washed with CHCl₃ and CHCl₃-MeOH (9:1), and the filtrate was concentrated in reduced pressure. The residue was purified by column chromatography on silica gel using a mixture of hexane-AcOEt (100/0-0/100) as eluent to give the intended compound as a colorless solid.

Reference Example 15

6-(5-Oxo-4,5-dihydro-1,2,4-oxadiazol-3-yl)spiro[chroman-2,4'-piperidin]-4-one hydrochloride

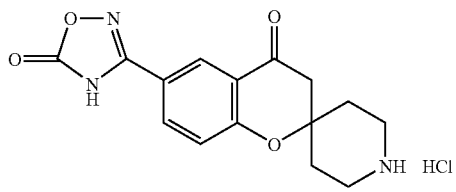

A suspension of 437 mg of tert-butyl 4-oxo-6-(5-oxo-4,5-dihydro-1,2,4-oxadiazol-3-yl)-spiro[chroman-2,4'-piperidine]-1'-carboxylate in 10 mL of 4N HCl in dioxane was stirred at rt for 1d, the resultant white solid was filtered, and washed with ether. The collected white solid was dried in vacuo at 50° C. to give the intended compound as a colorless solid.

Reference Example 16

1'-tert-Butoxycarbonyl-6-(4",4",5",5"-tetramethyl-1",3",2"-dioxaborolan-2"-yl)spiro[chroman-2,4'-piperidin]-4-one

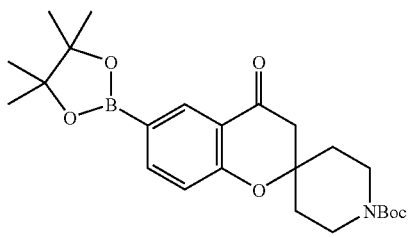

Tert-Butyl 6-bromo-4-oxospiro[chroman-2,4'-piperidine]-1'-carboxylate (99.0 g, 250 mmol), bis(pinacolato)diboran (70.2 g, 275 mmol), Pd(OAc)₂ (2.80 g, 12.5 mmol), DPPF (13.9 g, 25.0 mmol), and AcOK (29.1 g, 300 mmol) were suspended in dioxane (500 ml) and heated at 100° C. for 20 h. After cooling down to room temperature, MeOH (500 ml) was added and further stirred for 1 h. The resulted precipitate was filtered and the cake was washed with MeOH to obtain the intended compound as a pale brown solid.

Reference Example 17

5"-{1'-tert-Butoxycarbonyl]-4-oxospiro[chroman-2,4'-piperidin]-6-yl}nicotinic acid methyl ester

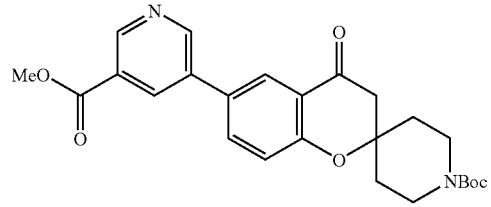

1'-tert-butoxycarbonyl-6-(4",4",5",5"-tetramethyl-1",3",2"-dioxaborolan-2"-yl)spiro[chroman-2,4'-piperidin]-4-one (2.00 g, 4.51 mmol), 5-bromonicotinic acid methyl ester (1.17 g, 5.42 mmol), Pd(OAc)₂ (50.6 mg, 0.226 mmol), DPPF (250 mg, 0.451 mmol), and K₃PO₄ (1.91 g, 9.02 mmol) were suspended in DME (500 ml) and heated at 100° C. for 18 h. The reaction mixture was filtered through Celite, the residue on the Celite was washed with chloroform, and the filtrate and the washing were combined and concentrated under a reduced pressure. The resulting residue was purified through silica gel column chromatography (hexane/EtOAc=10/0 to 2/8) to obtain the intended compound as a pale yellow foam.

Reference Example 18

5"-{4-Oxospiro[chroman-2,4'-piperidin]-6-yl}nicotinic acid methyl ester di-hydrochloride

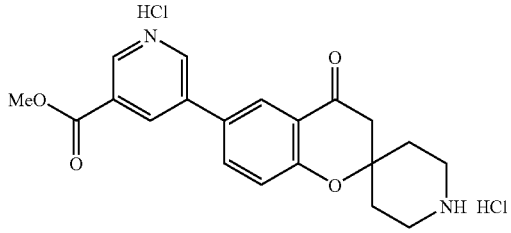

5"-{1'-tert-butoxycarbonyl]-4-oxospiro[chroman-2,4'-piperidin]-6-yl}nicotinic acid methyl ester (22.0 g, 48.6 mmol) was suspended in MeOH (110 ml) and 4N HCl in dioxane (220 ml) was added thereto, and stirred at room temperature for 14 h. The solvents were removed in vacuo and the resulting solid was washed with MeOH/Et₂O (50 ml/200 ml) to obtain the intended compound as a colorless solid.

Reference Example 19

3"-{1'-tert-Butoxycarbonyl]-4-oxospiro[chroman-2,4'-piperidin]-6-yl}benzoic acid

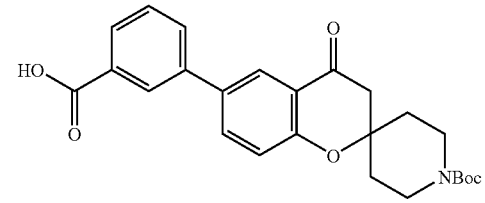

Tert-butyl 6-bromo-4-oxospiro[chroman-2,4'-piperidine]-1'-carboxylate (39.6 g, 100 mmol), 3-carboxy-phenylboronicacid (16.6 g, 100 mmol), Pd(PPh₃)₄ (5.78 g, 5.00 mmol), and 2M Na₂CO₃ aq. (250 ml, 500 mmol) were suspended in 1,4-dioxane (400 ml) and heated at 100° C. for 18 h. The reaction mixture was diluted with CHCl₃ and dil HCl aq. (1.1 mol), the aqueous layer was extracted with CHCl₃. The combined organic layer was washed with H₂O and brine, dried over MgSO₄. The desiccant was removed through filtration and the filtrate was concentrated under reduced pressure. The residue was triturated with EtOAc and the insoluble solid was collected through filtration to obtain the intended compound as a colorless solid.

Reference Example 20

3-(4-Oxospiro[chroman-2,4'-piperidin]-6-yl)benzoic acid hydrochloride

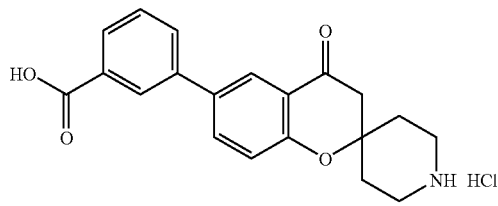

The intended compound was produced according to the procedure described in Reference Example 18 but using 3"-{1'-tert-butoxycarbonyl]-4-oxospiro[chroman-2,4'-piperidin)-6-yl}benzoic acid. in place of 5"-{1'-tert-butoxycarbonyl]-4-oxospiro[chroman-2,4'-piperidin]-6-yl}nicotinic acid methyl ester.

Reference Example 21

Methyl 3"-{1'-tert-butoxycarbonyl]-4-oxospiro[chroman-2,4'-piperidin]-6-yl}benzoate

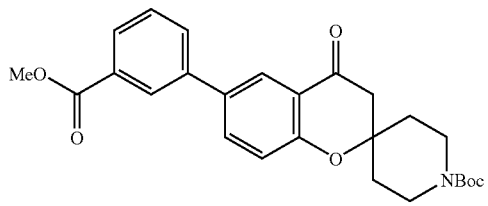

3"-{1'-tert-butoxycarbonyl]-4-oxospiro[chroman-2,4'-piperidin]-6-yl}benzoic acid (24.0 g, 54.9 mmol) was dissolved in CHCl₃ (120 ml), and MeOH (24 ml), WSC—HCl (15.8 g, 82.4 mmol) and DMAP (10.0 g, 82.4 mmol) was added thereto in this order, and the mixture was stirred at room temperature overnight. The reaction mixture was diluted with CHCl₃ and diluted HCl aq. (220 mmol). The organic layer was washed with 0.5N NaOH aq., brine and dried over MgSO₄ and silica gel. The desiccant was removed through filtration and the filtrate was concentrated under reduced pressure. The residue was triturated with MeOH and the insoluble solid was collected through filtration to obtain the intended compound as a pale yellow solid.

Reference Example 22

Methyl 5-{4-oxospiro[chroman-2,4'-piperidin]-6-yl}benzoate hydrochloride

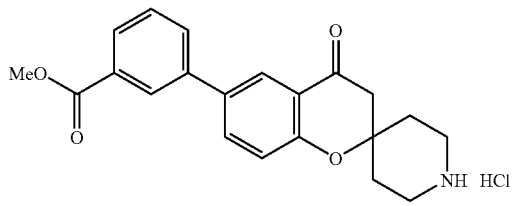

The intended compound was produced according to the Reference Example 18 but using methyl 3"-{1-tert-butoxycarbonyl]-4-oxospiro[chroman-2,4'-piperidin]-6-yl}benzoate in place of 5'-{1'-tert-butoxycarbonyl]-4-oxospiro[chroman-2,4'-piperidin]-6-yl}nicotinic acid methyl ester.

Reference Example 23

5"-{1'-tert-Butoxycarbonyl]-4-oxospiro[chroman-2,4'-piperidin]-6-yl}nicotinamide

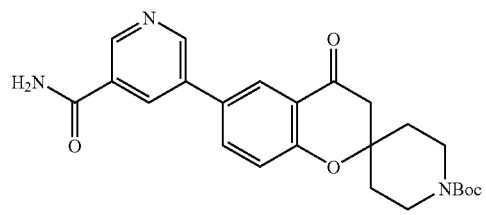

The intended compound was produced according to the procedure described in Reference Example 17 but using 5-bromonicotinamide in place of 5-bromonicotinic acid methyl ester.

Reference Example 24

5"-{4-Oxosipiro[chroman-2,4'-piperidin]-6-yl}nicotinamide di-hydrochloride

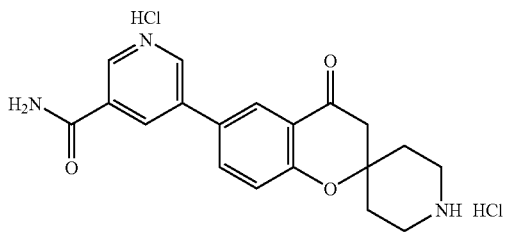

5"-{1'-tert-butoxycarbonyl]-4-oxospiro[chroman-2,4'-piperidin]-6-yl}nicotinamide (1.30 g) was suspended in dioxane (10 ml) and 4N HCl in dioxane (20 ml) was added thereto, and stirred at room temperature for 18 h. The resulted precipitate was filtered, washed with dioxane and Et₂O to obtain the intended compound as a colorless solid.

Reference Example 25

4-Oxospiro[chroman-2,4'-piperidine]-6-carboxylic acid hydrochloride

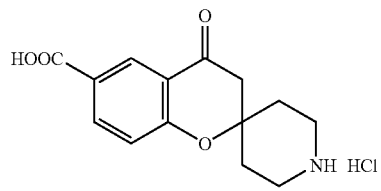

Tert-butyl 6-cyano-4-oxospiro[chroman-2,4'-piperidine]-1'-carboxylate (20.0 g, 58.5 mmol) was suspended in dioxane (50 ml)-6N HCl aq. (200 ml) and was heated at 120° C. for 20 h. After removal of the solvents in vacuo, the residue was triturated with H₂O and the insoluble solid was collected through filtration to obtain the intended compound as a colorless solid.

Reference Example 26 tert-Butyl 6-carboxy-4-oxospiro[chroman-2,4'-piperidine]-1'-carboxylate

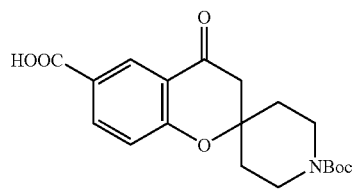

4-Oxospiro[chroman-2,4'-piperidine]-6-carboxylic acid hydrochloride (15.0 g, 50.3 mmol) was dissolved in 1,4-dioxane (150 ml) and H₂O (150 ml), NaHCO₃ (10.6 g, 126 mmol) and DIBOC (13.2 g, 60.4 mmol) were added thereto in this order. After stirred at room temperature for 13 h, the reaction mixture was diluted with Et₂O and 5N NaOH aq. (12.1 ml). The aqueous layer was washed with Et₂O and acidified with 6N HCl aq. (PH=ca. 3), then extracted with CHCl₃. The organic layer was washed with brine and dried over MgSO₄. The desiccant was removed through filtration and the filtrate was concentrated under reduced pressure. The residue was triturated with MeOH—H₂O and the insoluble solid was collected through filtration to obtain the intended compound as a colorless solid.

Reference Example 27

3-(4-Oxospiro[chroman-2,4'-piperidin]-6-yl)benzamide hydrochloride

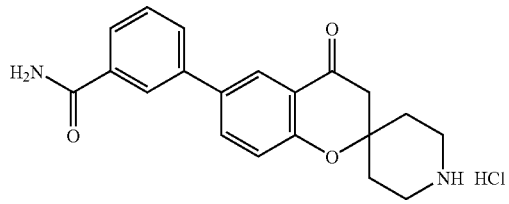

The intended compound was produced according to the procedure described in Reference Example 19 and 24 but using [3-(aminocarbonyl)phenyl]boronic acid in place of 3-carboxy-phenylboronicacid.

Reference Example 28

Methyl 4-(4-oxo-spiro[chroman-2,4'-piperidin]-6-yl)pyridine-2-carboxylate dihydrochloride

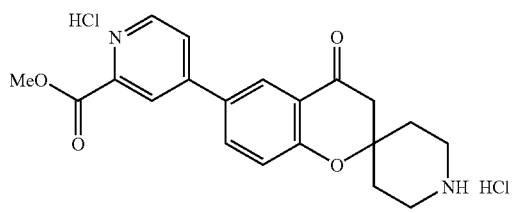

The intended compound was produced according to the procedure described in Reference Example 17 and 18 but using methyl 4-bromopyridine-2-carboxylate in place of 5-bromonicotinic acid methyl ester.

Reference Example 29

Methyl 2-(4-oxo-[chroman-2,4'-piperidin]-6-yl)pyridine-4-carboxylate dihydrochloride

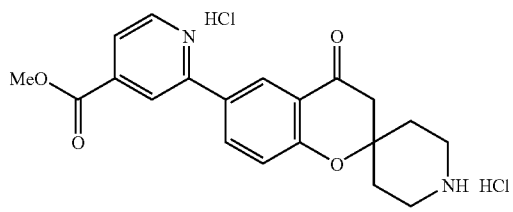

The intended compound was produced according to the procedure described in Reference Example 17 and 18 but using methyl 2-bromopyridine-4-carboxylate in place of 5-bromonicotinic acid methyl ester.

Reference Example 30

Methyl 5-(4-oxo-spiro[chroman-2,4'-piperidin]-6-yl)pyridine-2-carboxylate dihydrochloride

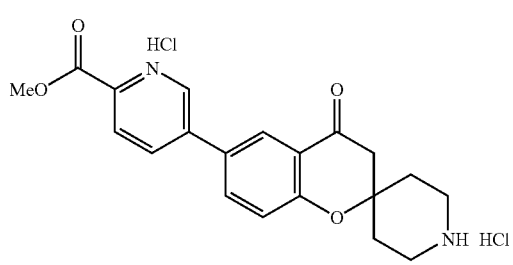

The intended compound was produced according to the procedure described in Reference Example 17 and 18 but using methyl 5-bromopyridine-2-carboxylate in place of 5-bromonicotinic acid methyl ester.

Reference Example 31 tert-Butyl 6-[6-(methoxy)pyridin-3-yl]-4-oxo-spiro[chroman-2,4'-piperidine]-1'-carboxylate

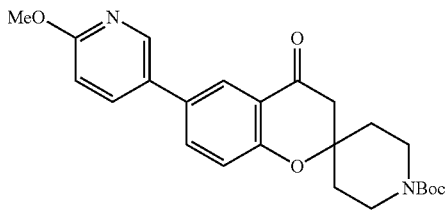

The intended compound was produced according to the procedure described in Reference Example 19 but using [6-(methoxy)pyridin-3-yl]boronic acid in place of 3-carboxyphenylboronicacid.

Reference Example 32

6-[6-(Methoxy)pyridin-3-yl]spiro[chroman-2,4'-piperidin]-4-one dihydrochloride

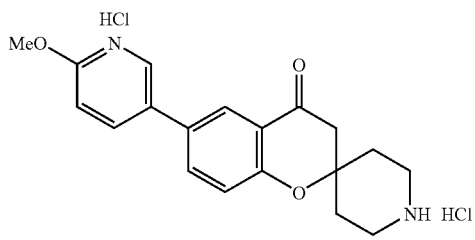

The intended compound was produced according to the procedure described in Reference Example 24 but using 6-[6-(methoxy)pyridin-3-yl]-4-oxo-spiro[chroman-2,4'-piperidine)-1'-carboxylate in place of 5''-{1'-tert-butoxycarbonyl]-4-oxospiro[chroman-2,4'-piperidin]-6-yl}nicotinamide.

Reference Example 33

6-(6-Oxo-1,6-dihydropyridin-3-yl)spiro[chroman-2,4'-piperidin]-4-one hydrochloride

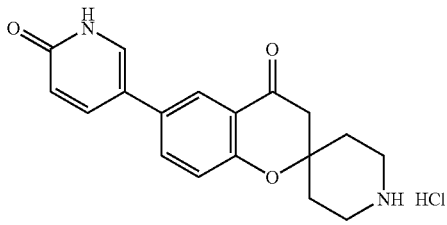

Tert-Butyl 6-[6-(methoxy)pyridin-3-yl]-4-oxo-spiro[chroman-2,4'-piperidine]-1'-carboxylate (550 mg) was suspended in conc. HCl aq. (10 ml) and stirred at 100 deg. for 20 h. After removal of the solvent, the resulted solid was washed with MeOH and Et$_2$O to obtain the intended compound as a colorless solid.

Reference Example 34 tert-Butyl 6-[(1-methyl-1H-pyrazol-5-yl)amino]-4-oxo-spiro[chroman-2,4'-piperidine]-1'-carboxylate

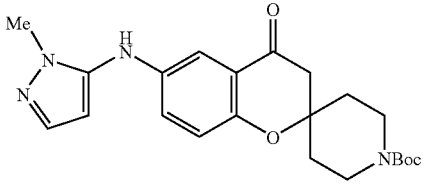

Tert-Butyl 6-bromo-4-oxospiro[chroman-2,4'-piperidine]-1'-carboxylate (16.3 g), 5-amino-1-methyl-1H-pyrazole (4.00 g), palladium acetate (922 mg), 2-(di-t-butylphosphino)biphenyl (1.23 g) and cesium carbonate (16.1 g) were suspended in 1,4-dioxane (20 mL), and heated under reflux at 110° C. for 5 hours. The reaction liquid was filtered through Celite, the residue on the Celite was washed with chloroform, and the filtrate was concentrated under reduced pressure. The resulting residue was purified through silica gel column chromatography (hexane/EtOAc) to obtain the intended compound as a yellow amorphous solid.

Reference Example 35

6-[(1-Methyl-1H-pyrazol-5-yl)amino]spiro[chroman-2,4'-piperidin]-4-one hydrochloride

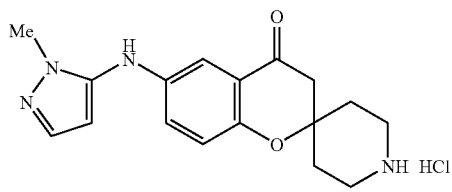

The intended compound was produced according to the procedure described in Reference Example 18 but using tert-Butyl 6-[(1-methyl-1H-pyrazol-5-yl)amino)-4-oxo-spiro[chroman-2,4'-piperidine]-1'-carboxylate in place of 5''-{1'-tert-butoxycarbonyl]-4-oxospiro[chroman-2,4'-piperidin]-6-yl}nicotinic acid methyl ester.

Reference Example 36

1'-tert-Butoxycarbonyl-[4-oxospiro[chroman-2,4'-piperidine]-6-yl]-carboxylic acid carbamoylmethyl amide

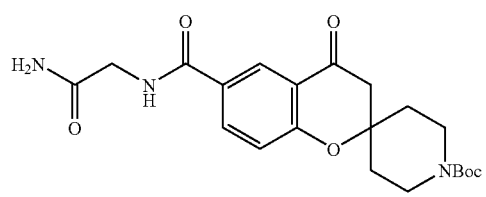

Tert-butyl 6-carboxy-4-oxospiro[chroman-2,4'-piperidine]-1'-carboxylate (7.50 g, 20.8 mmol), glycinamide hydrochloride (2.76 g, 24.9 mmol), EDCI (4.78 g, 24.9 mmol), HOBT (3.78 g, 24.9 mmol), and TEA (5.80 ml, 41.6 mmol) were suspended in DMF (75 ml) and stirred at room

Reference Example 37

4-Oxospiro[chroman-2,4'-piperidine]-6-carboxylic acid carbamoylmethyl amide hydrochloride

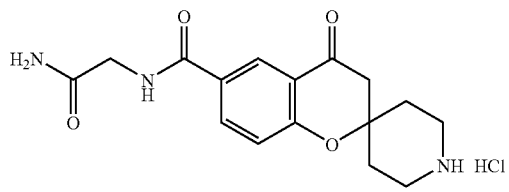

The intended compound was produced according to the Reference Example 18 but using 1'-tert-butoxycarbonyl-[4-oxospiro[chroman-2,4'-piperidine]-6-yl]-carboxylic acid N-carbamoylmethylamide in place of 5"-{1'-tert-butoxycarbonyl]-4-oxospiro[chroman-2,4'-piperidin]-6-yl}nicotinic acid methyl ester.

Reference Example 38 tert-Butyl 6-(2-{[(2,2-dimethylpropanoyl)oxy]methyl}-2H-tetrazol-5-yl)-4-oxo-spiro[chroman-2,4'-piperidine]-1'-carboxylate

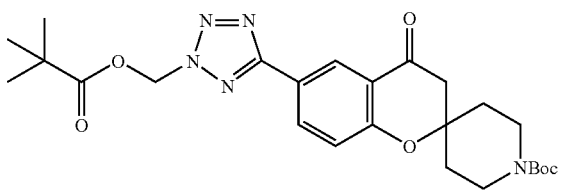

To a solution of tert-butyl 4-oxo-6-(tetrazol-5-yl)spiro[chroman-2,4'-piperidine]-1'-carboxylate (60.0 g) in DMF (500 ml) was added potassium tert-butoxide (18.4 g) chloromethyl 2,2-dimethylpropanoate (23.6 ml), potassium iodide (27.2 g) at 0° C. and further stirred at room temperature for 20 hours. The reaction mixture was diluted with EtOAc and H2O, extracted with EtOAc, washed with H₂O and brine, dried over MgSO₄. After filtration, the solvent was removed in vacuo and the residue was purified with silica gel column chromatography (hexane/EtOAc) to give the intended compound as pale yellow foam.

Reference Example 39

[5-(4-Oxospiro[chroman-2,4'-piperidin]-6-yl)-2H-tetrazol-2-yl]methyl 2,2-dimethylpropanoate hydrochloride

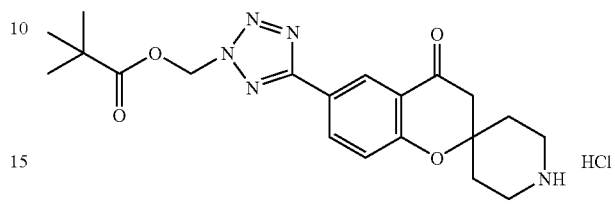

To a solution of tert-Butyl 6-(2-{[(2,2-dimethylpropanoyl)oxy]methyl}-2H-tetrazol-5-yl)-4-oxo-spiro[chroman-2,4'-piperidine]-1'-carboxylate (68.0 g) in EtOAc (1.36 L) was added 4N HCl in EtOAc (340 ml) at 0° C. and the mixture was further stirred for 21 h at room temperature. The resulted precipitate was filtered and washed with EtOAc to give intended compound as a pale yellow solid.

Reference Example 40

Tert-Butyl 6-(1-methyl-1H-pyrazol-4-yl)-4-oxo-spiro[chroman-2,4'-piperidine]-1'-carboxylate

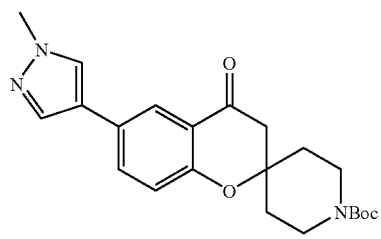

Tert-butyl 6-bromo-4-oxospiro-[chroman-2,4'-piperidine]-1'-carboxylate (1 g) and 1-methyl-4-(4,4,5,5-tetramethyl-1,3,2-dioxaborolan-2-yl)-1H-pyrazole (682 mg) were dissolved in dioxane in a nitrogen atmosphere, and aqueous 2 M sodium carbonate solution (3.8 mL) and tetrakis(triphenylphosphine)palladium (144 mg) were added thereto, and degassed. The reaction liquid was stirred overnight at 100° C., cooled to room temperature, then water was added thereto, and filtered through Celite. The filtrate was extracted with chloroform, and the organic layer was dried with sodium sulfate. Sodium sulfate was removed through filtration, the filtrate was concentrated under reduced pressure, and the residue was purified through silica gel column chromatography (hexane/ethyl acetate=100/0 to 0/100) to obtain the intended product as a pale yellow solid.

Reference Example 41

6-(1-Methyl-1H-pyrazol-4-yl)spiro[chroman-2,4'-piperidin]-4-one hydrochloride

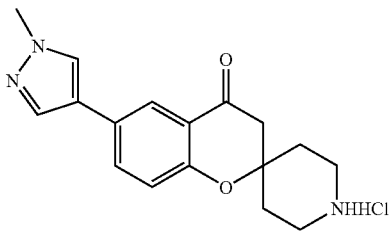

4 N hydrogen chloride/dioxane solution was added to tert-butyl 6-(1-methyl-1H-pyrazol-4-yl)-4-oxo-spiro[chroman-2,4'-piperidine]-1'-carboxylate (1.0 g), and stirred overnight at room temperature. Ether was added to the reaction liquid, the solid was taken out through filtration, washed with ether, and dried under reduced pressure to obtain the intended product as a white solid.

Reference Example 42

Dimethyl 5-trifluoromethanesulfonyloxyisophthalate

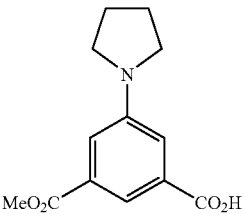

With cooling with ice, trifluoromethanesulfonic acid anhydride (4.04 mL, 24.0 mmol) was added to a mixture of dimethyl 5-hydroxyisophthalate (4.20 g, 20.0 mmol), triethylamine (6.69 mL, 48.0 mmol) and chloroform (40 mL), and stirred for 1 hour with cooling with ice. The reaction mixture was diluted with chloroform, shaken with aqueous saturated sodium hydrogencarbonate solution, then the organic layer was dried with sodium sulfate and concentrated under reduced pressure. The residue was purified through silica gel column chromatography to obtain the title compound as a colorless solid.

Reference Example 43

Dimethyl 5-(1-pyrrolidinyl)isophthalate

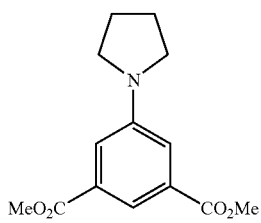

In a nitrogen atmosphere, a mixture of dimethyl 5-trifluoromethanesulfonyloxyisophthalate (1.37 g, 4.00 mmol), pyrrolidine (0.50 mL, 6.00 mmol), tris(dibenzylideneacetone)dipalladium(0) (37 mg, 0.040 mmol), 2-(di-tert-butylphosphino)biphenyl (24 mg, 0.080 mmol), potassium phosphate (1.19 g, 5.60 mmol) and 1,2-dimethoxyethane (12 mL) was stirred at 80° C. for 12 hours. After left cooled, the reaction mixture was diluted with ethyl acetate, filtered through Celite, and the filtrate was concentrated under reduced pressure. The residue was purified through silica gel column chromatography to obtain the title compound as a yellow solid.

Reference Example 44

Methyl 5-(1-pyrrolidinyl)isophthalate

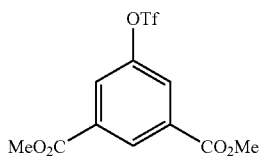

Aqueous 1 N sodium hydroxide solution (1.00 mL, 1.00 mmol) was added to a tetrahydrofuran (6 mL)-methanol (2 mL) solution of dimethyl 5-(1-pyrrolidinyl)isophthalate (263 mg, 1.00 mmol), and stirred at room temperature for 17 hours. The reaction mixture was concentrated under reduced pressure, water (5 mL) was added to the residue, and washed with diethyl ether. The aqueous layer was made acidic with 5 N hydrochloric acid added thereto, and extracted with ethyl acetate. The organic layer was dried with sodium sulfate and concentrated under reduced pressure. Chloroform was added to the residue, and filtered, and the filtrate was concentrated under reduced pressure to obtain the title compound as a yellow solid.

Reference Example 45

3-Methoxycarbonyl-5-(1-pyrrolidinyl)benzamide

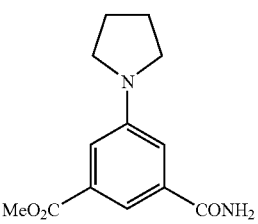

N,N'-carbonylimidazole (114 mg, 0.70 mmol) was added to a DMF (3 mL) solution of methyl 5-(1-pyrrolidinyl)isophthalate (146 mg, 0.59 mmol), and stirred at room temperature for 1 hour. Ammonium chloride (94 mg, 1.76 mmol) and triethylamine (0.246 mL, 1.76 mmol) were added to it, and further stirred at room temperature for 13 hours. The reaction mixture was concentrated under reduced pressure, water was added to the residue, and the formed insoluble matter was taken out through filtration, washed and dried to obtain the title compound as a pale yellow solid.

Reference Example 46

Methyl 3-(1-pyrrolidinol)-5-(1,2,4-triazol-3-yl)benzoate

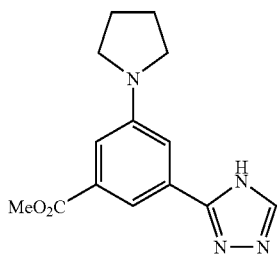

A mixture of 3-methoxycarbonyl-5-(1-pyrrolidinyl)benzamide (122 mg, 0.49 mmol) and N,N-dimethylformamide dimethyl acetal (3.0 mL) was stirred at 110° C. for 30 minutes. The mixture was concentrated under reduced pressure, then the residue was dissolved in acetic acid (1.0 mL), an acetic acid solution (1.0 mL) of hydrazine hydrate (30 mg, 0.59 mmol) was added to it, and stirred at 90° C. for 1 hour. The reaction mixture was concentrated under reduced pressure, then aqueous saturated sodium hydrogencarbonate solution was added to the residue, and extracted with ethyl acetate. The organic layer was washed with aqueous saturated sodium chloride solution, dried with sodium sulfate, and concentrated under reduced pressure. The residue was purified through silica gel column chromatography to obtain the title compound as a pale yellow solid.

Reference Example 47

3-(1-Pyrrolidinyl)-5-(1,2,4-triazol-3-yl)benzoic acid

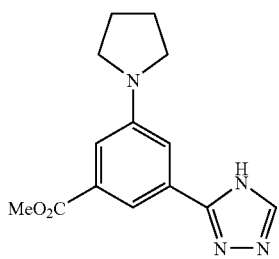

Aqueous 5 N sodium hydroxide solution (0.21 mL, 1.05 mmol) was added to a THF (0.7 mL)-methanol (0.7 mL) suspension of methyl 3-(1-pyrrolidinyl)-5-(1,2,4-triazol-3-yl)benzoate (95.8 mg, 0.35 mmol), and stirred at room temperature for 18 hours. 5 N hydrochloric acid (0.21 mL, 1.05 mmol) was added to the reaction mixture and concentrated under reduced pressure. 40% methanol/chloroform was added to the residue, the mixture was filtered, and the filtrate was concentrated under reduced pressure. Diethyl ether was added to the residue, the formed insoluble matter was taken out through filtration, washed and dried to obtain the title compound as a pale yellow solid.

Reference Example 48

Methyl 3-ethoxy-5-trifluoromethanesulfonyloxybenzoate

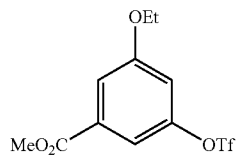

With cooling with ice, potassium carbonate (152 mg, 1.10 mmol) and iodoethane (0.088 mL, 1.10 mmol) were added to a DMF solution (2.0 mL) of methyl 3-hydroxy-5-trifluoromethane-sulfonyloxybenzoate (300 mg, 1.00 mmol), and stirred at room temperature for 14 hours. The reaction mixture was diluted with diethyl ether (30 mL), then washed with water and aqueous saturated sodium chloride solution, dried with sodium sulfate, and concentrated under reduced pressure. The residue was purified through silica gel column chromatography to obtain the title compound as a colorless oil.

Reference Example 49

Methyl 3-cyano-5-ethoxybenzoate

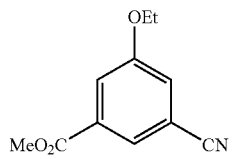

A mixture of methyl 3-ethoxy-5-trifluoromethanesulfonyloxybenzoate (308 mg, 0.94 mmol), zinc cyanide (165 mg, 1.41 mmol), tetrakis(triphenylphosphine)palladium(0) (54 mg, 0.05 mmol) and DMF (2.0 mL) was stirred in a nitrogen atmosphere at 80° C. for 12 hours. After left cooled, the reaction mixture was diluted with ethyl acetate (30 mL), washed with aqueous 14% ammonia and aqueous saturated sodium chloride solution, dried with sodium sulfate, and concentrated under reduced pressure. The residue was purified through silica gel column chromatography to obtain the title compound as a colorless solid.

Reference Example 50

Methyl 3-ethoxy-5-(tetrazol-5-yl)benzoate

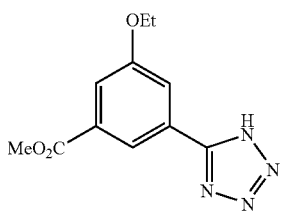

A mixture of methyl 3-cyano-5-ethoxybenzoate (182 mg, 0.89 mmol), sodium azide (173 mg, 2.66 mmol), triethylamine hydrochloride (366 mg, 2.66 mmol) and DMF (4.4 mL) was stirred in a nitrogen atmosphere at 100° C. for 12 hours. After left cooled, aqueous 5 N sodium hydroxide solution (0.53 mL, 2.66 mmol) was added to the reaction mixture, and washed with chloroform. The aqueous layer was made to have a pH of 2 with 5 N hydrochloric acid, and extracted with chloroform. The organic layer was dried with sodium sulfate, concentrated under reduced pressure, and the residue was purified through silica gel column chromatography to obtain the title compound as a colorless solid.

Reference Example 51

3-Ethoxy-5-(tetrazol-5-yl)benzoic acid

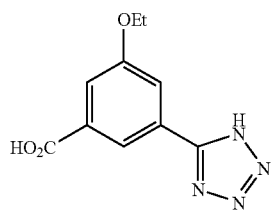

Aqueous 5 N sodium hydroxide solution (0.46 mL, 2.23 mmol) was added to a THF (2.0 mL)-methanol (2.0 mL) solution of methyl 3-ethoxy-5-(tetrazol-5-yl)benzoate (190 mg, 0.77 mmol), and stirred at room temperature for 18 hours. 5 N hydrochloric acid (0.46 mL, 2.23 mmol) was added to the reaction mixture, and concentrated under reduced pressure. 20% methanol/chloroform was added to the residue, the mixture was filtered, and the filtrate was concentrated under reduced pressure to obtain the title compound as a colorless solid.

Reference Example 52

Methyl 4-(benzo[b]thiophen-2-yl)benzoate

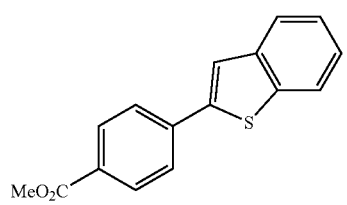

A mixture of methyl 4-bromobenzoate (430 mg, 2.00 mmol), 2-benzo[b]thiopheneboronic acid (392 mg, 2.20 mmol), palladium(0) acetate (2.2 mg, 0.010 mmol), potassium carbonate (691 mg, 5.00 mmol), tetrabutylammonium bromide (645 mg, 2.00 mmol) and water (2.2 mL) was stirred in a nitrogen atmosphere at 70° C. for 1 hour. Water was added to the reaction mixture, and extracted with ethyl acetate. The organic layer was washed with aqueous saturated sodium chloride solution, dried with sodium sulfate, and concentrated under reduced pressure. The residue was purified through silica gel column chromatography to obtain the title compound as a pale yellow solid.

Reference Example 53

4-(Benzo[b]thiophen-2-yl)benzoic acid

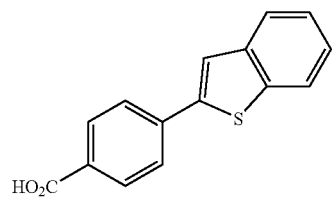

Aqueous 5 N sodium hydroxide solution (0.28 mL, 1.40 mmol) was added to a methanol (2.3 mL) solution of methyl 4-(benzo[b]thiophen-2-yl)benzoate (124 mg, 0.462 mmol), and refluxed for 3 hours. After left cooled, 5 N hydrochloric acid (0.28 mL, 1.40 mmol) was added to the reaction mixture, and concentrated under reduced pressure. 20% methanol/THF was added to the residue, the mixture was filtered, and the filtrate was concentrated under reduced pressure. Diethyl ether was added to the residue, the insoluble matter was taken out through filtration, and dried to obtain the title compound as a pale yellow solid.

Reference Example 54

Methyl 3-methoxy-5-trifluoromethanesulfonyloxybenzoate

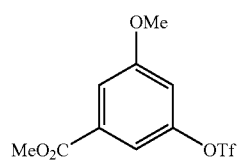

With cooling with ice, potassium carbonate (152 mg, 1.10 mmol) and iodomethane (0.137 mL, 2.20 mmol) were added to a DMF solution (3.0 mL) of methyl 3-hydroxy-5-trifluoromethane-sulfonyloxybenzoate (300 mg, 1.00 mmol), and stirred at room temperature for 17 hours. The reaction mixture was diluted with diethyl ether (30 mL), washed with water and aqueous saturated sodium chloride solution, dried with sodium sulfate, and concentrated under reduced pressure. The residue was purified through silica gel column chromatography to obtain the title compound as a colorless oil.

Reference Example 55

Methyl 3-(indol-5-yl)-5-methoxybenzoate

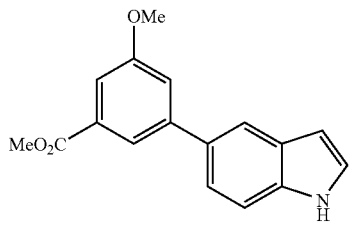

A mixture of methyl 3-methoxy-5-trifluoromethanesulfonyloxybenzoate (314 mg, 1.00 mmol), 5-indoleboronic acid (193 mg, 1.20 mmol), tetrakis(triphenylphosphine)palladium (0) (57.8 mg, 0.050 mmol), potassium phosphate (318 mg, 1.50 mmol) and 1,2-dimethoxyethane (5.0 ml) was stirred in a nitrogen atmosphere at 85° C. for 13 hours. After left cooled, the reaction mixture was diluted with ethyl acetate, filtered through Celite, and the filtrate was concentrated under reduced pressure. The residue was purified through silica gel column chromatography to obtain the title compound as a colorless oil.

Reference Example 56

3-(Indol-5-yl)-5-methoxy-benzoic acid

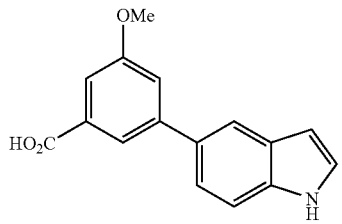

Aqueous 1 N sodium hydroxide solution (0.38 mL, 0.38 mmol) was added to a methanol (2.0 mL) solution of methyl 3-(indol-5-yl)-5-methxoybenzoate (71.9 mg, 0.26 mmol), and stirred at room temperature for 18 hours. 1N hydrochloric acid (0.38 mL, 0.38 mmol) was added to the reaction mixture, and concentrated under reduced pressure. 30% methanol/chloroform was added to the residue, the mixture was filtered, and the filtrate was concentrated under reduced pressure. Hexane was added to the residue, the insoluble matter was taken out through filtration, washed with hexane and dried to obtain the title compound as a pale yellow solid.

Reference Example 57

Methyl 5-benzyloxybiphenyl-3-carboxylate

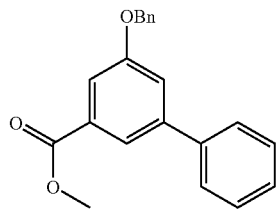

Phenylboronic acid (1.2 g), Pd(PPh$_3$)$_4$ (364 mg) and potassium phosphate (4 g) were added in that order to a DME (60 mL) solution of methyl 3-benzyloxy-5-{[(trifluoromethyl) sulfonyl]-oxy}benzoate (2.5 g), and stirred at 85° C. for 7 hours. The reaction liquid was filtered through Celite, concentrated under reduced pressure, and the residue was diluted with ethyl acetate, water was added to it, and extracted with ethyl acetate. The organic layer was washed with water and saturated saline water, dried with anhydrous sodium sulfate, filtered, and the solvent was evaporated away. The residue was purified through silica gel column chromatography (hexane/ethyl acetate) to obtain the title compound as a colorless oil.

Reference Example 58

Methyl 5-hydroxybiphenyl-3-carboxylate

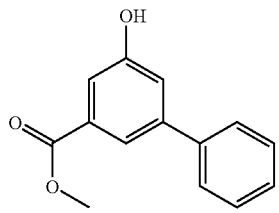

In a nitrogen atmosphere, 10% palladium-carbon (900 mg) was added to a mixed solution of EtOH (40 mL)-THF (8 mL) of methyl 5-benzyloxybiphenyl-3-carboxylate (1.55 g), and stirred in a hydrogen atmosphere at room temperature for 2 hours. The reaction liquid was filtered through Celite, and concentrated under reduced pressure to obtain the title compound as a white powder. Not purified, this was used in the next step.

Reference Example 59

Methyl 5-{[(trifluoromethyl)sulfonyl]oxy}biphenyl-3-carboxylate

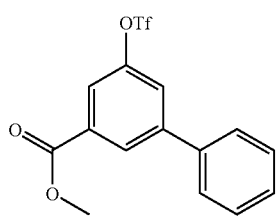

With cooling with ice, pyridine (1.2 mL) and trifluoromethanesulfonic acid anhydride (1.2 mL) were added to a CHCl$_3$ (40 mL) solution of methyl 5-hydroxybiphenyl-3-carboxylate, and stirred for 30 minutes with cooling with ice. Aqueous ammonium chloride was added to the reaction liquid, extracted with ethyl acetate, and the organic layer was washed with water, aqueous saturated sodium bicarbonate solution and saturated saline water. This was dried with anhydrous sodium sulfate, filtered and concentrated under reduced pressure to obtain the title compound as a yellow oil. Not purified, this was used in the next step.

Reference Example 60

Methyl 5-cyanobiphenyl-3-carboxylate

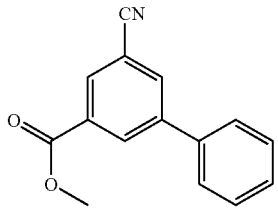

Zinc cyanide (1.1 g) and Pd(PPh$_3$)$_4$ (281 mg) were added to a DMF (45 mL) solution of methyl 5-{[(trifluoromethyl)sulfonyl]oxy}biphenyl-3-carboxylate (1.68 g), and stirred at 90° C. for 1 hour and 30 minutes. The reaction liquid was filtered through Celite, the solvent was partly evaporated away, and the residue was diluted with ethyl acetate, aqueous ammonia was added to it, and the solution was extracted with ethyl acetate. The organic layer was washed with water and saturated saline water, dried with anhydrous sodium sulfate, filtered, and the solvent was evaporated away. The residue was purified through silica gel column chromatography (hexane/ethyl acetate) to obtain the title compound as a white powder.

Reference Example 61

Methyl 5-(tetrazol-5-yl)biphenyl-3-carboxylate

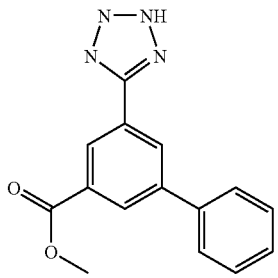

Sodium azide (880 mg) and triethylamine hydrochloride (1.9 g) were added to a DMF (40 mL) solution of methyl 5-cyanobiphenyl-3-carboxylate (1.09 g), and stirred at 100° C. for 9 hours. With cooling with ice, diluted hydrochloric acid was added to it, the formed precipitate was taken out through filtration, washed with water, and dried to obtain the title compound as a white powder.

Reference Example 62

5-(Tetrazol-5-yl)biphenyl-3-carboxylic acid

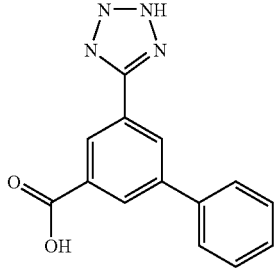

Aqueous 2 N sodium hydroxide solution (4 mL) was added to an MeOH (40 mL) solution of methyl 5-(tetrazol-5-yl)biphenyl-3-carboxylate (1.18 g), and stirred at room temperature for 45 minutes and then at 50° C. for 5 hours. Further, aqueous 2 N sodium hydroxide solution (2 mL) was added to it, and stirred at 50° C. for 2 hours. With cooling with ice, 2 N hydrochloric acid (12 mL) and water were added to it, the formed precipitate was taken out through filtration, washed with water and dried to obtain the title compound as a white powder.

Reference Example 63

2-Chloro-6-benzyloxypyridine-4-carboxylic acid

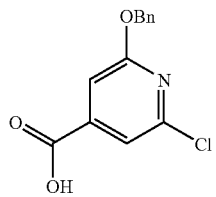

With cooling with ice, benzyl alcohol (3.4 mL) was dropwise added to a DMF (100 mL) suspension of sodium hydride (3.2 g). This was stirred at that temperature for 1 hour, then a DMF (30 mL) solution of 2,6-dichloropyridine-4-carboxylic acid (6.38 g) was dropwise added to the reaction solution with cooling with ice, and stirred at that temperature for 1 hour and 30 minutes and then overnight at 90° C. With cooling with ice, diluted hydrochloric acid was added to it, and extracted with ethyl acetate. The organic layer was washed with saturated saline water, dried with anhydrous sodium sulfate, filtered and concentrated under reduced pressure. A mixed solution of hexane/ethyl acetate=2/1 was added to the residue, and the formed precipitate was removed. The filtrate was concentrated under reduced pressure to obtain the title compound as a yellow oil. Not purified, this was used in the next step.

Reference Example 64

Methyl 2-chloro-6-benzyloxypyridine-4-carboxylate

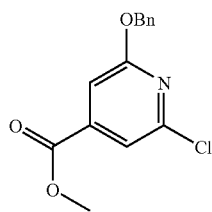

With cooling with ice, oxalyl chloride (5.8 mL) and DMF (3 drops) were added to a CHCl$_3$ (40 mL) solution of 2-chloro-6-benzyloxypyridine-4-carboxylic acid, and stirred at that temperature for 1 hour. DMF (3 drops) was added to it, and stirred overnight at room temperature, then oxalyl chloride (2.9 mL) and DMF (3 drops) were added to it, and stirred at room temperature for 3 hours. The solvent was evaporated away, CHCl$_3$-MeOH was added to the residue, and stirred at room temperature for 30 minutes. Sodium bicarbonate water was added to the reaction solution, extracted with chloroform, and the organic layer was washed with water, saturated sodium bicarbonate water and saturated saline water, and

Reference Example 65

Methyl 2-phenyl-6-benzyloxypyridine-4-carboxylate

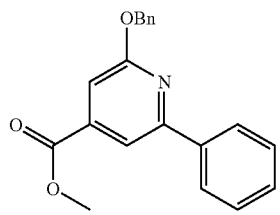

Phenylboronic acid (3.4 g), Pd(OAc)$_2$ (528 mg), tBu2-P-Ph-Ph (1.4 g) and potassium fluoride (4.1 g) were added in that order to a THF (200 mL) solution of methyl 2-chloro-6-benzyloxypyridine-4-carboxylate (6.5 g), and stirred overnight at 50° C. The reaction liquid was filtered through Celite, and concentrated under reduced pressure. The residue was purified through silica gel column chromatography (hexane/ethyl acetate) to obtain the title compound as a yellow oil.

Reference Example 66

Methyl 2-oxo-6-phenyl-1,2-dihydropyridine-4-carboxylate

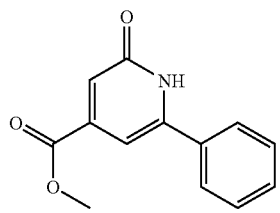

In a nitrogen atmosphere, 10% palladium-carbon (3.2 g) was added to an EtOH (50 mL)-THF (5 mL) mixed solution of methyl 2-phenyl-6-benzyloxypyridine-4-carboxylate (5.3 g), and in a hydrogen atmosphere, this was stirred at room temperature for 9 hours. The reaction liquid was filtered through Celite, concentrated under reduced pressure, and a mixed solution of hexane/ethyl acetate=2/1 was added thereto. The precipitate was taken out through filtration, washed with that solution, and dried to obtain the title compound as a white powder. The filtrate was concentrated, and the residue was purified through silica gel column chromatography (from hexane/ethyl acetate to chloroform/methanol), and combined with the previous powder to obtain the title compound as a white powder.

Reference Example 67

Methyl 2-phenyl-6-{[(trifluoromethyl)sulfonyl]oxy}pyridine-4-carboxylate

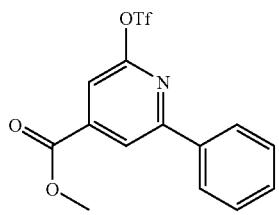

With cooling with ice, trifluoromethanesulfonic acid anhydride (3.7 mL) was added to a pyridine (80 mL) solution of methyl 2-oxo-6-phenyl-1,2-dihydropyridine-4-carboxylate (2.8 g), and this was stirred for 10 minutes with cooling with ice, and then at room temperature for 2 hours. With further cooling with ice, trifluoromethanesulfonic acid anhydride (1 mL) was added to it, stirred at that temperature for 5 minutes and then overnight at room temperature. The reaction liquid was concentrated under reduced pressure, then ethyl acetate was added thereto, and the formed precipitate was taken away through filtration. Water was added to the filtrate, extracted with ethyl acetate, and the organic layer was washed with water and saturated saline water. This was dried with anhydrous sodium sulfate, filtered, concentrated under reduced pressure, and the residue was purified through silica gel column chromatography (hexane/ethyl acetate) to obtain the title compound as a yellow powder.

Reference Example 68

Methyl 2-cyano-6-phenylpyridine 4-carboxylate

Zinc cyanide (4 g) and Pd(PPh$_3$)$_4$ (1.16 g) were added to a DMF (60 mL) solution of methyl 2-phenyl-6-{[(trifluoromethyl)sulfonyl]oxy}pyridine-4-carboxylate (3.7 g), and stirred at 90° C. for 3 hours. The reaction liquid was filtered through Celite, the solvent was partly evaporated away, the residue was diluted with ethyl acetate, water was added to it, and the solution was extracted with ethyl acetate. The organic layer was washed with water and saturated saline water, dried with anhydrous sodium sulfate, filtered and the solvent was evaporated away. The residue was purified through silica gel column chromatography (hexane/ethyl acetate) to obtain the title compound as a yellow powder.

(Continued from previous page) dried with anhydrous sodium sulfate. This was filtered, concentrated under reduced pressure, and the residue was purified through silica gel column chromatography (hexane/ethyl acetate) to obtain the title compound as a yellow oil.

Example 69

Methyl 2-phenyl-6-(tetrazol-5-yl)pyridine-4-carboxylate

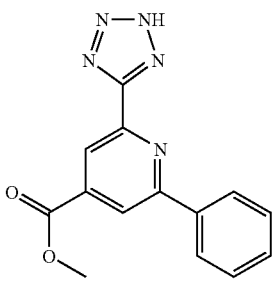

Sodium azide (1.7 g) and triethylamine hydrochloride (3.5 g) were added to a DMF (80 mL) solution of methyl 2-cyano-6-phenylpyridine-4-carboxylate (2 g), and stirred overnight at 100° C. With cooling with ice, diluted hydrochloric acid was added to it, and extracted with a mixed solution of chloroform/methanol=10/1. The organic layer was washed with water and saturated saline water, dried with anhydrous sodium sulfate, filtered, and the solvent was evaporated away to obtain the title compound as a brown solid.

Reference Example 70

2-Phenyl-6-(tetrazol-5-yl)pyridine-4-carboxylic acid

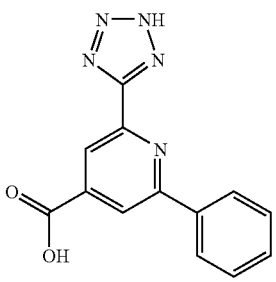

Aqueous 2 N sodium hydroxide solution (8.4 mL) was added to an MeOH (85 mL) solution of methyl 2-phenyl-6-(tetrazol-5-yl)pyridine-4-carboxylate (3.19 g), and stirred at 50° C. for 4 hours. With cooling with ice, 2N hydrochloric acid (16.8 mL) and water were added to it, the formed precipitate was taken out through filtration, washed with water and dried to obtain the title compound as a flesh-colored powder.

Reference Example 71

Methyl 2-chloro-6-phenylpyridine-4-carboxylate

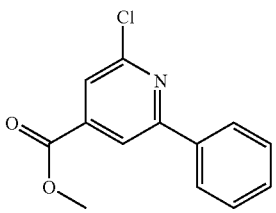

Phenylboronic acid (326 mg), PdCl$_2$(PPh$_3$)$_2$ (84 mg) and cesium carbonate (3.9 g) were added in that order to a THF (10 mL) solution of 2,6-dichloropyridine-4-carboxylic acid (500 mg), and stirred under heat with refluxing for 1.5 hours. The reaction liquid was filtered through Celite, concentrated under reduced pressure, and the residue was purified through silica gel column chromatography (hexane/ethyl acetate) to obtain a crude product of the title compound as a yellow oil. Not purified, this was used in the next step.

Reference Example 72

2-Methoxy-6-phenylpyridine-4-carboxylic acid

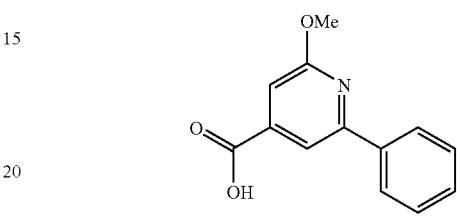

25% NaOMe/methanol solution (92 μL) was added to an MeOH (2 mL) solution of methyl 2-chloro-6-phenylpyridine-4-carboxylate (1100 mg), and stirred at room temperature for 2 hours. Further, 25% NaOMe/methanol solution (92 μL) was added to it, and stirred under heat with refluxing for 2 hours and 30 minutes. DMA (3 mL) was added to it, and stirred overnight at 130° C., then 25% NaOMe/methanol solution (92 μL) was added to it, and stirred at 130° C. for 7 hours. With cooling with ice, diluted hydrochloric acid was added to it, the formed precipitate was taken out through filtration, washed with water, dried, and purified through reversed-phase high-performance liquid chromatography [acetonitrile/water+0.11% trifluoroacetic acid] to obtain the title compound as a white powder.

Reference Example 73

Methyl 3-cyano-5-benzyloxybenzoate

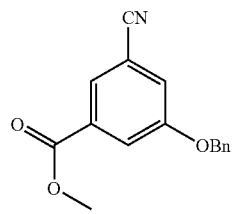

Zinc cyanide (1.9 g) and Pd(PPh$_3$)$_4$ (456 mg) were added to a DMF (60 mL) solution of methyl 3-benzyloxy-5-{[(trifluoromethyl)sulfonyl]oxy}benzoate (3.08 g), and stirred at 90° C. for 2 hours. The reaction liquid was filtered through Celite, the solvent was partly evaporated away, the residue was diluted with ethyl acetate, aqueous ammonia was added to it, and the solution was extracted with ethyl acetate. The organic layer was washed with water and saturated saline water, then dried with anhydrous sodium sulfate, filtered, and the solvent was evaporated away. The residue was purified through silica gel column chromatography (hexane/ethyl acetate) to obtain the title compound as a white powder.

Reference Example 74

Methyl 3-benzyloxy-5-(tetrazol-5-yl)benzoate

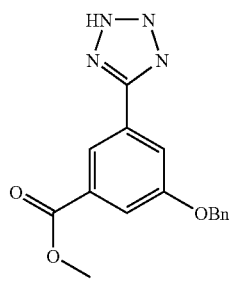

Sodium azide (1.5 g) and triethylamine hydrochloride (3.2 g) were added to a DMF (70 mL) solution of methyl 3-cyano-5-benzyloxybenzoate (2.07 g), and stirred at 100° C. for 6 hours and then overnight at room temperature. With cooling with ice, diluted hydrochloric acid was added to it, the precipitate was taken out through filtration, washed with water, and dried to obtain the title compound as a white powder.

Reference Example 75

Methyl 3-benzyloxy-5-[({[2-(trimethylsilyl)ethyl]oxy}methyl)tetrazol-5-yl]benzoate

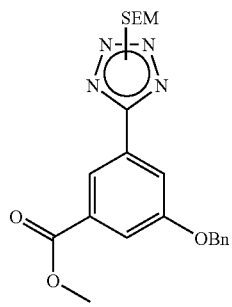

With cooling with ice, diisopropylethylamine (1.5 mL) and trimethylsilylethoxymethyl chloride (1.6 mL) were added to a CHCl₃ (70 mL) solution of methyl 3-benzyloxy-5-(tetrazol-5-yl)benzoate (2.32 g), and stirred at room temperature for 1 hour. Sodium bicarbonate water was added to the reaction liquid, and extracted with chloroform. The organic layer was washed with water and saturated saline water, dried with anhydrous sodium sulfate, filtered, and concentrated under reduced pressure to obtain the title compound as a brown oil. Not purified, this was used in the next step.

Reference Example 76

Methyl 3-hydroxy-5-[({[2-(trimethylsilyl)ethyl]oxy}methyl)tetrazol-5-yl]benzoate

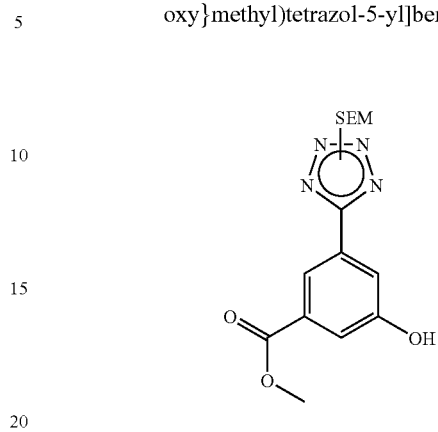

In a nitrogen atmosphere, 10% palladium-carbon (2.4 g) was added to an EtOH (35 mL)-THF (35 mL) mixed solution of methyl 3-benzyloxy-5-[({[2-(trimethylsilyl)ethyl]oxy}methyl)-tetrazol-5-yl]benzoate (4.02 g), and in a hydrogen atmosphere this was stirred at room temperature for 2 hours. The reaction liquid was filtered through Celite, concentrated under reduced pressure, and dried to obtain the title compound as a white powder. Not purified, this was used in the next step.

Reference Example 77

Methyl 3-{[(trifluoromethyl)sulfonyl]oxy}-5-[({[2-(trimethylsilyl)ethyl]oxy}methyl)tetrazol-5-yl]benzoate

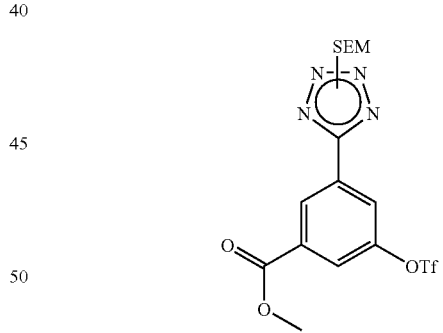

With cooling with ice, trifluoromethanesulfonic acid anhydride (480 µL) was added to a pyridine (8 mL) solution of methyl 3-hydroxy-5-[({([2-(trimethylsilyl)ethyl]oxy}methyl)tetrazol-5-yl]benzoate (500 mg), and stirred for 15 minutes with cooling with ice, and then at room temperature for 15 minutes. The reaction liquid was concentrated under reduced pressure, aqueous ammonium chloride was added to the residue, and extracted with ethyl acetate. The organic layer was washed with water and saturated saline water, dried with anhydrous sodium sulfate, filtered, concentrated under reduced pressure, and the residue was purified through silica gel column chromatography (hexane/ethyl acetate) to obtain the title compound as a colorless oil.

Reference Example 78

Methyl 3-{[ethoxymethyl]tetrazol-5-yl}-5-pyrrolidin-1-ylbenzoate

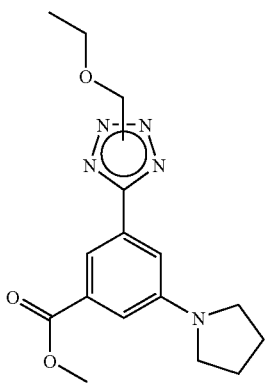

Pyrrolidine (41 mg), Pd$_2$(dba)$_3$ (35 mg), tBu$_2$-P-Ph-Ph (23 mg) and potassium phosphate (241 mg) were added in that order to a DME (5 mL) solution of methyl 3-{[(trifluoromethyl)-sulfonyl]oxy}-5-[({[2-(trimethylsilyl)ethyl]oxy}methyl)tetrazol-5-yl]benzoate (183 mg), and stirred at 85° C. for 4 hours. The reaction liquid was filtered through Celite, the solvent was evaporated away, the residue was diluted with ethyl acetate, water was added thereto, and the solution was extracted with ethyl acetate. The organic layer was washed with saturated saline water, dried with anhydrous sodium sulfate, filtered, and the solvent was evaporated away. The residue was purified through silica gel column chromatography (hexane/ethyl acetate) to obtain the title compound as a red oil.

Reference Example 79

Methyl 3-pyrrolidin-1-yl-5-(tetrazol-5-yl)benzoate

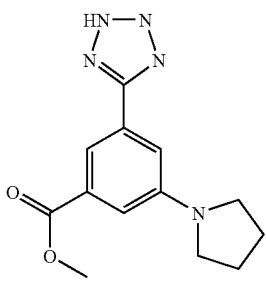

A trifluoroacetic acid (5 mL) solution of methyl 3-{[ethoxymethyl]tetrazol-5-yl}-5-pyrrolidin-1-ylbenzoate (127 mg) was stirred at room temperature for 2 hours and then at 80° C. for 2 hours. The reaction liquid was concentrated under reduced pressure, the residue was purified through reversed-phase high-performance liquid chromatography [acetonitrile/water+0.1% trifluoroacetic acid] to obtain the title compound as a yellow powder.

Reference Example 80

3-Pyrrolidin-1-yl-5-(tetrazol-5-yl)benzoic acid

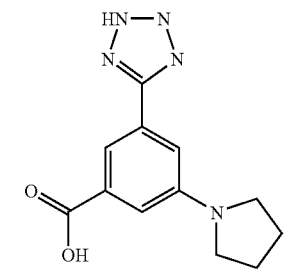

Aqueous 2 N sodium hydroxide solution (1.26 mL) was added to an MeOH (5 mL) solution of methyl 3-pyrrolidin-1-yl-5-(tetrazol-5-yl)benzoate (35.6 mg), and stirred at 50° C. for 2 hours and 30 minutes. With cooling with ice, 2 N hydrochloric acid (2.52 mL) and water were added to it, and the formed precipitate was taken out through filtration, washed with water and dried to obtain the title compound as a yellow powder.

Reference Example 81

1-Cyclopropyl-1H-pyrrole-2-carbaldehyde

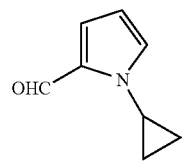

In a 500-ml egg plant-type flask, POCl$_3$ (44.46 mL, 0.48 mol) was dropwise added to a DMF (37 mL, 0.48 mol) solution of 1-cyclopropyl-1H-pyrrole (46.46 g, 0.43 mol) with cooling with ice, and then stirred overnight at room temperature. The reaction mixture was poured into 5 N sodium hydroxide solution (336 mL) with cooling with ice, and the reaction solution was made basic with 5 N sodium hydroxide solution added thereto. The mixture solution was extracted with dichloromethane, dried with sodium sulfate, filtered, concentrated, and purified through silica gel column chromatography (Biotage [SiO$_2$, 75+M]) with a hexane/ethyl acetate developer system to obtain the title compound as a colorless oil.

Reference Example 82

Ethel 4-acetoxy-1-cyclopropyl-1H-indole-6-carboxylate

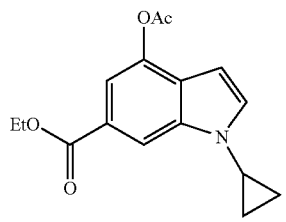

In a 2.0-liter egg plant-type flask, sodium metal pieces (14.57 g, 0.63 mol) were gradually added to ethanol (400 mL) to prepare a sodium ethoxide solution. To the solution, dropwise added was an ethanol solution (100 mL) of 1-cyclopropyl-1H-pyrrole-2-carbaldehyde (38.91 g, 0.29 mol) and diethyl succinate (48.23 mL, 0.29 mol) at 50° C., and stirred overnight with heating under reflux. With cooling with ice, aqueous 5 N hydrochloric acid solution (140 mL) was added to the reaction mixture, and ethanol was removed under reduced pressure. The resulting mixture was extracted with chloroform, dried with sodium sulfate, filtered and concentrated to obtain a red oil. The crude product was dissolved in acetic anhydride (400 mL) in a 1-liter egg plant-type flask, and sodium acetate (47.40 g, 0.56 mol) was added to it. The reaction solution was stirred for 30 minutes with heating under reflux, then left cooled at room temperature and filtered. The filtrate was concentrated and purified through silica gel column chromatography (Biotage [SiO$_2$, 75+L]) with a hexane/ethyl acetate developer system to obtain the title compound as a red oil.

Reference Example 83

Ethyl 1-cyclopropyl-4-hydroxy-1H-indole-6-carboxylate

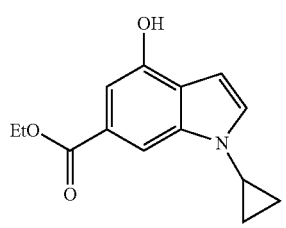

In a 2.0-liter egg plant-type flask, potassium carbonate (69.58 g, 0.50 mol) was added to an ethanol (360 mL) solution of ethyl 4-acetoxy-1-cyclopropyl-1H-indole-6-carboxylate (72.33 g, 0.25 mol), and stirred at room temperature for 4 hours. Ethanol was removed from the reaction solution under reduced pressure, the residue was diluted with ethyl acetate, washed with water and saturated saline water, dried with sodium sulfate, and concentrated to obtain a crude product. This was crystallized with toluene and hexane to obtain the title compound as a pale brown crystal.

Reference Example 84

Ethyl 1-cyclopropyl-4-{[(trifluoromethyl)sulfonyl]oxy}-1H-indole-6-carboxylate

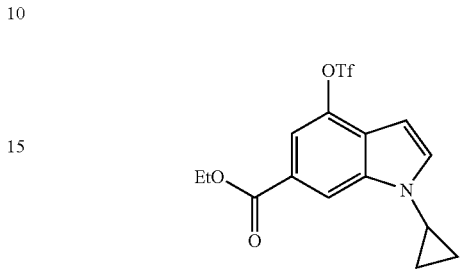

In a 500-mL egg plant-type flask, a chloroform (50 mL) solution of trifluoromethanesulfonic acid anhydride (6.30 mL, 37.5 mmol) was dropwise added to a chloroform (100 mL) solution of ethyl 1-cyclopropyl-4-hydroxy-1H-indole-6-carboxylate (6.12 g, 25 mmol) and pyridine (6.06 mL, 75 mmol) with cooling with ice, and stirred at that temperature for 30 minutes, then poured into aqueous hydrochloric acid solution, extracted with chloroform, washed with aqueous saturated sodium hydrogencarbonate solution, and dried with sodium sulfate. The reaction solution was filtered, concentrated, and purified through silica gel column chromatography (Biotage [SiO$_2$, 40+M]) with a hexane/ethyl acetate developer system to obtain the title compound as a colorless oil.

Reference Example 85

Ethyl 4-cyano-1-cyclopropyl-1H-indole-6-carboxylate

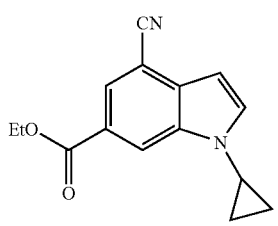

In a 300-mL egg plant-type flask, tetrakistriphenylphosphine palladium (2.31 g, 2.0 mmol) was added to a DMF (50 mL) solution of ethyl 1-cyclopropyl-4-{[(trifluoromethyl)sulfonyl]oxy}-1H-indole-6-carboxylate (7.54 g, 20 mmol) and zinc cyanide (4.70 g, 40 mmol), then purged with nitrogen, and stirred at 90° C. for 1.5 hours. After left cooled, this was diluted with ethyl acetate (100 mL), and aqueous 25% ammonia (50 mL) and water (50 mL) were added thereto, stirred at room temperature for 30 minutes, extracted with ethyl acetate, and washed with water and saturated saline water in that order. The reaction solution was dried with sodium sulfate, filtered, concentrated, and purified through silica gel column chromatography (Biotage [SiO2, 40+M]) with a hexane/ethyl acetate developer system to obtain the title compound as a yellow solid.

Reference Example 86

Ethyl 1-cyclopropyl-4-(tetrazol-5-yl)-1H-indole-6-carboxylate

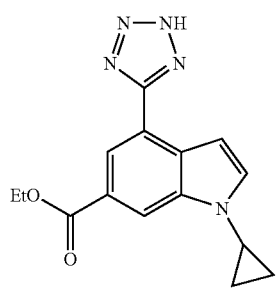

In a 100-mL egg plant-type flask, sodium azide (486 mg, 7.48 mmol) was added to a DMF (10 mL) solution of ethyl 4-cyano-1-cyclopropyl-1H-indole-6-carboxylate (475 mg, 1.87 mmol) and triethylamine hydrochloride (1.03 g, 7.48 mmol), and stirred overnight at 110° C. The reaction solution was diluted with ethyl acetate, made acidic with aqueous hydrochloric acid solution added thereto, and the separated organic layer was washed with water and saturated saline water in that order, dried with sodium sulfate, filtered and concentrated. The crude product was washed with hexane to obtain the title compound as a colorless solid.

Reference Example 87

1-Cyclopropyl-4-(tetrazol-5-yl)-1H-indole-6-carboxylic acid

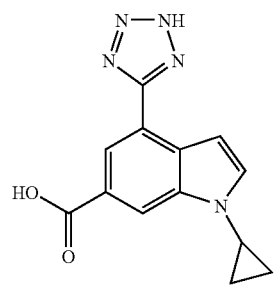

In a 500-mL egg plant-type flask, aqueous 5 N sodium hydroxide solution (11 mL, 55 mmol) was added to an MeOH solution (70 mL) of ethyl 1-cyclopropyl-4-(tetrazol-5-yl)-1H-indole-6-carboxylate (5.40 g), and stirred at 60° C. for 8 hours. The reaction solution was left cooled, aqueous 5 N hydrochloric acid solution (12 mL) was added thereto, and the formed precipitate was taken out through filtration. This was washed with water and dried under reduced pressure to obtain the title compound as a colorless solid.

Reference Example 88

Methyl 2,6-dimethoxybiphenyl-4-carboxylate

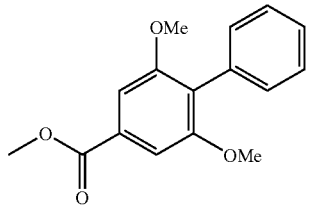

PdCl$_2$(dppf) (14.8 g) was added to a CH$_3$CN (900 mL) solution of methyl 4-bromo-3,5-dimethoxybenzoate (25.0 g), phenylboronic acid (22.2 g), Bu$_4$NBr (5.86 g) and K$_3$PO$_4$ (77.2 g), and stirred under heat for 14 hours. This was filtered through Celite, and the filtrate was concentrated and purified through column chromatography to obtain the title compound as a colorless solid.

Reference Example 89

2,6-Dimethoxybiphenyl-4-carboxylic acid

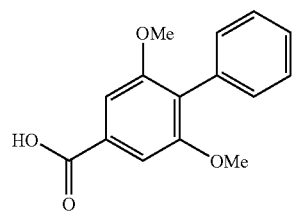

Aqueous 5 N sodium hydroxide solution (44 mL) was added to a THF (150 mL)-MeOH (150 mL) solution of methyl 2,6-dimethoxybiphenyl-4-carboxylate (20.0 g), and stirred at 40° C. for 5 hours. The reaction solution was poured into aqueous 0.5 M KHSO$_4$ solution, and extracted with ethyl acetate. The combined organic layers were washed with aqueous saturated sodium chloride solution, dried with anhydrous sodium sulfate, and concentrated. The residue was recrystallized from hexane/ethyl acetate to obtain the title compound as a colorless crystal.

Reference Example 90

Methyl 4-bromo-3,5-dihydroxybenzoate

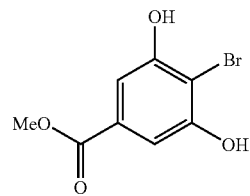

In a 2.0-liter egg plant-type flask, a hydrochloric acid/methanol solution (500 mL) of 4-bromo-3,5-dihydroxybenzoic acid (50 g, 0.21 mol) was stirred with heating under reflux for 6 hours. Methanol was removed under reduced pressure to obtain a crude crystal. This was washed with hexane and chloroform to obtain the title compound as a colorless solid.

Reference Example 91

Methyl 4-bromo-3,5-diethoxybenzoate

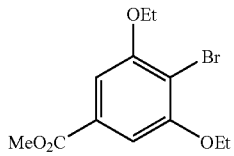

Methyl 4-bromo-3,5-dihydroxybenzoate (10 g) was dissolved in DMF (80 mL), and potassium carbonate (13.2 g) and ethyl iodide (7.6 mL) were added to it, and stirred overnight at room temperature. The reaction liquid was poured into water with cooling with ice, extracted with ethyl acetate, the organic layer was washed with water and saturated saline water, and dried with sodium sulfate. Sodium sulfate was removed through filtration, the filtrate was concentrated under reduced pressure, and the residue was purified through silica gel column chromatography (hexane/ethyl acetate=1/0 to 90/10) to obtain the title compound as a white solid.

Reference Example 92

Methyl 3,5-diethoxy-4-(1-methyl-1H-pyrazol-4-yl)benzoate

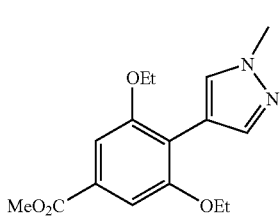

Methyl 4-bromo-3,5-diethoxybenzoate (1 g) and 1-methyl-4-(4,4,5,5-tetramethyl-1,3,2-dioxaborolan-2-yl)-1H-pyrazole (895 mg) were dissolved in DME in a nitrogen atmosphere, and potassium phosphate (2.1 g) and 1,1'-bis(diphenylphosphino)ferrocene palladium (D) chloride-CH$_2$Cl$_2$ complex (269 mg) were added to it at room temperature, and degassed. The reaction liquid was stirred overnight at 90° C., then cooled to room temperature, and water was added to it, and this was filtered through Celite. The filtrate was extracted with chloroform, washed with saturated saline water, and dried with sodium sulfate. Sodium sulfate was removed through filtration, the filtrate was concentrated under reduced pressure, and the residue was purified through silica gel column chromatography (hexane/ethyl acetate=100/0 to 50/50 to 35/65) to obtain the title compound as a pale yellow solid.

Reference Example 93

3,5-Diethoxy-4-(1-methyl-1H-pyrazol-4-yl)benzoic acid

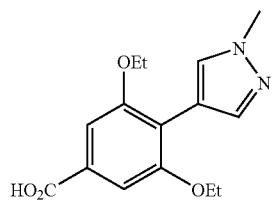

3,5-Diethoxy-4-(1-methyl-1H-pyrazol-4-yl)-benzoic acid methyl ester (895 mg) was dissolved in a mixed methanol/THF solution (16 mL, 5/3), aqueous 1 M NaOH solution (6 mL) was added to it, and stirred at 50° C. for 5 hours. The reaction liquid was cooled to room temperature, and aqueous 1 M HCl solution (6 mL) was added to it, and the solvent was evaporated away under reduced pressure. The resulting solid was taken out through filtration, washed with water and ether, and dried under reduced pressure to obtain the title compound as a pale yellow solid.

Reference Example 94

Methyl 4-bromo-3,5-bis{[(trifluoromethyl)sulfonyl]oxy}benzoate

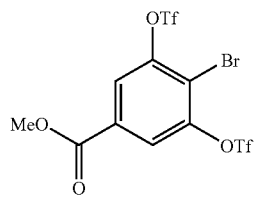

At −50° C., trifluoromethanesulfonic acid anhydride (28.8 mL, 176 mmol) was dropwise added to a chloroform solution (400 mL) of methyl 4-bromo-3,5-dihydroxybenzoate (19.8 g, 80 mmol) and diisopropylethylamine (60 mL, 352 mmol), and stirred for 30 minutes with cooling with ice. This was again cooled to −50° C., and diisopropylethylamine (21 mL, 128 mmol) and trifluoromethanesulfonic acid anhydride (10.5 mL, 64 mmol) were added thereto in that order, and stirred at that temperature for 30 minutes. Water was added to the reaction solution, extracted with chloroform, washed with aqueous saturated sodium hydrogencarbonate solution, dried with sodium sulfate, filtered and concentrated to obtain an oil. The residue was purified through silica gel column chromatography (Biotage [SiO$_2$, 40+M]×3) with a hexane/ethyl acetate developer system to obtain a brown oily crude product containing the title compound.

Reference Example 95

Methyl 4-bromo-3-hydroxy-5-{[(trifluoromethyl)sulfonyl]oxy}benzoate

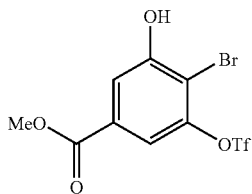

In a 1-liter egg plant-type flask, cesium carbonate (24.8 g, 76.3 mmol) was added to a DME (200 mL) solution of methyl 4-bromo-3,5-bis{[(trifluoromethyl)sulfonyl]oxy}benzoate (26.0 g), and stirred at 60° C. for 3 hours. DME was removed under reduced pressure, the residue was diluted with ethyl acetate, washed with water and saturated saline water in that order, dried with sodium sulfate, filtered and concentrated to obtain a crude product as a brown solid. This was washed with a mixed solvent of toluene and hexane to obtain the title compound as a colorless solid.

Reference Example 96

Methyl 4-bromo-3-methoxy-5-{[(trifluoromethyl)sulfonyl]oxy}benzoate

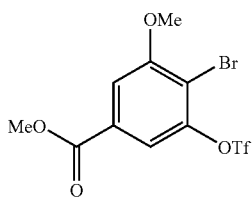

In a 1-liter egg plant-type flask, methyl iodide (6.67 mL, 105 mmol) was added to a DMF (200 mL) solution of methyl 4-bromo-3-hydroxy-5-{[(trifluoromethyl)sulfonyl]oxy}benzoate (19.9 g) and potassium carbonate (14.5 g, 105 mmol), and stirred at room temperature for 4 hours. The reaction solution was diluted with ethyl acetate, washed with water and saturated saline water, dried with sodium sulfate, filtered, and concentrated to obtain a crude product. This was purified through silica gel column chromatography (Biotage [SiO2, 40+M]) with a hexane/ethyl acetate developer system to obtain the title compound as a colorless solid.

Reference Example 97

Methyl 4-bromo-3-hydroxy-5-methoxybenzoate

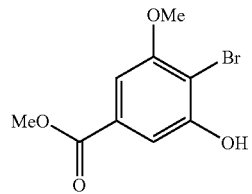

In a 1.0-liter egg plant-type flask, 1.0 M TBAF-THF solution (86 mL, 86 mmol) was added to a THF (200 mL) solution of methyl 4-bromo-3-methoxy-5-{[(trifluoromethyl)sulfonyl]oxy}-benzoate (16.9 g, 43 mmol), and stirred at room temperature for 2 hours. THF was removed under reduced pressure, the residue was diluted with diethyl ether, washed with aqueous phosphate buffer (pH 6.8) solution and saturated saline water in that order, dried with sodium sulfate, filtered and concentrated to obtain a crude product containing the title compound.

Reference Example 98

Methyl 4-bromo-3-ethoxy-5-methoxybenzoate

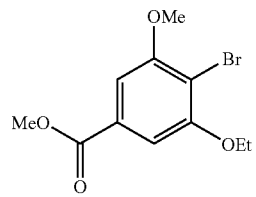

In a 1.0-liter egg plant-type flaks, ethyl iodide (6.91 mL, 86 mmol) was added to a DMF (150 mL) solution of the previously-obtained methyl 4-bromo-3-hydroxy-5-methoxybenzoate and potassium carbonate (11.9 g, 86 mmol), and stirred overnight at room temperature. Water was added to the reaction solution, the formed precipitate was taken out through filtration and dried under reduced pressure to obtain the title compound as a colorless solid.

Reference Example 99

Methyl 3-ethoxy-5-methoxy-4-(1-methyl-1H-pyrazol-4-yl)benzoate

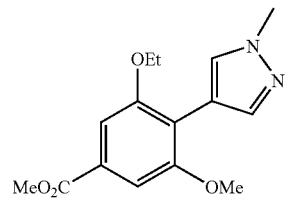

Methyl 3-ethoxy-4-bromo-5-methoxybenzoate (300 mg) and 1-methyl-4-(4,4,5,5-tetramethyl-1,3,2-dioxaborolan-2-yl)-1H-pyrazole (324 mg) were dissolved in DME in a nitrogen atmosphere, and potassium phosphate (661 mg) and 1,1'-bis(diphenylphosphino)ferrocene palladium(II) chloride-CH$_2$Cl$_2$ complex (85 mg) were added to it at room temperature and degassed. The reaction liquid was stirred overnight at 90° C., then cooled to room temperature, water was added to it, and filtered through Celite. The filtrate was extracted with chloroform, washed with saturated saline water, and dried with sodium sulfate. Sodium sulfate was removed through filtration, the filtrate was concentrated under reduced pressure, and the residue was purified through silica gel column chromatography (hexane/ethyl acetate=100/0 to 40/60) to obtain the title compound as a white solid.

Reference Example 100

3-Ethoxy-5-methoxy-4-(1-methyl-1H-pyrazol-4-yl)benzoic acid

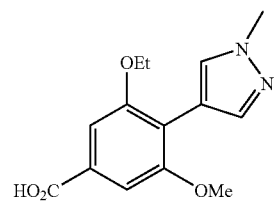

Methyl 3-ethoxy-5-methoxy-4-(1-methyl-1H-pyrazol-4-yl)benzoate (157 mg) was dissolved in a mixed solvent of methanol/THF (9 mL, 1/2), and aqueous 1 M NaOH solution (2.1 mL) was added to it and stirred at room temperature for 5 hours. Aqueous 1 M HCl solution (2.1 mL) was added to it, and the solvent was concentrated under reduced pressure. The obtained solid was removed through filtration, washed with water and ether, and dried under reduced pressure to obtain the title compound as a white solid.

Reference Example 101

Methyl 4-[1-(ethoxy)ethenyl]-3,5-dimethoxybenzoate

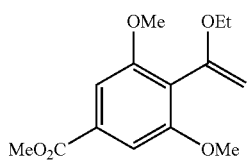

Methyl 3,5-dimethoxy-4-bromobenzoate (500 mg) was dissolved in toluene in a nitrogen atmosphere, and 1-ethoxyvinyltributyltin (742 μL) and tetrakis(triphenylphosphine)palladium (211 mg) were added to it, and stirred overnight at 110° C. The reaction liquid was cooled to room temperature, then aqueous potassium fluoride solution was added to it, and stirred at room temperature. The reaction liquid was filtered through Celite, the Celite was washed with ethyl acetate, and the filtrate was washed with saturated saline water. The organic layer was dried with sodium sulfate, the sodium sulfate was removed through filtration, the filtrate was concentrated under reduced pressure, and the residue was purified through silica gel column chromatography (hexane/ethyl acetate=100/0 to 85/15) to obtain the title compound.

Reference Example 102

Methyl 4-(bromoacetyl)-3,5-dimethoxybenzoate

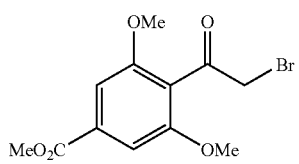

Methyl 4-[1-ethoxy)ethenyl]-3,5-dimethoxybenzoate (130 mg) was dissolved in a dioxane/water mixed solvent (11 mL, 10/1), and N-bromosuccinimide (87 mg) was added to it at 0° C., and stirred at room temperature for 1 hour. The reaction liquid was added to sodium bicarbonate water, extracted with ethyl acetate, and the organic layer was dried with sodium sulfate. Sodium sulfate was removed through filtration, and the filtrate was concentrated under reduced pressure to obtain a crude product containing the title compound.

Reference Example 103

Methyl 4-(azidoacetyl)-3,5-dimethoxybenzoate

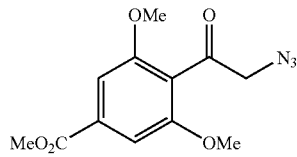

Methyl 4-(bromoacetyl)-3,5-dimethoxybenzoate was dissolved in DMF, sodium azide (96 mg) was added to it, and stirred at room temperature for 1 hour. The reaction liquid was poured into water, extracted with ethyl acetate, the organic layer was washed with water and saturated saline water, and dried with sodium sulfate. Sodium sulfate was removed through filtration, and the filtrate was concentrated under reduced pressure. The residue was purified through silica gel column chromatography (hexane/ethyl acetate=100/0 to 60/40) to obtain the title compound.

Reference Example 104

Methyl 4-(aminoacetyl)-3,5-dimethoxybenzoate hydrochloride

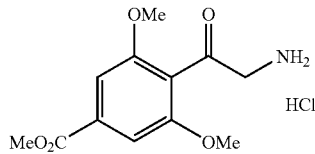

Methyl 4-(azidoacetyl)-3,5-dimethoxybenzoate (90 mg) was dissolved in methanol, and in a nitrogen atmosphere, 10% palladium-carbon (20 mg) was added to it, and then purged with hydrogen. The reaction liquid was stirred at room temperature for 4 hours, then filtered through Celite, hydrogen chloride-methanol was added to the filtrate, and the solvent was evaporated away under reduced pressure to obtain a crude product containing the title compound.

Reference Example 105

Methyl 4-(2-methyl-1,3-oxazol-5-yl)-3,5-dimethoxybenzoate

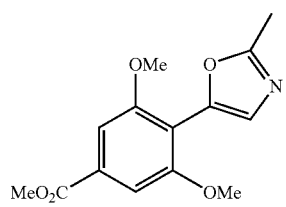

Methyl 4-(aminoacetyl)-3,5-dimethoxybenzoate hydrochloride was dissolved in triethyl orthoacetate, paratoluenesulfonic acid monohydrate (10 mg) was added to it, and stirred at 140° C. for 6 hours. The reaction liquid was cooled to room temperature, then triethyl orthoacetate was evaporated away under reduced pressure, and the residue was purified through silica gel column chromatography (hexane/ethyl acetate=100/0 to 30/70) to obtain the title compound.

Reference Example 106

4-(2-Methyl-1,3-oxazol-5-yl)-3,5-dimethoxybenzoic acid

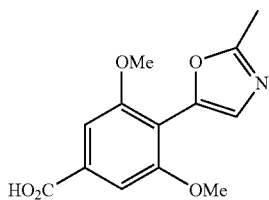

Methyl 4-(2-methyl-1,3-oxazol-5-yl)-3,5-dimethoxybenzoate (23 mg) was dissolved in methanol, aqueous 1 M NaOH solution (332 μL) was added to it, and stirred at room temperature for 5 hours. Aqueous 1 M HCl solution (332 μL) was added to it, and the solvent was concentrated under reduced pressure to obtain a crude product containing the title compound.

Reference Example 107

Methyl 3,5-diethoxy-4-(isoxazol-4-yl)benzoate

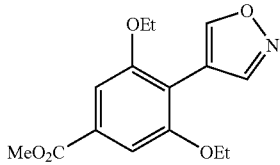

Methyl 4-bromo-3,5-diethoxybenzoate (456 mg) and 4-(4,4,5,5-Tetramethyl-[1,3,2]dioxaborolan-2-yl)-isoxazole (438 mg) were dissolved in THF in a nitrogen atmosphere, and potassium phosphate (954 mg), palladium acetate (33 mg) and dicyclohexyl-(2',6'-dimethoxy-biphenyl-2-yl)-phosphane (62 mg) were added to it, and degassed. The reaction liquid was stirred overnight at 85° C., then cooled to room temperature, water was added to it, and filtered through Celite. The filtrate was extracted with chloroform, washed with saturated saline water, and the organic layer was dried with sodium sulfate. Sodium sulfate was removed through filtration, the filtrate was concentrated under reduced pressure, and the residue was purified through silica gel column chromatography (hexanelethyl acetate=100/0 to 80/20) to obtain the title compound as a pale yellow solid.

Reference Example 108

3,5-Diethoxy-4-(isoxazol-4-yl)benzoic acid

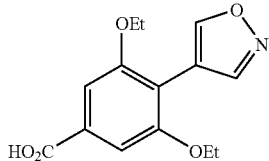

Methyl 3,5-diethoxy-4-(isoxazol-4-yl)benzoate (91 mg) was dissolved in a mixed solvent of methanol/THF (8 mL, 3/5), aqueous 1 M NaOH solution (1.2 mL) was added to it, and stirred at room temperature for 5 hours. Aqueous 1 M HCl solution (1.2 mL) was added to it, and the solvent was concentrated under reduced pressure. The formed solid was taken out through filtration, washed with water, and dried under reduced pressure to obtain the title compound as a pale yellow solid.

Reference Example 109

3-Methyl-1-pyridin-2-yl-1H-pyrazol-5-ol

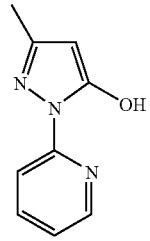

In a 1.0-liter egg plant-type flask, an ethanol solution (300 mL) of 2-hydrazinopyridine (16.3 g, 0.15 mol) and ethyl 3-oxobutanoate (20.5 g, 0.16 mol) was stirred overnight with heating under reflux. Ethanol was removed from the reaction solution under reduced pressure to obtain the title compound as a brown oily crude product.

Reference Example 110

5-Chloro-3-methyl-1-pyridin-2-yl-1H-pyrazole-4-carbaldehyde

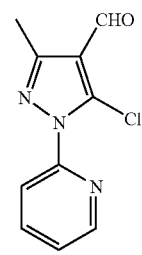

In a 1.0-liter egg plant-type flask, POCl$_3$ (56 mL, 0.60 mL) was dropwise added to a DMF (17.4 mL, 0.23 mol) solution of 3-methyl-1-pyridin-2-yl-1H-pyrazol-5-ol with cooling with ice, and stirred overnight at 80° C. The reaction solution was poured onto crushed ice, and stirred at room temperature. The formed precipitate was filtered, and dried under reduced pressure to obtain the title compound as a pale brown solid.

Reference Example 111

3-Methyl-1-pyridin-2-yl-1H-thieno[2,3-c]pyrazole-5-carboxylic acid

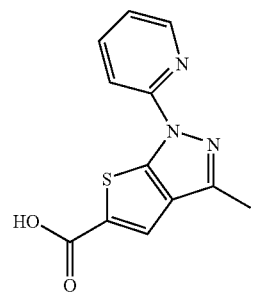

In a 1.0-liter egg plant-type flask, mercaptoacetic acid (10.3 g, 0.15 mol) and potassium hydroxide (35.6 g, 0.54 mol) were added to an ethanol (600 mL) solution of 5-chloro-3-methyl-1-pyridin-2-yl-1H-pyrazole-4-carbaldehyde (30.0 g, 0.14 mol), and stirred for 2 hours with heating under reflux. Ethanol was removed from the reaction solution under reduced pressure, then the residue was diluted with water and made acidic with aqueous 5 N hydrochloric acid solution added thereto, and the formed precipitate was taken out through filtration, washed with methanol and ethyl acetate in that order, and dried under reduced pressure to obtain the title compound as a pale brown solid.

Reference Example 112

Methyl 3-ethoxy-4-(1-methyl-pyrazol-4-yl)benzoate

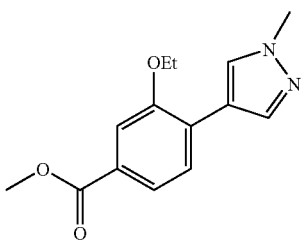

1-Methyl-(4,4,5,5-tetramethyl-1,3,2-dioxaborolan-2-yl)-1H-pyrazole (183 mg, 0.88 mmol), potassium phosphate (374 mg, 1.76 mmol) and dichloro(1,1-bis(diphenylphosphino)-ferrocene)palladium(II) dichloromethane adduct (9.6 mg, 0.012 mmol) were added to an acetonitrile solution (3 mL) of methyl 4-bromo-3-ethoxybenzoate (152 mg, 0.59 mmol), and stirred overnight at 100° C. The reaction liquid was cooled to room temperature, and water was added to it. This was extracted with ethyl acetate, washed with saturated saline water, and dried with magnesium sulfate. The solution was filtered, and concentrated under reduced pressure, and the resulting residue was purified through silica gel column chromatography (hexane/ethyl acetate=50/50) to obtain the title compound as a white solid.

Reference Example 113

3-Ethoxy-4-(1-methylpyrazol-4-yl)benzoic acid

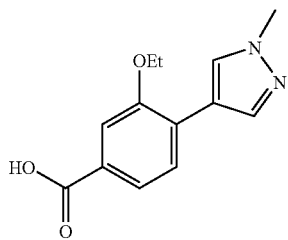

Aqueous 5 N sodium hydroxide solution (0.6 mL, 3.0 mmol) was added to a methano chloroform (1/1) solution (5 mL) of methyl 3-ethoxy-4-(1-methylpyrazol-4-yl)benzoate (149 mg, 0.57 mmol), and stirred overnight at room temperature. 5 N hydrochloric acid water (0.6 mL, 3.0 mmol) was added to the reaction liquid. The aqueous layer was extracted twice with chloroform, washed with saturated saline water, and dried with magnesium sulfate. The solution was filtered and concentrated under reduced pressure to obtain the title compound as a white solid.

Reference Example 114

Ethyl indazole-6-carboxylate hydrochloride

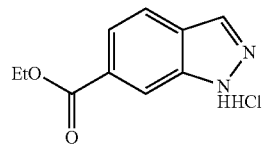

In a 200-mL egg plant-type flask, acetic anhydride (9.46 mL, 100 mmol) was added to a CHCl$_3$ solution (200 mL) of sodium acetate (5.89 g, 60 mmol) and 5-(ethyloxy)-2-methylaniline (8.96 g, 50 mmol), and stirred for 30 minutes with heating under reflux. Next, isoamyl nitrite (13.31 mL, 100 mmol) and 18-crown-6-ether (1.32 g, 5 mmol) were added to the reaction solution, and stirred overnight with heating under reflux. This was diluted with water, extracted with CHCl$_3$, washed with aqueous saturated sodium hydrogencarbonate solution, and dried with sodium sulfate. The solution was filtered and concentrated to obtain a crude product. This was stirred in a hydrochloric acid/methanol solution at 60° C. for 30 minutes, and concentrated. The formed solid was washed with hexane and ethyl acetate to obtain the title compound of hydrochloride as a pale yellow solid.

Reference Example 115

Ethyl 3-iodo-indazole-6-carboxylate

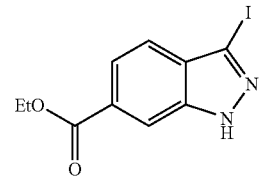

In a 3.0-liter egg plant type flask, iodine (6.09 g, 24 mmol) and KOH (4.49 g, 68 mmol) were added to a DMF solution (60 mL) of ethyl 1H-indazole-6-carboxylate (4.52 g, 20 mmol), and stirred at room temperature for 2 hours. Saturated ammonium chloride water was added to it, extracted with ethyl acetate, washed with water and saturated saline water in that order, and dried with sodium sulfate. The reaction solution was filtered, concentrated, and the resulting solid was washed with a mixed solution of hexane and ethyl acetate to obtain the title compound as a yellow solid.

Reference Example 116

Methyl 3-iodo-1-methyl-1H-indazole-6-carboxylate

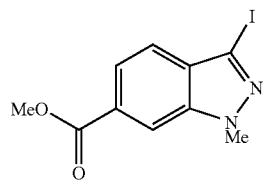

In a 100-mL egg plant-type flask, MeI (381 mL, 6 mmol) was added to a DMF solution (10 ml) of ethyl 3-iodo-1H- indazole-6-carboxylate (948 mg, 3 mmol) and K₂CO₃ (830 mg, 6 mmol), and stirred overnight at room temperature. Further, and K₂CO₃ (830 mg, 6 mmol) and methyl iodide (381 μL, 6 mmol) were added to it, and stirred at 50° C. for 1 hour. After the starting materials disappeared, methanol was added to the reaction solution and stirred at that temperature for 30 minutes. This was diluted with a mixed solvent of hexane and ethyl acetate, and washed with water and saturated saline water in that order, dried with sodium sulfate, filtered, concentrated and purified through silica gel column chromatography to obtain the title compound as a colorless solid.

Reference Example 117

Methyl 1-methyl-3-phenyl-1H-indazole-6-carboxylate

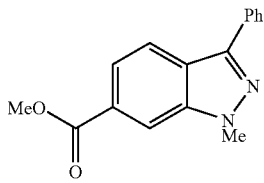

In a 100-mL egg plant-type flask, PdCl₂(dppf) (178 mg, 0.22 mmol) was added to a THF (20 mL)-water (2 mL) mixed solution of methyl 3-iodo-1-methyl-1H-indazole-6-carboxylate (690 mg, 22 mmol), phenylboric acid (399 mg, 3.27 mmol) and K₂CO₃ (1.35 g, 9.81 mmol), and stirred overnight at 80° C. in an argon atmosphere. This was diluted with ethyl acetate, washed with water and saturated saline water, dried with sodium sulfate, filtered and concentrated. The resulting crude product was purified through silica gel column chromatography to obtain the title compound.

Reference Example 118

1-Methyl-3-phenyl-1H-indazole-6-carboxylic acid

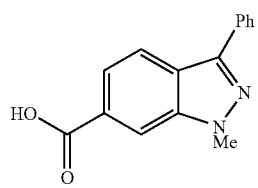

In a 50-mL egg plant-type flask, aqueous 5 N sodium hydroxide solution (1.3 mL, 6.5 mmol) was added to a THF (5 mL)-methanol (5 mL) mixed solution of methyl 1-methyl-3-phenyl-1H-indazole-6-carboxylate (604 mg, 22 mmol), and stirred overnight at 60° C. With cooling with ice, aqueous 5 N hydrochloric acid solution (1.3 mL, 6.5 mmol) was added to the reaction solution, and concentrated to obtain a mixture of the title compound with salt, as a colorless solid.

Reference Example 119 tert-Butyl 6-chloro-5-(methoxycarbonyl)-3-pyridinyl]-4-oxospiro[chroman-2,4'-piperidine]-1'-carboxylate

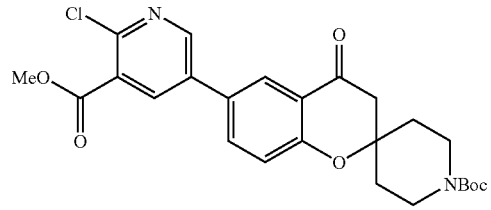

The mixture of methyl 5-bromo-2-chloronicotinate (1.10 g), Pd(PPh3)₄ (0.23 g), K3PO4 (2.55 g) and 1'-tert-butoxycarbonyl-6-(4",4",5",5"-tetramethyl-1",3",2"-dioxaborolan-2"-yl)spiro[chroman-2,4'-piperidin]-4-one (1.77 g) in DME (17 ml) was stirred at 150° C. for 15 min under microwave irradiation. The cooled reaction mixture was diluted with CHCl3, washed with water, and dried over sodium sulfate. After filtration and concentration, the residue was purified by silica gel chromatography (hexane/EtOAc) and crystallized from methanol to give title compound as a colorless solid.

Reference Example 120 tert-Butyl 6-[5-(methoxycarbonyl)-6-methyl-3-pyridinyl]-4-oxospiro[chroman-2,4'-piperidine]-1'-carboxylate

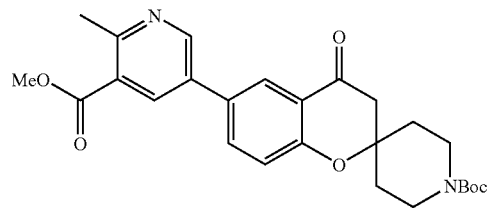

The mixture of tetramethyltin (1.14 ml), and PdCl2 (PPh3)2 (97 mg), tert-butyl 6-[6-chloro-5-(methoxycarbonyl)-3-pyridinyl]-4-oxospiro[chroman-2,4'-piperidine]-1'-carboxylate (1.35 g) in dioxane (13 ml) was stirred at 180° C. for 15 min under microwave irradiation. The reaction mixture was evaporated, and purified by silica gel chromatography (hexane/ethyl acetate) to give the intended compound.

Reference Example 121

Methyl 2-methyl-5-(4-oxospiro[chroman-2,4'-piperidin]-6-yl)nicotinate dihydrochloride

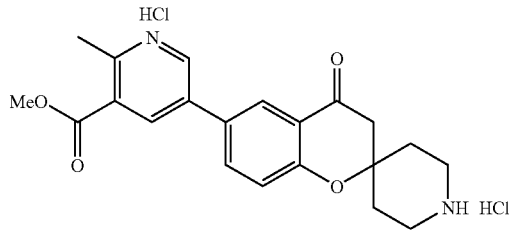

The intended compound was produced according to the procedure described in Reference Example 18 but using tert-Butyl 6-[5-(methoxycarbonyl)-6-methyl-3-pyridinyl]-4-oxospiro[chroman-2,4'-piperidine]-1'-carboxylate.

Reference Example 122

6-(4-oxospiro[chroman-2,4'-piperidin]-6-yl)nicotinamide dihydrochloride

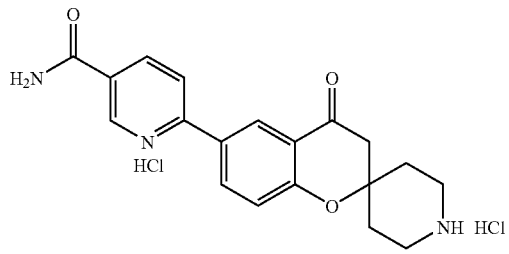

The intended compound was produced according to the procedure described in Reference Example 17 and 24 but using 6-chloronicotinamide in place of 5-bromonicotinic acid methyl ester.

Reference Example 123

Methyl 2-fluoro-5-(4-oxospiro[chroman-2,4'-piperidin]-6-yl)benzoate hydrochloride

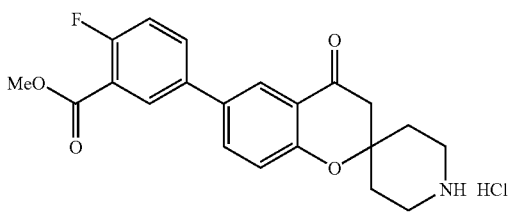

The intended compound was produced according to the procedure described in Reference Example 19, 21 and 22 but using 5-(dihydroxyboryl)-2-fluorobenzoic acid in place of 3-carboxy-phenylboronicacid.

Reference Example 124

Methyl 6-(4-oxospiro[chroman-2,4'-piperidin]-6-yl)pyridine-3-carboxylate dihydrochloride

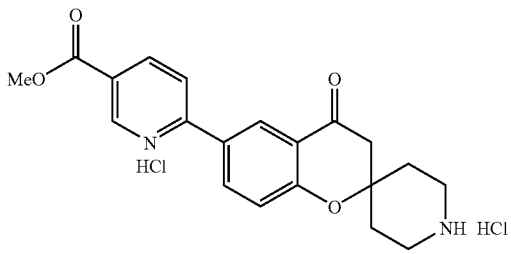

The intended compound was produced according to the procedure described in Reference Example 17 and 18 but using 5-(dihydroxyboryl)-2-fluorobenzoic acid in place of 3-carboxyphenylboronic acid.

Reference Example 125

6-(1,1-dioxidothiomorpholin-4-yl)spiro[chroman-2,4'-piperidin]-4-o ne hydrochloride

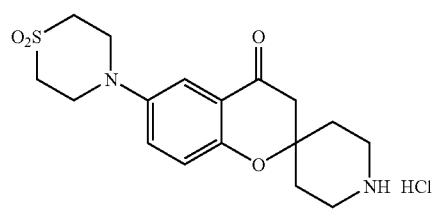

The intended compound was produced according to the procedure described in Reference Example 34 and 18 but using thiomorpholine 1,1-dioxide in place of 5-amino-1-methyl-1H-pyrazole.

Reference Example 126 tert-Butyl 6-[(methoxycarbonyl)amino]-4-oxospiro[chroman-2,4'-piperidine]-1'-carboxylate

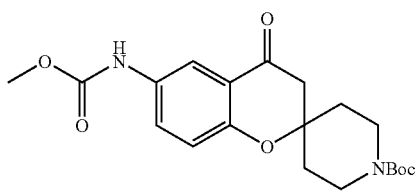

Methyl chloridocarbonate was added to a solution of tert-butyl 6-amino-4-oxospiro[chroman-2,4'-piperidine]-1'-carboxylate in pyridine and stirred at room temperature for 6 hours. The solvent was removed under reduced pressure and the residue was purified by silicagel column chromatography (hexane/EtOAc) to obtain the intended compound as pale yellow foam.

Reference Example 127

Methyl(4-oxospiro[chroman-2,4'-piperidin]-6-yl)carbamate hydrochloride

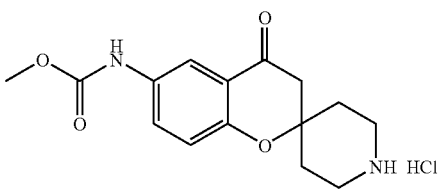

The intended compound was produced according to the procedure described in Reference Example 24 but using tert-butyl 6-[(methoxycarbonyl)amino]-4-oxospiro[chroman-2,4'-piperidine]-1'-carboxylate in place of 5''-{1'-tert-butoxycarbonyl]-4-oxospiro[chroman-2,4'-piperidin]-6-yl}nicotinamide.

Reference Example 128

N-(2,2-difluoroethyl)-4-oxospiro[chroman-2,4'-piperidine]-6-carboxamide hydrochloride

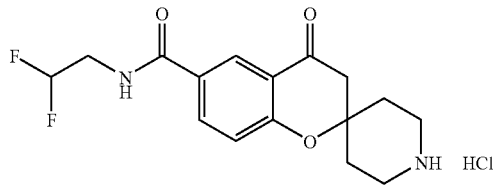

The intended compound was produced according to the procedure described in Reference Example 36 and 24 but using 2,2-difluoroethanamine in place of glycinamide hydrochloride.

Reference Example 129

1-Acetyl-5-bromo-3-methyl-1H-indazole

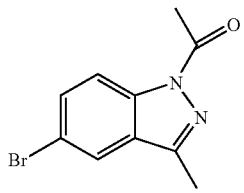

Acetic anhydride (4.73 ml) was added to the mixture of 4-bromo-2-ethylaniline (5.0 g) and KOAc (2.94 g) in CHCl3 (70 ml) and stirred for 30 min at reflux. Then isoamyl nitrite (6.65 ml) and 18-crown-6-ether (660 mg) was added to the reaction mixture and stirred for 12 h at reflux. The reaction mixture was diluted with CHCl3, washed with water, and dried over sodium sulfate. After filtration and concentration, the residue was purified by silica gel chromatography (hexane/ethyl acetate), and crystallized from mixed solvent of hexane and CHCl3 to give the title compound as a yellow solid.

Reference Example 130

5-Bromo-3-methyl-1H-indazole hydrochloride

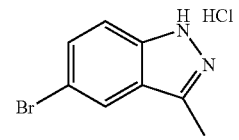

1-Acetyl-5-bromo-3-methyl-1H-indazole (1.23 g) was added to the solution of hydrochloride in methanol (30 ml), and stirred for 30 min at 60° C. The mixture was concentrated under reduced pressure, and the residue was crystallized from mixed solvent of hexane and EtOAc to give the title compound as a yellow solid.

Reference Example 131

5-Bromo-3-methyl-1-phenyl-1H-indazole

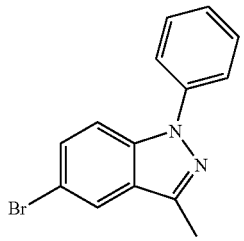

The mixture of 5-bromo-3-methyl-1H-indazole hydrochloride (999 mg), Cu(OAc)$_2$ (1.13 g), pyridine (978 ul) and phenylbronic acid (982 mg) in dichloromethane (20 ml) was stirred at room temperature for over night. The mixture was filtered with celite pad, and the filtrate was evaporated under reduced pressure. The green residue was purified by silica gel chromatography (hexane/EtOAc) to give the intended compound as brown oil.

Reference Example 132

Methyl 3-methyl-1-phenyl-1H-indazole-5-carboxylate

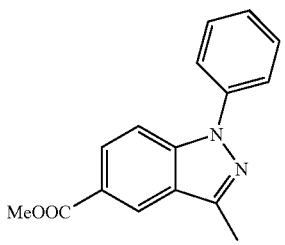

The mixture of 5-bromo-3-methyl-1-phenyl-1H-indazole (642 mg), Pd(OAc)$_2$ (52 mg), DPPF (123 mg), diisopropyl ethyl amine (1.14 ml) in DMF (5 ml)-MeOH (5 ml) was purged with CO and stirred at 70° C. under CO atmosphere for over night. The cooled reaction mixture was evaporated and the residue was purified by silica gel column chromatography (hexane/EtOAc) to give the title compound as brown oil.

Reference Example 133

3-Methyl-1-phenyl-1H-indazole-5-carboxylic acid

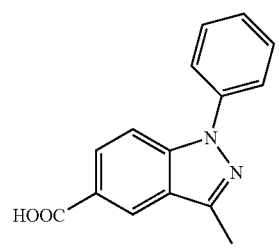

5N NaOH aqueous solution (6 ml) was added to the solution of methyl 3-methyl-1-phenyl-1H-indazole-5-carboxylate (2.66 g) in methanol 30 ml and stirred at 50° C. for over night. The cooled reaction mixture was quenched with 1N HCl aqueous solution (33 ml) and white precipitate was collected and dried in vacuo at 60° C. to give the title compound as a colorless solid Reference Example 134

Methyl 4-(1-cyclopropyl-1H-pyrazol-4-yl)-3,5-diethoxybenzoate

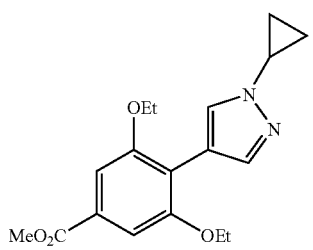

To a mixture of methyl 3,5-diethoxy-4-(1H-pyrazol-4-yl)benzoate (20 mg), cyclopropylboronic acid (24 mg) in THF (2 ml) were added Cu(OAc)$_2$ (37 mg), pyridine (45 ul) and TEA (48 ul) at room temperature and irradiated with microwave at 120° C. for 15 min. After cooling to room temperature, the mixture was diluted with EtOAc, filtered through celite pad and the filtrate was evaporated under reduced pressure. The residue was purified by p-TLC (hexane/EtOAc) to give the title product as a colorless solid.

Reference Example 135

4-(1-cyclopropyl-1H-pyrazol-4-yl)-3,5-diethoxybenzoic acid

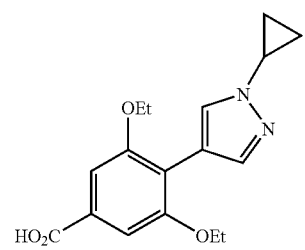

To a solution of Methyl 4-(1-cyclopropyl-1H-pyrazol-4-yl)-3,5-diethoxybenzoate (20 mg) in MeOH (3 ml) was added aqueous 1N NaOH (240 ul) at room temperature, and the reaction mixture was stirred for over night. The mixture was concentrated under reduced pressure and aqueous 1N HCl (240 ul) was added to the residue. The mixture was concentrated under reduced pressure and dried in vacuo to give the crude title compound which was used in the next step without further purification.

Reference Example 136

1-(difluoromethyl)-4-iodo-1H-pyrazole

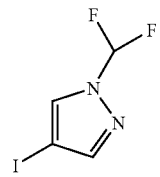

To a mixture of 4-iodo-1H-pyrazole (3 g) in DMF (80 ml) were added H2O (16 ml), potassium carbonate (6.41 g) and dichloroacetic acid (7.01 ml) at room temperature, and the reaction mixture was stirred at 100° C. for over night. Then, additional potassium carbonate (6.41 g) and dichloroacetic acid (7.81 ml) were added to the reaction mixture and the mixture was stirred at 100° C. for further 8 h. After cooling to room temperature, the mixture was poured into H2O, extracted with EtOAc and dried over sodium sulphate. After filtration and concentration, the residue was purified by silicagel column chromatography (hexane/EtOAc) to give the title compound as colorless oil.

Reference Example 137

4-Bromo-3,5-diethoxybenzoic acid

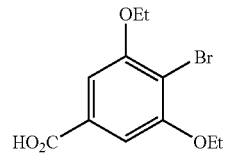

To a stirred solution of methyl 4-bromo-3,5-diethoxybenzoate (3 g) in a mixture of THF (25 ml) and MeOH (10 ml) was added aqueous 1N NaOH (20 ml) and the reaction mixture was stirred at room temperature for 6 h. The mixture was concentrated under reduced pressure, the residue was diluted with H2O and diethylether. The aqueous layer was acidified with 1N HCl aq., the mixture was extracted with CHCl3 and dried over sodium sulphate. After filtration and concentration, the residue was dried in vacuo to give the crude title compound as a colorless solid. Thus obtained crude product was used in the next step without further purification.

Reference Example 138 tert-Butyl 4-bromo-3,5-diethoxybenzoate

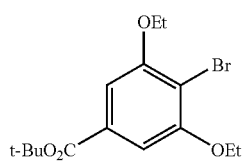

To a mixture of 4-Bromo-3,5-diethoxybenzoic acid (2.8 g) in DMF (25 ml) was added CDI (1.8 g) at room temperature and the mixture was stirred at 40° C. for 2 h. To the reaction mixture, t-BuOH (1.85 ml) and DBU (1.752 ml) were added and further stirred at 40° C. for over night. After cooling to room temperature, the mixture was poured into ice-H2O and extracted with EtOAc. The organic layer was washed with H2O, brine and dried over sodium sulphate. After filtration and concentration, the residue was purified by silica gel column chromatography (hexane/EtOAc) to give the title compound as a colorless solid.

Reference Example 139

[4-(tert-butoxycarbonyl)-2,6-diethoxyphenyl]boronic acid

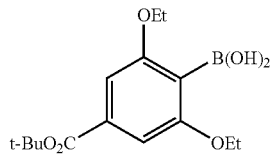

To a stirred solution of tert-butyl 4-bromo-3,5-diethoxybenzoate (1 g) in THF (20 ml) was added n-BuLi (1.6M in hexane, 3.6 ml) at −78° C. under argon atmosphere and stirred at the same temperature for 1 h. To the mixture was added B(OMe)$_3$ (777 ul) at −78° C. and the mixture was allowed to warm up to at room temperature. After stirring for further 1 h, the mixture was poured into ice-HCl aq., extracted with EtOAc, washed with brine and dried over sodium sulphate. After filtration and concentration, the residue was purified by silicagel column chromatography (hexane/EtOAc) to give the title product as a colorless solid.

Reference Example 140 tert-butyl 4-[1-(difluoromethyl)-1H-pyrazol-4-yl]-3,5-diethoxybenzoate

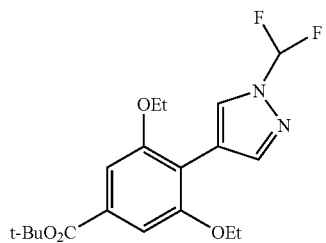

[4-(tert-butoxycarbonyl)-2,6-diethoxyphenyl]boronic acid (50 mg), 4-iodopyrazole (59 mg), K3PO4 (103 mg), S-phos (6.6 mg), Pd(OAc)2 and H2O was suspended in THF (3 ml) at N2 atmosphere and the mixture was stirred at 90° C. for over night. The reaction mixture was cooled to room temperature, and diluted with H2O. The mixture was extracted with EtOAc, washed with brine and dried over sodium sulphate. After filtration and concentration, the residue was purified by silicagel column chromatography (hexane/EtOAc) to give the title compound as a colorless solid.

Reference Example 141

4-[1-(difluoromethyl)-1H-pyrazol-4-yl]-3,5-diethoxybenzoic acid

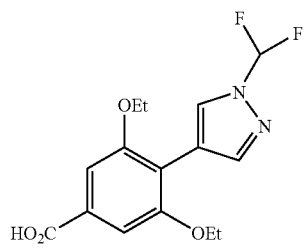

To a stirred solution of tert-butyl[1-(difluoromethyl)-1H-pyrazol-4-yl]-3,5-diethoxybenzoate (35 mg) in CHCl3 (1.5 ml) was added TFA (1.5 ml) and the reaction mixture was stirred at room temperature for 4 h. The solvents were removed under reduced pressure and CHCl3 was added to the residue. The solvent was removed under reduced pressure the residue was dried in vacuo to give the crude title compound as a pale brown solid. Thus obtained crude product was used in the next step without further purification.

The usefulness of the compounds of the invention as medicines is demonstrated, for example, by the following pharmacological test example.

BIOLOGICAL ASSAYS

A. Pharmacological Test Example (Acetyl CoA Carboxylase (ACC) Activity Inhibition Test)

A test compound is dissolved in dimethyl sulfoxide (DMSO) to a concentration of 10 mM and then diluted with DMSO to give a 100-fold concentrated solution of the compound compared with target assay concentration. The ACC enzyme activity inhibition test is carried out according to a modification of Thampy & Wakil's method (*J. Biol. Chem.*, Vol. 260, pp. 6318-6323 (1985)). Concretely, 0.8 μl of the diluted test compound is added to each well of 96-well assay plate (Perkin Elmer Opti Plate), then 40 μl of a substrate solution (50 mM Hepes sodium (pH 7.5), 2 mM DTT, 10 mM ATP, 500 μM acetyl CoA, 0.17 mM NaH[$^{14}$C]O$_3$ (58 mCi/mmol, by Amersham), 8 mM NaHCO$_3$) is added to each well, and 40 μL of an enzyme solution (1 to 2 mM human ACC1 or human ACC2, 50 mM Hepes sodium (pH 7.5), 2 mM DTT, 40 mM MgCl$_2$, 40 mM tripotassium citrate 1 mg/ml fetal bovine serum albumin) is added thereto. Then, the upper side of the plate is sealed up, and the plate is incubated with gently stirring at 37° C. for 40 minutes. Next, 20 μl of 1 N HCl is added to each well to stop the enzyme reaction, and the assay plate is stirred overnight to remove the unreacted NaH[$^{14}$C]O$_3$. Next, 100 μl of a scintillator (Perkin Elmer's Microscinti 40) is added to each well and the plate is stirred, then the radioactivity of the fixed [$^{14}$C] is counted using a microplate scintillation counter (Perkin Elmer's Topcount), the radioactivity of which represents the enzyme activity in each well. The human ACC1 and human ACC2 enzyme-inhibition activities of the test compounds are calculated, based on the radioactivity of the well added by DMSO without test compound as a control.

The compounds of the invention were tested according to this method and the compounds tested all inhibited both ACC1 and ACC2. The results are shown in the following Table.

| Inhibition (%) by 1 μmol/liter Chemical | | |
|---|---|---|
| Compound | human ACC1 | human ACC2 |
| Example 5 | 94% | 97% |
| Example 12 | 100% | 99% |
| Example 25 | 100% | 99% |
| Example 29 | 99% | 99% |
| Example 37 | 100% | 99% |
| Example 42 | 98% | 99% |
| Example 51 | 98% | 89% |
| Example 56 | 99% | 98% |
| Example 63 | 93% | 97% |
| Example 68 | 99% | 99% |
| Example 71 | 99% | 99% |
| Example 77 | 99% | 99% |
| Example 79 | 99% | 99% |

Representative compounds of the present invention, including the compounds of Examples 1-81, were tested in the above assay and found to have a percent inhibition of greater than or equal to 50% for ACC-1 and a percent inhibition of greater than or equal to 50% for ACC-2 in the acetyl CoA carboxylase (ACC) activity inhibition test.

B. Effect of ACC1/2 Inhibitor on In Vivo Body Weight, Fat Mass, Fatty Liver and Plasma Glucose Levels Effect of ACC1/2 inhibitor on body weight, fat mass, fatty liver and plasma glucose level can be determined in either high fat diet induced obese or KKAy diabetic mice.

Male C57black/6J mice at approximately 6 weeks old are individually housed and maintained on chow diet for 2 weeks prior to the study. Then the mice are fed with a 60% fat diet for 5 weeks before dosing. The mice (n=8) on the high fat diet are orally dosed with either vehicle control (0.5% methylcellulose solution) or an ACC1/2 inhibitor (various doses) for 6 weeks. Body weight is determined on a daily basis and fat mass is measured by NMR every other week. Hepatic triglyceride content is determined at week 6. Effective ACC1/2 inhibitors result reduced body weight gain, reduced fat mass gain, and reduced hepatic triglyceride content in ACC1/2 inhibitor treated male C57black/6J mice in contrast to the vehicle control group.

Male KKAy mice at approximately 8 weeks old are individually housed and maintained on for 2 weeks prior to the study. The mice (n=10) are orally dosed with either vehicle control (0.5% methylcellulose solution) organ ACC1/2 inhibitor (various doses) for 2 weeks. At week 2, blood is collected at 23 hours post dose and plasma glucose concentration is determined. Effective ACC1/2 inhibitors result in reduced plasma glucose levels in ACC1/2 inhibitor treated KKAy mice in contrast to the vehicle control group.

C. Human Study for Effect on Food Intake and Glucose/Insulin Levels 800 people with a BMI ≧30 who have impaired fasting plasma glucose levels, impaired glucose tolerance, or elevated serum insulin, indicative of a prediabetic insulin resistant state, and who may have elevated serum glucose levels, indicative of type II diabetes, are advised to diet and increase their physical activity. After a two-week placebo run-in period, which includes a standardized program of diet, physical activity, and lifestyle changes, the patients are randomized into 2 treatment groups: placebo; and an effective dose of a compound of formula (I). The compound of formula (I) is given once or more per day, as previously determined to be effective. Patients are treated for 6 months, body weights are measured biweekly, and appetite, hunger, satiety are measured weekly using standard questionnaires. Serum glucose, insulin levels and body weight are determined at day 0, monthly, and after the final dose.

Effective compounds result in body weight loss or an improvement in serum insulin levels, indicative of improved insulin sensitivity or lower fasting blood glucose levels.

Formulation Preparation Example 1

20.0 g of the compound of Example 1, 417 g of lactose, 80 g of crystalline cellulose and 80 g of partially-alphatized starch are mixed in a V-shape mixer, and 3.0 g of magnesium stearate is added to it and mixed. The mixture powder is tabletted according to an ordinary method to obtain 3000 tablets each having a diameter of 7.0 mm and a weight of 150 mg.

| Ingredients of Tablet (150 mg) | |
|---|---|
| Compound of Example 1 | 5.0 mg |
| Lactose | 104.25 mg |
| Crystalline cellulose | 20.0 mg |
| Partially-alphatized starch | 20.0 mg |
| Magnesium stearate | 0.75 mg |

Formulation Preparation Example 2

10.8 g of hydroxypropyl cellulose 2910 and 2.1 g of polyethylene glycol 6000 are dissolved in 172.5 g of pure water, and 2.1 g of titanium oxide is dispersed therein to prepare a coating liquid. Using a high-coater-mini, 2500 tablets of Preparation Example 1 that is prepared separately is sprayed with the coating liquid to obtain film-coated tables each having a weight of 155 mg.

| Ingredients of Tablet (155 mg) | |
|---|---|
| Tablet of Preparation Example 1 | 150 mg |
| Hydroxypropyl cellulose 2910 | 3.6 mg |
| Polyethylene glycol 6000 | 0.7 mg |
| Titanium dioxide | 0.7 mg |

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

What is claimed is:

1. The compound, or a salt thereof, wherein the compound is represented by a general formula (I-1):

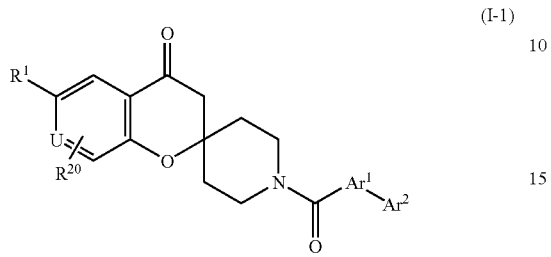

wherein Ar$^1$ represents a group formed from an aromatic ring selected from a group consisting of benzene, pyrazole, isoxazole, pyridine, indole, 1H-indazole, 1H-furo[2,3-c]pyrazole, 1H-thieno[2,3-c]pyrazole, benzimidazole, 1,2-benzisoxazole, imidazo[1,2-a]pyridine, imidazo[1,5-a]pyridine and 1H-pyrazolo[3,4-b]pyridine, having Ar$^2$, and optionally having one or two or more substituents selected from R$^3$;

Ar$^2$ represents an aromatic group selected from a group consisting of a phenyl group, a furyl group, a thienyl group, a pyrazolyl group, a thiazolyl group, an oxazolyl group, an isoxazolyl group, a 1,2,4-triazolyl group, a 1,2,4-oxadiazolyl group, a 1,3,4-oxadiazolyl group, a tetrazolyl group, a pyridyl group, a pyrazinyl group, a pyrimidinyl group, an indolyl group and a benzo[b]thienyl group, optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C1-C6 alkoxycarbonyl group, a C1-C6 alkylsulfonyl group, a C1-C6 alkylsulfonylamino group and a tetrazolyl group;

R$^1$ represents a group of -Q$^1$-N(R$^a$)-Q$^2$-R$^b$;

or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N(R$^c$)R$^d$; or a C1-C6 alkyl group or a C2-C6 alkenyl group having the aryl or heterocyclic group;

R$^{20}$ represents a hydrogen atom, a halogen atom, a C1-C6 alkyl group or a C1-C6 alkoxy group;

R$^3$ represents a halogen atom, a nitro group, a cyano group, a hydroxyl group, a carboxyl group, a C2-C6 alkenyl group, a cyclo-C3-C6 alkyl group, or a group of —N(R$^e$)R$^f$;

a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group may be interrupted by an oxygen atom, a sulfur atom or an imino group;

a C1-C6 alkyl group optionally having a substituent selected from a group consisting of a halogen atom, a hydroxyl group, a cyclo-C3-C6 alkyl group and a C1-C6 alkoxy group; or a phenyl group, a 1,2,4-triazolyl group or a tetrazolyl group optionally having a substituent selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group;

Q$^1$ and Q$^2$ are a single bond, R$^a$ is a hydrogen atom, and R$^b$ is a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group;

R$^c$, and R$^d$, each independently represent a hydrogen atom, a C1-C6 alkyl group, or a halo-C1-C6 alkyl group;

R$^e$ and R$^f$ each independently represent a hydrogen atom, a C1-C6 alkyl group, or a halo-C1-C6 alkyl group, or taken together, they may form a C2-C5 alkylene group optionally interrupted by an oxygen atom, a sulfur atom or an imino group; and U represents a methine group.

2. The compound as claimed in claim 1, or a salt or ester thereof, which is the following:

(1) 1'-{[4-(Benzo[b]thiophen-2-yl)phenyl]carbonyl}-6-(tetrazol-5-yl)-spiro[chroman-2,4'-piperidin]-4-one, (2) 1'-{[2,6-Bis(4-fluorophenyl)pyridin-4-yl]carbonyl}-6-(tetrazol-5-yl)-spiro[chroman-2,4'-piperidin]-4-one, (3) 1'-{[2-Methoxy-6-phenylpyridin-4-yl]carbonyl}-6-(tetrazol-5-yl)spiro[chroman-2,4'-piperidin]-4-one.

(4) 1'-{[3-(1H-indol-5-yl)$_5$-methoxyphenyl]carbonyl}-6-(tetrazol-5-yl)-spiro[chroman-2,4'-piperidin]-4-one, (5) 1'-{[2,6-Dimethoxybiphenyl-4-yl]carbonyl}-6-(tetrazol-5-yl)-spiro[chroman-2,4'-piperidin]-4-one, (6) 1'-{[2,6-Dimethoxybiphenyl-4-yl]carbonyl}-6-(tetrazol-5-yl)-spiro[chroman-2,4'-piperidin]-4-one sodium salt, (7) 1'-{[3-Pyrrolidin-1-yl-5-(1,2,4-triazol-3-yl)phenyl]carbonyl}-6-(tetrazol-5-yl)spiro[chroman-2,4'-piperidin]-4-one sodium salt, (8) 6-[(1-Methyl-1H-pyrazol-5-yl)amino]-1'-{[2-phenyl-6-(tetrazol-5-yl)pyridin-4-yl]carbonyl}spiro[chroman-2,4'-piperidin]-4-one, (9) [5-(4-Oxo-1'-{[3-(pyrrolidin-1-yl-5-(1,2,4-triazol-3-yl)phenyl]carbonyl}-spiro[chroman-2,4'-piperidin]-6-yl)-tetrazol-2-yl]methyl-2,2-dimethylpropanoate,

(10) [5-(1'-{[2,6-Dimethoxybiphenyl-4-yl]carbonyl}-4-oxospiro[chroman-2,4'-piperidin]-6-yl)-tetrazol-2-yl]methyl-2,2-dimethylpropanoate,

(11) 1'-{[3-Ethoxy-5-(tetrazol-5-yl)phenyl]carbonyl}-6-[(1-methyl-1H-pyrazol-5-yl)amino]spiro[chroman-2,4'-piperidin]-4-one sodium salt,

(12) 1'-{[3,5-Diethoxy-4-(1-methyl-1H-pyrazol-4-yl)phenyl]carbonyl}-6-(tetrazol-5-yl)spiro[chroman-2,4'-piperidin]-4-one,

(14) 6-(1-Methyl-1H-pyrazol-4-yl)-1'-{[5-(tetrazol-5-yl)biphenyl-3-yl]carbonyl}spiro[chroman-2,4'-piperidin]-4-one,

(15) 1'-{[3-Ethoxy-4-(1-methyl-1H-pyrazol-4-yl)phenyl]carbonyl}-6-(tetrazol-5-yl)spiro[chroman-2,4'-piperidin]-4-one,

(16) 6-[(1-Methyl-1H-pyrazol-5-yl)amino]-1'-{[3-(pyrrolidin-1-yl)-5-(tetrazol-5-yl)phenyl]carbonyl}spiro[chroman-2,4'-piperidin]-4-one,

(17) 5-(4-Oxo-1'-{[5-(tetrazol-5-yl)biphenyl-3-yl]carbonyl}-spiro[chroman-2,4'-piperidin]-6-yl)pyridine-3-carboxamide sodium salt,

(18) 1'-{[3,5-Diethoxy-4-(1H-pyrazol-4-yl)phenyl]carbonyl}-6-(tetrazol-5-yl)spiro[chroman-2,4'-piperidin]-4-one,

(19) 1'-{[3,5-Diethoxy-4-(1H-pyrazol-4-yl)phenyl]carbonyl}-6-(5-oxo-4,5-dihydro-1,2,4-oxadiazol-3-yl)spiro[chroman-2,4'-piperidin]-4-one,

(20) 1'-{[3,5-Diethoxy-4-(1-methyl-1H-pyrazol-4-yl)phenyl]carbonyl}-6-(5-oxo-4,5-dihydro-1,2,4-oxadiazol-3-yl)spiro[chroman-2,4'-piperidin]-4-one,

(22) 1'-{[3,5-Diethoxy-4-(1-methyl-1H-pyrazol-4-yl)phenyl]carbonyl}-6-(5-oxo-4,5-dihydro-1H-1,2,4-triazol-3-yl)spiro[chroman-2,4'-piperidin]-4-one,

(23) 1'-{[3,5-Diethoxy-4-isoxazol-4-ylphenyl]carbonyl}-6-(tetrazol-5-yl)spiro[chroman-2,4'-piperidin]-4-one,

(24) 5-(1'-{[2,6-Dimethoxybiphenyl-4-yl]carbonyl}-4-oxospiro[chroman-2,4'-piperidin]-6-yl)pyridine-3-carboxylic acid,

(25) 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid,

(26) 5-(1'-{[3,5-Diethoxy-4-(1-methyl-1H-pyrazol-4-yl)phenyl]carbonyl}-4-oxospiro[chroman-2,4'-piperidin]-6-yl)pyridine-3-carboxylic acid sodium salt,

(27) [5-(1'-{[3,5-Diethoxy-4-(1-methyl-1H-pyrazol-4-yl)phenyl]carbonyl}-4-oxospiro[chroman-2,4'-piperidin]-6-yl)-2H-tetrazol-2-yl]methyl 2,2-dimethylpropanoate,

(29) 1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one,

(30) 1'-{[3-Ethoxy-5-methoxy-4-(1-methyl-1H-pyrazol-4-yl)phenyl]carbonyl}-6-(tetrazol-5-yl)spiro[chroman-2,4'-piperidin]-4-one sodium salt,

(31) 1'-{[3,5-Diethoxy-4-(6-fluoropyridin-3-yl)phenyl]carbonyl}-6-(tetrazol-5-yl)spiro[chroman-2,4'-piperidin]-4-one,

(32) 1'-{[3,5-Diethoxy-4-(2-fluoropyridin-4-yl)phenyl]carbonyl}-6-(tetrazol-5-yl)spiro[chroman-2,4'-piperidin]-4-one,

(33) 1'-{[4-(2-Methyl-1,3-oxazol-5-yl)-3,5-dimethoxyphenyl]carbonyl}-6-(tetrazol-5-yl)spiro[chroman-2,4'-piperidin]-4-one,

(34) Sodium 5-(1'-{[3,5-diethoxy-4-(6-fluoropyridin-3-yl)phenyl]carbonyl}-4-oxo-spiro[chroman-2,4'-piperidin]-6-yl)pyridine-3-carboxylate,

(35) Sodium 5-(1'-{[3,5-Diethoxy-4-(1-methyl-1H-pyrazol-4-yl)phenyl]carbonyl}-4-oxospiro[chroman-2,4'-piperidin]-6-yl)pyridine-2-carboxylate,

(36) Sodium 2-(1'-{[3,5-diethoxy-4-(1-methyl-1H-pyrazol-4-yl)phenyl]carbonyl}-4-oxospiro[chroman-2,4'-piperidin]-6-yl)pyridine-4-carboxylate,

(37) 4-(1'-{(3,5-Diethoxy-4-(1-methyl-1H-pyrazol-4-yl)phenyl)carbonyl}) oxospiro[chroman-2,4'-piperidin]-6-yl)pyridine-2-carboxylic acid,

(38) 1'-{[1-(1-Methylethyl)-6-phenyl-1H-pyrazolo[3,4-b]pyridin-4-yl]carbonyl}-6-(tetrazol-5-yl)spiro[chroman-2,4'-piperidin]-4-one,

(39) 1'-[(1,3-Diphenyl-1H-thieno[2,3-c]pyrazol-5-yl)carbonyl]-6-(tetrazol-5-yl)spiro[chroman-2,4'-piperidin]-4-one,

(40) 1'-{[1-Cyclopropyl-4-(tetrazol-5-yl)-1H-indol-6-yl]carbonyl}-6-[(1-methyl-1H-pyrazol-5-yl)amino]spiro[chroman-2,4'-piperidin]-4-one,

(42) 1'-{([1-Cyclopropyl-4-(tetrazol-5-yl)-1H-indol-6-yl]carbonyl}-6-(1-methyl-1H-pyrazol-4-yl)spiro[chroman-2,4'-piperidin]-4-one,

(43) 1'-[(3-Cyclopropyl-1-pyridin-2-yl-1H-thieno[2,3-c]pyrazol-5-yl)carbonyl]-6-(tetrazol-5-yl)spiro[chroman-2,4'-piperidin]-4-one,

(44) 1'-{[1-Cyclopropyl-4-(tetrazol-5-yl)-1H-indol-6-yl]carbonyl}-6-[6-(methyloxy)pyridin-3-yl]spiro[chroman-2,4'-piperidin]-4-one,

(45) 1'-{[1-Cyclopropyl-4-(tetrazol-5-yl)-1H-indol-6-yl]carbonyl}-6-(6-oxo-1,6-dihydropyridin-3-yl)spiro[chroman-2,4'-piperidin]-4-one,

(46) 3-(1'-{[1-Cyclopropyl-4-(tetrazol-5-yl)-1H-indol-6-yl]carbonyl}-4-oxospiro[chroman-2,4'-piperidin]-6-yl)benzamide,

(47) 1'-[(1,3-Diphenyl-1H-indazol-6-yl)carbonyl]-6-(tetrazol-5-yl)spiro[chroman-2,4'-piperidin]-4-one,

(48) 1'-{[4-Methoxy-1-phenyl-1H-indol-6-yl]carbonyl}-6-(tetrazol-5-yl)spiro[chroman-2,4'-piperidin]-4-one,

(49) 1'-[(3-Phenyl-1-pyridin-2-yl-1H-thieno[2,3-c]pyrazol-5-yl)carbonyl]-6-(tetrazol-5-yl)spiro[chroman-2,4'-piperidin]-4-one,

(50) 1'-[(3-Chloro-1-phenyl-1H-indol-5-yl)carbonyl]-6-(tetrazol-5-yl)spiro[chroman-2,4'-piperidin]-4-one,

(51) 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one,

(52) 1'-[(3-Methyl-1-pyridin-2-yl-1H-thieno[2,3-c]pyrazol-5-yl)carbonyl]-6-(tetrazol-5-yl)spiro[chroman-2,4'-piperidin]-4-one sodium salt,

(53) 1'-[(2-Cyclopropyl-1-phenyl-1H-benzimidazol-5-yl)carbonyl]-6-(tetrazol-5-yl)spiro[chroman-2,4'-piperidin]-4-one,

(54) 1'-[(1-Methyl-3-phenyl-1H-indol-6-yl)carbonyl]-6-(tetrazol-5-yl)spiro[chroman-2,4'-piperidin]-4-one,

(55) 1'-[(1-Ethyl-3-phenyl-1H-thieno[2,3-c]pyrazol-5-yl)carbonyl]-6-(tetrazol-5-yl)spiro[chroman-2,4'-piperidin]-4-one,

(56) 1'-[(1-Methyl-3-phenyl-1H-indazol-6-yl)carbonyl]-6-(tetrazol-5-yl)spiro[chroman-2,4'-piperidin]-4-one,

(57) 1'-[(3-Methyl-1-phenyl-1H-indazol-5-yl)carbonyl]-6-(tetrazol-5-yl)spiro[chroman-2,4'-piperidin]-4-one,

(58) Sodium 5-{1'-[(3-methyl-1-pyridin-2-yl-1H-thieno[2,3-c]pyrazol-5-yl)-carbonyl]-4-oxospiro[chroman-2,4'-piperidin]-6-yl}pyridine-3-carboxylate,

(59) Sodium 5-(1'-[(3-methyl-1-phenyl-1H-indazol-5-yl)carbonyl]-4-oxo-spiro[chroman-2,4'-piperidin]-6-yl)pyridine-3-carboxylate,

(60) Sodium 4-(1'-[(3-methyl-1-pyridin-2-yl-1H-thieno[2,3-c]pyrazol-5-yl)-carbonyl]-4-oxospiro[chroman-2,4'-piperidin]-6-yl)pyridine-2-carboxylate,

(61) 1'-{[3-(Difluoromethyl)-1-pyridin-2-yl-1H-thieno[2,3-c]pyrazol-5-yl]carbonyl}-6-(tetrazol-5-yl)spiro[chroman-2,4'-piperidin]-4-one,

(62) Methyl 5-{1'-[3-ethoxy-5-methoxy-4-(1-methyl-1H-pyrazol-4-yl)benzoyl]-4-oxospiro[chromman-2,4'-piperidin]-6-yl}nicotinate,
(63) (5-{1'-[3-ethoxy-5-methoxy-4-(1-methyl-1H-pyrazol-4-yl)benzoyl]-4-oxospiro[chroman-2,4'-piperidin]-6-yl}-2H-tetrazol-2-yl)methylpivalate,
(64) 4-{1'-[(3-methyl-1-phenyl-1H-indazol-5-yl)carbonyl]-4-oxospiro[chroman-2,4'-piperidin]-6-yl}-2-pyridinecarboxylic acid,
(65) 2-methyl-5-{1'-[(3-methyl-1-phenyl-1H-indazol-5-yl)carbonyl]-4-oxospiro[chroman-2,4'-piperidin]-6-yl}nicotinic acid,
(66) 3-carboxy-5-{1'-[4-(1-cyclopropyl-1H-pyrazol-4-yl)-3,5-diethoxybenzoyl]-4-oxospiro[chroman-2,4'-piperidin]-6-yl}pyridinium trifluoroacetate,
(67) 5-(1'-{4-[1-(difluoromethyl)-1H-pyrazol-4-yl]-3,5-diethoxybenzoyl}-4-oxospiro[chroman-2,4'-piperidin]-6-yl)nicotinic acid,
(68) 6-{1'-[3,5-dimethoxy-4-(1-methyl-1H-pyrazol-4-yl)benzoyl]-4-oxospiro[chroman-2,4'-piperidin]-6-yl}nicotinamide,
(71) Sodium 6-{1'-[3,5-diethoxy-4-(1-methyl-1H-pyrazol-4-yl)benzoyl]-4-oxospiro[chroman-2,4'-piperidin]-6-yl}nicotinate,
(72) 6-(1,1-dioxido-4-thiomorpholinyl)-1'-[3-ethoxy-5-methoxy-4-(1-methyl-1H-pyrazol-4-yl)benzoyl]spiro[chroman-2,4'-piperidin]-4-one,
(75) 5-{1'-[3-Ethoxy-5-methoxy-4-(1-methyl-1H-pyrazol-4-yl)benzoyl]-4-oxospiro[chroman-2,4'-piperidin]-6-yl}nicotinic acid,
(76) 6-(4-acetyl-1-piperazinyl)-1'-[3-ethoxy-5-methoxy-4-(1-methyl-1H-pyrazol-4-yl)benzoyl]spiro[chroman-2,4'-piperidin]-4-one,
(77) 6-{1'-[3-ethoxy-5-methoxy-4-(1-methyl-1H-pyrazol-4-yl)benzoyl]-4-oxospiro[chroman-2,4'-piperidin]-6-yl}nicotinamide,
(79) 1'-[3-Ethoxy-5-methoxy-4-(1-methyl-1H-pyrazol-4-yl)benzoyl]-6-(1-methyl-1H-pyrazol-4-yl)spiro[chroman-2,4'-piperidin]-4-one,
(80) 1'-[(3-Methyl-1-phenyl-1H-furo[2,3-c]pyrazol-5-yl)carbonyl]-6-(tetrazol-5-yl)spiro[chroman-2,4'-piperidin]-4-one, or
(81) Sodium 5-[3-cyclopropyl-5-({6-[(1-methyl-1H-pyrazol-5-yl)amino]-4-oxospiro[chroman-2,4'-piperidin]-1'-yl}carbonyl)-1H-indol-1-yl]tetrazolide.

3. A pharmaceutical composition comprising a therapeutically effective amount of the compound of claim 1 or a salt or ester thereof, and a pharmaceutically acceptable additive.

\* \* \* \* \*